(12) United States Patent
Donald et al.

(10) Patent No.: US 12,128,095 B2
(45) Date of Patent: *Oct. 29, 2024

(54) ESCHERICHIA COLI COMPOSITIONS AND METHODS THEREOF

(71) Applicant: Pfizer Inc., New York, NY (US)

(72) Inventors: Robert G. K. Donald, South Orange, NJ (US); Annaliesa Sybil Anderson, Upper Saddle River, NJ (US); Laurent Oliver Chorro, New York, NY (US); Jianxin Gu, Paramus, NJ (US); Jin-Hwan Kim, Suffern, NY (US); Srinivas Kodali, Hillsborough, NJ (US); Jason Arnold Lotvin, West Nyack, NY (US); Justin Keith Moran, West Nyack, NY (US); Rosalind Pan, Morris Plains, NJ (US); Avvari Krishna Prasad, Chapel Hill, NC (US); Mark Edward Ruppen, Cresco, PA (US); Suddham Singh, Monroe, NY (US); Ling Chu, Suffern, NY (US); Scott Ellis Lomberk, Suffern, NY (US); Karen Kiyoko Takane, Brooklyn, NY (US); Nishith Merchant, Parlin, NJ (US); Wei Chen, Cliffside Park, NJ (US)

(73) Assignee: Pfizer Inc., New York, NY (US)

( * ) Notice: Subject to any disclaimer, the term of this patent is extended or adjusted under 35 U.S.C. 154(b) by 149 days.

This patent is subject to a terminal disclaimer.

(21) Appl. No.: 17/672,126

(22) Filed: Feb. 15, 2022

(65) Prior Publication Data

US 2022/0168410 A1     Jun. 2, 2022

Related U.S. Application Data

(63) Continuation of application No. 16/534,457, filed on Aug. 7, 2019, now Pat. No. 11,260,119.

(60) Provisional application No. 62/881,361, filed on Jul. 31, 2019, provisional application No. 62/784,940, filed on Dec. 26, 2018, provisional application No. 62/722,370, filed on Aug. 24, 2018.

(51) Int. Cl.
| | |
|---|---|
| *A61K 39/108* | (2006.01) |
| *A61K 39/00* | (2006.01) |
| *A61P 31/04* | (2006.01) |
| *A61P 37/04* | (2006.01) |
| *C08B 37/00* | (2006.01) |

(52) U.S. Cl.
CPC .......... *A61K 39/0258* (2013.01); *A61P 31/04* (2018.01); *A61P 37/04* (2018.01); *C08B 37/006* (2013.01); *A61K 2039/6037* (2013.01); *A61K 2039/627* (2013.01)

(58) Field of Classification Search
CPC ........ A61K 39/0258; A61K 2039/6037; A61K 2039/627; A61P 37/04; A61P 31/04; C08B 37/006
USPC ...................................................... 424/194.1
See application file for complete search history.

(56) References Cited

U.S. PATENT DOCUMENTS

| | | |
|---|---|---|
| 4,709,017 A | 11/1987 | Collier et al. |
| 4,950,740 A | 8/1990 | Greenfield et al. |
| 5,340,740 A | 8/1994 | Petitte et al. |
| 5,370,872 A | 12/1994 | Cryz et al. |
| 5,614,382 A | 3/1997 | Metcalf |
| 5,656,479 A | 8/1997 | Petitte et al. |
| 5,830,510 A | 11/1998 | Petitte et al. |
| 5,843,711 A | 12/1998 | Collier et al. |
| 5,917,017 A | 6/1999 | Collier et al. |
| 6,114,168 A | 9/2000 | Samarut et al. |
| 6,194,388 B1 | 2/2001 | Krieg et al. |
| 6,207,646 B1 | 3/2001 | Krieg et al. |
| 6,214,806 B1 | 4/2001 | Krieg et al. |
| 6,218,371 B1 | 4/2001 | Krieg et al. |
| 6,239,116 B1 | 5/2001 | Krieg et al. |
| 6,339,068 B1 | 1/2002 | Krieg et al. |
| 6,455,673 B1 | 9/2002 | Collier |
| 6,500,668 B2 | 12/2002 | Samarut et al. |
| 6,749,831 B1 | 6/2004 | Bennett-Guerrero et al. |
| 7,247,307 B2 | 7/2007 | Szu et al. |
| 8,871,214 B2 | 10/2014 | Serino et al. |
| 9,060,965 B2 | 6/2015 | Costantino et al. |
| 9,492,559 B2 | 11/2016 | Emini et al. |
| 9,517,274 B2 | 12/2016 | Gu et al. |
| 9,585,950 B2 | 3/2017 | Wacker et al. |

(Continued)

FOREIGN PATENT DOCUMENTS

| | | |
|---|---|---|
| CA | 2004810 | 6/1990 |
| EP | 0 372 501 A2 | 12/1989 |

(Continued)

OTHER PUBLICATIONS

PCT International Search Report and Written Opinion for International Application No. PCT/IB2021/062022 mailed on Jun. 3, 2022.

(Continued)

*Primary Examiner* — Yih-Horng Shiao
(74) *Attorney, Agent, or Firm* — Rebecca Wright

(57) ABSTRACT

In one aspect, the invention relates to an immunogenic composition comprising modified O-polysaccharide molecules derived from *E. coli* lipopolysaccharides and conjugates thereof. Multivalent vaccines may be prepared by combining two or more monovalent immunogenic compositions for different *E. coli* serotypes. In one embodiment, the modified O-polysaccharide molecules are produced by a recombinant bacterium that includes a wzz gene.

29 Claims, 31 Drawing Sheets

Specification includes a Sequence Listing.

(56) References Cited

U.S. PATENT DOCUMENTS

| | | |
|---|---|---|
| 9,700,612 B2 | 7/2017 | Kowarik et al. |
| 9,849,169 B2 | 12/2017 | Nagy et al. |
| 11,260,119 B2 | 3/2022 | Donald et al. |
| 2006/0228380 A1 | 10/2006 | Hausdorff et al. |
| 2007/0184071 A1 | 8/2007 | Hausdorff et al. |
| 2007/0184072 A1 | 8/2007 | Hausdorff et al. |
| 2007/0231340 A1 | 10/2007 | Hausdorff et al. |
| 2007/0231876 A1 | 10/2007 | Biemans et al. |
| 2007/0253984 A1 | 11/2007 | Kandke et al. |
| 2012/0276137 A1 | 11/2012 | Freese et al. |
| 2013/0122033 A1 | 5/2013 | De Santis et al. |
| 2015/0216996 A1 | 8/2015 | Gu et al. |
| 2015/0328328 A1 | 11/2015 | Han et al. |
| 2016/0015797 A1 | 1/2016 | Bouzari |
| 2016/0106826 A1 | 4/2016 | Ghunaim et al. |
| 2016/0158333 A1 | 6/2016 | White et al. |
| 2016/0193330 A1 | 7/2016 | Eldridge et al. |
| 2016/0220666 A1 | 8/2016 | Eldridge et al. |
| 2016/0324950 A1 | 11/2016 | Anderson et al. |
| 2017/0260240 A1 | 9/2017 | Simon et al. |
| 2019/0275134 A1 | 9/2019 | Poolman |
| 2019/0275135 A1 | 9/2019 | Poolman |
| 2020/0002727 A1 | 1/2020 | Feary et al. |
| 2020/0061177 A1 | 2/2020 | Donald et al. |
| 2021/0268095 A1 | 9/2021 | Donald et al. |
| 2022/0152181 A1 | 5/2022 | Anderson et al. |
| 2022/0202923 A1 | 6/2022 | Che et al. |

FOREIGN PATENT DOCUMENTS

| | | |
|---|---|---|
| EP | 0413378 B1 | 2/1991 |
| EP | 0 378 881 B1 | 6/1993 |
| EP | 0 427 347 B1 | 2/1995 |
| EP | 0 471 177 B1 | 10/1995 |
| EP | 0 689 454 B1 | 9/1997 |
| EP | 0 594 610 B1 | 9/1998 |
| EP | 0 735 898 B1 | 3/1999 |
| EP | 0 761 231 B1 | 1/2000 |
| GB | 2 220 211 A | 1/1990 |
| WO | 90/03184 A1 | 4/1990 |
| WO | 91/01146 A1 | 2/1991 |
| WO | 93/003765 A1 | 3/1993 |
| WO | 93/17712 A2 | 9/1993 |
| WO | 94/03208 A1 | 2/1994 |
| WO | 96/11711 A1 | 4/1996 |
| WO | 97/01640 A2 | 1/1997 |
| WO | 98/36772 A1 | 8/1998 |
| WO | 98/57659 A1 | 12/1998 |
| WO | 98/58668 A2 | 12/1998 |
| WO | 99/11241 A1 | 3/1999 |
| WO | 99/44636 A2 | 9/1999 |
| WO | 99/52549 A1 | 10/1999 |
| WO | 00/004922 A1 | 2/2000 |
| WO | 00/07621 A2 | 2/2000 |
| WO | 00/23105 A2 | 4/2000 |
| WO | 00/37105 A2 | 6/2000 |
| WO | 00/39299 A2 | 7/2000 |
| WO | 00/41720 A1 | 7/2000 |
| WO | 00/48630 A1 | 8/2000 |
| WO | 00/56358 A2 | 9/2000 |
| WO | 00/61761 A2 | 10/2000 |
| WO | 00/62800 A2 | 10/2000 |
| WO | 01/04148 A2 | 1/2001 |
| WO | 01/21152 A1 | 3/2001 |
| WO | 01/21207 A2 | 3/2001 |
| WO | 01/72337 A1 | 10/2001 |
| WO | 01/98334 A2 | 12/2001 |
| WO | 02/04496 A2 | 1/2002 |
| WO | 02/053181 A1 | 7/2002 |
| WO | 02/091998 A1 | 11/2002 |
| WO | 03/054007 A2 | 7/2003 |
| WO | 2004/081515 A2 | 9/2004 |
| WO | 2004/083251 A2 | 9/2004 |
| WO | 2006/032499 A1 | 3/2006 |
| WO | 2006/110381 A1 | 10/2006 |
| WO | 2006/134423 A2 | 12/2006 |
| WO | 2007/026190 A2 | 3/2007 |
| WO | 2008/079653 A1 | 7/2008 |
| WO | 2008/142034 A2 | 11/2008 |
| WO | 2008/143709 A2 | 11/2008 |
| WO | 2009/000826 A1 | 12/2008 |
| WO | 2010/125480 A1 | 11/2010 |
| WO | 2013/164334 A1 | 11/2013 |
| WO | 2013/188539 A2 | 12/2013 |
| WO | 2014/013375 A1 | 1/2014 |
| WO | 2014/027302 A1 | 2/2014 |
| WO | 2014/057109 A1 | 4/2014 |
| WO | 2014/072405 A1 | 5/2014 |
| WO | 2015/052344 A1 | 4/2015 |
| WO | 2015/124769 A1 | 8/2015 |
| WO | 2016/012587 A1 | 1/2016 |
| WO | 2016/115328 A1 | 7/2016 |
| WO | 2016/168324 A1 | 10/2016 |
| WO | 2016/183501 A1 | 11/2016 |
| WO | 2017/035181 A1 | 3/2017 |
| WO | 2017/085586 A1 | 5/2017 |
| WO | 2019/016187 A1 | 1/2019 |
| WO | 2019/175147 A1 | 9/2019 |
| WO | 2020/039359 A2 | 2/2020 |
| WO | 2021/084429 A1 | 5/2021 |
| WO | 2021/144369 A1 | 7/2021 |
| WO | 2021/165928 A2 | 8/2021 |
| WO | 2022/090893 A2 | 5/2022 |
| WO | 2022/137078 A1 | 6/2022 |

OTHER PUBLICATIONS

Pearson et al, "Improved tools for biological sequence comparison", PNAS 85:2444-2448 (1988).

Podschun et al, "*Klebsiella* spp. As Nosocomial Pathogens: Epidemiology, Taxonomy, Typing Methods, and Pathogenicity Factors", Clinical Microbiology Reviews 11(4):589-603 (1998).

Rodriguez et al, "Allosteric Coupling in the Bacterial Adhesive Protein FimH", The Journal of Biological Chemistry 288(33):24128-24139 (2013).

Rogers et al, "*Escherichia coli* O25b-ST131: a pandemic, multiresistant, community-associated strain", Journal of Antimicrobial Chemotherapy 66:1-14 (2011).

Ruiz-Argüello et al, "Thermostability of the human respiratory syncytial virus fusion protein before and after activation: implications for the membrane-fusion mechanism", Journal of General Virology 85(12):3677-3687 (2004).

Russo et al, "Medical and economic impact of extraintestinal infections due to *Escherichia coli*: focus on an increasingly important endemic problem", Microbes and Infection 5:449-456 (2003).

Schembri et al, "Expression and purification of the mannose recognition domain of the FimH adhesin", FEMS Microbiology Letters 188:147-151 (2000).

Schrag et al, "Epidemiology of Invasive Early-Onset Neonatal Sepsis, 2005 to 2014", Pediatrics 138(6):e20162013 (2016).

Schwartz et al, "Population Dynamics and Niche Distribution of Uropathogenic *Escherichia coli* during Acute and Chronic Urinary Tract Infection", Infection and Immunity 79(10):4250-4259 (2011).

Schwartz et al, "Positively selected FimH residues enhance virulence during urinary tract infection by altering FimH conformation", PNAS 110(39):15530-15537 (2013).

Sjölander et al, "ISCOMs: an adjuvant with multiple functions", Journal of Leukocyte Biology 64:713-723 (1998).

Starks et al, "Optimization and qualification of an assay that demonstrates that a FimH vaccine induces functional antibody responses in women with histories of urinary tract infections", Human Vaccines & Immunotherapeutics 17(1):283-292 (2021).

Stoll et al, "Early Onset Neonatal Sepsis: The Burden of Group B Streptococcal and *E. coli* Disease Continues", Pediatrics 127(5):817-826 (2011).

Summers et al, A Manual of Methods for Baculovirus Vectors and Insect Cell Culture Procedures; Texas Agricultural Experiment Station Bulletin No. 1555 (1987).

(56) References Cited

OTHER PUBLICATIONS

Thelwall et al, "Annual Epidemiological Commentary: Mandatory MRSA, MSSSA and *E. coli* bacteraemia and C. difficile infection data 2015/2016", Jul. 7, 2016, Public Health England.

Thumbikat et al, "Bacteria-Induced Uroplakin Signaling Mediates Bladder Response to Infection", PLoS Pathogens 5(5):e1000415 (2009).

Uchida et al, "Mutation in the Structural Gene for Diphtheria Toxin Carried by Temperate Phage Beta", Nature New Biology 233:8-11 (1971).

Uchida et al, "Diphtheria toxin and related proteins. I. Isolation and properties of mutant proteins serologically related to diphtheria toxin", J Biol Chem 248(11):3838-3844 (1973).

Urlaub et al, "Isolation of Chinese hamster cell mutants deficient in dihydrofolate reductase activity", Proc. Natl. Acad. Sci. USA 77(7):4216-4220 (1980).

Vetsch et al, "Chaperone-independent Folding of Type 1 Pilus Domains", J. Mol. Biol. 322(4):827-840 (2002).

Vinogradov et al, "Structures of Lipopolysaccharides from Klebsiella pneumoniae: Elucidation of the Structure of the Linkage Region Between Core and Polysaccharide O Chain and Identification of the Residues at the Non-Reducing Termini of the O Chains", The Journal of Biological Chemistry 277(28):25070-25081 (2002).

Weissman et al, "Clonal analysis reveals high rate of structural mutations in fimbrial adhesins of extraintestinal pathogenic *Escherichia coli*", Mol Microbiol. 59(3):975-988 (2006).

Wick et al, "Kaptive Web: User-Friendly Capsule and Lipopolysaccharide Serotype Prediction for Klebsiella Genomes", Journal of Clinical Microbiology 56(6):e00197-18 (2018).

Wirth et al, "Sex and virulence in *Escherichia coli*: an evolutionary perspective", Molecular Microbiology 60(5):1136-1151 (2006).

Yinnon et al, "Klebsiella bacteraemia: community versus nosocomial infection", Q J Med 89(12):933-941 (1996).

Zowawi et al, "The emerging threat of multidrug-resistant Gram-negative bacteria in urology", Nature Reviews Urology 12:570-584 (2015).

Meiland, R., et al., "Fimch antiserum inhibits the adherence of *Escherichia coli* to cells collected by voided urine specimens of diabetic women" J Urol 171:1589-1593 (2004).

Mellata, M., et al, "Novel vaccine antigen combinations elicit protective immune responses against *Escherichia coli* sepsis", Vaccine, 34(5):656-662 (2016).

Meloni, E., et al., "Simplified low-cost production of O-antigen from *Salmonella typhimurium* Generalized Modules for Membrane Antigens (GMMA)", Journal of Biotechnology 198:46-52 (2015).

Micoli, F., et al., "A Scalable Method for O-antigen Purification Applied to Various *Salmonella* Serovars", Anal Biochem, 434(1):136-145 (2013).

Mobley H. and Alteri C., "Development of a Vaccine against *Escherichia coli* Urinary Tract Infections", Pathogens 5 (2016).

Morales-Barroso, I., et al., "Bacteraemia due to non-ESBL-producing *Escherichia coli* O25b:H4 sequence type 131: insights into risk factors, clinical features and outcomes", Int J Antimicrob Agents doi:10.1016/j.ijantimicag (2016).

Moriel, D., et al., "Identification of Protective and Broadly Conserved Vaccine Antigens from the Genome of Extraintestinal Pathogenic *Escherichia coli*", Proc Natl Acad Sci, 107(20):9072-9077 (2010).

Motley, M. & Fries, B., "A New Take on an Old Remedy: Generating Antibodies against Multidrug-Resistant Gram-Negative Bacteria in a Postantibiotic World", mSphere, 2(5) e00397-17 (2017).

Mulford, C. and Osborn M., "An intermediate step in translocation of lipopolysaccharide to the outer membrane of *Salmonella typhimurium*", Proc Natl Acad Sci U S A 80:1159-1163 (1983).

Muller-Leonnies, S., et al., "Neutralizing and Cross-Reactive Antibodies Against Enterobacterial Lipopolysaccharide", Int J Med Microbiol., 297(5):321-40 (2007).

Murray, G., et al., "Regulation of *Salmonella typhimurium* lipopolysaccharide O antigen chain length is required for virulence; identification of FepE as a second Wzz", Mol Microbiol, 47:1395-1406 (2003).

Naumenko, O., "Structure and Gene Cluster of the O-antigen of *Escherichia coli* O54", Carbohydrate Research, 462:34-38 (2018).

Naumenko, O., et al., "Structural Studies on the O-polysaccharide of *Escherichia coli* O57", Carbohydrate Research 465:1-3 (2018).

O'Brien, V., et al, "Drug and Vaccine Development for the Treatment and Prevention of Urinary Tract Infections", Microbiol Spectrum 4(1): 1-42 (2016).

Osawa, K., et al., "Modulation of O-antigen chain length by the wzz gene in *Escherichia coli* O157 influences its sensitivities to serum complement", Microbiol Immunol 57:616-623 (2013).

Perepelov, A., et al., "Structure and Gene Cluster of the O-antigen of *Escherichia coli* O76", Carbohydrate Research, 377:14-14 (2013).

Perepelov, A., et al., "Structure and Gene Cluster of the O-antigen of *Escherichia coli* O36", Carbohydrate Research, 390:46-49 (2014).

Perepelov, A., et al., "Structure and Gene Cluster of the O-antigen of *Escherichia coli* O140", Carbohydrate Research 411:33-36 (2015).

Phalipon, A., et al., "A Synthetic Carbohydrate-Protein Conjugate Vaccine Candidate Against Shigella Flexneri 2a Infection", J Immunol., 182(4):2241-7 (2009).

Phan, M., et al., "The Serum Resistome of a Globally Disseminated Multidrug Resistant Uropathogenic *Escherichia coli* Clone", PLoS Genetics 9:e1003834 (2013).

Poolman, J., et al., Extraintestinal Pathogenic *Escherichia coli*, a Comon Human Pathogen: Challenges for Vaccine Development and Progress in the Field, Journal of Infectious Diseases, 213(1):6-13 (2016).

Rabbani, S., et al, "Conformational switch of the bacterial adhesin FimH in the absence of the regulatory domain: Engineering a minimalistic allosteric system", J. Biol. Chem., 293(5): 1835-1849 (2018).

Reyes E., et al., Mechanisms of O-Antigen Structural Variation of Bacterial Lipopolysaccharide (LPS). Chapter 3, The Complex World of Polysaccharides. IntechOpen (2012).

Ronald, L., et al, "Adaptive mutations in the signal peptide of the type 1 fimbrial adhesin of uropathogenic *Escherichia coli*" PNAS, 105(31): 10937-10942 (2008).

Sarkar, S., "Role of Capsule and O Antigen in the Virulence of Uropathogenic *Escherichia coli*", PLoS One 9: e94786 (2014).

Sato, T., et al. , "Tigecycline Nonsusceptibility Occurs Exclusively in Fluoroquinolone-Resistant *Escherichia coli* Clinical Isolates, Including the Major Multidrug-Resistant Lineages", Antimicrob Agents Chemother, O25b:H4-ST131-H30R and O1-ST648. 61 (2017).

Sauer, M., et al, "Catch-bond mechanism of the bacterial adhesin FimH", Nat. Commun. 7:10738 doi: 10.1038/ncomms 10738 (2016).

Shang, W., et al., "Chemical Synthesis of the Outer Core Oligosaccharide of *Escherichia coli* R3 and Immunological Evaluation" Org Biomol Chem., 13(14):4321-4330 (2015).

Sheikh, A., et al, "Highly conserved type 1 pili promote enterotoxigenic *E. coli* pathogen-host interactions", PLoS Negl Trop Dis 11(5): e0005586 (2017).

Sihra, N., et al, "Nonantibiotic prevention and management of recurrent urinary tract infection", Nat Rev Urol 15: 750-776 (2018).

Smith, SN, "Dissemination and systemic colonization of uropathogenic *Escherichia coli* in a murine model of bacteremia" MBio 1 (2010).

Stenutz, R., et al., The Structures of *Escherichia coli* O-polysaccharide Antigens, FEMS Microbiol Rev., 30 (3):382-403 (2006).

Szijarto, V., et al., "Diagnostic Potential of Monoclonal Antibodies Specific to the Unique O-Antigen of Multidrug-Resistant Epidemic *Escherichia coli* Clone ST131-O25b:H4", Clin Vaccine Immunol., 21(7):930-939 (2014).

Szijarto, V., et al., "Bactericidal monoclonal antibodies specific to the lipopolysaccharide O antigen from multidrug-resistant *Escherichia coli* clone ST131-O25b:H4 elicit protection in mice", Antimicrob Agents Chemother 59:3109-3116 (2015).

Taylor, C., et al., Mutations in the waaR Gene of *Escherichia coli* Which Disrupt Lipopolysaccharide Outer Core Biosynthesis Affect Cell Surface Retention of Group 2 Capsular Polysaccharides, J Bacteriol. 88(3):1165-1168 (2006).

(56) References Cited

OTHER PUBLICATIONS

Tchesnokova, V., et al, "Type 1 Fimbrial Adhesin FimH Elicits an Immune Response That Enhances Cell Adhesion of *Escherichia coli*", Infection and Immunity, 79(10): 3895-3904 (2011).
Tocilj, A., et al., "Bacterial polysaccharide co-polymerases share a common framework for control of polymer length" Nat Struct Mol Biol 15:130-138 (2008).
Van Den Dobbelsteen, G.P., et al., "Immunogenicity and safety of a tetravalent *E. coli* O-antigen bioconjugate vaccine in animal models", Vaccine 34:4152-4160 (2016).
Vimont, S., et al., "The CTX-M-15-producing *Escherichia coli* clone O25b: H4-ST131 has high intestine colonization and urinary tract infection abilities" PLoS One 7:e46547 (2012).
Whitfield, C., et al., Molecular Insights Into the Assembly and Diversity of the Outer Core Oligosaccharide in Lipopolysaccharides from *Escherichia coli* and *Salmonella*, J Endotoxin Res., 9(4):244-249 (2003).
Wizemann, T., et al, "Adhesins as Targets for Vaccine Development", Emerg Infect Dis, 5(3):395-403 (1999).
Wolf, M., Occurrence, Distribution, and Associations of O and H serogroups, Colonization Factor Antigens, and Toxins of Enterotoxigenic *Escherichia coli*, Clin Microbiol Rev., 10(4):569-84 (1997).
Woodward, R., et al., "In vitro bacterial polysaccharide biosynthesis: defining the functions of Wzy and Wzz." Nat Chem Biol., 6(6):418-23 (2010).
Zhou, G., et al., "Uroplakin Ia is the urothelial receptor for uropathogenic *Escherichia coli*: evidence from in vitro FimH binding", J Cell Sci 114:4095-4103 (2001).
Kisiela et al, "Conformational inactivation induces immunogenicity of the receptor-binding pocket of a bacterial adhesin—Supporting Information", 10.1073/pnas.1314395110 (2013).
Al-Hasan et al, "Antimicrobial resistance trends of *Escherichia coli* bloodstream isolates: a population-based study, 1998-2007", Journal of Antimicrobial Chemotherapy 64(1):169-174 (2009).
Anderson et al, "Bloodstream Infections in Community Hospitals in the 21st Century: A Multicenter Cohort Study", PLoS One 9(3):e91713 (2014).
Baraldo et al, "N19 Polyepitope as a Carrier for Enhanced Immunogenicity and Protective Efficacy of Meningococcal Conjugate Vaccines", Infection and Immunity 72(8):4884-4887 (2004).
Barnhart et al, "PapD-like chaperones provide the missing information for folding of pilin proteins", PNAS 97(14):7709-7714 (2000).
Barnhart et al, "Chaperone-Subunit-Usher Interactions Required for Donor Strand Exchange during Bacterial Pilus Assembly", Journal of Bacteriology 185(9):2723-2730 (2003).
Bauchart et al, "Pathogenomic comparison of human extraintestinal and avian pathogenic *Escherichia coli*—Search for factors involved in host specificity or zoonotic potential", Microbial Pathogenesis 49(3):105-115 (2010).
Bouckaert et al, "Receptor binding studies disclose a novel class of high-affinity inhibitors of the *Escherichia coli* FimH adhesin", Molecular Microbiology 55(2):441-455 (2005).
Brown et al, "Structure of the streptococcal cell wall C5a peptidase", Proc. Natl. Acad. Sci. USA 102(51):18391-18396 (2005).
Buckles et al, "Role of the K2 Capsule in *Escherichia coli* Urinary Tract Infection and Serum Resistance", The Journal of Infectious Diseases 199(11):1689-1697 (2009).
Burns et al, "Loss of Resistance to Ingestion and Phagocytic Killing by O- and K- Mutants of a Uropathogenic *Escherichia coli* O75:K5 Strain", Infection and Immunity 67(8):3757-3762 (1999).
Céspedes et al, "Genetic Diversity and Virulence Determinants of *Escherichia coli* Strains Isolated from Patients with Crohn's Disease in Spain and Chile", Frontiers in Microbiology 8:Article 639 (2017).
Chen et al, "Carbapenemase-producing Klebsiella pneumoniae: molecular and genetic decoding", Trends in Microbiology 22(12):686-696 (2014).
Clarke et al, "Coordination of Polymerization, Chain Termination, and Export in Assembly of the *Escherichia coli* Lipopolysaccharide O9a Antigen in an ATP-binding Cassette Transporter-dependent Pathway", The Journal of Biological Chemistry 284(44):30662-30672 (2009).
Cusumano et al, "Treatment and Prevention of Urinary Tract Infection with Orally Active FimH Inhibitors", Science Translational Medicine 3(109):109ra115 (2011).
Diancourt et al, "Multilocus Sequence Typing of Klebsiella pneumoniae Nosocomial Isolates", Journal of Clinical Microbiology 43(8):4178-4182 (2005).
Douglas et al, "Exotoxin A of Pseudomonas aeruginosa: Substitution of Glutamic Acid 553 with Aspartic Acid Drastically Reduces Toxicity and Enzymatic Activity", Journal of Bacteriology 169(11):4967-4971), (year 1987).
Dreux et al, "Point Mutations in FimH Adhesin of Crohn's Disease-Associated Adherent-Invasive *Escherichia coli* Enhance Intestinal Inflammatory Response", PLoS Pathogens 9(1):e1003141 (2013).
Falugi et al, "Rationally designed strings of promiscuous CD4+ T cell epitopes provide help to Haemophilus influenzae type b oligosaccharide: a model for new conjugate vaccines", Eur. J. Immunol. 31:3816-3824 (2001).
Follador et al, "The diversity of Klebsiella pneumoniae surface polysaccharides", Microbial Genomics 2:e000073 (2016).
Ghosh et al, "Incidence of multidrug resistance, pathogenicity island markers, and pathoadaptive FimH mutations in uropathogenic *Escherichia coli* isolated from asymptomatic hospitalized patients", Folia Microbiologica 64(4):587-600 (2019).
Graham et al, "Characteristics of a Human Cell Line Transformed by DNA from Human Adenovirus Type 5", J. Gen. Virol. 36(1):59-74 (1977).
Greenfield et al, "Biosynthesis of the Polymannose Lipopolysaccharide O-antigens from *Escherichia coli* Serotypes O8 and O9a Requires a Unique Combination of Single- and Multiple-active Site Mannosyltransferases", The Journal of Biological Chemistry 287(42):35078-35091 (2012).
Guachalla et al, "Discovery of monoclonal antibodies cross-reactive to novel subserotypes of K. pneumoniae O3", Scientific Reports 7:6635 (2017).
Hannan et al, "Early Severe Inflammatory Responses to Uropathogenic *E. coli* Predispose to Chronic and Recurrent Urinary Tract Infection", PLoS Pathogens 6(8):e1001042 (2010).
Hull et al, "Construction and Expression of Recombinant Plasmids Encoding Type 1 or D-Mannose-Resistant Pili from a Urinary Tract Infection *Escherichia coli* Isolate", Infection and Immunity 33(3):933-938 (1981).
Iebba et al, "Microevolution in fimH Gene of Mucosa-Associated *Escherichia coli* Strains Isolated from Pediatric Patients with Inflammatory Bowel Disease", Infection and Immunity 80(4):1408-1417 (2012).
Iredell et al, "Antibiotic resistance in Enterobacteriaceae: mechanisms and clinical implications", BMJ 352:h6420 (2016).
Joensen et al, "Rapid and Easy In Silico Serotyping of *Escherichia coli* Isolates by Use of Whole-Genome Sequencing Data", Journal of Clinical Microbiology 53(8):2410-2426 (2015).
Jolley et al, "Open-access bacterial population genomics: BIGSdb software, the PubMLST.org website and their applications", Wellcome Open Research 3:124 (2018).
Ktnik-Prastowska et al, "Glycosylation of uroplakins. Implications for bladder physiopathology", Glycoconjugate Journal 31:623-636 (2014).
Khatun et al, "Immunology of carbohydrate-based vaccines", Advanced Drug Delivery Reviews 165-166:117-126 (2020).
Kido et al, "A Single Amino Acid Substitution in a Mannosyltransferase, WbdA, Converts the *Escherichia coli* O9 Polysaccharide into O9a: Generation of a New O-Serotype Group", Journal of Bacteriology 182(9):2567-2573 (2000).
King et al, "Lipopolysaccharide O antigen size distribution is determined by a chain extension complex of variable stoichiometry in *Escherichia coli* O9a", Proc. Natl. Acad. Sci. USA 111(17):6407-6412 (2014).
Kisiela et al, "Inhibition and Reversal of Microbial Attachment by an Antibody with Parasteric Activity against the FimH Adhesin of Uropathogenic *E. coli*", PLoS Pathogens 11(5):e1004857 (2015).

(56) References Cited

OTHER PUBLICATIONS

Kuo et al, "Characterization of a Recombinant Pneumolysin and Its Use as a Protein Carrier for Pneumococcal Type 18C Conjugate Vaccines", Infection and Immunity 63(7):2706-2713 (1995).

Kurupati et al, "Identification of vaccine candidate antigens of an ESBL producing Klebsiella pneumoniae clinical strain by immunoproteome analysis", Proteomics 6:836-844 (2006).

Le Trong et al, "Donor strand exchange and conformational changes during E. coli fimbrial formation", Journal of Structural Biology 172(3):380-388 (2010).

Liu et al, "Identification of FimH derivatives as adjuvant vaccinated with Pac that enhance protection against Streptococcus mutans colonization", Molecular and Cellular Probes 45:19-25 (2019).

Magala et al, "RMSD analysis of structures of the bacterial protein FimH identifies five conformations of its lectin domain", Proteins 88(4):593-603 (2019).

Marder et al, "Multistate Outbreak of Escherichia coli O157:H7 Associated with Bagged Salad", Foodborne Pathogens and Disease 11(8):593-595 (2014).

Mather, "Establishment and Characterization of Two Distinct Mouse Testicular Epithelial Cell Lines", Biology of Reproduction 23:243-252 (1980).

Mather et al, "Culture of Testicular Cells in Hormone-Supplemented Serum-Free Medium", Annals N.Y. Acad. Sci. 383:44-68 (1982).

Milstein et al, "Hybrid hybridomas and their use in immunohistochemistry", Nature 305(5934):537-540 (1983).

Munera et al, "Recognition of the N-terminal lectin domain of FimH adhesin by the usher FimD is required for type 1 pilus biogenesis", Molecular Microbiology 64(2):333-346 (2007).

Munera et al, "Specific residues in the N-terminal domain of FimH stimulate type 1 fimbriae assembly in Escherichia coli following the initial binding of the adhesin to FimD usher", Molecular Microbiology 69(4):911-925 (2008).

Needleman et al, "A General Method Applicable to the Search for Similarities in the Amino Acid Sequence of Two Proteins", J. Mol. Biol. 48(3):443-453 (1970).

Nicolas-Chanoine et al, "Escherichia coli ST131, an Intriguing Clonal Group", Clinical Microbiology Reviews 27(3):543-574 (2014).

PCT International Search Report and Written Opinion for International Application No. PCT/IB2019/057025 issued on Feb. 17, 2020.

PCT International Search Report and Written Opinion for International Application No. PCT/IB2021/051457 issued on Aug. 16, 2021.

PCT International Search Report and Written Opinion for International Application No. PCT/IB2020/060081 issued on Dec. 21, 2020.

Abbanat, D., et al., "Development and Qualification of an Opsonophagocytic Killing Assay To Assess Immunogenicity of a Bioconjugated Escherichia coli Vaccine", Clin Vaccine Immunol 24(12):e00123-17 (2017).

Alonso-Caballero, A., et al., "Mechanical architecture and folding of E. coli type 1 pilus domains", Nat Commun 9, 2758 (2018).

Amor, K., et al., "Distribution of core oligosaccharide types in lipopolysaccharides from Escherichia coli", Infect Immun 68:1116-1124 (2000).

Appelmelk, B., et al., "Frequencies of lipopolysaccharide core types in Escherichia coli strains from bacteraemic patients", Microbiology 140:1119-24 (1994).

Aprikian, P., et al, "The Bacterial Fimbrial Tip Acts as a Mechanical Force Sensor", PLoS Biol 9(5):e1000617 (2011).

Baliban, S., et al., "Development of a glycoconjugate vaccine to prevent invasive Salmonella typhimurium infections in sub-Saharan Africa", PLoS Negl Trop Dis. 11(4): e0005493 (2017).

Bameri, Z., et al., "High Yield Expression and Modified Purification of Novel Recombinant Truncated Protein FimH. MrpH against Urinary Tract Infections by Escherichia coli and Proteus mirabilis", Journal of Clinical and Diagnostic Research 12(1): KC06-KC09 (2018).

Behrens, R., et al., "Efficacy and safety of a patch vaccine containing heat-labile toxin from Escherichia coli against travellers' diarrhoea: a phase 3, randomised, double-blind, placebo-controlled field trial in travellers from Europe to Mexico and Guatemala", Lancet Infect Dis. 14(3):197-204 (2014).

Bennett-Guerrero, E., et al., "Preparation and preclinical Evaluation of a Novel Liposomal Complete-Core Lipopolysaccharide Vaccine", Infect Immun. 68(11):6202-6208 (2000).

Bourgeois, A., et al., "Status of Vaccine Research and Development for Enterotoxigenic Escherichia coli", Vaccine 34(26):2880-2886 (2016).

Brumbaugh, A., et al., Preventing Urinary Tract Infection: Progress Toward an Effective Escherichia coli Vaccine. Expert Rev Vaccines. 11(6):663-76 (2012).

Chakraborty, S., Human Experimental Challenge With Enterotoxigenic Escherichia coli Elicits Immune Responses to Canonical and Novel Antigens Relevant to Vaccine Development, The Journal of Infectious Diseases 218(9):1436-1446 (2018).

Chen, S., et al., "Positive selection identifies an in vivo role for FimH during urinary tract infection in addition to mannose binding", PNAS 106(52): 22439-22444 (2009).

Chmielewski, M., et al., "FimH-based display of functional eukaryotic proteins on bacteria surfaces", Scientific Reports 9:8410 s41598-019-44883 (2019).

Clermont, O., et al., Determination of Escherichia coli O Types by Allele-Specific Polymerase Chain Reaction: Application to the O types Involved in Human Septicemia, Diagn Microbiol Infect Dis. 57(2):129-36 (2007).

Cryz, S.J., "Synthesis and Characterization of a Polyvalent Escherichia coli O-polysaccharide-toxin A Conjugate Vaccine", Vaccine 13(5):449-453 (1995).

Debroy, C., et al., Comparison of O-Antigen Gene Clusters of All O-Serogroups of Escherichia coli and Proposal for Adopting a New Nomenclature for O-Typing. PLoS One 11(1):e0147434 (2016).

Durant, L., et al., "Identification of candidates for a subunit vaccine against extraintestinal pathogenic Escherichia coli", Infect Immun 75:1916-1925 (2007).

Feenstra, T., et al, "Adhesion of Escherichia coli under flow conditions reveals potential novel effects of FimH mutations", Eur J Clin Microbiol Infect Dis 36:467-478 (2017).

Feldman, M., et al., "Engineering N-linked protein glycosylation with diverse O antigen lipopolysaccharide structures in Escherichia coli", Proceedings of the National Academy of Sciences of the United States of America 102:3016-3021 (2005).

Forde, B., et al., "The complete genome sequence of Escherichia coli EC958: a high quality reference sequence for the globally disseminated multidrug resistant E. coli O25b:H4-ST131 clone", PLoS One, 9:e104400 (2014).

Franco, A., et al., "A Wzz (Cld) Protein Determines the Chain Length of K Lipoploysaccharide in Escherichia coli O8 and O9 Strains", Journal of Bacteriology 178(7):1903-1907 (1996).

Frenck, R., et al., Long-term Immunogenicity and Safety of ExPEC4V Vaccine Against Extraintestinal Pathogenic Escherichia coli Disease in Healthy Participants. Presented at the American Society for Microbiology, Jun. 7-11, Atlanta, GA. (2018).

Giedraitiene, A., et al., "Prevalence of O25b-ST131 clone among Escherichia coli strains producing CTX-M-15, CTX-M-14 and CTX-M-92 beta-lactamases", Infect Dis (Lond) 49:106-112 (2017).

Green, S., et al., "Murine model of chemotherapy-induced extraintestinal pathogenic Escherichia coli translocation", Infect Immun 83:3243-3256 (2015).

Jagan E. and Mobley H., "Uropathogenic Escherichia coli outer membrane antigens expressed during urinary tract infection", Infect Immun 75:3941-3949 (2007).

Han D., et al., "Regulation of the O-antigen polysaccharide chain length by Wzz—a review", Acta Microbiologica Sinica 54(9):971-976 (2014).

Hannan T., and Hunstad DA, "A Murine Model for Escherichia coli Urinary Tract Infection" Methods Mol Biol 1333:159-175 (2016).

Haraoka M., et al. "Neutrophil recruitment and resistance to urinary tract infection", J Infect Dis 180:1220-1229 (1999).

Hefzy, E. and Hassuna, N., "Fluoroquinolone-Resistant Sequence Type 131 Subgroups O25b and O16 Among Extraintestinal Escherichia

(56) References Cited

OTHER PUBLICATIONS

*coli* Isolates from Community-Acquired Urinary Tract Infections", Microb Drug Resist 23:224-229 (2017).
Heinrichs, D., et al., "The Assembly System for the Lipopolysaccharide R2 Core-Type of *Escherichia coli* is a hybrid of those found in *Escherichia coli* K-12 and *Salmonella enterica* Structure and function of the R2 WaaK and WaaL homologs", J Biol Chem. 273(15):8849-59 (1998).
Hong, Y. and Reeves P., "Model for the Controlled Synthesis of O-Antigen Repeat Units Involving the WaaL Ligase" mSphere 1 E00074-15 (2016).
Huttner, A., et al., "Safety, Immunogenicity, and Preliminary Clinical Efficacy of a Vaccine Against Extraintestinal Pathogenic *Escherichia coli* in Women with a History of Recurrent Urinary Tract Infection: a Randomised, Single-Blind, Placebo-Controlled Phase 1b Trial", Lancet Infect Dis, doi:10.1016/s1473-3099(17)30108-1 (2017).
Huttner, A., et al., "The Development and Early Clinical Testing of the ExPEC4V Conjugate Vaccine Against Uropathogenic *Escherichia coli*", Clin Microbiol Infect. 24(10):1046-1050 (2018).
Iguchi, A., et al., "A Complete View of the Genetic Diversity of the *Escherichia coli* O-antigen Biosynthesis Gene Cluster", DNA Res. 22(1):101-107 (2015).
Inoue, M., et al., "Safety, Tolerability and Immunogenicity of the ExPEC4V (JNJ-63871860) Vaccine for Prevention of invasive Extraintestinal Pathogenic *Escherichia coli* Disease: A phase 1, Randomized, Double-Blind, Placebo-Controlled Study in Healthy Japanese Participants", Hum Vaccin & Immunother. 14(9):2150-2157 (2018).
Jiang, L., et al., "Structure and Gene Cluster of the O-antigen of *Escherichia coli* O68", Carbohydrate Research 397:27-30 (2014).
Johnson S., et al., "Correlation of opsonophagocytosis and passive protection assays using human anticapsular antibodies in an infant mouse model of bacteremia for *Streptococcus pneumoniae*", J Infect Dis, 180:133-140 (1999).
Jonsson, K., et al., "Structural Determination of the O-antigenic Polysaccharide from *Escherichia coli* O74", Carbohydrade Research 344:1592-1595 (2009).
Kalynych, S., et al., "Structure-Guided Investigation of Lipopolysaccharide O-Antigen Chain Length Regulators Reveals Regions Critical for Modal Length Control", J Bacteriol. 193(15): 3710-3721 (2011).
Kalynych, S., et al., "Progress in Understanding the Assembly Process of Bacterial O-antigen", FEMS Microbiol Rev., 38(5):1048-1065 (2014).
Kisiela, D., et al, "Conformational inactivation induces immunogenicity of the receptor-binding pocket of a bacterial adhesin", PNAS, 110(47):19089-19094 (2013).
Knirel, Y.A., "Structure of O-Antigens", Bacterial Lipopolysaccharides: Structure, Chemical Synthesis, Biogenesis and Interaction with Host Cells; Chapter 3, pp. 41-115; Springer 2011.
Konadu, E., et al., Preparation, Characterization, and Immunological Properties in Mice of *Escherichia coli* O157 O-Specific Polysaccharide-Protein Conjugat Vaccines, Infection and Immunity, 62(11):5048-5054 (1994).
Lane, M., et al., "Expression of flagella is coincident with uropathogenic *Escherichia coli* ascension to the upper urinary tract", Proceedings of the National Academy of Sciences, 104:16669-16674 (2007).
Angermann, S., et al, "Prevention of Mucosal *Escherichia coli* Infection by FimH-Adhesin-Based Systemic Vaccination", Science, 267(5312): 607-611 (1997).
Larzabal, M., et al, "Human and Veterinary Vaccines against Pathogenic *Escherichia coli*", IntechOpen, 21 pages (2018).
Lerouge and Vanderleyden, "O-antigen structural variation: mechanisms and possible roles in animal/plant-microbe interactions", FEMS Microbiology Reviews 26(1):17-47 (2001).
Letrong, I., et al, "Structural Basis for Mechanical Force Regulation of the Adhesin FimH via Finger Trap-like b Sheet Twisting", Cell, 141:645-655 (2010).
Ma, Z., et al, "Glycoconjugate Vaccine Containing *Escherichia coli* O157:H7 O-Antigen Linked with Maltose-Binding Protein Elicits Humoral and Cellular Responses", PLOS One, 9(8): 1-10 (2014).
Costantino et al, "The design of semi-synthetic and synthetic glycoconjugate vaccines", Expert Opinion Drug Discovery 6(10):1045-1066 (2011).
Franco et al, "The Wzz (Cld) Protein in *Escherichia coli*: Amino Acid Sequence Variation Determines O-Antigen Chain Length Specificity", Journal of Bacteriology 180(10):2670-2675 (1998).
Rojas-Macias et al, "Development of the ECODAB into a relational database for *Escherichia coli* O-antigens and other bacterial polysaccharides", Glycobiology 25(3):341-347 (2015).
U.S. Appl. No. 16/534,457, filed Aug. 7, 2019.

FIG. 2

```
                          1         10        20        30        40        50        60        70        80        90
                          |         |         |         |         |         |         |         |         |         |
K12\W3110\WzzB            MRVENNNVSGQNHDPEQIDLIDLLVQLWRGKMTIISVIVAIALAIGYLAVAEKWTSAIITQPDVGQIAGYNNAMNVIYGQAAPKVSDLQETLIGRFS
O25a\ETEC\ATCC\WzzB       MRVENNNVSGQNHDPEQIDLIDLLVQLWRGKMTIISVIVAIALAIGYLAVAEKWTSAIITQPDVGQIAGYNNAMNVIYGQAAPKVSDLQETLIGRFS
O25a:K5:H1\WzzB           MRVENNNVSGQNHDPEQIDLIDLLVQLWRGKMTIISVIVAIALAIGYLAVAEKWTSAIITQPDVGQIAGYNNAMNVIYGQAAPKVSDLQETLIGRFS
O25b\2401\WzzB            MRVENNNVSGQNHDPEQIDLIDLLVQLWRGKMTIISVIVAIALAIGYLAVAEKWTSAIITQPDVGQIAGYNNAMNVIYGQAAPKVSDLQETLIGRFS
Salmonella\LT2\WzzB       MTVDSNTSSGRGNDPEQIDLIELLLQLWRGKMTIIVAVIIAILLAVGYLMIAKEKWTSAIITQPDAAQVATYTNALNVLYGGNAPKISEVQANFISRFS 100       110       120       130       140       150       160       170       180       190
                          |         |         |         |         |         |         |         |         |         |
K12\W3110\WzzB            SAFSALAETLDNQERREKLTIEPSVKNQQLPLTVSYVGQTAEGAQMKLAQYIQQVDDKVNQBLEKDLKDNIALGRKNLQDSLRTQEVVAQEQKDLRIRQI
O25a\ETEC\ATCC\WzzB       FAFSALAETLDNQKEPEKLTIEPSVKNQQLPLTVSYVGQTAERDAQMKLAQYIQQVDDKVNQBLRKDLKDNLALGRKNLQDSLRTQEVVAQEQKDLRIRQI
O25a:K5:H1\WzzB           SAFSALAETLDNQEDREPEKLTIEPSVKNQQLPLTVSYVGQTAEGAQMKLAQYIQQVDDKVNQBLEKDLKDNIALGRKNLQDSLRTQEVVAQEQKDLRIRQI
O25b\2401\WzzB            SAFSALAETLDNQEEPEKLTIEPSVKNQQLPLTVSYVGQTAEGAQMKLAQYIQQVDDKVNQBLEKDLKDNIALGRKNLQDSLRTQEVVAQEQKDLRIRQI
Salmonella\LT2\WzzB       SAFSALSEVLDNQKEREKLTIBQSVKGQALPLSVSYVSTTARGAQRRLABYIQQVDERVAKELEVDLKDNIFLQTKTLQESLETQEVVAQEQKDLRIKQI 200       210       220       230       240       250       260       270       280       290
                          |         |         |         |         |         |         |         |         |         |
K12\W3110\WzzB            QEALQYANQAQVTKPQIQQTGEBDITQDTLFLLGSEALESMIKHEATRPLVFSPNYYQTRQNLLDIBSLKVDDLDIHAYRYVMKPMLPIRRDSPKKAITLI
O25a\ETEC\ATCC\WzzB       QEALQYANQAQVTKPQIQQTGEBDITQDTLFLLGSEALESMIKHEATRPLVFSPNYYQTRQNLLDIBSLKVDDLDIHAYRYVMKPTLPIRRDSPKKAITLI
O25a:K5:H1\WzzB           QEALQYANQAQVTKPQIQQTGEBDITQDTLFLLGSEALESMIKHEATRPLVFSPNYYQTRQNLLDIBSLKVDDLDIHAYRYVMKPTLPIRRDSPKKAITLI
O25b\2401\WzzB            QEALQYANQAQVTKPQVQQT-EBVTQDTLFLLGSEALESMIKHEATRPLVFSPNYYQTRQNLLDIBSLKVDDLDIHAYRYVMKPTLPIRRDSPKKAITLI
Salmonella\LT2\WzzB       EEALRYADEAKITQPQIQQT-QDVTQDTMFLLGSDALKSMIQNEATRPLVFSPAYYQTKQTLIDIKNLKVTADTVHVYRYVMKPTLPVRRDSPKTAITLV 300       310       320
                          |         |         |
K12\W3110\WzzB            LAVLLGGMVGAGIVLGRNALRNYNAK*-      (SEQ ID NO: 23)
O25a\ETEC\ATCC\WzzB       LAVLLGGMVGAGIVLGRNALRNYNSK--      (SEQ ID NO: 22)
O25a:K5:H1\WzzB           LAVLLGGMVGAGIVLGRNALRNYNAK*-      (SEQ ID NO: 21)
O25b\2401\WzzB            LAVLLGGMVGAGIVLGRNALRNYNAK*-      (SEQ ID NO: 20)
Salmonella\LT2\WzzB       LAVLLGGMIGAGIVLGRNALRSYKPKAL      (SEQ ID NO: 24)
```

FIG. 5

```
                        1         10        20        30        40        50        60        70        80        90
                        |         |         |         |         |         |         |         |         |         |
O157\FepE               MSSLNIKQGSDAHFPDYPLASPSNNEIDLLNLISVLWRAKKTVMAVVFAFACAGLLISFILPQKWTSAAVVTPPEPVQWQELEKTFTKLRVLDLDIKIDR
O25a\ETEC\ATCC\FepE     MSSLNIKQGSDAHFPDYPLASPSNNEIDLLNLISVLWRAKKTVMAVVFAFACAGLLISFILPQKWTSAAVVTPPEPVQWQELEKTFTKLRVLDLDIKIDR
O25a:K5:H1\FepE         MSSLNIKQGSEAHFPEYPLASPSNNEIDLLNLIEVLWRAKKTVMAVVFAFACAGLLISFILPQKWTSAAVVTPPEPVQWQELEKTFTKLRVLDLDIKIDR
O25b\2401\FepE          MSSLNIKQGSDAHFPDYPLASPSNNEIDLLNLISVLWRAKKTVMAVVFAFACAGLLISFILPQKWTSAAVVTPPEPVQWQELEKSFTKLRVLDLDIKIDR
Salmonella\LT2\FepE     MPSLNVKQEKNQSFAGYSLPPANSHEIDLFSLIEVLWQAKRRILATVFRAFACVGLLLSFLLPQKWTSQAIVTPAESVQWQLERTLTALRVLDMEVSVDR 110       120       130       140       150       160       170       180       190
                                  |         |         |         |         |         |         |         |         |
O157\FepE               TEAFNLFIKKFQSVSLLEEYLRSSPYVMDQLKEAKIDELDLHRAIVALSEKMKAVDDNASKKKDEPSLYTSWTLSFTAPTSEEAQTVLSGYIDYISALVV
O25a\ETEC\ATCC\FepE     TEAFNLFIKKFQSVSLLEEYLRSSPYVMDQLKEAKIDELDLHRAIVALSEKMKAVDDNASKKKDEPSLYTSWTLSFTAPTSEEAQTVLSGYIDYISTLVV
O25a:K5:H1\FepE         TEAFNLFIKKFQSVSLLEEYLRSSPYVMDQLKEAKIDPLDLHRAIVALSEKMKAVDDNASKKKDESALYTSWTLSFTAPTSEEAQKVLAGYIDYISALVV
O25b\2401\FepE          TEAFNLFIKKFQSVSLLEEYLRSSPYVMDQLKEAKIDELDLHRAIVALSEKMKAVDDNASKKKDEPSLYTSWTLSFTAPTSEEAQTVLSGYIDYISTLVV
Salmonella\LT2\FepE     GSVFNLFIKKFSSPSLLEEYLRSSPYVMDQLKGAQIDEQDLHRAIVLLSEKMKAVDSNVGK-KNETSLFTSWTLSFTAPTREEAQKVLAGYIQYISDIVV 210       220       230       240       250       260       270       280       290
                                  |         |         |         |         |         |         |         |         |
O157\FepE               KESIENVRNKLEIKTQFEKEKLAQDRIKMKNQLDANIQRLNYSLDIANAAGIKKPVYSNGQAVKDDPDFSISLGADGIERKLEIEKAVTDVAELNGELRN
O25a\ETEC\ATCC\FepE     KESLENVRNKLEIKTQFEKEKLAQDRIKTKNQLDANIQRLNYSLDIANAAGIKKPVYSNGQAVKDDPDFSISLGADGIERKLEIEKAVTDVAELNGELRN
O25a:K5:H1\FepE         KESIENVRNKLEIKTQFEKEKLAQDRIKTKNQLDANIQRLNYSLDIANAAGIKKPVYSNGQAVKDDPDFSISLGADGIERKLEIEKAVTDVAELNGELRN
O25b\2401\FepE          KESLENVRNKLEIKTQFEKEKLAQDRIKTKNQLDANIQRLNYSLDIANAAGIKKPVYSNGQAVKDDPDFSISLGADGIERKLEIEKAVTDVAELNGELRN
Salmonella\LT2\FepE     KETLENIRNQLEIKTRYEQEKLAMDRVRLKNQLDANIQRLHYSLEIANAAGIKRPVYSNGQAVKDDPDFSISLGADGISRKLEIEKGVTDVABIDGDLRN 310       320       330       340       350       360       370
                                  |         |         |         |         |         |         |
O157\FepE               RQYLVEQLTKANINDVNFTPFKYQLSPSLPVKKDGPSKAIIVILSALIGGMVACGSVLLRYAMASRKQDAMMADH--LV (SEQ ID NO: 18)
O25a\ETEC\ATCC\FepE     RQYLVEQLTKAHVNDVNFTPFKYQLSPSLPVKKDGPGKAIIVILSALIGGMVACGGVLLRYAMASRKQDAMMADH--LV (SEQ ID NO: 17)
O25a:K5:H1\FepE         RQYLVEQLTKTNINDVNFTPFKYQLRPSLPVKKDGQGKAIIVILSALVGGMVACGGVLLRHAMASRKQDAMMADH--LV (SEQ ID NO: 16)
O25b\2401\FepE          RQYLVEQLTKAHVNDVNFTPFKYQLSPSLPVKKDGPGKAIIVILSALIGGMVACGGVLLRYAMASRKQDAMMADH--LV (SEQ ID NO: 15)
Salmonella\LT2\FepE     RQYHVBQLAAMNVSDVKFTPFKYQLSPSLPVKKDGPGKAIIILAALIGGMMACGGVLLRHAMVSRKMENALAIDERLV (SEQ ID NO: 19)
```

SPS PAGE

O25 Immuno-Blot

FIG. 9A

| Serogroup | Structure |
|---|---|
| O1A, O1A1 | →3)-α-L-Rha-(1→3)-α-L-Rha-(1→4)-β-L-Rha-(1→3)-β-D-GlcNAc-(1→ \| β-D-ManNAc-(1→2) |
| O1B | →3)-α-L-Rha-(1→2)-α-L-Rha-(1→2)-α-D-Gal-(1→3)-β-D-GlcNAc-(1→ \| β-D-ManNAc-(1→2) |
| O1C | →3)-α-L-Rha-(1→2)-α-L-Rha-(1→3)-α-D-Gal-(1→3)-β-D-GlcNAc-(1→ \| β-D-ManNAc-(1→2) |
| O2 | →3)-α-L-Rha-(1→2)-α-L-Rha-(1→4)-β-L-Rha-(1→3)-β-D-GlcNAc-(1→ \| α-D-Fuc3NAc-(1→2) |
| O3 | β-L-RhaNAc(1→4)α-D-Glc-(1→4)\|→3)-β-D-GlcNAc-(1→3)-α-D-Gal-(1→3)-β-D-GlcNAc-(1→ |
| O4:K52 | →2)-α-L-Rha-(1→6)-α-D-Glc-(1→3)-α-L-FucNAc-(1→3)-β-D-GlcNAc(1→ |
| O4:K6 | α-D-Glc-(1→3) \| →2)-α-L-Rha-(1→6)-α-D-Glc-(1→3)-α-L-FucNAc-(1→3)-β-D-GlcNAc(1→ |
| O5ab | →4)-β-D-Qui3NAc-(1→3)-β-D-Ribf-(1→4)-β-D-Gal-(1→3)-α-D-GalNAc(1→ |
| O5ac(strain 180/C3) | →2)-β-D-Qui3NAc-(1→3)-β-D-Ribf-(1→4)-β-D-Gal-(1→3)-α-D-GalNAc(1→ |
| O6:K2, K13; K15 | →4)-α-D-GalNAc-(1→3)-β-D-Man-(1→4)-β-D-Man-(1→3)-α-D-GlcNAc-(1→ \| β-D-Glc-(1→2) |
| O6:K54 | →4)-α-D-GalNAc-(1→3)-β-D-Man-(1→4)-β-D-Man-(1→3)-α-D-GlcNAc-(1→ \| β-D-GlcNAc-(1→2) |
| O7 | α-L-Rha-(1→3) \| →3)-β-D-Qui4NAc-(1→2)-α-D-Man-(1→4)-β-D-Gal-(1→3)-α-D-GlcNAc-(1→ |
| O10 | →3)-α-L-Rha-(1→3)-α-L-Rha-(1→3)-α-D-Gal-(1→3)-β-D-GlcNAc-(1→ \| α-D-Fuc4NAcyl-(1→2) |
| | Acyl=acetyl (60%) or (R)-3-hydroxybutyryl (40%) |
| O16 | →2)-β-D-Galf-(1→6)-α-D-Glc-(1→3)-α-L-Rha2Ac-(1→3)-α-D-GlcNAc-(1→ |
| O17 | α-D-Glc-(1→6) \| →6)-α-D-Man-(1→2)-α-D-Man-(1→3)-α-D-GlcNAc(1→ |
| O18A, O18ac | →2)-α-L-Rha-(1→6)-α-D-Glc-(1→4)-α-D-Gal-(1→3)-α-D-GlcNAc-(1→ \| β-D-GlcNAc-(1→3) |
| O18A1 | α-D-Glc-(1→6) \| →2)-α-L-Rha-(1→6)-α-D-Glc-(1→4)-α-D-Gal-(1→3)-α-D-GlcNAc-(1→ \| β-D-GlcNAc-(1→3) |
| O18B | →3)-α-L-Rha-(1→6)-α-D-Glc-(1→4)-α-D-Gal-(1→3)-α-D-GlcNAc-(1→ \| β-D-Glc-(1→3) |
| O18B1 | α-D-Glc-(1→4) \| →3)-α-L-Rha-(1→6)-α-D-Glc-(1→4)-α-D-Gal-(1→3)-α-D-GlcNAc-(1→ \| β-D-Glc-(1→3) |
| O21 | β-D-Gal-(1→4) \| →3)-β-D-Glc-(1→4)-β-D-Gal-(1→3)-β-D-GalNAc-(1→3)-α-D-GlcNAc-(1→ \| β-D-GlcNAc-(1→2) |
| O23A | α-D-Glc-(1→6) \| →6)-α-D-Glc-(2→3)-β-D-Glc-(1→3)-β-D-GalNAc-(1→ \| β-D-GlcNAc(1→3) |
| O24 | →7)-α-Neu5Ac-(2→3)-β-D-Glc-(1→3)-β-D-GalNAc-(1→ \| α-D-Glc-(1→2) |

FIG. 9B continued

O73 (Strain 73-1) a-D-Glc-(1 → 3)|→ 4)-a-D-Man-(1 → 2)-a-D-Man-(1 → 2)-b-D-Man-(1 → 3)-a-D-GalNAc(1 →
O75 b-D-Man-(1 → 4)|→ 3)-a-D-Gal-(1 → 4)-a-L-Rha-(1 → 3)-b-D-GlcNAc-(1 →
O77 → 6)-a-D-Man-(1 → 2)-a-D-Man-(1 → 2)-b-D-Man-(1 → 3)-a-D-GlcNAc(1 →
O78 → 4)-b-D-GlcNAc-(1 → 4)-b-D-Man-(1 → 4)-a-D-Man-(1 → 3)-b-D-GlcNAc-(1 →
O86 a-D-Gal-(1 → 3)|→ 4)-a-L-Fuc-(1 → 2)-b-D-Gal-(1 → 3)-a-D-GalNAc-(1 → 3)-b-D-GalNAc-(1 →
O88 a-L-6dTal-(1 → 3)|→ 4)-a-D-Man-(1 → 3)-a-D-Man-(1 → 3)-b-D-GlcNAc-(1 →
O90 → 4)-a-L-Fuc2/3Ac-(1 → 2)-b-D-Gal-(1 → 3)-a-D-GalNAc-(1 → 3)-b-D-GalNAc-(1 →
O98 → 3)-a-L-QuiNAc-(1 → 4)-a-D-GalNAcA-(1 → 3)-a-L-QuiNAc-(1 → 3)-b-D-GlcNAc-(1 →
O104 → 4)-a-D-Gal-(1 → 4)-a-Neu5,7,9Ac3-(2 → 3)-b-D-Gal-(1 → 3)-b-D-GalNAc-(1 →
O111 a-Col-(1 → 6)|→ 4)-a-D-Glc-(1 → 4)-a-D-Gal-(1 → 3)-b-D-GlcNAc-(1 →|a-Col-(1 → 3)
O113 → 4)-a-D-GalNAc-(1 → 4)-a-D-GalA-(1 → 3)-a-D-Gal-(1 → 3)-b-D-GlcNAc-(1 →|b-D-Gal-(1 → 3)
O114 → 4)-b-D-Qui3N(N-acetyl-L-seryl)-(1 → 3)-b-D-Ribf-(1 → 4)-b-D-Gal-(1 → 3)-a-D-GlcNAc(1 →

FIG. 9C

O119  β-D-RhaNAc3NFo-(1→3) | →2)-β-D-Man-(1→3)-α-D-Gal-(1→4)-α-L-Rha-(1→3)-α-D-GlcNAc-(1→
O121  →3)-β-D-Qui4N(N-acetyl-glycyl)-(1→4)-α-D-GalNAc3AcA6N-(1→4)-α-D-GalNAcA-(1→3)-α-D-GlcNAc-(1→
O124  4-O-[(R)-1-carboxyethyl]-β-D-Glc-(1→6)-α-D-Glc-(1→4) |→3)-α-D-Gal-(1→6)-β-D-Galf-(1→3)-β-D-GalNAc-(1→
O125  α-D-Glc-(1→3) |→4)-β-D-GalNAc-(1→2)-α-D-Man-(1→3)-α-L-Fuc-(1→3)-α-D-GalNAc-(1→ | β-D-Gal-(1→3)
O126  →2)-β-D-Man-(1→3)-β-D-Gal-(1→3)-β-D-GlcNAc-(1→ | α-L-Fuc-(1→2)
O127  →2)-α-L-Fuc-(1→2) |→6)-β-D-Gal-(1→3)-β-D-GalNAc-(1→3)-α-D-GalNAc-(1→
O128  α-L-Fuc-(1→2) |→6)-β-D-Gal-(1→3)-β-D-GalNAc-(1→4)-α-D-Gal-(1→3)-β-D-GalNAc-(1→
O136  →4)-β-Pse5Ac7Ac-(2→4)-β-D-Gal-(1→4)
       -β-D-GlcNAc-(1→β-Pse5Ac7Ac=5,7-diacetamido-3,5,7,9-tetradeoxy-L-glycero-β-L-manno-nonulosonic acid
O138  →2)-α-L-Rha-(1→3)-α-L-Rha-(1→4)-α-D-GalNAcA-(1→3)-β-D-GlcNAc-(1→
O141  α-L-Rha-(1→3) |→4)-α-D-Man-(1→3)-α-D-Man6Ac-(1→3)-β-D-GlcNAc-(1→ | β-D-GlcA-(1→2)
O142  →2)-α-L-Rha-(1→6)-α-D-GalNAc-(1→4)-α-D-GalNAc-(1→3)-α-D-GalNAc-(1→ | β-D-GlcNAc-(1→3)
O143  →2)-β-D-GalA6R3,4Ac-(1→3)-α-D-GalNAc-(1→4)-β-D-GlcA-(1→3)-β-D-GlcNAc-(1→ R=1,3-dihydroxy-2-propylamino
O147  →2)-α-L-Rha-(1→2)-α-L-Rha-(1→4)-β-D-GalA-(1→3)-β-D-GalNAc-(1→
O149  →3)-β-D-GlcNAc-(S)-4,6Py-(1→3)-β-L-Rha-(1→4)-β-D-GlcNAc-(1→ (S)-4,6Py=4,6-O-[(S)-1-carboxyethylidene]-
O152  β-L-Rha-(1→4) |→3)-α-D-GlcNAc-(1-P→6)-α-D-Glc-(1→2)-β-D-Glc-(1→3)-β-D-GlcNAc-(1→
O157  →2)-α-D-Rha4NAc-(1→3)-α-L-Fuc-(1→4)-β-D-Glc-(1→3)-β-D-GalNAc-(1→ | α-L-Rha-(1→3)
O158  α-D-Glc-(1→6) |→4)-α-D-Glc-(1→3)-β-D-GalNAc-(1→4)-α-D-GalA-(1→3)-α-L-Fuc-(1→3)-β-D-GlcNAc-(1→
O159  α-L-Fuc-(1→4) |→6)-α-D-Glc-(1→4)-α-D-GlcNAc-(1→4)-α-D-GalA-(1→6)-β-D-Gal-(1→3)-β-D-GalNAc-(1→
O164  β-D-Glc-(1→6)-α-D-Glc(1→4) |→3)-β-D-Gal-(1→6)-β-D-Galf-(1→3)-β-D-Glc-(1→3)-β-D-GalNAc-(1→
O173  α-L-Fuc-(1→4) |→3)-β-D-Gal-(1-P→6)-α-D-Glc-(1→2)-β-D-Glc-(1→3)-β-D-GlcNAc-(1→
62D1  α-D-Gal(1→6) |→2)-β-D-Qui3NAc-(1→3)-α-L-Rha-(1→3)-α-D-Gal-(1→3)-β-D-GalNAc-(1→3)-α-D-FucNAc-(1→ Suggested as Erwinia herbicola

FIG. 10A

O22   →6)-α-D-Glc-(1→4)-β-D-GlcA-(1→4)-β-D-GalNAc3Ac-(1→3)-α-D-Gal-(1→3)-β-D-GalNAc-(1→

O35   →3)-α-L-Rha-(1→2)-α-L-Rha-(1→3)-α-L-Rha-(1→2)-α-L-Rha-(1→3)-β-D-GlcNAc-(1→ | α-D-GalNAcA6N-(1→2)

O65   →2)-β-D-Qui3NAc-(1→4)-α-D-GalA6N-(1→4)-α-D-GalNAc-(1→4)-β-D-GalA-(1→3)-α-D-GlcNAc-(1→

O66   →2)-β-D-Man-(1→3)-α-D-GlcNAc-(1→2)-β-D-Glc3Ac-(1→3)-α-L-6dTal-(1→3)-α-D-GlcNAc-(1→

O83   →6)-α-D-Glc-(1→4)-β-D-GlcA-(1→6)-β-D-Gal-(1→4)-β-D-Gal-(1→4)-β-D-GlcNAc-(1→

O91   →4)-α-D-Qui3NAcyl-(1→4)-β-D-Gal-(1→4)-β-D-GlcNAc-(1→4)-β-D-GlcA6NGly-(1→3)-β-D-GlcNAc-(1→ Acyl=(R)-3-hydroxybutyryl O105  β-D-Ribf-(1→3) | →4)-α-D-GlcA2Ac3Ac-(1→2)-α-L-Rha4Ac-(1→3)-β-L-Rha-(1→4)-β-L-Rha-(1→3)-β-D-GlcNAc6Ac-(1→

O116  →2)-β-D-Qui4NAc-(1→6)-α-D-GlcNAc-(1→4)-α-D-GalA-(1→3)-β-D-GlcNAc-(1→

O117  →4)-β-D-GalNAc-(1→3)-α-L-Rha-(1→4)-α-D-Glc-(1→4)-β-D-Gal-(1→3)-α-D-GalNAc-(1→

O139  β-D-Glc-(1→3) | →3)-α-L-Rha-(1→4)-α-D-GalA-(1→2)-α-L-Rha-(1→3)-α-L-Rha-(1→2)-α-L-Rha-(1→3)-α-D-GlcNAc-(1→  Ratnayake (1994a)

O153  →2)-β-D-Ribf-(1→4)-β-D-Gal-(1→4)-α-D-GlcNAc-(1→4)-α-D-GlcNAc-(1→

O167  α-D-Galf-(1→4) | →2)-β-D-GalA6N(L)Ala-(1→3)-α-D-GlcNAc-(1→2)-β-D-Galf-(1→5)-β-D-Galf-(1→3)-β-D-GlcNAc-(1→

O172  →3)-α-L-FucNAc-(1→4)-α-D-Glc6Ac-(1-P→4)-α-D-Glc-(1→3)-α-L-FucNAc-(1→3)-α-D-GlcNAc-(1→

FIG. 10B

| | |
|---|---|
| O8 | →2)-α-D-Man-(1→2)-α-D-Man-(1→3)-β-D-Man-(1→ |
| O9a | →2)-α-D-Man-(1→2)-α-D-Man-(1→3)-α-D-Man-(1→3)-α-D-Man-(1→ |
| O9 | →2)-[α-D-Man-(1→2)]2-α-D-Man-(1→3)-α-D-Man-(1→3)-α-D-Man-(1→ |
| | Vasil'ev & Zakharova (1976) |
| O20ab | →2)-β-D-Ribf-(1→4)-α-D-Gal-(1→ |
| O20ac | α-D-Gal-(1→3) \| →2)-β-D-Ribf-(1→4)-α-D-Gal-(1→ |
| O52 | →3)-β-D-Fucf-(1→3)-β-D-6dmanHep2Ac-(1→ |
| O97 | →3)-α-L-Rha-(1→3)-β-L-Rha-(1→ \|\| β-D-Xulf-(2→2)β-D-Xulf-(2→2) |
| O101 | →6)-α-D-GlcNAc-(1→4)-α-D-GalNAc-(1→ |

ESCHERICHIA COLI COMPOSITIONS AND METHODS THEREOF

CROSS REFERENCE TO RELATED APPLICATIONS

This application claims priority to U.S. Provisional Application Ser. No. 62/722,370, filed on Aug. 24, 2018, U.S. Provisional Application Ser. No. 62/784,940, filed on Dec. 26, 2018, and U.S. Provisional Application Ser. No. 62/881,361, filed on Jul. 31, 2019, each of which are incorporated by reference in their entirety.

FIELD OF THE INVENTION

The present invention relates to *Escherichia coli* compositions and methods thereof.

BACKGROUND OF THE INVENTION

The cell wall of Gram-negative bacteria includes an outer membrane and a peptidoglycan layer on the inside of the outer membrane. The outer membrane includes phospholipids, lipopolysaccharides (LPS), lipoproteins and membrane proteins. A lipopolysaccharide is found in an outer layer of the membrane and a phospholipid in an inner layer thereof.

The LPS includes a lipid A membrane anchor that links a core oligosaccharide to a polymer of O-polysaccharides containing repeated saccharide monomer units, which form short, long or very long O-chains. While the core oligosaccharide is mostly conserved within individual bacterial species, the O-polysaccharide can be variable amongst serotypes. *Escherichia coli* (*E. coli*) is a Gram-negative bacterium known to cause life-threatening bacterial sepsis. Both capsular (K) and lipopolysaccharide (LPS) O-antigens are important virulence factors.

There is marked interest in the use of O-polysaccharides as the basis of vaccines for *E. coli*. However, previous attempts to develop *E. coli* glycoconjugate vaccines using conventional chemical conjugation or bioconjugation approaches have failed to generate robust functional immune responses for all serotypes. Accordingly, there exists an unmet need for immunogenic compositions against *E. coli* that generate robust functional immune responses.

SUMMARY OF THE INVENTION

To meet these and other needs, the present invention relates to compositions and methods of use thereof for eliciting immune responses against *E. coli* serotypes.

In one embodiment, the present invention relates to saccharides, conjugates, and compositions comprising the same, resulting from *E. coli* strains that have been engineered to express longer O-antigen lipopolysaccharides (LPS) with improved properties for bioprocess development and a higher density of immunogenic epitopes. For example, in one embodiment, the *E. coli* strain was engineered to express the *Salmonella enterica* fepE gene from a high copy plasmid, which resulted in the production of long chain LPS in *E. coli* strains of different O-antigen serotypes.

Initial strain development focused on the O-antigen of serotype O25b, which is associated with hard-to-treat, emerging multidrug resistant isolates. The wzzB gene was deleted from a clinical *E. coli* O25b strain. After transformation with the *Salmonella* fepE plasmid, the now engineered *E. coli* O25b strain produced exclusively long chain LPS. After chemical extraction with acetic acid to release the O-antigen from the bacterial surface, the resulting long chain O25b polysaccharide was amenable to conventional purification and conjugation techniques. Unlike O-antigens produced through bioconjugation, these longer chain O-antigens retain the inner and outer core oligosaccharides, which independently have the potential to elicit functional antibodies that are both bactericidal and capable of blocking sepsis. Exemplary O25b glycoconjugates were surprisingly significantly more immunogenic in mammals than the unconjugated polysaccharide.

Accordingly, in one aspect, the invention relates to a saccharide including an increase of at least 5 repeating units, compared to the corresponding wild-type O-polysaccharide of an *E. coli*.

In one embodiment, the composition includes a structure selected from Formula O1, Formula O2, Formula O3, Formula O4, Formula O5, Formula O6, Formula O7, Formula O8, Formula O9, Formula O10, Formula O11, Formula O12, Formula O13, Formula O14, Formula O15, Formula O16, Formula O17, Formula O18, Formula O19, Formula O20, Formula O21, Formula O22, Formula O23, Formula O24, Formula O25, Formula O25b, Formula O26, Formula O27, Formula O28, Formula O29, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45, Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula 62D$_1$, Formula O63, Formula O64, Formula O65, Formula O66, Formula O68, Formula O69, Formula O70, Formula O71, Formula O73, Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144, Formula O145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, and Formula O187, wherein n is an integer from 1 to 1000. See Table 1 and FIGS. 9A-C and FIGS. 10A-B.

As used herein, unless expressly stated otherwise, the term "wherein n is" refers to the "n" in the Formula(s)

selected from the group. In one embodiment, the composition includes a structure selected from Formula O1 (e.g., Formula O1A, Formula O1B, and Formula O1C), Formula O2, Formula O3, Formula O4 (e.g., Formula O4: K52 and Formula O4: K6), Formula O5 (e.g., Formula O5ab and Formula O5ac (strain 180/C3)), Formula O6 (e.g., Formula O6: K2; K13; K15 and Formula O6: K54), Formula O7, Formula O8, Formula O9, Formula O10, Formula O11, Formula O12, Formula O13, Formula O14, Formula O15, Formula O16, Formula O17, Formula O18 (e.g., Formula O18A, Formula O18ac, Formula O18A1, Formula O18B, and Formula O18B1), Formula O19, Formula O20, Formula O21, Formula O22, Formula O23 (e.g., Formula O23A), Formula O24, Formula O25 (e.g., Formula O25a and Formula O25b), Formula O26, Formula O27, Formula O28, Formula O29, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45 (e.g., Formula O45 and Formula O45rel), Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula 62D$_1$, Formula O63, Formula O64, Formula O65, Formula O66, Formula O68, Formula O69, Formula O70, Formula O71, Formula O73 (e.g., Formula O73 (strain 73-1)), Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144, Formula O145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, and Formula O187, wherein n is an integer from 1 to 1000. See Table 1 and FIGS. 9A-C and FIGS. 10A-B.

In one embodiment, the composition includes a structure selected from Formula O1 (e.g., Formula O1A, Formula O1B, and Formula O1C), Formula O2, Formula O3, Formula O4 (e.g., Formula O4: K52 and Formula O4: K6), Formula O5 (e.g., Formula O5ab and Formula O5ac (strain 180/C3)), Formula O6 (e.g., Formula O6: K2; K13; K15 and Formula O6: K54), Formula O7, Formula O10, Formula O16, Formula O17, Formula O18 (e.g., Formula O18A, Formula O18ac, Formula O18A1, Formula O18B, and Formula O18B1), Formula O21, Formula O23 (e.g., Formula O23A), Formula O24, Formula O25 (e.g., Formula O25a and Formula O25b), Formula O26, Formula O28, Formula O44, Formula O45 (e.g., Formula O45 and Formula O45rel), Formula O55, Formula O56, Formula O58, Formula O64, Formula O69, Formula O73 (e.g., Formula O73 (strain 73-1)), Formula O75, Formula O77, Formula O78, Formula O86, Formula O88, Formula O90, Formula O98, Formula O104, Formula O111, Formula O113, Formula O114, Formula O119, Formula O121, Formula O124, Formula O125, Formula O126, Formula O127, Formula O128, Formula O136, Formula O138, Formula O141, Formula O142, Formula O143, Formula O147, Formula O149, Formula O152, Formula O157, Formula O158, Formula O159, Formula O164, Formula O173, Formula 62D$_1$, Formula O22, Formula O35, Formula O65, Formula O66, Formula O83, Formula O91, Formula O105, Formula O116, Formula O117, Formula O139, Formula O153, Formula O167, and Formula O172, wherein n is an integer from 1 to 1000. See Table 1 and FIGS. 9A-C and FIG. 10A.

In one embodiment, the composition includes a structure selected from Formula O1 (e.g., Formula O1A, Formula O1B, and Formula O1C), Formula O2, Formula O3, Formula O4 (e.g., Formula O4: K52 and Formula O4: K6), Formula O5 (e.g., Formula O5ab and Formula O5ac (strain 180/C3)), Formula O6 (e.g., Formula O6: K2; K13; K15 and Formula O6: K54), Formula O7, Formula O10, Formula O16, Formula O17, Formula O18 (e.g., Formula O18A, Formula O18ac, Formula O18A1, Formula O18B, and Formula O18B1), Formula O21, Formula O23 (e.g., Formula O23A), Formula O24, Formula O25 (e.g., Formula O25a and Formula O25b), Formula O26, Formula O28, Formula O44, Formula O45 (e.g., Formula O45 and Formula O45rel), Formula O55, Formula O56, Formula O58, Formula O64, Formula O69, Formula O73 (e.g., Formula O73 (strain 73-1)), Formula O75, Formula O77, Formula O78, Formula O86, Formula O88, Formula O90, Formula O98, Formula O104, Formula O111, Formula O113, Formula O114, Formula O119, Formula O121, Formula O124, Formula O125, Formula O126, Formula O127, Formula O128, Formula O136, Formula O138, Formula O141, Formula O142, Formula O143, Formula O147, Formula O149, Formula O152, Formula O157, Formula O158, Formula O159, Formula O164, Formula O173, and Formula 62D$_1$, wherein n is an integer from 1 to 1000. See Table 1 and FIG. 9A-C.

In one embodiment, the composition does not include a structure selected from Formula O8, Formula O9a, Formula O9, Formula O20ab, Formula O20ac, Formula O52, Formula O97, and Formula O101. In another embodiment, the composition includes a structure selected from Formula O8, Formula O9a, Formula O9, Formula O20ab, Formula O20ac, Formula O52, Formula O97, and Formula O101, wherein n is an integer from 1 to 10. See Table 1 and FIG. 10B.

In one embodiment, the *E. coli* is *E. coli* serotype is selected from any one of O1, O2, O3, O4, O5, O6, O7, O8, O9, O10, O11, O12, O13, O14, O15, O16, O17, O18, O19, O20, O21, O22, O23, O24, O25, O25b, O26, O27, O28, O29, O30, O32, O33, O34, O35, O36, O37, O38, O39, O40, O41, O42, O43, O44, O45, O46, O48, O49, O50, O51, O52, O53, O54, O55, O56, O57, O58, O59, O60, O61, O62, 62D$_1$, O63, O64, O65, O66, O68, O69, O70, O71, O73, O74, O75, O76, O77, O78, O79, O80, O81, O82, O83, O84, O85, O86, O87, O88, O89, O90, O91, O92, O93, O95, O96, O97, O98, O99, O100, O101, O102, O103, O104, O105, O106, O107, O108, O109, O110, O111, O112, O113, O114, O115, O116, O117, O118, O119, O120, O121, O123, O124, O125, O126, O127, O128, O129, O130, O131, O132, O133, O134, O135, O136, O137, O138, O139, O140, O141, O142, O143, O144, O145, O146, O147, O148, O149, O150, O151, O152, O153, O154, O155, O156, O157, O158, O159, O160, O161, O162, O163, O164, O165, O166, O167, O168, O169, O170, O171, O172, O173, O174, O175, O176, O177, O178, O179, O180, O181, O182, O183, O184, O185, O186, and O187.

In one embodiment, the *E. coli* is *E. coli* serotype is selected from the group consisting of O1, O2, O3, O4, O5, O6, O7, O8, O9, O10, O11, O12, O13, O14, O15, O16, O17, O18, O19, O20, O21, O22, O23, O24, O25, O25b, O26, O27, O28, O29, O30, O32, O33, O34, O35, O36, O37, O38, O39, O40, O41, O42, O43, O44, O45, O46, O48, O49, O50, O51, O52, O53, O54, O55, O56, O57, O58, O59, O60, O61, O62, 62D$_1$, O63, O64, O65, O66, O68, O69, O70, O71, O73, O74, O75, O76, O77, O78, O79, O80, O81, O82, O83, O84, O85, O86, O87, O88, O89, O90, O91, O92, O93, O95, O96, O97, O98, O99, O100, O101, O102, O103, O104, O105, O106, O107, O108, O109, O110, O111, O112, O113, O114, O115, O116, O117, O118, O119, O120, O121, O123, O124, O125, O126, O127, O128, O129, O130, O131, O132, O133, O134, O135, O136, O137, O138, O139, O140, O141, O142, O143, O144, O145, O146, O147, O148, O149, O150, O151, O152, O153, O154, O155, O156, O157, O158, O159, O160, O161, O162, O163, O164, O165, O166, O167, O168, O169, O170, O171, O172, O173, O174, O175, O176, O177, O178, O179, O180, O181, O182, O183, O184, O185, O186, and O187.

In one embodiment, the saccharide is produced by expressing a wzz family protein in a Gram-negative bacterium to generate said saccharide. In one embodiment, the saccharide is produced by increasing repeating units of O-polysaccharides produced by a Gram-negative bacterium in culture comprising expressing (not necessarily overexpressing) wzz family proteins in a Gram-negative bacterium to generate said saccharide. In a preferred embodiment, the wzz family protein is selected from any one of wzzB, wzz, wzz$_{SF}$, wzz$_{ST}$, fepE, wzz$_{fepE}$, wzz1 and wzz2. In a preferred embodiment, the expressed (not necessarily overexpressed) wzz family protein is selected from the group consisting of wzzB, wzz, wzz$_{SF}$, wzz$_{ST}$, fepE, wzz$_{fepE}$, wzz1 and wzz2. In an alternative embodiment, the saccharide is synthetically synthesized. In one embodiment, the saccharide is covalently bound (conjugated) to a carrier protein. Preferably, the carrier protein is CRM$_{197}$.

In one aspect, the invention relates to a composition that includes the saccharide and/or conjugates thereof and a pharmaceutically acceptable diluent.

In another aspect, the invention relates to a method for inducing an immune response in a subject, including administering to the subject an effective amount of the composition. In one embodiment, the immune response includes induction of an anti-*E. coli* O-specific polysaccharide antibody.

BRIEF DESCRIPTION OF THE DRAWINGS

FIG. 10A-B—FIG. 10A depicts structures of O-antigens synthesized by the polymerase-dependent pathway with five or six residues in the backbone; FIG. 10B depicts O-antigens believed to be synthesized by the ABC-transporter-dependent pathway.

FIG. 15A depicts results from Rabbit A-1 (Unconjugated Poly); FIG. 15B depicts results from Rabbit A-3 (Unconjugated Poly); FIG. 15C depicts results from Rabbit A-4 (Unconjugated Poly); FIG. 15D depicts results from Rabbit 2-1 (low activation); FIG. 15E depicts results from Rabbit 2-2 (low activation); and FIG. 15F depicts results from Rabbit 2-3 (low activation).

FIG. 16A depicts results wherein —■—represents results from 025b 2831 vs PD3 antisera; —●—O25b 2831 wt vs prebleed; —●—O25b 2831/fepE vs PD3 antisera; —▼—O25b 2831/fepE vs prebleed. FIG. 16B depicts results wherein —●—represents results from O25b 2401 vs PD3 antisera; —■—O25b 2401 vs prebleed; —▲—O25b 2401/fepE vs PD3 antisera; —▼—O25b 2401/fepE vs prebleed. FIG. 16C depicts results wherein —●—represents results from *E. coli* K12 vs PD3 antisera; —■—*E. coli* K12 vs prebleed.

FIG. 19A shows OPA titers of Rabbit 2-3 pre-immune serum —●—and post-immune serum wk 13 —■—. FIG. 19B shows OPA titers of Rabbit 1-2 pre-immune serum —●—and post-immune serum wk 19 —■—. FIG. 19C shows Rabbit 1-2 wk 19 OPA Titer Specificity, in which OPA activity of Rabbit 1-2 immune serum is blocked by pre-incubation with 100 µg/ml of purified unconjugated O25b long O-antigen polysaccharide, wherein —■—represents results from Rabbit 1-2 immune serum wk 19; and —▼—represents results from Rabbit 1-2 wk 19 w/R1 Long-OAg.

FIG. 20B and FIG. 20C show graphs depicting O-antigen O25b IgG levels elicited by unconjugated O25b long O-antigen polysaccharide (FIG. 20B, O25b Free Poly (2 µg)) and derived O25b RAC/DMSO long O-antigen glycoconjugate (FIG. 20C, O25b-CRM$_{197}$ RAC Long (2 µg)), wherein — . . . —(dotted line) represents Naïve CD1 O25b IgG level.

SEQUENCE IDENTIFIERS

Figure 1A:
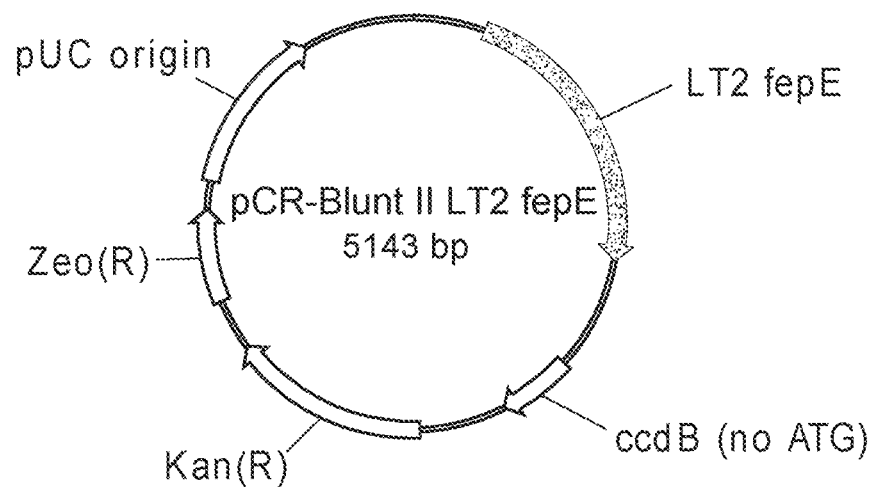
FIG. 1A-B—FIG. 1A depicts a pUC replicon, 500-700× copies per cell, Chain length regulator (FIG. 1A) and P15a replicon-10-12× copies per cell, O-antigen operon (FIG. 1B) plasmids FIG. 2—WzzB amino acid sequence alignments, showing K12\W3110\WzzB (SEQ ID NO: 23); O25a\ETEC\ATCC\WzzB (SEQ ID NO: 22); O25a: K5: H1\WzzB (SEQ ID NO: 21); O25b\2401\WzzB (SEQ ID NO: 20); and O25b\2401\WzzB (SEQ ID NO: 20).

SEQ ID NO: 1 sets forth a primer sequence for LT2wzzB_S, described in Table 4.
SEQ ID NO: 2 sets forth a primer sequence for LT2wzzB_AS, described in Table 4.
SEQ ID NO: 3 sets forth a primer sequence for O25bFepE_S, described in Table 4.
SEQ ID NO: 4 sets forth a primer sequence for O25bFepE_A, described in Table 4.
SEQ ID NO: 5 sets forth a primer sequence for wzzB P1_S, described in Table 4.
SEQ ID NO: 6 sets forth a primer sequence for wzzB P2_AS, described in Table 4.
SEQ ID NO: 7 sets forth a primer sequence for wzzB P3_S, described in Table 4.
SEQ ID NO: 8 sets forth a primer sequence for wzzB P4_AS, described in Table 4.
SEQ ID NO: 9 sets forth a primer sequence for O157 FepE_S, described in Table 4.
SEQ ID NO: 10 sets forth a primer sequence for O157 FepE_AS, described in Table 4.
SEQ ID NO: 11 sets forth a primer sequence for pBAD33_adaptor_S, described in Table 4.
SEQ ID NO: 12 sets forth a primer sequence for pBAD33_adaptor_AS, described in Table 4.
SEQ ID NO: 13 sets forth a primer sequence for JUMP-START_r, described in Table 4.
SEQ ID NO: 14 sets forth a primer sequence for gnd_f, described in Table 4.
SEQ ID NO: 15 sets forth a O25b 2401 FepE amino acid sequence shown in FIG. 5.
SEQ ID NO: 16 sets forth a O25a: K5: H1 FepE amino acid sequence shown in FIG. 5.
SEQ ID NO: 17 sets forth a 025a ETEC ATCC FepE amino acid sequence shown in FIG. 5.
SEQ ID NO: 18 sets forth a O157 FepE amino acid sequence shown in FIG. 5.

SEQ ID NO: 19 sets forth a *Salmonella* LT2 FepE amino acid sequence shown in FIG. 5.

SEQ ID NO: 20 sets forth a O25b 2401 WzzB amino acid sequence shown in FIG. 2.

SEQ ID NO: 21 sets forth a O25a: K5: H1 WzzB amino acid sequence shown in FIG. 2.

SEQ ID NO: 22 sets forth a 025a ETEC ATCC WzzB amino acid sequence shown in FIG. 2.

SEQ ID NO: 23 sets forth a K12 W3110 WzzB amino acid sequence shown in FIG. 2.

SEQ ID NO: 24 sets forth a *Salmonella* LT2 WzzB amino acid sequence shown in FIG. 2.

DETAILED DESCRIPTION OF THE INVENTION

The inventors surprisingly discovered *E. coli* antigens resulting from engineering of different Wzz proteins (e.g., WzzB), including the surprising discovery of immunogenic conjugates and methods of use thereof. The inventors further surprisingly discovered glycoconjugates containing such saccharides being covalently conjugated to a carrier protein, such as, for example, through a bivalent, heterobifunctional linker referred to herein as a (2-((2-oxoethyl)thio)ethyl) carbamate (eTEC) spacer. The inventors also surprisingly discovered glycoconjugates containing the saccharides conjugated to a carrier protein, such as, for example, through reductive amination (RAC). In particular, RAC in an aprotic solvent, preferably in an DMSO (RAC/DMSO) or in aqueous solution. The invention further relates to immunogenic compositions comprising such glycoconjugates, and methods for the use of such glycoconjugates and immunogenic compositions. In addition, the inventors surprisingly discovered that, in some embodiments, a glycoconjugate containing a high molecular weight saccharide having an intermediate or long O-antigen chain may be more immunogenic as compared to glycoconjugates having relatively short O-antigen chains. Moreover, the inventors discovered that, in some embodiments, glycoconjugates produced by multiple-ended activation of the saccharide prior to conjugation to the carrier protein, such as, for example, by methods comprising RAC or single-end conjugation or eTEC, may be more immunogenic than glycoconjugates produced by single-ended activation of the saccharide prior to conjugation to the carrier protein.

In one embodiment, the saccharide is produced by expression (not necessarily overexpression) of different Wzz proteins (e.g., WzzB) to control of the size of the saccharide. As used herein, the term "saccharide" refers to a single sugar moiety or monosaccharide unit as well as combinations of two or more single sugar moieties or monosaccharide units covalently linked to form disaccharides, oligosaccharides, and polysaccharides. The saccharide may be linear or branched.

In one embodiment, the saccharide is produced in a recombinant Gram-negative bacterium. In one embodiment, the saccharide is produced in a recombinant *E. coli* cell. In one embodiment, the saccharide is produced in a recombinant *Salmonella* cell. Exemplary bacteria include *E. coli* O25K5H1, *E. coli* BD559, *E. coli* GAR2831, *E. coli* GAR865, *E. coli* GAR868, *E. coli* GAR869, *E. coli* GAR872, *E. coli* GAR878, *E. coli* GAR896, *E. coli* GAR1902, *E. coli* O25a ETC NR-5, *E. coli* O157: H7: K-, *Salmonella enterica* serovar *Typhimurium* strain LT2, *E. coli* GAR2401, *Salmonella enterica* serotype *Enteritidis* CVD 1943, *Salmonella enterica* serotype *Typhimurium* CVD 1925, *Salmonella enterica* serotype Paratyphi A CVD 1902, and *Shigella flexneri* CVD 1208S. In one embodiment, the bacterium is not *E. coli* GAR2401. This genetic approach towards saccharide production allows for efficient production of O-polysaccharides and O-antigen molecules as vaccine components.

The term "wzz protein," as used herein, refers to a chain length determinant polypeptide, such as, for example, wzzB, wzz, $wzz_{SF}$, $wzz_{ST}$, fepE, $wzz_{fepE}$, wzz1 and wzz2. The GenBank accession numbers for the exemplary wzz gene sequences are AF011910 for E4991/76, AF011911 for F186, AF011912 for M70/1-1, AF011913 for 79/311, AF011914 for Bi7509-41, AF011915 for C664-1992, AF011916 for C258-94, AF011917 for C722-89, and AF011919 for EDL933. The GenBank accession numbers for the G7 and Bi316-41 wzz genes sequences are U39305 and U39306, respectively. Further GenBank accession numbers for exemplary wzz gene sequences are NP_459581 for *Salmonella enterica* subsp. *enterica* serovar *Typhimurium* str. LT2 FepE; AIG66859 for *E. coli* 0157: H7 Strain EDL933 FepE; NP_461024 for *Salmonella enterica* subsp. *enterica* serovar *Typhimurium* str. LT2 WzzB. NP_416531 for *E. coli* K-12 substr. MG1655 WzzB, NP_415119 for *E. coli* K-12 substr. MG1655 FepE. In preferred embodiments, the wzz family protein is any one of wzzB, wzz, $wzz_{SF}$, $wzz_{ST}$, fepE, $wzz_{fepE}$, wzz1 and wzz2, most preferably wzzB, more preferably fepE.

Exemplary wzzB Sequences Include:

```
>O25b 2401 WzzB
                                        (SEQ ID NO: 20)
MRVENNNVSGQNHDPEQIDLIDLLVQLWRGKMTIIISVIVAIALAIGYLA

VAKEKWTSTAIITQPDVGQIAGYNNAMNVIYGQAAPKVSDLQETLIGRFS

SAFSALAETLDNQEEPEKLTIEPSVKNQQLPLTVSYVGQTAEGAQMKLAQ

YIQQVDDKVNQELEKDLKDNIALGRKNLQDSLRTQEVVAQEQKDLRIRQI

QEALQYANQEQVTKPQVQQTEDVTQDTLFLLGSEALESMIKHEATRPLVF

SSNYYQTRQNLLDIESLKVDDLDIHAYRYVMKPTLPIRRDSPKKAITLIL

AVLLGGMVGAGIVLGRNALRNYNAK

>O25a:K5:H1 WzzB
                                        (SEQ ID NO: 21)
MRVENNNVSGQNNDPEQIDLIDLLVQLWRGKMTIIISVIVAIALAIGYLA

VAKEKWTSTAIITQPDVGQIAGYNNAMNVIYGQAAPKVSDLQETLIGRFS

SAFSALAETLDNQDEPEKLTIEPSVKNQQLPLTVSYVGQTAEGAQMKLAQ

YIQQVDDKVNQELEKDLKDNIALGRKNLQDSLRTQEVVAQEQKDLRIRQI

QEALQYANQAQVTKPQIQQTGEDITQDTLFLLGSEALESMIKHEATRPLV

FSPNYYQTRQNLLDIESLKVDDLDIHAYRYVMKPTLPIRRDSPKKAITLI

LAVLLGGMVGAGIVLGRNALRNYNAK

>O25a ETEC ATCC WzzB
                                        (SEQ ID NO: 22)
MRVENNNVSGQNHDPEQIDLIDLLVQLWRGKMTIIISVVVAIALAIGYLA

VAKEKWTSTAIITQPDVGQIAGYNNAMNVIYGQAAPKVSDLQETLIGRFS

FAFSALAETLDNQKEPEKLTIEPSVKNQQLPLTVSYVGQTAEDAQMKLAQ

YIQQVDDKVNQELEKDLKDNLALGRKNLQDSLRTQEVVAQEQKDLRIRQI

QEALQYANQAQVTKPQIQQTGEDITQDTLFLLGSEALESMIKHEATRPLV
```

FSPNYYQTRQNLLDIENLKVDDLDIHAYRYVMKPTLPIRRDSPKKAITLI

LAVLLGGMVGAGIVLGRNALRNYNSK

>K12 W3110 WzzB
(SEQ ID NO: 23)
MRVENNNVSGQNHDPEQIDLIDLLVQLWRGKMTIIISVIVAIALAIGYLA

VAKEKWTSTAIITQPDVGQIAGYNNAMNVIYGQAAPKVSDLQETLIGRFS

SAFSALAETLDNQEEREKLTIEPSVKNQQLPLTVSYVGQTAEGAQMKLAQ

YIQQVDDKVNQELEKDLKDNIALGRKNLQDSLRTQEVVAQEQKDLRIRQI

QEALQYANQAQVTKPQIQQTGEDITQDTLFLLGSEALESMIKHEATRPLV

FSPNYYQTRQNLLDIESLKVDDLDIHAYRYVMKPMLPIRRDSPKKAITLI

LAVLLGGMVGAGIVLGRNALRNYNAK

>*Salmonella* LT2 WzzB
(SEQ ID NO: 24)
MTVDSNTSSGRGNDPEQIDLIELLLQLWRGKMTIIVAVIIAILLAVGYLM

IAKEKWTSTAIITQPDAAQVATYTNALNVLYGGNAPKISEVQANFISRFS

SAFSALSEVLDNQKEREKLTIEQSVKGQALPLSVSYVSTTAEGAQRRLAE

YIQQVDEEVAKELEVDLKDNITLQTKTLQESLETQEVVAQEQKDLRIKQI

EEALRYADEAKITQPQIQQTQDVTQDTMFLLGSDALKSMIQNEATRPLVF

SPAYYQTKQTLLDIKNLKVTADTVHVYRYVMKPTLPVRRDSPKTAITLVL

AVLLGGMIGAGIVLGRNALRSYKPKAL

Exemplary FepE Sequences Include:

>O25b GAR2401 FepE
(SEQ ID NO: 15)
MSSLNIKQGSDAHFPDYPLASPSNNEIDLLNLISVLWRAKKTVMAVVFAF

ACAGLLISFILPQKWTSAAVVTPPEPVQWQELEKSFTKLRVLDLDIKIDR

TEAFNLFIKKFQSVSLLEEYLRSSPYVMDQLKEAKIDELDLHRAIVALSE

KMKAVDDNASKKKDEPSLYTSWTLSFTAPTSEEAQTVLSGYIDYISTLVV

KESLENVRNKLEIKTQFEKEKLAQDRIKTKNQLDANIQRLNYSLDIANAA

GIKKPVYSNGQAVKDDPDFSISLGADGIERKLEIEKAVTDVAELNGELRN

RQYLVEQLTKAHVNDVNFTPFKYQLSPSLPVKKDGPGKAIIVILSALIGG

MVACGGVLLRYAMASRKQDAMMADHLV

>O25a:K5:H1 FepE
(SEQ ID NO: 16)
MSSLNIKQGSEAHFPEYPLASPSNNEIDLLNLIEVLWRAKKTVMAVVFAF

ACAGLLISFILPQKWTSAAVVTPPEPVQWQELEKTFTKLRVLDLDIKIDR

TEAFNLFIKKFQSVSLLEEYLRSSPYVMDQLKEAKIDPLDLHRAIVALSE

KMKAVDDNASKKKDESALYTSWTLSFTAPTSEEAQKVLAGYIDYISALVV

KESIENVRNKLEIKTQFEKEKLAQDRIKTKNQLDANIQRLNYSLDIANAA

GIKKPVYSNGQAVKDDPDFSISLGADGIERKLEIEKAVTDVAELNGELRN

RQYLVEQLTKTNINDVNFTPFKYQLRPSLPVKKDGQGKAIIVILSALVGG

MVACGGVLLRHAMASRKQDAMMADHLV

>O25a ETEC ATCC FepE
(SEQ ID NO: 17)
MSSLNIKQGSDAHFPDYPLASPSNNEIDLLNLISVLWRAKKTVMAVVFAF

ACAGLLISFILPQKWTSAAVVTPPEPVQWQELEKSFTKLRVLDLDIKIDR

TEAFNLFIKKFQSVSLLEEYLRSSPYVMDQLKEAKIDELDLHRAIVALSE

KMKAVDDNASKKKDEPSLYTSWTLSFTAPTSEEAQTVLSGYIDYISTLVV

KESLENVRNKLEIKTQFEKEKLAQDRIKTKNQLDANIQRLNYSLDIANAA

GIKKPVYSNGQAVKDDPDFSISLGADGIERKLEIEKAVTDVAELNGELRN

RQYLVEQLTKAHVNDVNFTPFKYQLSPSLPVKKDGPGKAIIVILSALIGG

MVACGGVLLRYAMASRKQDAMMADHLV

>O157 FepE
(SEQ ID NO: 18)
MSSLNIKQGSDAHFPDYPLASPSNNEIDLLNLISVLWRAKKTVMAWFAFA

CAGLLISFILPQKWTSAAWTPPEPVQWQELEKTFTKLRVLDLDIKIDRTE

AFNLFIKKFQSVSLLEEYLRSSPYVMDQLKEAKIDELDLHRAIVALSEKM

KAVDDNASKKKDEPSLYTSWTLSFTAPTSEEAQTVLSGYIDYISALWKES

IENVRNKLEIKTQFEKEKLAQDRIKMKNQLDANIQRLNYSLDIANAAGIK

KPVYSNGQAVKDDPDFSISLGADGIERKLEIEKAVTDVAELNGELRNRQY

LVEQLTKANINDVNFTPFKYQLSPSLPVKKDGPGKAIIVILSALIGGMVA

CGSVLLRYAMASRKQDAMMADHLV

>*Salmonella* LT2 FepE
(SEQ ID NO: 19)
MPSLNVKQEKNQSFAGYSLPPANSHEIDLFSLIEVLWQAKRRILATVFAF

ACVGLLLSFLLPQKWTSQAIVTPAESVQWQGLERTLTALRVLDMEVSVDR

GSVFNLFIKKFSSPSLLEEYLRSSPYVMDQLKGAQIDEQDLHRAIVLLSE

KMKAVDSNVGKKNETSLFTSWTLSFTAPTREEAQKVLAGYIQYISDIVVK

ETLENIRNQLEIKTRYEQEKLAMDRVRLKNQLDANIQRLHYSLEIANAAG

IKRPVYSNGQAVKDDPDFSISLGADGISRKLEIEKGVTDVAEIDGDLRNR

QYHVEQLAAMNVSDVKFTPFKYQLSPSLPVKKDGPGKAIIIILAALIGGM

MACGGVLLRHAMVSRKMENALAIDERLV

In some embodiments, a modified saccharide (modified as compared to the corresponding wild-type saccharide) may be produced by expressing (not necessarily overexpressing) a wzz family protein (e.g., fepE) from a Gram-negative bacterium in a Gram-negative bacterium and/or by switching off (i.e., repressing, deleting, removing) a second wzz gene (e.g., wzzB) to generate high molecular weight saccharides, such as lipopolysaccharides, containing intermediate or long O-antigen chains. For example, the modified saccharides may be produced by expressing (not necessarily overexpressing) wzz2 and switching off wzz1. Or, in the alternative, the modified saccharides may be produced by expressing (not necessarily overexpressing) wzzfepE and switching off wzzB. In another embodiment, the modified saccharides may be produced by expressing (not necessarily overexpressing) wzzB but switching off wzzfepE. In another embodiment, the modified saccharides may be produced by expressing fepE. Preferably, the wzz family protein is derived from a strain that is heterologous to the host cell.

In some embodiments, the saccharide is produced by expressing a wzz family protein having an amino acid sequence that is at least 30%, 50%, 70%, 75%, 80%, 85%, 90%, 95%, 98%, 99% or 100% sequence identity to any one of SEQ ID NO: 20, SEQ ID NO: 21, SEQ ID NO: 22, SEQ ID NO: 23, SEQ ID NO: 24, SEQ ID NO: 15, SEQ ID NO: 16, SEQ ID NO: 17, SEQ ID NO: 18, and SEQ ID NO: 19.

In one embodiment, the wzz family protein includes a sequence selected from any one of SEQ ID NO: 20, SEQ ID NO: 21, SEQ ID NO: 22, SEQ ID NO: 23, SEQ ID NO: 24, SEQ ID NO: 15, SEQ ID NO: 16, SEQ ID NO: 17, SEQ ID NO: 18, and SEQ ID NO: 19. Preferably, the wzz family protein has at least 30%, 50%, 70%, 75%, 80%, 85%, 90%, 95%, 98%, 99% or 100% sequence identity to SEQ ID NO: 15, SEQ ID NO: 16, SEQ ID NO: 17, SEQ ID NO: 18, and SEQ ID NO: 19. In some embodiments, the saccharide is produced by expressing a protein having an amino acid sequence that is at least 30%, 50%, 70%, 75%, 80%, 85%, 90%, 95%, 98%, 99% or 100% sequence identity to an fepE protein.

In one aspect, the invention relates to saccharides produced by expressing a wzz family protein, preferably fepE, in a Gram-negative bacterium to generate high molecular weight saccharides containing intermediate or long O-antigen chains, which have an increase of at least 1, 2, 3, 4, or 5 repeating units, as compared to the corresponding wild-type O-polysaccharide. In one aspect, the invention relates to saccharides produced by a Gram-negative bacterium in culture that expresses (not necessarily overexpresses) a wzz family protein (e.g., wzzB) from a Gram-negative bacterium to generate high molecular weight saccharides containing intermediate or long O-antigen chains, which have an increase of at least 1, 2, 3, 4, or 5 repeating units, as compared to the corresponding wild-type O-antigen. See description of O-polysaccharides and O-antigens below for additional exemplary saccharides having increased number of repeat units, as compared to the corresponding wild-type saccharides. A desired chain length is the one which produces improved or maximal immunogenicity in the context of a given vaccine construct.

In another embodiment, the saccharide includes any one Formula selected from Table 1, wherein the number of repeat units n in the saccharide is greater than the number of repeat units in the corresponding wild-type O-polysaccharide by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more repeat units. Preferably, the saccharide includes an increase of at least 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 repeat units, as compared to the corresponding wild-type O-polysaccharide. See, for example, Table 21. Methods of determining the length of saccharides are known in the art. Such methods include nuclear magnetic resonance, mass spectroscopy, and size exclusion chromatography, as described in Example 5.

In a preferred embodiment, the invention relates to a saccharide produced in a recombinant E. coli host cell, wherein the gene for an endogenous wzz O-antigen length regulator (e.g., wzzB) is deleted and is replaced by a (second) wzz gene from a Gram-negative bacterium heterologous to the recombinant E. coli host cell (e.g., Salmonella fepE) to generate high molecular weight saccharides, such as lipopolysaccharides, containing intermediate or long O-antigen chains. In some embodiments, the recombinant E. coli host cell includes a wzz gene from Salmonella, preferably from Salmonella enterica.

In one embodiment, the host cell includes the heterologous gene for a wzz family protein as a stably maintained plasmid vector. In another embodiment, the host cell includes the heterologous gene for a wzz family protein as an integrated gene in the chromosomal DNA of the host cell. Methods of stably expressing a plasmid vector in an E. coli host cell and methods of integrating a heterologous gene into the chromosome of an E. coli host cell are known in the art. In one embodiment, the host cell includes the heterologous genes for an O-antigen as a stably maintained plasmid vector. In another embodiment, the host cell includes the heterologous genes for an O-antigen as an integrated gene in the chromosomal DNA of the host cell. Methods of stably expressing a plasmid vector in an E. coli host cell and a Salmonella host cell are known in the art. Methods of integrating a heterologous gene into the chromosome of an E. coli host cell and a Salmonella host cell are known in the art.

In one aspect, the recombinant host cell is cultured in a medium that comprises a carbon source. Carbon sources for culturing E. coli are known in the art. Exemplary carbon sources include sugar alcohols, polyols, aldol sugars or keto sugars including but not limited to arabinose, cellobiose, fructose, glucose, glycerol, inositol, lactose, maltose, mannitol, mannose, rhamnose, raffinose, sorbitol, sorbose, sucrose, trehalose, pyruvate, succinate and methylamine. In a preferred embodiment, the medium includes glucose. In some embodiments, the medium includes a polyol or aldol sugar, for example, mannitol, inositol, sorbose, glycerol, sorbitol, lactose and arabinose as the carbon source. All of the carbon sources may be added to the medium before the start of culturing, or it may be added step by step or continuously during culturing.

An exemplary culture medium for the recombinant host cell includes an element selected from any one of $KH_2PO_4$, $K2HPO_4$, $(NH_4)_2SO_4$, sodium citrate, $Na_2SO_4$, aspartic acid, glucose, $MgSO_4$, $FeSO_4\text{-}7H_2O$, $Na_2MoO_4\text{-}2H_2O$, $H_3BO_3$, $CoCl_2\text{-}6H_2O$, $CuCl_2\text{-}2H_2O$, $MnCl_2\text{-}4H_2O$, $ZnCl_2$ and $CaCl_2)\text{-}2H_2O$. Preferably, the medium includes $KH_2PO_4$, $K2HPO_4$, $(NH_4)_2SO_4$, sodium citrate, $Na_2SO_4$, aspartic acid, glucose, $MgSO_4$, $FeSO_4\text{-}7H_2O$, $Na_2MoO_4\text{-}2H_2O$, $H_3BO_3$, $CoCl_2\text{-}6H_2O$, $CuCl_2\text{-}2H_2O$, $MnCl_2\text{-}4H_2O$, $ZnCl_2$ and $CaCl_2)\text{-}2H_2O$.

The medium used herein may be solid or liquid, synthetic (i.e. man-made) or natural, and may include sufficient nutrients for the cultivation of the recombinant host cell. Preferably, the medium is a liquid medium.

In some embodiments, the medium may further include suitable inorganic salts. In some embodiments, the medium may further include trace nutrients. In some embodiments, the medium may further include growth factors. In some embodiments, the medium may further include an additional carbon source. In some embodiments, the medium may further include suitable inorganic salts, trace nutrients, growth factors, and a supplementary carbon source. Inorganic salts, trace nutrients, growth factors, and supplementary carbon sources suitable for culturing E. coli are known in the art.

In some embodiments, the medium may include additional components as appropriate, such as peptone, N—Z Amine, enzymatic soy hydrosylate, additional yeast extract, malt extract, supplemental carbon sources and various vitamins. In some embodiments, the medium does not include such additional components, such as peptone, N—Z Amine, enzymatic soy hydrosylate, additional yeast extract, malt extract, supplemental carbon sources and various vitamins.

Illustrative examples of suitable supplemental carbon sources include, but are not limited to other carbohydrates, such as glucose, fructose, mannitol, starch or starch hydrolysate, cellulose hydrolysate and molasses; organic acids, such as acetic acid, propionic acid, lactic acid, formic acid, malic acid, citric acid, and fumaric acid; and alcohols, such as glycerol, inositol, mannitol and sorbitol.

In some embodiments, the medium further includes a nitrogen source. Nitrogen sources suitable for culturing *E. coli* are known in the art. Illustrative examples of suitable nitrogen sources include, but are not limited to ammonia, including ammonia gas and aqueous ammonia; ammonium salts of inorganic or organic acids, such as ammonium chloride, ammonium nitrate, ammonium phosphate, ammonium sulfate and ammonium acetate; urea; nitrate or nitrite salts, and other nitrogen-containing materials, including amino acids as either pure or crude preparations, meat extract, peptone, fish meal, fish hydrolysate, corn steep liquor, casein hydrolysate, soybean cake hydrolysate, yeast extract, dried yeast, ethanol-yeast distillate, soybean flour, cottonseed meal, and the like.

In some embodiments, the medium includes an inorganic salt. Illustrative examples of suitable inorganic salts include, but are not limited to salts of potassium, calcium, sodium, magnesium, manganese, iron, cobalt, zinc, copper, molybdenum, tungsten and other trace elements, and phosphoric acid.

In some embodiments, the medium includes appropriate growth factors. Illustrative examples of appropriate trace nutrients, growth factors, and the like include, but are not limited to coenzyme A, pantothenic acid, pyridoxine-HCl, biotin, thiamine, riboflavin, flavine mononucleotide, flavine adenine dinucleotide, DL-6,8-thioctic acid, folic acid, Vitamin $B_{12}$, other vitamins, amino acids such as cysteine and hydroxyproline, bases such as adenine, uracil, guanine, thymine and cytosine, sodium thiosulfate, p- or r-aminobenzoic acid, niacinamide, nitriloacetate, and the like, either as pure or partially purified chemical compounds or as present in natural materials. The amounts may be determined empirically by one skilled in the art according to methods and techniques known in the art.

In another embodiment, the modified saccharide (as compared to the corresponding wild-type saccharide) described herein is synthetically produced, for example, in vitro. Synthetic production or synthesis of the saccharides may facilitate the avoidance of cost- and time-intensive production processes. In one embodiment, the saccharide is synthetically synthesized, such as, for example, by using sequential glycosylation strategy or a combination of sequential glycosylations and [3+2] block synthetic strategy from suitably protected monosaccharide intermediates. For example, thioglycosides and glycosyl trichloroacetimidate derivatives may be used as glycosyl donors in the glycosylations. In one embodiment, a saccharide that is synthetically synthesized in vitro has the identical structure to a saccharide produced by recombinant means, such as by manipulation of a wzz family protein described above.

The saccharide produced (by recombinant or synthetic means) includes a structure derived from any *E. coli* serotype including, for example, any one of the following *E. coli* serotypes: O1 (e.g., O1A, O1B, and O1C), O2, O3, O4 (e.g., O4: K52 and O4: K6), O5 (e.g., O5ab and O5ac (strain 180/C3)), O6 (e.g., O6: K2; K13; K15 and O6: K54), O7, O8, O9, O10, O11, O12, O13, O14, O15, O16, O17, O18 (e.g., O18A, O18ac, O18A1, O18B, and O18B1), O19, O20, O21, O22, O23 (e.g., O23A), O24, O25 (e.g., O25a and O25b), O26, O27, O28, O29, O30, O32, O33, O34, O35, O36, O37, O38, O39, O40, O41, O42, O43, O44, O45 (e.g., O45 and O45rel), O46, O48, O49, O50, O51, O52, O53, O54, O55, O56, O57, O58, O59, O60, O61, O62, 62D$_1$, O63, O64, O65, O66, O68, O69, O70, O71, O73 (e.g., O73 (strain 73-1)), O74, O75, O76, O77, O78, O79, O80, O81, O82, O83, O84, O85, O86, O87, O88, O89, O90, O91, O92, O93, O95, O96, O97, O98, O99, O100, O101, O102, O103, O104, O105, O106, O107, O108, O109, O110, O111, O112, O113, O114, O115, O116, O117, O118, O119, O120, O121, O123, O124, O125, O126, O127, O128, O129, O130, O131, O132, O133, O134, O135, O136, O137, O138, O139, O140, O141, O142, O143, O144, O145, O146, O147, O148, O149, O150, O151, O152, O153, O154, O155, O156, O157, O158, O159, O160, O161, O162, O163, O164, O165, O166, O167, O168, O169, O170, O171, O172, O173, O174, O175, O176, O177, O178, O179, O180, O181, O182, O183, O184, O185, O186, and O187.

The individual polysaccharides are typically purified (enriched with respect to the amount of polysaccharide-protein conjugate) through methods known in the art, such as, for example, dialysis, concentration operations, diafiltration operations, tangential flow filtration, precipitation, elution, centrifugation, precipitation, ultra-filtration, depth filtration, and/or column chromatography (ion exchange chromatography, multimodal ion exchange chromatography, DEAE, and hydrophobic interaction chromatography). Preferably, the polysaccharides are purified through a method that includes tangential flow filtration.

Purified polysaccharides may be activated (e.g., chemically activated) to make them capable of reacting (e.g., either directly to the carrier protein or via a linker such as an eTEC spacer) and then incorporated into glycoconjugates of the invention, as further described herein.

In one preferred embodiment, the saccharide of the invention is derived from an *E. coli* serotype, wherein the serotype is O25a. In another preferred embodiment, the serotype is O25b. In another preferred embodiment, the serotype is O1A. In another preferred embodiment, the serotype is O2. In another preferred embodiment, the serotype is O6. In another preferred embodiment, the serotype is O17. In another preferred embodiment, the serotype is O15. In another preferred embodiment, the serotype is O18A. In another preferred embodiment, the serotype is O75. In another preferred embodiment, the serotype is O4. In another preferred embodiment, the serotype is O16. In another preferred embodiment, the serotype is O13. In another preferred embodiment, the serotype is O7. In another preferred embodiment, the serotype is O8. In another preferred embodiment, the serotype is O9.

As used herein, reference to any of the serotypes listed above, refers to a serotype that encompasses a repeating unit structure (O-unit, as described below) known in the art and is unique to the corresponding serotype. For example, the term "O25a" serotype (also known in the art as serotype "O25") refers to a serotype that encompasses Formula O25 shown in Table 1. As another example, the term "O25b" serotype refers to a serotype that encompasses Formula O25b shown in Table 1.

As used herein, the serotypes are referred generically herein unless specified otherwise such that, for example, the term Formula "O18" refers generically to encompass Formula O18A, Formula O18ac, Formula 18A1, Formula O18B, and Formula O18B1.

As used herein, the term "O1" refers generically to encompass the species of Formula that include the generic term "O1" in the Formula name according to Table 1, such as any one of Formula O1A, Formula O1A1, Formula O1B, and Formula O1C, each of which is shown in Table 1. Accordingly, an "O1 serotype" refers generically to a serotype that encompasses any one of Formula O1A, Formula O1A1, Formula O1B, and Formula O1C.

As used herein, the term "06" refers generically to species of Formula that include the generic term "06" in the Formula name according to Table 1, such as any one of Formula O6: K2; K13; K15; and O6: K54, each of which is shown in Table 1. Accordingly, an "06 serotype" refers generically to a serotype that encompasses any one of Formula O6: K2; K13; K15; and O6: K54.

Other examples of terms that refer generically to species of a Formula that include the generic term in the Formula name according to Table 1 include: "04", "05", "018", and "045".

As used herein, the term "O2" refers to Formula O2 shown in Table 1. The term "02 O-antigen" refers to a saccharide that encompasses Formula O2 shown in Table 1.

As used herein, reference to an O-antigen from a serotype listed above refers to a saccharide that encompasses the formula labeled with the corresponding serotype name. For example, the term "O25B O-antigen" refers to a saccharide that encompasses Formula O25B shown in Table 1.

As another example, the term "O1 O-antigen" generically refers to a saccharide that encompasses a Formula including the term "O1," such as the Formula O1A, Formula O1A1, Formula O1B, and Formula O1C, each of which are shown in Table 1.

As another example, the term "06 O-antigen" generically refers to a saccharide that encompasses a Formula including the term "06," such as Formula O6: K2; Formula O6: K13; Formula O6: K15 and Formula O6: K54, each of which are shown in Table 1.

O-Polysaccharide

As used herein, the term "O-polysaccharide" refers to any structure that includes an O-antigen, provided that the structure does not include a whole cell or Lipid A. For example, in one embodiment, the O-polysaccharide includes a lipopolysaccharide wherein the Lipid A is not bound. The step of removing Lipid A is known in the art and includes, as an example, heat treatment with addition of an acid. An exemplary process includes treatment with 1% acetic acid at 100° C. for 90 minutes. This process is combined with a process of isolating Lipid A as removed. An exemplary process for isolating Lipid A includes ultracentrifugation.

In one embodiment, the O-polysaccharide refers to a structure that consists of the O-antigen, in which case, the O-polysaccharide is synonymous with the term O-antigen. In one preferred embodiment, the O-polysaccharide refers to a structure that includes repeating units of the O-antigen, without the core saccharide. Accordingly, in one embodiment, the O-polysaccharide does not include an *E. coli* R1 core moiety. In another embodiment, the O-polysaccharide does not include an *E. coli* R2 core moiety. In another embodiment, the O-polysaccharide does not include an *E. coli* R3 core moiety. In another embodiment, the O-polysaccharide does not include an *E. coli* R4 core moiety. In another embodiment, the O-polysaccharide does not include an *E. coli* K12 core moiety. In another preferred embodiment, the O-polysaccharide refers to a structure that includes an O-antigen and a core saccharide. In another embodiment, the O-polysaccharide refers to a structure that includes an O-antigen, a core saccharide, and a KDO moiety.

Methods of purifying an O-polysaccharide, which includes the core oligosaccharide, from LPS are known in the art. For example, after purification of LPS, purified LPS may be hydrolyzed by heating in 1% (v/v) acetic acid for 90 minutes at 100 degrees Celsius, followed by ultracentrifugation at 142,000×g for 5 hours at 4 degrees Celsius. The supernatant containing the O-polysaccharide is freeze-dried and stored at 4 degrees Celsius. In certain embodiments, deletion of capsule synthesis genes to enable simple purification of O-polysaccharide is described.

The O-polysaccharide can be isolated by methods including, but not limited to mild acid hydrolysis to remove lipid A from LPS. Other embodiments may include use of hydrazine as an agent for O-polysaccharide preparation. Preparation of LPS can be accomplished by known methods in the art.

In certain embodiments, the O-polysaccharides purified from wild-type, modified, or attenuated Gram-negative bacterial strains that express (not necessarily overexpress) a Wzz protein (e.g., wzzB) are provided for use in conjugate vaccines. In preferred embodiments, the O-polysaccharide chain is purified from the Gram-negative bacterial strain expressing (not necessarily overexpressing) wzz protein for use as a vaccine antigen either as a conjugate or complexed vaccine.

In one embodiment, the O-polysaccharide has a molecular weight that is increased by about 1-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 21-fold, 22-fold, 23-fold, 24-fold, 25-fold, 26-fold, 27-fold, 28-fold, 29-fold, 30-fold, 31-fold, 32-fold, 33-fold, 34-fold, 35-fold, 36-fold, 37-fold, 38-fold, 39-fold, 40-fold, 41-fold, 42-fold, 43-fold, 44-fold, 45-fold, 46-fold, 47-fold, 48-fold, 49-fold, 50-fold, 51-fold, 52-fold, 53-fold, 54-fold, 55-fold, 56-fold, 57-fold, 58-fold, 59-fold, 60-fold, 61-fold, 62-fold, 63-fold, 64-fold, 65-fold, 66-fold, 67-fold, 68-fold, 69-fold, 70-fold, 71-fold, 72-fold, 73-fold, 74-fold, 75-fold, 76-fold, 77-fold, 78-fold, 79-fold, 80-fold, 81-fold, 82-fold, 83-fold, 84-fold, 85-fold, 86-fold, 87-fold, 88-fold, 89-fold, 90-fold, 91-fold, 92-fold, 93-fold, 94-fold, 95-fold, 96-fold, 97-fold, 98-fold, 99-fold, 100-fold or more, as compared to the corresponding wild-type O-polysaccharide. In a preferred embodiment, the O-polysaccharide has a molecular weight that is increased by at least 1-fold and at most 5-fold, as compared to the corresponding wild-type O-polysaccharide. In another embodiment, the O-polysaccharide has a molecular weight that is increased by at least 2-fold and at most 4-fold, as compared to the corresponding wild-type O-polysaccharide. An increase in molecular weight of the O-polysaccharide, as compared to the corresponding wild-type O-polysaccharide, is preferably associated with an increase in number of O-antigen repeat units. In one embodiment, the increase in molecular weight of the O-polysaccharide is due to the wzz family protein.

In one embodiment, the O-polysaccharide has a molecular weight that is increased by about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 kDa or more, as compared to the corresponding wild-type O-polysaccharide. In one embodiment, the O-polysaccharide of the invention has a molecular weight that is increased by at least 1 and at most 200 kDa, as compared to the corresponding wild-type O-polysaccharide. In one embodiment, the molecular weight is increased by at least 5 and at most 200 kDa. In one embodiment, the molecular weight is increased by at least 10 and at most 200 kDa. In one embodiment, the molecular weight is increased by at least 12 and at most 200 kDa. In one embodiment, the molecular weight is increased by at least 15 and at most 200 kDa. In one embodiment, the molecular weight is increased by at least 18 and at most 200 kDa. In one embodiment, the molecular weight is increased by at least 20 and at most 200 kDa. In one embodiment, the molecular weight is increased by at least 21 and at most 200 kDa. In one embodiment, the molecular weight is increased by at least 22 and at most 200 kDa. In one embodiment, the molecular weight is increased by at least 30 and at most 200 kDa. In one embodiment, the molecular weight is increased by at least 1 and at most 100 kDa. In one embodiment, the molecular weight is increased by at least 5 and at most 100 kDa. In one embodiment, the molecular weight is increased by at least 10 and at most 100 kDa. In one embodiment, the molecular weight is increased by at least 12 and at most 100 kDa. In one embodiment, the molecular weight is increased by at least 15 and at most 100 kDa. In one embodiment, the molecular weight is increased by at least 20 and at most 100 kDa. In one embodiment, the molecular weight is increased by at least 1 and at most 75 kDa. In one embodiment, the molecular weight is increased by at least 5 and at most 75 kDa. In one embodiment, the molecular weight is increased by at least 10 and at most 75 kDa. In one embodiment, the molecular weight is increased by at least 12 and at most 75 kDa. In one embodiment, the molecular weight is increased by at least 15 and at most 75 kDa. In one embodiment, the molecular weight is increased by at least 18 and at most 75 kDa. In one embodiment, the molecular weight is increased by at least 20 and at most 75 kDa. In one embodiment, the molecular weight is increased by at least 30 and at most 75 kDa. In one embodiment, the molecular weight is increased by at least 10 and at most 90 kDa. In one embodiment, the molecular weight is increased by at least 12 and at most 85 kDa. In one embodiment, the molecular weight is increased by at least 10 and at most 75 kDa. In one embodiment, the molecular weight is increased by at least 10 and at most 70 kDa. In one embodiment, the molecular weight is increased by at least 10 and at most 60 kDa. In one embodiment, the molecular weight is increased by at least 10 and at most 50 kDa. In one embodiment, the molecular weight is increased by at least 10 and at most 49 kDa. In one embodiment, the molecular weight is increased by at least 10 and at most 48 kDa. In one embodiment, the molecular weight is increased by at least 10 and at most 47 kDa. In one embodiment, the molecular weight is increased by at least 10 and at most 46 kDa. In one embodiment, the molecular weight is increased by at least 20 and at most 45 kDa. In one embodiment, the molecular weight is increased by at least 20 and at most 44 kDa. In one embodiment, the molecular weight is increased by at least 20 and at most 43 kDa. In one embodiment, the molecular weight is increased by at least 20 and at most 42 kDa. In one embodiment, the molecular weight is increased by at least 20 and at most 41 kDa. Such an increase in molecular weight of the O-polysaccharide, as compared to the corresponding wild-type O-polysaccharide, is preferably associated with an increase in number of O-antigen repeat units. In one embodiment, the increase in molecular weight of the O-polysaccharide is due to the wzz family protein. See, for example, Table 21.

In another embodiment, the O-polysaccharide includes any one Formula selected from Table 1, wherein the number of repeat units n in the O-polysaccharide is greater than the number of repeat units in the corresponding wild-type O-polysaccharide by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more repeat units. Preferably, the saccharide includes an increase of at least 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 repeat units, as compared to the corresponding wild-type O-polysaccharide. See, for example, Table 21.

O-Antigen

The O-antigen is part of the lipopolysaccharide (LPS) in the outer membrane of Gram-negative bacteria. The O-antigen is on the cell surface and is a variable cell constituent. The variability of the O-antigen provides a basis for serotyping of Gram-negative bacteria. The current *E. coli* serotyping scheme includes O-polysaccharides 1 to 181.

The O-antigen includes oligosaccharide repeating units (O-units), the wild type structure of which usually contains two to eight residues from a broad range of sugars. The O-units of exemplary *E. coli* O-antigens are shown in Table 1, see also FIGS. 9A-C and FIGS. 10A-B.

In one embodiment, saccharide of the invention may be one oligosaccharide unit. In one embodiment, saccharide of the invention is one repeating oligosaccharide unit of the relevant serotype. In such embodiments, the saccharide may include a structure selected from any one of Formula O8, Formula O9a, Formula O9, Formula O20ab, Formula O20ac, Formula O52, Formula O97, and Formula O101.

In one embodiment, saccharide of the invention may be oligosaccharides. Oligosaccharides have a low number of repeat units (typically 5-15 repeat units) and are typically derived synthetically or by hydrolysis of polysaccharides. In such embodiments, the saccharide may include a structure selected from any one of Formula O8, Formula O9a, Formula O9, Formula O20ab, Formula O20ac, Formula O52, Formula O97, and Formula O101.

Preferably, all of the saccharides of the present invention and in the immunogenic compositions of the present invention are polysaccharides. High molecular weight polysaccharides may induce certain antibody immune responses due to the epitopes present on the antigenic surface. The isolation and purification of high molecular weight polysaccharides are preferably contemplated for use in the conjugates, compositions and methods of the present invention.

In some embodiments, the number of repeat O units in each individual O-antigen polymer (and therefore the length and molecular weight of the polymer chain) depends on the wzz chain length regulator, an inner membrane protein. Different wzz proteins confer different ranges of modal lengths (4 to >100 repeat units). The term "modal length" refers to the number of repeating O-units. Gram-negative bacteria often have two different Wzz proteins that confer two distinct OAg modal chain lengths, one longer and one shorter. The expression (not necessarily the overexpression) of wzz family proteins (e.g., wzzB) in Gram-negative bacteria may allow for the manipulation of O-antigen length, to shift or to bias bacterial production of O-antigens of certain length ranges, and to enhance production of high-yield large molecular weight lipopolysaccharides. In one embodiment, a "short" modal length as used herein refers to a low number of repeat O-units, e.g., 1-20. In one embodiment, a "long" modal length as used herein refers to a number of repeat O-units greater than 20 and up to a maximum of 40. In one embodiment, a "very long" modal length as used herein refers to greater than 40 repeat O-units.

In one embodiment, the saccharide produced has an increase of at least 10 repeating units, 15 repeating units, 20 repeating units, 25 repeating units, 30 repeating units, 35 repeating units, 40 repeating units, 45 repeating units, 50 repeating units, 55 repeating units, 60 repeating units, 65 repeating units, 70 repeating units, 75 repeating units, 80 repeating units, 85 repeating units, 90 repeating units, 95 repeating units, or 100 repeating units, as compared to the corresponding wild-type O-polysaccharide.

In another embodiment, the saccharide of the invention has an increase of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more repeat units, as compared to the corresponding wild-type O-polysaccharide. Preferably, the saccharide includes an increase of at least 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 repeat units, as compared to the corresponding wild-type O-polysaccharide. See, for example, Table 21. Methods of determining the length of saccharides are known in the art. Such methods include nuclear magnetic resonance, mass spectroscopy, and size exclusion chromatography, as described in Example 5.

Methods of determining the number of repeat units in the saccharide are also known in the art. For example, the number of repeat units (or "n" in the Formula) may be calculated by dividing the molecular weight of the polysaccharide (without the molecular weight of the core saccharide or KDO residue) by the molecular weight of the repeat unit (i.e., molecular weight of the structure in the corresponding Formula, shown for example in Table 1, which may be theoretically calculated as the sum of the molecular weight of each monosaccharide within the Formula). The molecular weight of each monosaccharide within the Formula is known in the art. The molecular weight of a repeat unit of Formula O25b, for example, is about 862 Da. The molecular weight of a repeat unit of Formula O1a, for example, is about 845 Da. The molecular weight of a repeat unit of Formula O2, for example, is about 829 Da. The molecular weight of a repeat unit of Formula O6, for example, is about 893 Da. When determining the number of repeat units in a conjugate, the carrier protein molecular weight and the protein: polysaccharide ratio is factored into the calculation. As defined herein, "n" refers to the number of repeating units (represented in brackets in Table 1) in a polysaccharide molecule. As is known in the art, in biological macromolecules, repeating structures may be interspersed with regions of imperfect repeats, such as, for example, missing branches. In addition, it is known in the art that polysaccharides isolated and purified from natural sources such as bacteria may be heterogenous in size and in branching. In such a case, n may represent an average or median value for n for the molecules in a population.

In one embodiment, the O-polysaccharide has an increase of at least one repeat unit of an O-antigen, as compared to the corresponding wild-type O-polysaccharide. The repeat units of O-antigens are shown in Table 1. In one embodiment, the O-polysaccharide includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more total repeat units. Preferably, the saccharide has a total of at least 3 to at most 80 repeat units. In another embodiment, the O-polysaccharide has an increase of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more repeat units, as compared to the corresponding wild-type O-polysaccharide.

In one embodiment, the saccharide includes an O-antigen wherein n in any of the O-antigen formulas (such as, for example, the Formulas shown in Table 1 (see also FIGS. 9A-C and FIGS. 10A-B)) is an integer of at least 1, 2, 3, 4, 5, 10, 20, 21, 22, 23, 24, 25, 26, 27, 28, 29, 30, 31, 32, 33, 34, 35, 36, 37, 38, 39, 40, and at most 200, 100, 99, 98, 97, 96, 95, 94, 93, 92, 91, 90, 89, 88, 87, 86, 81, 80, 79, 78, 77, 76, 75, 74, 73, 72, 71, 70, 69, 68, 67, 66, 65, 60, 59, 58, 57, 56, 55, 54, 53, 52, 51, or 50. Any minimum value and any maximum value may be combined to define a range. Exemplary ranges include, for example, at least 1 to at most 1000; at least 10 to at most 500; and at least 20 to at most 80, preferably at most 90. In one preferred embodiment, n is at least 31 to at most 90. In a preferred embodiment, n is 40 to 90, more preferably 60 to 85.

In one embodiment, the saccharide includes an O-antigen wherein n in any one of the O-antigen Formulas is at least 1 and at most 200. In one embodiment, n in any one of the O-antigen Formulas is at least 5 and at most 200. In one embodiment, n in any one of the O-antigen Formulas is at least 10 and at most 200. In one embodiment, n in any one of the O-antigen Formulas is at least 25 and at most 200. In one embodiment, n in any one of the O-antigen Formulas is at least 50 and at most 200. In one embodiment, n in any one of the O-antigen Formulas is at least 75 and at most 200. In one embodiment, n in any one of the O-antigen Formulas is at least 100 and at most 200. In one embodiment, n in any one of the O-antigen Formulas is at least 125 and at most 200. In one embodiment, n in any one of the O-antigen Formulas is at least 150 and at most 200. In one embodiment, n in any one of the O-antigen Formulas is at least 175 and at most 200. In one embodiment, n in any one of the O-antigen Formulas is at least 1 and at most 100. In one embodiment, n in any one of the O-antigen Formulas is at least 5 and at most 100. In one embodiment, n in any one of the O-antigen Formulas is at least 10 and at most 100. In one embodiment, n in any one of the O-antigen Formulas is at least 25 and at most 100. In one embodiment, n in any one of the O-antigen Formulas is at least 50 and at most 100. In one embodiment, n in any one of the O-antigen Formulas is at least 75 and at most 100. In one embodiment, n in any one of the O-antigen Formulas is at least 1 and at most 75. In one embodiment, n in any one of the O-antigen Formulas is at least 5 and at most 75. In one embodiment, n in any one of the O-antigen Formulas is at least 10 and at most 75. In one embodiment, n in any one of the O-antigen Formulas is at least 20 and at most 75. In one embodiment, n in any one of the O-antigen Formulas is at least 25 and at most 75. In one embodiment, n in any one of the O-antigen Formulas is at least 30 and at most 75. In one embodiment, n in any one of the O-antigen Formulas is at least 40 and at most 75. In one embodiment, n in any one of the O-antigen Formulas is at least 50 and at most 75. In one embodiment, n in any one of the O-antigen Formulas is at least 30 and at most 90. In one embodiment, n in any one of the O-antigen Formulas is at least 35 and at most 85. In one embodiment, n in any one of the O-antigen Formulas is at least 35 and at most 75. In one embodiment, n in any one of the O-antigen Formulas is at least 35 and at most 70. In one embodiment, n in any one of the O-antigen Formulas is at least 35 and at most 60. In one embodiment, n in any one of the O-antigen Formulas is at least 35 and at most 50. In one embodiment, n in any one of the O-antigen Formulas is at least 35 and at most 49. In one embodiment, n in any one of the O-antigen Formulas is at least 35 and at most 48. In one embodiment, n in any one of the O-antigen Formulas is at least 35 and at most 47. In one embodiment, n in any one of the O-antigen Formulas is at least 35 and at most 46. In one embodiment, n in any one of the O-antigen Formulas is at least 36 and at most 45. In one embodiment, n in any one of the O-antigen Formulas is at least 37 and at most 44. In one embodiment, n in any one of the O-antigen Formulas is at least 38 and at most 43. In one embodiment, n in any one of the O-antigen Formulas is at least 39 and at most 42. In one embodiment, n in any one of the O-antigen Formulas is at least 39 and at most 41.

For example, in one embodiment, n in the saccharide is 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90, most preferably 40. In another embodiment, n is at least 35 to at most 60. For example, in one embodiment, n is any one of 35, 36, 37, 38, 39, 40, 41, 42, 43, 44, 45, 46, 47, 48, 49, 50, 51, 52, 53, 54, 55, 56, 57, 58, 59, and 60, preferably 50. In another preferred embodiment, n is at least 55 to at most 75. For example, in one embodiment, n is 55, 56, 57, 58, 59, 60, 61, 62, 63, 64, 65, 66, 67, 68, or 69, most preferably 60.

The saccharide structure may be determined by methods and tools known art, such as, for example, NMR, including 1D, 1H, and/or 13C, 2D TOCSY, DQF-COSY, NOESY, and/or HMQC.

In some embodiments, the purified polysaccharide before conjugation has a molecular weight of between 5 kDa and 400 kDa. In other such embodiments, the saccharide has a molecular weight of between 10 kDa and 400 kDa; between 5 kDa and 400 kDa; between 5 kDa and 300 kDa; between 5 kDa and 200 kDa; between 5 kDa and 150 kDa; between 10 kDa and 100 kDa; between 10 kDa and 75 kDa; between 10 kDa and 60 kDa; between 10 kDa and 40 kDa; between 10 kDa and 100 kDa; 10 kDa and 200 kDa; between 15 kDa and 150 kDa; between 12 kDa and 120 kDa; between 12 kDa and 75 kDa; between 12 kDa and 50 kDa; between 12 and 60 kDa; between 35 kDa and 75 kDa; between 40 kDa and 60 kDa; between 35 kDa and 60 kDa; between 20 kDa and 60 kDa; between 12 kDa and 20 kDa; or between 20 kDa and 50 kDa. In further embodiments, the polysaccharide has a molecular weight of between 7 kDa to 15 kDa; 8 kDa to 16 kDa; 9 kDa to 25 kDa; 10 kDa to 100; 10 kDa to 60 kDa; 10 kDa to 70 kDa; 10 kDa to 160 kDa; 15 kDa to 600 kDa; 20 kDa to 1000 kDa; 20 kDa to 600 kDa; 20 kDa to 400 kDa; 30 kDa to 1,000 KDa; 30 kDa to 60 kDa; 30 kDa to 50 kDa or 5 kDa to 60 kDa. Any whole number integer within any of the above ranges is contemplated as an embodiment of the disclosure.

As used herein, the term "molecular weight" of polysaccharide or of carrier protein-polysaccharide conjugate refers to molecular weight calculated by size exclusion chromatography (SEC) combined with multiangle laser light scattering detector (MALLS).

A polysaccharide can become slightly reduced in size during normal purification procedures. Additionally, as described herein, polysaccharide can be subjected to sizing techniques before conjugation. Mechanical or chemical sizing maybe employed. Chemical hydrolysis may be conducted using acetic acid. Mechanical sizing may be conducted using High Pressure Homogenization Shearing. The molecular weight ranges mentioned above refer to purified polysaccharides before conjugation (e.g., before activation).

TABLE 1

*E. coli* serogroups/serotypes and O-unit moieties

| Serogroup/Serotype | Moiety Structure (O-unit) | Moiety structure referred to herein as: |
|---|---|---|
| O1A, O1A1 | [→3)-α-L-Rha-(1→3)-α-L-Rha-(1→3)-(β-L-Rha-(1→4)-β-D-GlcNAc-(1→ \| β-D-ManNAc-(1→2)]$_n$ | Formula O1A |
| O1B | [→3)-α-L-Rha-(1→2)-α-L-Rha-(1→2)-α-D-Gal-(1→3)-β-D-GlcNAc-(1→\|β-D-ManNAc-(1→2)]$_n$ | Formula O1B |
| O1C | [→3)-α-L-Rha-(1→2)-α-L-Rha-(1→3)-α-D-Gal-(1→3)-β-D-GlcNAc-(1→\|β-D-ManNAc-(1→2)]$_n$ | Formula O1C |
| O2 | [→3)-α-L-Rha-(1→2)-α-L-Rha-(1→3)-β-L-Rha-(1→4)-β-D-GlcNAc-(1→ \| α-D-Fuc3NAc-(1→2)]$_n$ | Formula O2 |
| O3 | [β-L-RhaNAc(1→4)α-D-Glc-(1→4)\| \| →3)-β-D-GlcNAc-(1→3)-α-D-Gal-(1→3)-(β-D-GlcNAc-(1→]$_n$ | Formula O3 |
| O4:K52 | [→2)-α-L-Rha-(1→6)-α-D-Glc-(1→3)-α-L-FucNAc-(1→3)-β-D-GlcNAc(1→]$_n$ | Formula O4:K52 |
| O4:K6 | [α-D-Glc-(1→3) \| →2)-α-L-Rha-(1→6)-α-D-Glc-(1→3)-α-L-FucNAc-(1→3)-β-D-GlcNAc(1→]$_n$ | Formula O4:K6 |
| O5ab | [→4)-β-D-Qui3NAc-(1→3)-β-D-Ribf-(1→4)-β-D-Gal-(1→3)-α-D-GalNAc(1→]$_n$ | Formula O5ab |
| O5ac (strain 180/C3) | [→2)-β-D-Qui3NAc-(1→3)-β-D-Ribf-(1→4)-β-D-Gal-(1→3)-α-D-GalNAc(1→]$_n$ | Formula O5ac (strain 180/C3) |
| O6:K2; K13; K15 | [→4)-α-D-GalNAc-(1→3)-β-D-Man-(1→4)-β-D-Man-(1→3)-α-D-GlcNAc-(1→ \| β-D-Glc-(1→2)]$_n$ | Formula O6:K2; K13; K15 |
| O6:K54 | [→4)-α-D-GalNAc-(1→3)-β-D-Man-(1→4)-β-D-Man-(1→3)-α-D-GlcNAc-(1→\|β-D-GlcNAc-(1→2)]$_n$ | Formula O6:K54 |
| O7 | [α-L-Rha-(1→3) \| →3)-β-D-Qui4NAc-(1→2)-α-D-Man-(1→4)-β-D-Gal-(1→3)-α-D-GlcNAc-(1→]$_n$ | Formula O7 |
| O10 | [→3)-α-L-Rha-(1→3)-α-L-Rha-(1→3)-α-D-Gal-(1→3)-β-D-GlcNAc-(1→ \| α-D-Fuc4NAcyl-(1→2) Acyl = acetyl (60%) or (R)-3-hydroxybutyryl (40%)]$_n$ | Formula O10 |

TABLE 1-continued

_E. coli serogroups/serotypes and O-unit moieties_

| Serogroup/ Serotype | Moiety Structure (O-unit) | Moiety structure referred to herein as: |
|---|---|---|
| O16 | [→2)-β-D-Galf-(1→6)-α-D-Glc-(1→3)-α-L-Rha2Ac-(1→3)-α-D-GlcNAc-(1→]$_n$ | Formula O16 |
| O17 | [α-D-Glc-(1→6) | →6)-α-D-Man-(1→2)-α-D-Man-(1→2)-β-D-Man-(1→3)-α-D-GlcNAc(1→]$_n$ | Formula O17 |
| O18A, O18ac | [→2)-α-L-Rha-(1→6)-α-D-Glc-(1→4)-α-D-Gal-(1→3)-α-D-GlcNAc-(1→ | β-D-GlcNAc-(1→3)]$_n$ | Formula O18A, Formula O18ac |
| O18A1 | [α-D-Glc-(1→6) | →2)-α-L-Rha-(1→6)-α-D-Glc-(1→4)-α-D-Gal-(1→3)-α-D-GlcNAc-(1→ | β-D-GlcNAc-(1→3)]$_n$ | Formula O18A1 |
| O18B | [43)-α-L-Rha-(1→6)-α-D-Glc-(1→4)-α-D-Gal-(1→3)-α-D-GlcNAc-(1→ | β-D-Glc-(1→3)]$_n$ | Formula O18B |
| O18B1 | [α-D-Glc-(1→4) | →3)-α-L-Rha-(1→6)-α-D-Glc-(1→4)-α-D-Gal-(1→3)-α-D-GlcNAc-(1→ | β-D-Glc-(1→3)]$_n$ | Formula O18B1 |
| O21 | [β-D-Gal-(1→4) | →3)-β-D-Gal-(1→4)-β-D-Glc-(1→3)-β-D-GalNAc-(1→ | β-D-GlcNAc-(1→2)]$_n$ | Formula O21 |
| O23A | [α-D-Glc-(1→6) | →6)-α-D-Glc-(1→4)-β-D-Gal-(1→3)-β-D-GalNAc-(1→3)-β-D-GlcNAc-(1→ | β-D-GlcNAc(1→3)]$_n$ | Formula O23A |
| O24 | [→7)-α-Neu5Ac-(2→3)-β-D-Glc-(1→3)-β-D-GalNAc-(1→ | α-D-Glc-(1→2)]$_n$ | Formula O24 |
| O25/O25a | [β-D-Glc-(1→6) | →4)-α-D-Glc-(1→3)-α-L-FucNAc-(1→3)-β-D-GlcNAc-(1→ | α-L-Rha-(1→3)]$_n$ | Formula O25a |
| O25b | β-Glcp-<br>1<br>↓<br>6<br>[α-Rhap-(1→3)–α-Glcp-(1→3)–α-Rhap2OAc-(1→3)-β-GlcpNAc-]$_n$ | Formula O25b |
| O26 | [→3)-α-L-Rha-(1→4)-α-L-FucNAc-(1→3)-β-D-GlcNAc-(1→]$_n$ | Formula O26 |
| O28 | [→2)-(R)-Gro-1-P→4)-β-D-GlcNAc-(1→3)-β-D-Galf2Ac-(1→3)-α-D-GlcNAc-(1→]$_n$ | Formula O28 |
| O36 | [α-L-Rhap-(1→2)-α-L-Fucp<br>1<br>↓<br>3<br>→4)-α-D-Manp-(1→3)-α-L-Fucp-(1→3)-β-D-GlcpNAc-(1→]|n | Formula O36 |
| O44 | [α-D-Glc-(1→4) | →6)-α-D-Man-(1→2)-α-D-Man-(1→2)-β-D-Man-(1→3)-α-D-GlcNAc(1→]$_n$ | Formula O44 |
| O45 | [→2)-β-D-Glc-(1→3)-α-L-6dTal2Ac-(1→3)-α-D-FucNAc-(1→]$_n$ | Formula O45 |
| O45rel | [→2)-β-D-Glc-(1→3)-α-L-6dTal2Ac-(1→3)-β-D-GlcNAc-(1→]$_n$ | Formula O45rel |
| O54 | [→4)-α-d-GalpA-(1→2)-α-l-Rhap-(1→2)-β-d-Ribf-(1→4)-β-d-Galp-(1→3)-β-d-GlcpNAc-(1→]$_n$ | Formula O54 |
| O55 | [→6)-β-D-GlcNAc-(1→3)-α-D-Gal-(1→3)-β-D-GalNAc-(1→ | α-Col-(1→2)-β-D-Gal-(1→3)]$_n$ | Formula O55 |
| O56 | [→7)-α-Neu5Ac-(2→3)-β-D-Glc-(1→3)-β-D-GlcNAc-(1→ | α-D-Gal-(1→2)]$_n$ | Formula O56 |
| O57 | [→3)-α-D-Galp-(1→3)-α-L-FucpNAc-(1→3)-α-D-GlcpNAc-(1→]n<br>2      4<br>↑      ↑<br>1      1<br>α-D-GalpA2/3Ac    β-D-Glcp | Formula O57 |
| O58 | [3-O-[(R)-1-carboxyethyl]-α-L-Rha-(1→3) | →4)-α-D-Man-(1→4)-α-D-Man2Ac-(1→3)-β-D-GlcNAc-(1→]$_n$ | Formula O58 |
| O64 | [β-D-Gal-(1→6) | →3)-α-D-ManNAc-(1→3)-β-D-GlcA-(1→3)-β-D-Gal-(1→3)-β-D-GlcNAc(1→]$_n$ | Formula O64 |

TABLE 1-continued

E. coli serogroups/serotypes and O-unit moieties

| Serogroup/Serotype | Moiety Structure (O-unit) | Moiety structure referred to herein as: |
|---|---|---|
| O68 | [α-L-Rhap   α-D-Glcp<br>    1           1<br>    ↓           ↓<br>    3           3<br>→6)-α-D-Manp-(1→2)-α-D-Manp-(1→2)-α-D-Manp-(1→2)-β-D-Manp-(1→3)-α-D-GlcpNAC-(1→]n | Formula O68 |
| O69 | [→2)-α-L-Rha-(1→2)-α-L-Rha-(1→2)-α-D-Gal-(1→3)-β-D-GlcNAc-(1→]$_n$ | Formula O69 |
| O73 (Strain 73-1) | [α-D-Glc-(1→3) ǀ →4)-α-D-Man-(1→2)-α-D-Man-(1→2)-β-D-Man-(1→3)-α-D-GalNAc(1→]$_n$ | Formula O73 (Strain 73-1) |
| O74 | →6)-α-D-GlcpNAc-(1→4)-β-D-GalpA-(1→3)-β-D-GlcpNAc-(1→]n<br>\|<br>[β-D-Fucp3NAc-(1→3) | Formula O74 |
| O75 | [β-D-Man-(1→4) ǀ →3)-α-D-Gal-(1→4)-α-L-Rha-(1→3)-β-D-GlcNAc-(1→]$_n$ | Formula O75 |
| O76 | [→4)-β-D-GlcpA-(1→4)-β-D-GalpNAc3Ac-(1→4)-α-D-GalpNAc-(1→3)-β-D-GalpNAc-(1→]$_n$ | Formula O76 |
| O77 | [→6)-α-D-Man-(1→2)-α-D-Man-(1→2)-β-D-Man-(1→3)-α-D-GlcNAc(1→]$_n$ | Formula O77 |
| O78 | [→4)-β-D-GlcNAc-(1→4)-β-D-Man-(1→4)-α-D-Man-(1→3)-β-D-GlcNAc-(1→]$_n$ | Formula O78 |
| O86 | [α-D-Gal-(1→3) ǀ →4)-α-L-Fuc-(1→2)-β-D-Gal-(1→3)-α-D-GalNAc-(1→3)-β-D-GalNAc-(1→]$_n$ | Formula O86 |
| O88 | [α-L-6dTal-(1→3) ǀ →4)-α-D-Man-(1→3)-α-D-Man-(1→3)-β-D-GlcNAc-(1→]$_n$ | Formula O88 |
| O90 | [→4)-α-L-Fuc2/3Ac-(1→2)-β-D-Gal-(1→3)-α-D-GalNAc-(1→3)-β-D-GalNAc-(1→]$_n$ | Formula O90 |
| O98 | [→)-α-L-QuiNAc-(1→4)-α-D-GalNAcA-(1→3)-α-L-QuiNAc-(1→3)-β-D-GlcNAc-(1→]$_n$ | Formula O98 |
| O104 | [→4)-α-D-Gal-(1→4)-α-Neu5,7,9Ac$_3$-(2→3)-β-D-Gal-(1→3)-β-D-GalNAc-(1→]$_n$ | Formula O104 |
| O111 | [α-Col-(1→6) ǀ →4)-α-D-Glc-(1→4)-α-D-Gal-(1→3)-β-D-GlcNAc-(1→ ǀ α-Col-(1→3)]$_n$ | Formula O111 |
| O113 | [→4)-α-D-GalNAc-(1→4)-α-D-GalA-(1→3)-α-D-Gal-(1→3)-β-D-GlcNAc-(1→ ǀ β-D-Gal-(1→3)]$_n$ | Formula O113 |
| O114 | [→4)-β-D-Qui3N(N-acetyl-L-seryl)-(1→3)-β-D-Ribf-(1→4)-β-D-Gal-(1→3)-α-D-GlcNAc(1→]$_n$ | Formula O114 |
| O119 | [β-D-RhaNAc3NFo-(1→3) ǀ →2)-β-D-Man-(1→3)-α-D-Gal-(1→4)-α-L-Rha-(1→3)-α-D-GlcNAc-(1→]$_n$ | Formula O119 |
| O121 | [→3)-β-D-Qui4N(N-acetyl-glycyl)-(1→4)-α-D-GalNAc3Ac6N-(1→4)-α-D-GalNAcA-(1→3)-α-D-GlcNAc-(1→]$_n$ | Formula O121 |
| O124 | [4-O-[(R)-1-carboxyethyl]-β-D-Glc-(1→6)-α-D-Glc(1→4) ǀ→3)-α-D-Gal-(1→6)-β-D-Galf-(1→3)-β-D-GalNAc-(1→]$_n$ | Formula O124 |
| O125 | [α-D-Glc-(1→3) ǀ →4)-β-D-GalNAc-(1→2)-α-D-Man-(1→3)-α-L-Fuc-(1→3)-α-D-GalNAc-(1→ ǀ β-D-Gal-(1→3)]$_n$ | Formula O125 |
| O126 | [→2)-β-D-Man-(1→3)-β-D-Gal-(1→3)-α-D-GlcNAc-(1→3)-β-D-GlcNAc-(1→ ǀ α-L-Fuc-(1→2)]$_n$ | Formula O126 |
| O127 | [→2)-α-L-Fuc-(1→2)-β-D-Gal-(1→3)-α-D-GalNAc-(1→3)-α-D-GalNAc-(1→]$_n$ | Formula O127 |
| O128 | [α-L-Fuc-(1→2) ǀ →6)β-D-Gal-(1→3)-β-D-GalNAc-(1→4)-α-D-Gal-(1→3)-β-D-GalNAc-(1→]$_n$ | Formula O128 |
| O136 | [→4)-β-Pse5Ac7Ac-(2→4)-β-D-Gal-(1→4)-β-D-GlcNAc-(1→β-Pse5Ac7Ac = 5,7-diacetamido-3,5,7,9-tetradeoxy-L-glycero-β-L-manno-nonulosonic acid]$_n$ | Formula O136 |
| O138 | [→2)-α-L-Rha-(1→3)-α-L-Rha-(1→4)-α-D-GalNAcA-(1→3)-β-D-GlcNAc-(1→]$_n$ | Formula O138 |

TABLE 1-continued

*E. coli* serogroups/serotypes and O-unit moieties

| Serogroup/Serotype | Moiety Structure (O-unit) | Moiety structure referred to herein as: |
|---|---|---|
| O140 | [α-D-Galf-(1→2)-α-L-Rhap<br>1<br>↓<br>4<br>→3)-β-D-Galp-(1→4)-α-D-Glcp-(1→4)-β-D-GlcpA-(1→3)-β-D-GalpNAc-(1→]$_n$ | Formula O140 |
| O141 | [α-L-Rha-(1→3) \| →4)-α-D-Man-(1→3)-α-D-Man6Ac-(1→3)-β-D-GlcNAc-(1→ \| β-D-GlcA-(1→2)]$_n$ | Formula O141 |
| O142 | [→2)-α-L-Rha-(1→6)-α-D-GalNAc-(1→4)-α-D-GalNAc-(1→3)-α-D-GalNAc-(1→ \| β-D-GlcNAc-(1→3)]$_n$ | Formula O142 |
| O143 | [→2)-β-D-GalA6R3,4Ac-(1→3)-α-D-GalNAc-(1→4)-β-D-GlcA-(1→3)-β-D-GlcNAc-(1→ R = 1,3-dihydroxy-2-propylamino]$_n$ | Formula O143 |
| O147 | [→2)-α-L-Rha-(1→2)-α-L-Rha-(1→4)-β-D-GalA-(1→3)-β-D-GalNAc-(1→]$_n$ | Formula O147 |
| O149 | [→3)-β-D-GlcNAc-(S)-4,6Py-(1→3)-β-L-Rha-(1→4)-β-D-GlcNAc-(1→ (S)-4,6Py = 4,6-O-[(S)-1-carboxyethylidene]-]$_n$ | Formula O149 |
| O152 | [β-L-Rha-(1→4) \| →3)-α-D-GlcNAc-(1-P→6)-α-D-Glc-(1→2)-β-D-Glc-(1→3)-β-D-GlcNAc-(1→]$_n$ | Formula O152 |
| O157 | [→2)-α-D-Rha4NAc-(1→3)-α-L-Fuc-(1→4)-β-D-Glc-(1→3)-α-D-GalNAc-(1→]$_n$ | Formula O157 |
| O158 | [α-D-Glc-(1→6) \| →4)-α-D-Glc-(1→3)-α-D-GalNAc-(1→3)-β-D-GalNAc-(1→ \| α-L-Rha-(1→3)]$_n$ | Formula O158 |
| O159 | [α-L-Fuc-(1→4) \| →3)-β-D-GlcNAc-(1→4)-α-D-GalA-(1→3)-α-L-Fuc-(1→3)-β-D-GlcNAc-(1→]$_n$ | Formula O159 |
| O164 | [β-D-Glc-(1→6)-α-D-Glc(1→4) \| →3)-β-D-Gal-(1→6)-β-D-Galf-(1→3)-β-D-GalNAc-(1→]$_n$ | Formula O164 |
| O173 | [α-L-Fuc-(1→4) \| →3)-α-D-Glc-(1-P→6)-α-D-Glc-(1→2)-β-D-Glc-(1→3)-β-D-GlcNAc-(1→]$_n$ | Formula O173 |
| 62D1 Suggested as *Erwinia herbicola* | [α-D-Gal(1→6) \| 2)-β-D-Qui3NAc-(1→3)-α-L-Rha-(1→3)-β-D-Gal-(1→3)-α-D-FucNAc-(1→]$_n$ | Formula 62D1 |
| O22 | [→6)-α-D-Glc-(1→4)-β-D-GlcA-(1→4)-β-D-GalNAc3Ac-(1→3)-α-D-Gal-(1→3)-β-D-GalNAc-(1→]$_n$ | Formula O22 |
| O35 | [→3)-α-L-Rha-(1→2)-α-L-Rha-(1→3)-α-L-Rha-(1→2)-α-L-Rha-(1→3)-β-D-GlcNAc-(1→ \| α-D-GalNAcA6N-(1→2)]$_n$ | Formula O35 |
| O65 | [→2)-β-D-Qui3NAc-(1→4)-α-D-GalA6N-(1→4)-α-D-GalNAc-(1→4)-β-D-GalA-(1→3)-α-D-GlcNAc-(1→]$_n$ | Formula O65 |
| O66 | [→2)-β-D-Man-(1→3)-α-D-GlcNAc-(1→2)-β-D-Glc3Ac-(1→3)-α-L-6dTal-(1→3)-α-D-GlcNAc(1→]$_n$ | Formula O66 |
| O83 | [→6)-α-D-Glc-(1→4)-β-D-GlcA-(1→6)-β-D-Gal-(1→4)-β-D-Gal-(1→4)-β-D-GlcNAc-(1→]$_n$ | Formula O83 |
| O91 | [→4)-α-D-Qui3NAcyl-(1→4)-β-D-Gal-(1→4)-β-D-GlcNAc-(1→4)-β-D-GlcA6NGly-(1→3)-β-D-GlcNAc-(1→ Acyl = (R)-3-hydroxybutyryl]$_n$ | Formula O91 |
| O105 | [β-D-Ribf-(1→3) \| →4)-α-D-GlcA2Ac3Ac-(1→2) -α-L-Rha4Ac-(1→3)-β-L-Rha-(1→4)-β-L-Rha-(1→3)-β-D-GlcNAc6Ac-(1→]$_n$ | Formula O105 |
| O116 | [→2)-β-D-Qui4NAc-(1→6)-α-D-GlcNAc-(1→4)-β-D-GalNAc-(1→4)-α-D-GalA-(1→3)-β-D-GlcNAc-(1→]$_n$ | Formula O116 |
| O117 | [→4)-β-D-GalNAc-(1→3)-α-L-Rha-(1→4)-α-D-Glc-(1→4)-β-D-Gal-(1→3)-α-D-GalNAc-(1→]$_n$ | Formula O117 |
| O139 | [β-D-Glc-(1→3) \| →3)-α-L-Rha-(1→4)-α-D-GalA-(1→2)-α-L-Rha-(1→3)-α-L-Rha-(1→2)-α-L-Rha-(1→3)-α-D-GlcNAc-(1→]$_n$ | Formula O139 |
| O153 | [→2)-β-D-Ribf-(1→4)-β-D-Gal-(1→4)-α-D-GlcNAc-(1→4)-β-D-Gal-(1→3)-α-D-GlcNAc-(1→]$_n$ | Formula O153 |
| O167 | [α-D-Galf-(1→4) \| →2)-β-D-GalA6N(L)Ala-(1→3)-α-D-GlcNAc-(1→2)-β-D-Galf-(1→5)-β-D-Galf-(1→3)-β-D-GlcNAc-(1→]$_n$ | Formula O167 |
| O172 | [→3)-α-L-FucNAc-(1→4)-β-D-Glc6Ac-(1-P→4)-α-D-Glc-(1→3)-α-L-FucNAc-(1→3)-α-D-GlcNAc-(1→]$_n$ | Formula O172 |
| O8 | [→2)-α-D-Man-(1→2)-α-D-Man-(1→3)-β-D-Man-(1→]$_n$ | Formula O8 |
| O9a | [→2)-α-D-Man-(1→2)-α-D-Man-(1→3)-α-D-Man-(1→3)-α-D-Man-(1→]$_n$ | Formula O9a |
| O9 | [→2)-[α-D-Man-(1→2)]2-α-D-Man-(1→3)-α-D-Man-(1→3)-α-D-Man-(1→]$_n$ | Formula O9 |
| O20ab | [→2)-β-D-Ribf-(1→4)-α-D-Gal-(1→]$_n$ | Formula O20ab |
| O20ac | [α-D-Gal-(1→3) \| →2)-β-D-Ribf-(1→4)-α-D-Gal-(1→]$_n$ | Formula O20ac |

TABLE 1-continued

E. coli serogroups/serotypes and O-unit moieties

| Serogroup/Serotype | Moiety Structure (O-unit) | Moiety structure referred to herein as: |
|---|---|---|
| O52 | [→3)-β-D-Fucf-(1→3)-β-D-6dmanHep2Ac-(1→]$_n$ | Formula O52 |
| O97 | [→3)-α-L-Rha-(1→3)-β-L-Rha-(1→ \| \| β-D-Xulf-(2→2)β-D-Xulf-(2→2)]$_n$ | Formula O97 |

† β-D-6dmanHep2Ac is 2-O-acetyl-6-deoxy-β-D-manno-heptopyranosyl.
‡ β-D-Xulf is β-D-threo-pentofuranosyl.

Core Oligosaccharide

The core oligosaccharide is positioned between Lipid A and the O-antigen outer region in wild-type E. coli LPS. More specifically, the core oligosaccharide is the part of the polysaccharide that includes the bond between the O-antigen and the lipid A in wild type E. coli. This bond includes a ketosidic bond between the hemiketal function of the innermost 3-deoxy-d-manno-oct-2-ulosonic acid (KDO)) residue and a hydroxyl-group of a GlcNAc-residue of the lipid A. The core oligosaccharide region shows a high degree of similarity among wild-type E. coli strains. It usually includes a limited number of sugars. The core oligosaccharide includes an inner core region and an outer core region.

More specifically, the inner core is composed primarily of L-glycero-D-manno-heptose (heptose) and KDO residues. The inner core is highly conserved. A KDO residue includes the following Formula KDO:

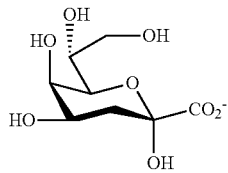

The outer region of the core oligosaccharide displays more variation than the inner core region, and differences in this region distinguish the five chemotypes in E. coli: R1, R2, R3, R4, and K-12. See FIG. 17, which illustrates generalized structures of the carbohydrate backbone of the outer core oligosaccharides of the five known chemotypes. HepII is the last residue of the inner core oligosaccharide. While all of the outer core oligosaccharides share a structural theme, with a (hexose) 3 carbohydrate backbone and two side chain residues, the order of hexoses in the backbone and the nature, position, and linkage of the side chain residues can all vary. The structures for the R1 and R4 outer core oligosaccharides are highly similar, differing in only a single β-linked residue.

The core oligosaccharides of wild-type E. coli are categorized in the art based on the structures of the distal oligosaccharide, into five different chemotypes: E. coli R1, E. coli R2, E. coli R3, E. coli R4, and E. coli K12.

In a preferred embodiment, the compositions described herein include glycoconjugates in which the O-polysaccharide includes a core oligosaccharide bound to the O-antigen. In one embodiment, the composition induces an immune response against at least any one of the core E. coli chemotypes E. coli R1, E. coli R2, E. coli R3, E. coli R4, and E. coli K12. In another embodiment, the composition induces an immune response against at least two core E. coli chemotypes. In another embodiment, the composition induces an immune response against at least three core E. coli chemotypes. In another embodiment, the composition induces an immune response against at least four core E. coli chemotypes. In another embodiment, the composition induces an immune response against all five core E. coli chemotypes.

In another preferred embodiment, the compositions described herein include glycoconjugates in which the O-polysaccharide does not include a core oligosaccharide bound to the O-antigen. In one embodiment, such a composition induces an immune response against at least any one of the core E. coli chemotypes E. coli R1, E. coli R2, E. coli R3, E. coli R4, and E. coli K12, despite the glycoconjugate having an O-polysaccharide that does not include a core oligosaccharide.

E. coli serotypes may be characterized according to one of the five chemotypes. Table 2 lists exemplary serotypes characterized according to chemotype. The serotypes in bold represent the serotypes that are most commonly associated with the indicated core chemotype. Accordingly, in a preferred embodiment, the composition induces an immune response against at least any one of the core E. coli chemotypes E. coli R1, E. coli R2, E. coli R3, E. coli R4, and E. coli K12, which includes an immune response against any one of the respective corresponding E. coli serotypes.

TABLE 2

Core Chemotype and associated E. coli Serotype

| Core chemotype | Serotype |
|---|---|
| R1 | O25a, O6, O2, O1, O75, O4, O16, O8, O18, O9, O13, O20, O21, O91, and O163. |
| R2 | O21, O44, O11, O89, O162, O9 |
| R3 | O25b, O15, O153, O21, O17, O11, O159, O22 O86, O93 |
| R4 | O2, O1, O86, O7,0102, O160, O166 |
| K-12 | O25b, O16 |

In some embodiments, the composition includes a saccharide that includes a structure derived from a serotype having an R1 chemotype, e.g., selected from a saccharide having Formula O25a, Formula O6, Formula O2, Formula O1, Formula O75, Formula O4, Formula O16, Formula O8, Formula O18, Formula O9, Formula O13, Formula O20, Formula O21, Formula O91, and Formula O163, wherein n is 1 to 100. In some embodiments, the saccharide in said composition further includes an E. coli R1 core moiety, e.g., shown in FIG. 17.

In some embodiments, the composition includes a saccharide that includes a structure derived from a serotype having an R1 chemotype, e.g., selected from a saccharide having Formula O25a, Formula O6, Formula O2, Formula O1, Formula O75, Formula O4, Formula O16, Formula O18, Formula O13, Formula O20, Formula O21, Formula O91, and Formula O163, wherein n is 1 to 100, preferably 31 to 100, more preferably 35 to 90, most preferably 35 to 65. In some embodiments, the saccharide in said composition further includes an *E. coli* R1 core moiety in the saccharide.

In some embodiments, the composition includes a saccharide that includes a structure derived from a serotype having an R2 chemotype, e.g., selected from a saccharide having Formula O21, Formula O44, Formula O11, Formula O89, Formula O162, and Formula O9, wherein n is 1 to 100, preferably 31 to 100, more preferably 35 to 90, most preferably 35 to 65.

Figure 17:
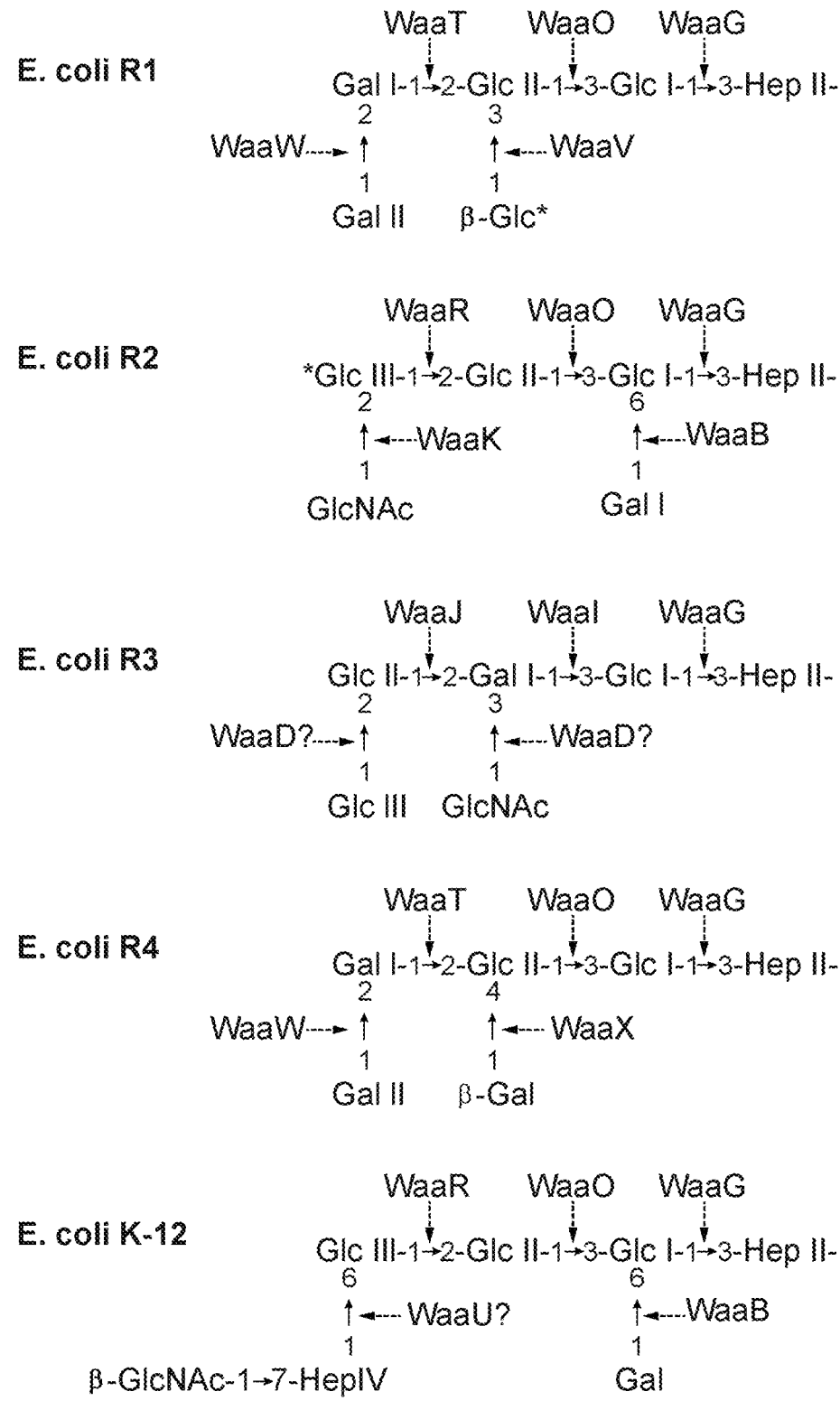
FIG. 17—Generalized structures of the carbohydrate backbone of the outer core oligosaccharides of the five known chemotypes. All glycoses are in the α-anomeric configuration unless otherwise indicated. The genes whose products catalyse formation of each linkage are indicated in dashed arrows. An asterisk denotes the residue of the core oligosaccharide to which attachment of O-antigen occurs.

In some embodiments, the saccharide in said composition further includes an *E. coli* R2 core moiety, e.g., shown in FIG. 17.

In some embodiments, the composition includes a saccharide that includes a structure derived from a serotype having an R3 chemotype, e.g., selected from a saccharide having Formula O25b, Formula O15, Formula O153, Formula O21, Formula O17, Formula O11, Formula O159, Formula O22, Formula O86, and Formula O93, wherein n is 1 to 100, preferably 31 to 100, more preferably 35 to 90, most preferably 35 to 65. In some embodiments, the saccharide in said composition further includes an *E. coli* R3 core moiety, e.g., shown in FIG. 17.

In some embodiments, the composition includes a saccharide that includes a structure derived from a serotype having an R4 chemotype, e.g., selected from a saccharide having Formula O2, Formula O1, Formula O86, Formula O7, Formula O102, Formula O160, and Formula O166, wherein n is 1 to 100, preferably 31 to 100, more preferably 35 to 90, most preferably 35 to 65. In some embodiments, the saccharide in said composition further includes an *E. coli* R4 core moiety, e.g., shown in FIG. 17.

In some embodiments, the composition includes a saccharide that includes a structure derived from a serotype having an K-12 chemotype (e.g., selected from a saccharide having Formula O25b and a saccharide having Formula O16), wherein n is 1 to 1000, preferably 31 to 100, more preferably 35 to 90, most preferably 35 to 65. In some embodiments, the saccharide in said composition further includes an *E. coli* K-12 core moiety, e.g., shown in FIG. 17.

In some embodiments, the saccharide includes the core saccharide. Accordingly, in one embodiment, the O-polysaccharide further includes an *E. coli* R1 core moiety. In another embodiment, the O-polysaccharide further includes an *E. coli* R2 core moiety. In another embodiment, the O-polysaccharide further includes an *E. coli* R3 core moiety. In another embodiment, the O-polysaccharide further includes an *E. coli* R4 core moiety. In another embodiment, the O-polysaccharide further includes an *E. coli* K12 core moiety.

In some embodiments, the saccharide does not include the core saccharide. Accordingly, in one embodiment, the O-polysaccharide does not include an *E. coli* R1 core moiety. In another embodiment, the O-polysaccharide does not include an *E. coli* R2 core moiety. In another embodiment, the O-polysaccharide does not include an *E. coli* R3 core moiety. In another embodiment, the O-polysaccharide does not include an *E. coli* R4 core moiety. In another embodiment, the O-polysaccharide does not include an *E. coli* K12 core moiety.

Conjugated O-Antigens

Chemical linkage of O-antigens or preferably O-polysaccharides to protein carriers may improve the immunogenicity of the O-antigens or O-polysaccharides. However, variability in polymer size represents a practical challenge for production. In commercial use, the size of the saccharide can influence the compatibility with different conjugation synthesis strategies, product uniformity, and conjugate immunogenicity. Controlling the expression of a Wzz family protein chain length regulator through manipulation of the O-antigen synthesis pathway allows for production of a desired length of O-antigen chains in a variety of Gram-negative bacterial strains, including *E. coli*.

In one embodiment, the purified saccharides are chemically activated to produce activated saccharides capable of reacting with the carrier protein. Once activated, each saccharide is separately conjugated to a carrier protein to form a conjugate, namely a glycoconjugate. As used herein, the term "glycoconjugate" refers to a saccharide covalently linked to a carrier protein. In one embodiment a saccharide is linked directly to a carrier protein. In another embodiment, a saccharide is linked to a protein through a spacer/linker.

Conjugates may be prepared by schemes that bind the carrier to the O-antigen at one or at multiple sites along the O-antigen, or by schemes that activate at least one residue of the core oligosaccharide.

In one embodiment, each saccharide is conjugated to the same carrier protein.

If the protein carrier is the same for 2 or more saccharides in the composition, the saccharides may be conjugated to the same molecule of the carrier protein (e.g., carrier molecules having 2 or more different saccharides conjugated to it).

In a preferred embodiment, the saccharides are each individually conjugated to different molecules of the protein carrier (each molecule of protein carrier only having one type of saccharide conjugated to it). In said embodiment, the saccharides are said to be individually conjugated to the carrier protein.

The chemical activation of the saccharides and subsequent conjugation to the carrier protein can be achieved by the activation and conjugation methods disclosed herein. After conjugation of the polysaccharide to the carrier protein, the glycoconjugates are purified (enriched with respect to the amount of polysaccharide-protein conjugate) by a variety of techniques. These techniques include concentration/diafiltration operations, precipitation/elution, column chromatography, and depth filtration. After the individual glycoconjugates are purified, they are compounded to formulate the immunogenic composition of the present invention.

Activation. The present invention further relates to activated polysaccharides produced from any of the embodiments described herein wherein the polysaccharide is activated with a chemical reagent to produce reactive groups for conjugation to a linker or carrier protein. In some embodiments, the saccharide of the invention is activated prior to conjugation to the carrier protein. In some embodiments, the degree of activation does not significantly reduce the molecular weight of the polysaccharide. For example, in some embodiments, the degree of activation does not cleave the polysaccharide backbone. In some embodiments, the degree of activation does not significantly impact the degree of conjugation, as measured by the number of lysine residues modified in the carrier protein, such as, $CRM_{197}$ (as determined by amino acid analysis). For example, in some embodiments, the degree of activation does not significantly increase the number of lysine residues modified (as determined by amino acid analysis) in the carrier protein by 3-fold, as compared to the number of lysine residues modified in the carrier protein of a conjugate with a reference polysaccharide at the same degree of activation. In some embodiments, the degree of activation does not increase the level of unconjugated free saccharide. In some embodiments, the degree of activation does not decrease the optimal saccharide/protein ratio.

In some embodiments, the activated saccharide has a percentage of activation wherein moles of thiol per saccharide repeat unit of the activated saccharide is between 1-100%, such as, for example, between 2-80%, between 2-50%, between 3-30%, and between 4-25%. The degree of activation is at least 1%, 2%, 3%, 4%, 5%, 6%, 7%, 8%, 9%, 10%, 11%, 12%, 13%, 14%, 15%, 16%, 17%, 18%, 19%, ≥20%, ≥30%, ≥40%, ≥50%, ≥60%, ≥70%, ≥80%, or ≥90%, or about 100%. Preferably, the degree of activation is at most 50%, more preferably at most 25%. In one embodiment, the degree of activation is at most 20%. Any minimum value and any maximum value may be combined to define a range.

In one embodiment, the polysaccharide is activated with 1-cyano-4-dimethylamino pyridinium tetrafluoroborate (CDAP) to form a cyanate ester. The activated polysaccharide is then coupled directly or via a spacer (linker) group to an amino group on the carrier protein (preferably $CRM_{197}$ or tetanus toxoid).

For example, the spacer may be cystamine or cysteamine to give a thiolated polysaccharide which could be coupled to the carrier via a thioether linkage obtained after reaction with a maleimide-activated carrier protein (for example using N—[Y-maleimidobutyrloxy] succinimide ester (GMBS)) or a haloacetylated carrier protein (for example using iodoacetimide, N-succinimidyl bromoacetate (SBA; SIB), N-succinimidyl (4-iodoacetyl)aminobenzoate (SIAB), sulfosuccinimidyl (4-iodoacetyl)aminobenzoate (sulfo-SIAB), N-succinimidyl iodoacetate (SIA), or succinimidyl 3-[bromoacetamido] proprionate (SBAP)). In one embodiment, the cyanate ester (optionally made by CDAP chemistry) is coupled with hexane diamine or adipic acid dihydrazide (ADH) and the amino-derivatised saccharide is conjugated to the carrier protein (e.g., $CRM_{197}$) using carbodiimide (e.g., EDAC or EDC) chemistry via a carboxyl group on the protein carrier.

Other suitable techniques for conjugation use carbodiimides, hydrazides, active esters, norborane, p-nitrobenzoic acid, N-hydroxysuccinimide, S—NHS, EDC, TSTU. Conjugation may involve a carbonyl linker which may be formed by reaction of a free hydroxyl group of the saccharide with CDI followed by reaction with a protein to form a carbamate linkage. This may involve reduction of the anomeric terminus to a primary hydroxyl group, optional protection/deprotection of the primary hydroxyl group, reaction of the primary hydroxyl group with CDI to form a CDI carbamate intermediate and coupling the CDI carbamate intermediate with an amino group on a protein (CDI chemistry).

Molecular weight. In some embodiments, the glycoconjugate comprises a saccharide having a molecular weight of between 10 kDa and 2,000 kDa. In other embodiments, the saccharide has a molecular weight of between 50 kDa and 1,000 kDa. In other embodiments, the saccharide has a molecular weight of between 70 kDa and 900 kDa. In other embodiments, the saccharide has a molecular weight of between 100 kDa and 800 kDa. In other embodiments, the saccharide has a molecular weight of between 200 kDa and 600 kDa. In further embodiments, the saccharide has a molecular weight of 100 kDa to 1000 kDa; 100 kDa to 900 kDa; 100 kDa to 800 kDa; 100 kDa to 700 kDa; 100 kDa to 600 kDa; 100 kDa to 500 kDa; 100 kDa to 400 kDa; 100 kDa to 300 kDa; 150 kDa to 1,000 kDa; 150 kDa to 900 kDa; 150 kDa to 800 kDa; 150 kDa to 700 kDa; 150 kDa to 600 kDa; 150 kDa to 500 kDa; 150 kDa to 400 kDa; 150 kDa to 300 kDa; 200 kDa to 1,000 kDa; 200 kDa to 900 kDa; 200 kDa to 800 kDa; 200 kDa to 700 kDa; 200 kDa to 600 kDa; 200 kDa to 500 kDa; 200 kDa to 400 kDa; 200 kDa to 300; 250 kDa to 1,000 kDa; 250 kDa to 900 kDa; 250 kDa to 800 kDa; 250 kDa to 700 kDa; 250 kDa to 600 kDa; 250 kDa to 500 kDa; 250 kDa to 400 kDa; 250 kDa to 350 kDa; 300 kDa to 1,000 kDa; 300 kDa to 900 kDa; 300 kDa to 800 kDa; 300 kDa to 700 kDa; 300 kDa to 600 kDa; 300 kDa to 500 kDa; 300 kDa to 400 kDa; 400 kDa to 1,000 kDa; 400 kDa to 900 kDa; 400 kDa to 800 kDa; 400 kDa to 700 kDa; 400 kDa to 600 kDa; 500 kDa to 600 kDa. In one embodiment, the glycoconjugate having such a molecular weight is produced by single-end conjugation. In another embodiment, the glycoconjugate having such a molecular weight is produced by reductive amination chemistry (RAC) prepared in aqueous buffer. Any whole number integer within any of the above ranges is contemplated as an embodiment of the disclosure.

In some embodiments, the glycoconjugate of the invention has a molecular weight of between 400 kDa and 15,000 kDa; between 500 kDa and 10,000 kDa; between 2,000 kDa and 10,000 kDa; between 3,000 kDa and 8,000 kDa; or between 3,000 kDa and 5,000 kDa. In other embodiments, the glycoconjugate has a molecular weight of between 500 kDa and 10,000 kDa. In other embodiments, glycoconjugate has a molecular weight of between 1,000 kDa and 8,000 kDa. In still other embodiments, the glycoconjugate has a molecular weight of between 2,000 kDa and 8,000 kDa or between 3,000 kDa and 7,000 kDa. In further embodiments, the glycoconjugate of the invention has a molecular weight of between 200 kDa and 20,000 kDa; between 200 kDa and 15,000 kDa; between 200 kDa and 10,000 kDa; between 200 kDa and 7,500 kDa; between 200 kDa and 5,000 kDa; between 200 kDa and 3,000 kDa; between 200 kDa and 1,000 kDa; between 500 kDa and 20,000 kDa; between 500 kDa and 15,000 kDa; between 500 kDa and 12,500 kDa; between 500 kDa and 10,000 kDa; between 500 kDa and 7,500 kDa; between 500 kDa and 6,000 kDa; between 500 kDa and 5,000 kDa; between 500 kDa and 4,000 kDa; between 500 kDa and 3,000 kDa; between 500 kDa and 2,000 kDa; between 500 kDa and 1,500 kDa; between 500 kDa and 1,000 kDa; between 750 kDa and 20,000 kDa; between 750 kDa and 15,000 kDa; between 750 kDa and 12,500 kDa; between 750 kDa and 10,000 kDa; between 750 kDa and 7,500 kDa; between 750 kDa and 6,000 kDa; between 750 kDa and 5,000 kDa; between 750 kDa and 4,000 kDa; between 750 kDa and 3,000 kDa; between 750 kDa and 2,000 kDa; between 750 kDa and 1,500 kDa; between 1,000 kDa and 15,000 kDa; between 1,000 kDa and 12,500 kDa; between 1,000 kDa and 10,000 kDa; between 1,000 kDa and 7,500 kDa; between 1,000 kDa and 6,000 kDa; between 1,000 kDa and 5,000 kDa; between 1,000 kDa and 4,000 kDa; between 1,000 kDa and 2,500 kDa; between 2,000 kDa and 15,000 kDa; between 2,000 kDa and 12,500 kDa; between 2,000 kDa and 10,000 kDa; between 2,000 kDa and 7,500 kDa; between 2,000 kDa and 6,000 kDa; between 2,000 kDa and 5,000 kDa; between 2,000 kDa and 4,000 kDa; or between 2,000 kDa and 3,000 kDa. In one embodiment, the glycoconjugate having such a molecular weight is produced by eTEC conjugation described herein. In another embodiment, the glycoconjugate having such a molecular weight is produced by reductive amination chemistry (RAC). In another embodiment, the glycoconjugate having such a molecular weight is produced by reductive amination chemistry (RAC) prepared in DMSO.

In further embodiments, the glycoconjugate of the invention has a molecular weight of between 1,000 kDa and 20,000 kDa; between 1,000 kDa and 15,000 kDa; between 2,000 kDa and 10,000 kDa; between 2000 kDa and 7,500 kDa; between 2,000 kDa and 5,000 kDa; between 3,000 kDa and 20,000 kDa; between 3,000 kDa and 15,000 kDa; between 3,000 kDa and 12,500 kDa; between 4,000 kDa and 10,000 kDa; between 4,000 kDa and 7,500 kDa; between 4,000 kDa and 6,000 kDa; or between 5,000 kDa and 7,000 kDa. In one embodiment, the glycoconjugate having such a molecular weight is produced by reductive amination chemistry (RAC). In another embodiment, the glycoconjugate having such a molecular weight is produced by reductive amination chemistry (RAC) prepared in DMSO. In another embodiment, the glycoconjugate having such a molecular weight is produced by eTEC conjugation described herein.

In further embodiments, the glycoconjugate of the invention has a molecular weight of between 5,000 kDa and 20,000 kDa; between 5,000 kDa and 15,000 kDa; between 5,000 kDa and 10,000 kDa; between 5,000 kDa and 7,500 kDa; between 6,000 kDa and 20,000 kDa; between 6,000 kDa and 15,000 kDa; between 6,000 kDa and 12,500 kDa; between 6,000 kDa and 10,000 kDa or between 6,000 kDa and 7,500 kDa.

The molecular weight of the glycoconjugate may be measured by SEC-MALLS. Any whole number integer within any of the above ranges is contemplated as an embodiment of the disclosure. The glycoconjugates of the invention may also be characterized by the ratio (weight/weight) of saccharide to carrier protein. In some embodiments, the ratio of polysaccharide to carrier protein in the glycoconjugate (w/w) is between 0.5 and 3 (e.g., about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, or about 3.0). In other embodiments, the saccharide to carrier protein ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the saccharide to carrier protein ratio (w/w) is between 0.8 and 1.2. In a preferred embodiment, the ratio of polysaccharide to carrier protein in the conjugate is between 0.9 and 1.1. In some such embodiments, the carrier protein is $CRM_{197}$.

The glycoconjugates may also be characterized by their molecular size distribution ($K_d$). Size exclusion chromatography media (CL-4B) can be used to determine the relative molecular size distribution of the conjugate. Size Exclusion Chromatography (SEC) is used in gravity fed columns to profile the molecular size distribution of conjugates. Large molecules excluded from the pores in the media elute more quickly than small molecules. Fraction collectors are used to collect the column eluate. The fractions are tested colorimetrically by saccharide assay. For the determination of $K_d$, columns are calibrated to establish the fraction at which molecules are fully excluded ($V_0$), ($K_d=0$), and the fraction representing the maximum retention ($V_i$), ($K_d=1$). The fraction at which a specified sample attribute is reached ($V_e$), is related to Kd by the expression, $K_d=(V_e-V_o)/(V_i-V_0)$.

Free saccharide. The glycoconjugates and immunogenic compositions of the invention may include free saccharide that is not covalently conjugated to the carrier protein, but is nevertheless present in the glycoconjugate composition. The free saccharide may be non-covalently associated with (i.e., non-covalently bound to, adsorbed to, or entrapped in or with) the glycoconjugate. In a preferred embodiment, the glycoconjugate comprises at most 50%, 45%, 40%, 35%, 30%, 25%, 20% or 15% of free polysaccharide compared to the total amount of polysaccharide. In a preferred embodiment the glycoconjugate comprises less than about 25% of free polysaccharide compared to the total amount of polysaccharide. In a preferred embodiment the glycoconjugate comprises at most about 20% of free polysaccharide compared to the total amount of polysaccharide. In a preferred embodiment the glycoconjugate comprises at most about 15% of free polysaccharide compared to the total amount of polysaccharide. In another preferred embodiment, the glycoconjugate comprises at most about 20%, 19%, 18%, 17%, 16%, 15%, 14%, 13%, 12%, 11%, 10%, 9%, 8%, 7%, 6%, 5%, 4%, 3%, 2%, or 1% of free polysaccharide compared to the total amount of polysaccharide. In a preferred embodiment the glycoconjugate comprises less than about 8% of free polysaccharide compared to the total amount of polysaccharide. In a preferred embodiment the glycoconjugate comprises at most about 6% of free polysaccharide compared to the total amount of polysaccharide. In a preferred embodiment the glycoconjugate comprises at most about 5% of free polysaccharide compared to the total amount of polysaccharide. See, for example, Table 12, Table 13, Table 14, Table 15, Table 16, Table 17, and Table 18.

Covalent linkage. In other embodiments, the conjugate comprises at least one covalent linkage between the carrier protein and saccharide for every 5 to 10 saccharide repeat units; every 2 to 7 saccharide repeat units; every 3 to 8 saccharide repeat units; every 4 to 9 saccharide repeat units; every 6 to 11 saccharide repeat units; every 7 to 12 saccharide repeat units; every 8 to 13 saccharide repeat units; every 9 to 14 saccharide repeat units; every 10 to 15 saccharide repeat units; every 2 to 6 saccharide repeat units, every 3 to 7 saccharide repeat units; every 4 to 8 saccharide repeat units; every 6 to 10 saccharide repeat units; every 7 to 11 saccharide repeat units; every 8 to 12 saccharide repeat units; every 9 to 13 saccharide repeat units; every 10 to 14 saccharide repeat units; every 10 to 20 saccharide repeat units; every 4 to 25 saccharide repeat units or every 2 to 25 saccharide repeat units. In frequent embodiments, the carrier protein is $CRM_{197}$. In another embodiment, at least one linkage between carrier protein and saccharide occurs for every 2, 3, 4, 5, 6, 7, 8, 9, 10, 11, 12, 13, 14, 15, 16, 17, 18, 19, 20, 21, 22, 23, 24 or 25 saccharide repeat units of the polysaccharide. In one embodiment, the carrier protein is $CRM_{197}$. Any whole number integer within any of the above ranges is contemplated as an embodiment of the disclosure.

Lysine residues. Another way to characterize the glycoconjugates of the invention is by the number of lysine residues in the carrier protein (e.g., $CRM_{197}$) that become conjugated to the saccharide which can be characterized as a range of conjugated lysines (degree of conjugation). The evidence for lysine modification of the carrier protein, due to covalent linkages to the polysaccharides, can be obtained by amino acid analysis using routine methods known to those of skill in the art. Conjugation results in a reduction in the number of lysine residues recovered, compared to the carrier protein starting material used to generate the conjugate materials. In a preferred embodiment, the degree of conjugation of the glycoconjugate of the invention is between 2 and 15, between 2 and 13, between 2 and 10, between 2 and 8, between 2 and 6, between 2 and 5, between 2 and 4, between 3 and 15, between 3 and 13, between 3 and 10, between 3 and 8, between 3 and 6, between 3 and 5, between 3 and 4, between 5 and 15, between 5 and 10, between 8 and 15, between 8 and 12, between 10 and 15 or between 10 and 12. In one embodiment, the degree of conjugation of the glycoconjugate of the invention is about 2, about 3, about 4, about 5, about 6, about 7, about 8, about 9, about 10, about 11, about 12, about 13, about 14 or about 15. In a preferred embodiment, the degree of conjugation of the glycoconjugate of the invention is between 4 and 7. In some such embodiments, the carrier protein is $CRM_{197}$.

The frequency of attachment of the saccharide chain to a lysine on the carrier protein is another parameter for characterizing the glycoconjugates of the invention. For example, in some embodiments, at least one covalent linkage between the carrier protein and the polysaccharide for every 4 saccharide repeat units of the polysaccharide. In another embodiment, the covalent linkage between the carrier protein and the polysaccharide occurs at least once in every 10 saccharide repeat units of the polysaccharide. In another embodiment, the covalent linkage between the carrier protein and the polysaccharide occurs at least once in every 15 saccharide repeat units of the polysaccharide. In a further embodiment, the covalent linkage between the carrier protein and the polysaccharide occurs at least once in every 25 saccharide repeat units of the polysaccharide.

O-acetylation. In some embodiments, the saccharides of the invention are O-acetylated. In some embodiments, the glycoconjugate comprises a saccharide which has a degree of O-acetylation of between 10-100%, between 20-100%, between 30-100%, between 40-100%, between 50-100%, between 60-100%, between 70-100%, between 75-100%, 80-100%, 90-100%, 50-90%, 60-90%, 70-90% or 80-90%. In other embodiments, the degree of O-acetylation is ≥10%, ≥20%, ≥30%, ≥40%, ≥ 50%, ≥60%, ≥70%, ≥80%, or >90%, or about 100%. By % of O-acetylation it is meant the percentage of a given saccharide relative to 100% (where each repeat unit is fully acetylated relative to its acetylated structure).

In some embodiments, the glycoconjugate is prepared by reductive amination. In some embodiments, the glycoconjugate is a single-end-linked conjugated saccharide, wherein the saccharide is covalently bound to a carrier protein directly. In some embodiments, the glycoconjugate is covalently bound to a carrier protein through a (2-((2-oxoethyl)thio)ethyl) carbamate (eTEC) spacer.

REDUCTIVE AMINATION. In one embodiment, the saccharide is conjugated to the carrier protein by reductive amination (such as described in U.S. Patent Appl. Pub. Nos. 2006/0228380, 2007/0231340, 2007/0184071 and 2007/0184072, WO 2006/110381, WO 2008/079653, and WO 2008/143709).

Reductive amination includes (1) oxidation of the saccharide, (2) reduction of the activated saccharide and a carrier protein to form a conjugate. Before oxidation, the saccharide is optionally hydrolyzed. Mechanical or chemical hydrolysis may be employed. Chemical hydrolysis may be conducted using acetic acid.

The oxidation step may involve reaction with periodate. The term "periodate" as used herein refers to both periodate and periodic acid. The term also includes both metaperiodate ($IO_4^-$) and orthoperiodate ($IO_6^{5-}$) and the various salts of periodate (e.g., sodium periodate and potassium periodate). In one embodiment the polysaccharide is oxidized in the presence of metaperiodate, preferably in the presence of sodium periodate ($NaIO_4$). In another embodiment the polysaccharide is oxidized in the presence of orthoperiodate, preferably in the presence of periodic acid.

In one embodiment, the oxidizing agent is a stable nitroxyl or nitroxide radical compound, such as piperidine-N-oxy or pyrrolidine-N-oxy compounds, in the presence of an oxidant to selectively oxidize primary hydroxyls. In said reaction, the actual oxidant is the N-oxoammonium salt, in a catalytic cycle. In an aspect, said stable nitroxyl or nitroxide radical compound are piperidine-N-oxy or pyrrolidine-N-oxy compounds. In an aspect, said stable nitroxyl or nitroxide radical compound bears a TEMPO (2,2,6,6-tetramethyl-1-piperidinyloxy) or a PROXYL (2,2,5,5-tetramethyl-1-pyrrolidinyloxy) moiety. In an aspect, said stable nitroxyl radical compound is TEMPO or a derivative thereof. In an aspect, said oxidant is a molecule bearing a N-halo moiety. In an aspect, said oxidant is selected from any one of N-ChloroSuccinimide, N-Bromosuccinimide, N-Iodosuccinimide, Dichloroisocyanuric acid, 1,3,5-trichloro-1,3,5-triazinane-2,4,6-trione, Dibromoisocyanuric acid, 1,3,5-tribromo-1,3,5-triazinane-2,4,6-trione, Diiodoisocyanuric acid and 1,3,5-triiodo-1,3,5-triazinane-2,4,6-trione. Preferably said oxidant is N-Chlorosuccinimide.

Following the oxidation step of the saccharide, the saccharide is said to be activated and is referred to as "activated" herein below. The activated saccharide and the carrier protein may be lyophilised (freeze-dried), either independently (discrete lyophilization) or together (co-lyophilized). In one embodiment the activated saccharide and the carrier protein are co-lyophilized. In another embodiment the activated polysaccharide and the carrier protein are lyophilized independently.

In one embodiment the lyophilization takes place in the presence of a non-reducing sugar, possible non-reducing sugars include sucrose, trehalose, raffinose, stachyose, melezitose, dextran, mannitol, lactitol and palatinit.

The next step of the conjugation process is the reduction of the activated saccharide and a carrier protein to form a conjugate (so-called reductive amination), using a reducing agent. Suitable reducing agents include the cyanoborohydrides, such as sodium cyanoborohydride, sodium triacetoxyborohydride or sodium or zinc borohydride in the presence of Bronsted or Lewis acids), amine boranes such as pyridine borane, 2-Picoline Borane, 2,6-diborane-methanol, dimethylamine-borane, t-BuMe'PrN—BH3, benzylamine-BH3 or 5-ethyl-2-methylpyridine borane (PEMB), borane-pyridine, or borohydride exchange resin. In one embodiment the reducing agent is sodium cyanoborohydride.

In an embodiment, the reduction reaction is carried out in aqueous solvent (e.g., selected from PBS, MES, HEPES, Bis-tris, ADA, PIPES, MOPSO, BES, MOPS, DIPSO, MOBS, HEPPSO, POPSO, TEA, EPPS, Bicine or HEPB, at a pH between 6.0 and 8.5, 7.0 and 8.0, or 7.0 and 7.5), in another embodiment the reaction is carried out in aprotic solvent. In an embodiment, the reduction reaction is carried out in DMSO (dimethylsulfoxide) or in DMF (dimethylformamide) solvent. The DMSO or DMF solvent may be used to reconstitute the activated polysaccharide and carrier protein which has been lyophilized.

At the end of the reduction reaction, there may be unreacted aldehyde groups remaining in the conjugates, these may be capped using a suitable capping agent. In one embodiment this capping agent is sodium borohydride ($NaBH_4$). Following the conjugation (the reduction reaction and optionally the capping), the glycoconjugates may be purified (enriched with respect to the amount of polysaccharide-protein conjugate) by a variety of techniques known to the skilled person. These techniques include dialysis, concentration/diafiltration operations, tangential flow filtration precipitation/elution, column chromatography (DEAE or hydrophobic interaction chromatography), and depth filtration. The glycoconjugates maybe purified by diafiltration and/or ion exchange chromatography and/or size exclusion chromatography. In an embodiment, the glycoconjugates are purified by diafiltration or ion exchange chromatography or size exclusion chromatography. In one embodiment the glycoconjugates are sterile filtered. In a preferred embodiment, a glycoconjugate from an *E. coli* serotype is selected from any one of O25B, O1, O2, and O6 is prepared by reductive amination. In a preferred embodiment, the glycoconjugates from *E. coli* serotypes O25B, O1, O2, and O6 are prepared by reductive amination.

In one aspect, the invention relates to a conjugate that includes a carrier protein, e.g., $CRM_{197}$, linked to a saccharide of Formula O25B, presented by

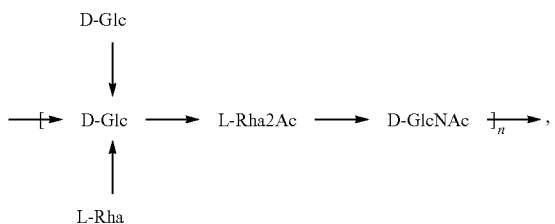

wherein n is any integer greater than or equal to 1. In a preferred embodiment, n is an integer of at least 31, 32, 33, 34, 35, 36, 37, 38, 39, 40, and at most 200, 100, 99, 98, 97, 96, 95, 94, 93, 92, 91, 90, 89, 88, 87, 86, 81, 80, 79, 78, 77, 76, 75, 74, 73, 72, 71, 70, 69, 68, 67, 66, 65, 60, 59, 58, 57, 56, 55, 54, 53, 52, 51, or 50. Any minimum value and any maximum value may be combined to define a range. Exemplary ranges include, for example, at least 1 to at most 1000; at least 10 to at most 500; and at least 20 to at most 80. In one preferred embodiment, n is at least 31 to at most 90, more preferably 40 to 90, most preferably 60 to 85.

In another aspect, the invention relates to a conjugate that includes a carrier protein, e.g., $CRM_{197}$, linked to a saccharide having any one of the following structures shown in Table 1 (see also FIGS. 9A-C and FIGS. 10A-B), wherein n is an integer greater than or equal to 1. Without being bound by theory or mechanism, in some embodiments, a stable conjugate is believed to require a level of saccharide antigen modification that is balanced against preserving the structural integrity of the critical immunogenic epitopes of the antigen.

Activation and formation of an Aldehyde. In some embodiments, the saccharide of the invention is activated and results in the formation of an aldehyde. In such embodiments wherein the saccharide is activated, the percentage (%) of activation (or degree of oxidation (DO)) refers to moles of a saccharide repeat unit per moles of aldehyde of the activated polysaccharide. For example, in some embodiments, the saccharide is activated by periodate oxidation of vicinal diols on a repeat unit of the polysaccharide, resulting in the formation of an aldehyde. Varying the molar equivalents (meq) of sodium periodate relative to the saccharide repeat unit and temperature during oxidation results in varying levels of degree of oxidation (DO).

The saccharide and aldehyde concentrations are typically determined by colorimetric assays. An alternative reagent is TEMPO (2,2,6,6-tetramethylpiperidine 1-oxyl radical)-N-chlorosuccinimide (NCS) combination, which results in the formation of aldehydes from primary alcohol groups.

In some embodiments, the activated saccharide has a degree of oxidation wherein the moles of a saccharide repeat unit per moles of aldehyde of the activated saccharide is between 1-100, such as, for example, between 2-80, between 2-50, between 3-30, and between 4-25. The degree of activation is at least 1, 2, 3, 4, 5, 6, 7, 8, 9, 10, 11, 12, 13, 14, 15, 16, 17, 18, 19, ≥20, ≥30, ≥40, ≥50, ≥60, ≥70, ≥80, or ≥90, or about 100. Preferably, the degree of oxidation (DO) is at least 5 and at most 50, more preferably at least 10 and at most 25. In one embodiment, the degree of activation is at least 10 and at most 25. Any minimum value and any maximum value may be combined to define a range. A degree of oxidation value may be represented as percentage (%) of activation. For example, in one embodiment, a DO value of 10 refers to one activated saccharide repeat unit out of a total of 10 saccharide repeat units in the activated saccharide, in which case the DO value of 10 may be represented as 10% activation.

In some embodiments, the conjugate prepared by reductive amination chemistry includes a carrier protein and a saccharide, wherein the saccharide includes a structure selected from any one of Formula O1 (e.g., Formula O1A, Formula O1B, and Formula O1C), Formula O2, Formula O3, Formula O4 (e.g., Formula O4: K52 and Formula O4: K6), Formula O5 (e.g., Formula O5ab and Formula O5ac (strain 180/C3)), Formula O6 (e.g., Formula O6: K2; K13; K15 and Formula O6: K54), Formula O7, Formula O8, Formula O9, Formula O10, Formula O11, Formula O12, Formula O13, Formula O14, Formula O15, Formula O16, Formula O17, Formula O18 (e.g., Formula O18A, Formula O18ac, Formula O18A1, Formula O18B, and Formula O18B1), Formula O19, Formula O20, Formula O21, Formula O22, Formula O23 (e.g., Formula O23A), Formula O24, Formula O25 (e.g., Formula O25a and Formula O25b), Formula O26, Formula O27, Formula O28, Formula O29, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45 (e.g., Formula O45 and Formula O45rel), Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula $62D_1$, Formula O63, Formula O64, Formula O65, Formula O66, Formula O68, Formula O69, Formula O70, Formula O71, Formula O73 (e.g., Formula O73 (strain 73-1)), Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144, Formula O145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, and Formula O187. In some embodiments, the saccharide in the conjugate includes a Formula, wherein n is an integer from 1 to 1000, from 5 to 1000, preferably 31 to 100, more preferably 35 to 90, most preferably 35 to 65.

SINGLE-END LINKED CONJUGATES. In some embodiments, the conjugate is single-end-linked conjugated saccharide, wherein the saccharide is covalently bound at one end of the saccharide to a carrier protein. In some embodiments, the single-end-linked conjugated polysaccharide has a terminal saccharide. For example, a conjugate is single-end linked if one of the ends (a terminal saccharide residue) of the polysaccharide is covalently bound to a carrier protein. In some embodiments, the conjugate is single-end linked if a terminal saccharide residue of the polysaccharide is covalently bound to a carrier protein through a linker. Such linkers may include, for example, a cystamine linker (A1), a 3,3'-dithio bis(propanoic dihydrazide) linker (A4), and a 2,2'-dithio-N,N'-bis(ethane-2,1-diyl) bis(2-(aminooxy) acetamide) linker (A6).

In some embodiments, the saccharide is conjugated to the carrier protein through a 3-deoxy-d-manno-oct-2-ulosonic acid (KDO) residue to form a single-end linked conjugate. See, for example, Example 18, Example 19, Example 20, and FIG. 24.

In some embodiments, the conjugate is preferably not a bioconjugate. The term "bioconjugate" refers to a conjugate between a protein (e.g., a carrier protein) and an antigen, e.g., an O antigen (e.g., O25B) prepared in a host cell background, wherein host cell machinery links the antigen to the protein (e.g., N-links). Glycoconjugates include bioconjugates, as well as sugar antigen (e.g., oligo- and polysaccharides)-protein conjugates prepared by means that do not require preparation of the conjugate in a host cell, e.g., conjugation by chemical linkage of the protein and saccharide.

Thiol Activated Saccharides. In some embodiments, the saccharide of the invention is thiol activated. In such embodiments wherein the saccharide is thiol activated, the percentage (%) of activation refers to moles of thiol per saccharide repeat unit of the activated polysaccharide. The saccharide and thiol concentrations are typically determined by Ellman's assay for quantitation of sulfhydryls. For example, in some embodiments, the saccharide includes activation of 2-Keto-3-deoxyoctanoic acid (KDO) with a disulfide amine linker. See, for example, Example 18 and FIG. 24. In some embodiments, the saccharide is covalently bound to a carrier protein through a bivalent, heterobifunctional linker (also referred to herein as a "spacer"). The linker preferably provides a thioether bond between the saccharide and the carrier protein, resulting in a glycoconjugate referred to herein as a "thioether glycoconjugate." In some embodiments, the linker further provides carbamate and amide bonds, such as, for example, (2-((2-oxoethyl) thio)ethyl) carbamate (eTEC). See, for example, Example 13.

In some embodiments, the single-end linked conjugate includes a carrier protein and a saccharide, wherein the saccharide includes a structure selected from any one of Formula O1 (e.g., Formula O1A, Formula O1B, and Formula O1C), Formula O2, Formula O3, Formula O4 (e.g., Formula O4: K52 and Formula O4: K6), Formula O5 (e.g., Formula O5ab and Formula O5ac (strain 180/C3)), Formula O6 (e.g., Formula O6: K2; K13; K15 and Formula O6: K54), Formula O7, Formula O8, Formula O9, Formula O10, Formula O11, Formula O12, Formula O13, Formula O14, Formula O15, Formula O16, Formula O17, Formula O18 (e.g., Formula O18A, Formula O18ac, Formula O18A1, Formula O18B, and Formula O18B1), Formula O19, Formula O20, Formula O21, Formula O22, Formula O23 (e.g., Formula O23A), Formula O24, Formula O25 (e.g., Formula O25a and Formula O25b), Formula O26, Formula O27, Formula O28, Formula O29, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45 (e.g., Formula O45 and Formula O45rel), Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula 62D$_1$, Formula O63, Formula O64, Formula O65, Formula O66, Formula O68, Formula O69, Formula O70, Formula O71, Formula O73 (e.g., Formula O73 (strain 73-1)), Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144, Formula O145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, and Formula O187. In some embodiments, the saccharide in the conjugate includes a Formula, wherein n is an integer from 1 to 1000, from 5 to 1000, preferably 31 to 100, more preferably 35 to 90, most preferably 35 to 65.

For example, in one embodiment, the single-end linked conjugate includes a carrier protein and a saccharide having a structure selected from Formula O8, Formula O9a, Formula O9, Formula O20ab, Formula O20ac, Formula O52, Formula O97, and Formula O101, wherein n is an integer from 1 to 10 eTEC Conjugates

In one aspect, the invention relates generally to glycoconjugates comprising a saccharide derived from *E. coli* described above covalently conjugated to a carrier protein through a (2-((2-oxoethyl)thio)ethyl) carbamate (eTEC)

spacer (as described, for example, in U.S. Pat. No. 9,517,274 and International Patent Application Publication WO2014027302, incorporated by reference herein in their entireties), including immunogenic compositions comprising such glycoconjugates, and methods for the preparation and use of such glycoconjugates and immunogenic compositions. Said glycoconjugates comprise a saccharide covalently conjugated to a carrier protein through one or more eTEC spacers, wherein the saccharide is covalently conjugated to the eTEC spacer through a carbamate linkage, and wherein the carrier protein is covalently conjugated to the eTEC spacer through an amide linkage. The eTEC spacer includes seven linear atoms (i.e., —C(O)NH(CH$_2$)$_2$SCH$_2$C(O)—) and provides stable thioether and amide bonds between the saccharide and carrier protein.

Figure 26:
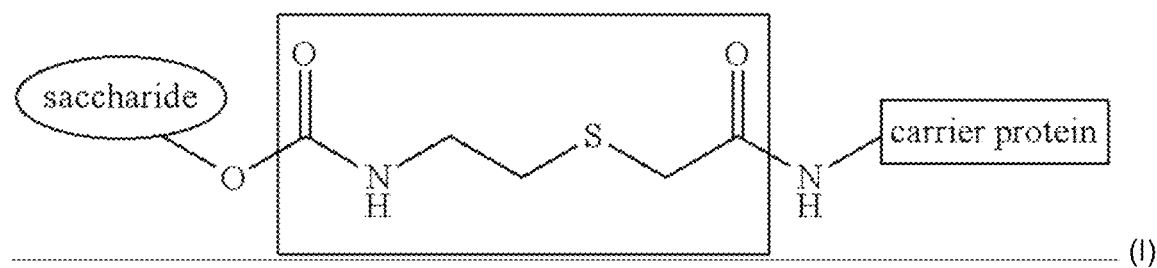
FIG. 26 depicts general formula (I) of an exemplary eTEC linked glycoconjugate of the invention, wherein the atoms that comprise the eTEC spacer are contained in the central box.

The eTEC linked glycoconjugates of the invention may be represented by the general formula (I), as shown in FIG. 26, where the atoms that comprise the eTEC spacer are contained in the central box.

In said glycoconjugates of the invention, the saccharide may be a polysaccharide or an oligosaccharide.

The carrier proteins incorporated into the glycoconjugates of the invention are selected from the group of carrier proteins generally suitable for such purposes, as further described herein or known to those of skill in the art. In particular embodiments, the carrier protein is CRM$_{197}$.

In another aspect, the invention provides a method of making a glycoconjugate comprising a saccharide described herein conjugated to a carrier protein through an eTEC spacer, comprising the steps of a) reacting a saccharide with a carbonic acid derivative in an organic solvent to produce an activated saccharide; b) reacting the activated saccharide with cystamine or cysteamine or a salt thereof, to produce a thiolated saccharide; c) reacting the thiolated saccharide with a reducing agent to produce an activated thiolated saccharide comprising one or more free sulfhydryl residues; d) reacting the activated thiolated saccharide with an activated carrier protein comprising one or more α-haloacetamide groups, to produce a thiolated saccharide-carrier protein conjugate; and e) reacting the thiolated saccharide-carrier protein conjugate with (i) a first capping reagent capable of capping unconjugated α-haloacetamide groups of the activated carrier protein; and/or (ii) a second capping reagent capable of capping unconjugated free sulfhydryl residues of the activated thiolated saccharide; whereby an eTEC linked glycoconjugate is produced.

In frequent embodiments, the carbonic acid derivative is 1,1'-carbonyl-di-(1,2,4-triazole) (CDT) or 1,1'-carbonyl-diimidazole (CDI). Preferably, the carbonic acid derivative is CDT and the organic solvent is a polar aprotic solvent, such as dimethylsulfoxide (DMSO). In preferred embodiments, the thiolated saccharide is produced by reaction of the activated saccharide with the bifunctional symmetric thioalkylamine reagent, cystamine or a salt thereof. Alternatively, the thiolated saccharide may be formed by reaction of the activated saccharide with cysteamine or a salt thereof. The eTEC linked glycoconjugates produced by the methods of the invention may be represented by general Formula (I).

In frequent embodiments, the first capping reagent is N-acetyl-L-cysteine, which reacts with unconjugated α-haloacetamide groups on lysine residues of the carrier protein to form an S-carboxymethylcysteine (CMC) residue covalently linked to the activated lysine residue through a thioether linkage.

In other embodiments, the second capping reagent is iodoacetamide (IAA), which reacts with unconjugated free sulfhydryl groups of the activated thiolated saccharide to provide a capped thioacetamide. Frequently, step e) comprises capping with both a first capping reagent and a second capping reagent. In certain embodiments, step e) comprises capping with N-acetyl-L-cysteine as the first capping reagent and IAA as the second capping reagent.

In some embodiments, the capping step e) further comprises reaction with a reducing agent, for example, DTT, TCEP, or mercaptoethanol, after reaction with the first and/or second capping reagent.

The eTEC linked glycoconjugates and immunogenic compositions of the invention may include free sulfhydryl residues. In some instances, the activated thiolated saccharides formed by the methods provided herein will include multiple free sulfhydryl residues, some of which may not undergo covalent conjugation to the carrier protein during the conjugation step. Such residual free sulfhydryl residues are capped by reaction with a athiol-reactive capping reagent, for example, iodoacetamide (IAA), to cap the potentially reactive functionality. Other thiol-reactive capping reagents, e.g., maleimide containing reagents and the like are also contemplated.

In addition, the eTEC linked glycoconjugates and immunogenic compositions of the invention may include residual unconjugated carrier protein, which may include activated carrier protein which has undergone modification during the capping process steps.

In some embodiments, step d) further comprises providing an activated carrier protein comprising one or more α-haloacetamide groups prior to reacting the activated thiolated saccharide with the activated carrier protein. In frequent embodiments, the activated carrier protein comprises one or more α-bromoacetamide groups.

In another aspect, the invention provides an eTEC linked glycoconjugate comprising a saccharide described herein conjugated to a carrier protein through an eTEC spacer produced according to any of the methods disclosed herein.

In some embodiments, the carrier protein is CRM$_{197}$ and the covalent linkage via an eTEC spacer between the CRM$_{197}$ and the polysaccharide occurs at least once in every 4, 10, 15 or 25 saccharide repeat units of the polysaccharide.

For each of the aspects of the invention, in particular embodiments of the methods and compositions described herein, the eTEC linked glycoconjugate comprises a saccharide described herein, such as, a saccharide derived from *E. coli*.

In another aspect, the invention provides a method of preventing, treating or ameliorating a bacterial infection, disease or condition in a subject, comprising administering to the subject an immunologically effective amount of an immunogenic composition of the invention, wherein said immunogenic composition comprises an eTEC linked glycoconjugate comprising a saccharide described herein. In some embodiments, the saccharide is derived from *E. coli*.

In some embodiments, the eTEC linked glycoconjugate comprises a carrier protein and a saccharide, in which said saccharide comprises a structure selected from any one of Formula O1 (e.g., Formula O1A, Formula O1B, and Formula O1C), Formula O2, Formula O3, Formula O4 (e.g., Formula O4: K52 and Formula O4: K6), Formula O5 (e.g., Formula O5ab and Formula O5ac (strain 180/C3)), Formula O6 (e.g., Formula O6: K2; K13; K15 and Formula O6: K54), Formula O7, Formula O8, Formula O9, Formula O10, Formula O11, Formula O12, Formula O13, Formula O14, Formula O15, Formula O16, Formula O17, Formula O18 (e.g., Formula O18A, Formula O18ac, Formula O18A1, Formula O18B, and Formula O18B1), Formula O19, Formula O20, Formula O21, Formula O22, Formula O23 (e.g., Formula O23A), Formula O24, Formula O25 (e.g., Formula O25a and Formula O25b), Formula O26, Formula O27, Formula O28, Formula O29, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45 (e.g., Formula O45 and Formula O45rel), Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula 62D$_1$, Formula O63, Formula O64, Formula O65, Formula O66, Formula O68, Formula O69, Formula O70, Formula O71, Formula O73 (e.g., Formula O73 (strain 73-1)), Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144, Formula O145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, and Formula O187. In some embodiments, the saccharide in the conjugate includes a Formula, wherein n is an integer from 1 to 1000, from 5 to 1000, preferably 31 to 100, more preferably 35 to 90, most preferably 35 to 65.

The number of lysine residues in the carrier protein that become conjugated to the saccharide can be characterized as a range of conjugated lysines. For example, in some embodiments of the immunogenic compositions, the CRM$_{197}$ may comprise 4 to 16 lysine residues out of 39 covalently linked to the saccharide. Another way to express this parameter is that about 10% to about 41% of CRM$_{197}$ lysines are covalently linked to the saccharide. In other embodiments, the CRM$_{197}$ may comprise 2 to 20 lysine residues out of 39 covalently linked to the saccharide. Another way to express this parameter is that about 5% to about 50% of CRM$_{197}$ lysines are covalently linked to the saccharide.

In frequent embodiments, the carrier protein is CRM$_{197}$ and the covalent linkage via an eTEC spacer between the CRM$_{197}$ and the polysaccharide occurs at least once in every 4, 10, 15 or 25 saccharide repeat units of the polysaccharide.

In other embodiments, the conjugate comprises at least one covalent linkage between the carrier protein and saccharide for every 5 to 10 saccharide repeat units; every 2 to 7 saccharide repeat units; every 3 to 8 saccharide repeat units; every 4 to 9 saccharide repeat units; every 6 to 11 saccharide repeat units; every 7 to 12 saccharide repeat units; every 8 to 13 saccharide repeat units; every 9 to 14 saccharide repeat units; every 10 to 15 saccharide repeat units; every 2 to 6 saccharide repeat units, every 3 to 7 saccharide repeat units; every 4 to 8 saccharide repeat units; every 6 to 10 saccharide repeat units; every 7 to 11 saccharide repeat units; every 8 to 12 saccharide repeat units; every 9 to 13 saccharide repeat units; every 10 to 14 saccharide repeat units; every 10 to 20 saccharide repeat units; or every 4 to 25 saccharide repeat units.

In another embodiment, at least one linkage between carrier protein and saccharide occurs for every 2, 3, 4, 5, 6, 7, 8, 9, 10, 11, 12, 13, 14, 15, 16, 17, 18, 19, 20, 21, 22, 23, 24 or 25 saccharide repeat units of the polysaccharide.

Carrier Proteins

A component of the glycoconjugate of the invention is a carrier protein to which the saccharide is conjugated. The terms "protein carrier" or "carrier protein" or "carrier" may be used interchangeably herein. Carrier proteins should be amendable to standard conjugation procedures.

One component of the conjugate is a carrier protein to which the O-polysaccharide is conjugated. In one embodiment, the conjugate includes a carrier protein conjugated to the core oligosaccharide of the O-polysaccharide (see FIG. 17). In one embodiment, the conjugate includes a carrier protein conjugated to the O-antigen of the O-polysaccharide.

The terms "protein carrier" or "carrier protein" or "carrier" may be used interchangeably herein. Carrier proteins should be amendable to standard conjugation procedures.

In a preferred embodiment, the carrier protein of the conjugates is independently selected from any one of TT, DT, DT mutants (such as CRM$_{197}$), H. influenzae protein D, PhtX, PhtD, PhtDE fusions (particularly those described in WO 01/98334 and WO 03/54007), detoxified pneumolysin, PorB, N19 protein, PspA, OMPC, toxin A or B of C. Difficile and PsaA. In an embodiment, the carrier protein of the conjugates of the invention is DT (Diphtheria toxoid). In another embodiment, the carrier protein of the conjugates of the invention is TT (tetanus toxoid). In another embodiment, the carrier protein of the conjugates of the invention is PD (Haemophilus influenzae protein D-see, e.g., EP 0 594 610 B).

In a preferred embodiment, the saccharides are conjugated to CRM$_{197}$ protein. The CRM$_{197}$ protein is a nontoxic form of diphtheria toxin but is immunologically indistinguishable from the diphtheria toxin. CRM$_{197}$ is produced by C. diphtheriae infected by the nontoxigenic phage β197tox created by nitrosoguanidine mutagenesis of the toxigenic corynephage beta. The CRM$_{197}$ protein has the same molecular weight as the diphtheria toxin but differs therefrom by a single base change (guanine to adenine) in the structural gene. This single base change causes an amino acid substitution glutamic acid for glycine) in the mature protein and eliminates the toxic properties of diphtheria toxin. The CRM$_{197}$ protein is a safe and effective T-cell dependent carrier for saccharides.

Accordingly, in some embodiments, the conjugates of the invention include CRM$_{197}$ as the carrier protein, wherein the saccharide is covalently linked to CRM$_{197}$.

In a preferred embodiment, the carrier protein of the glycoconjugates is selected in the group consisting of DT (Diphtheria toxin), TT (tetanus toxoid) or fragment C of TT, CRM$_{197}$ (a nontoxic but antigenically identical variant of diphtheria toxin), other DT mutants (such as CRM$_{176}$, CRM228, CRM 45 (Uchida et al J. Biol. Chem. 218;

3838-3844, 1973), CRM9, CRM45, CRM102, CRM103 or CRM107; and other mutations described by Nicholls and Youle in Genetically Engineered Toxins, Ed: Frankel, Maecel Dekker Inc, 1992; deletion or mutation of Glu-148 to Asp, Gln or Ser and/or Ala 158 to Gly and other mutations disclosed in U.S. Pat. No. 4,709,017 or U.S. Pat. No. 4,950,740; mutation of at least one or more residues Lys 516, Lys 526, Phe 530 and/or Lys 534 and other mutations disclosed in U.S. Pat. No. 5,917,017 or U.S. Pat. No. 6,455,673; or fragment disclosed in U.S. Pat. No. 5,843, 711), pneumococcal pneumolysin (Kuo et al (1995) Infect Immun 63; 2706-13) including ply detoxified in some fashion for example dPLY-GMBS (WO 04081515, PCT/EP2005/010258) or dPLY-formol, PhtX, including PhtA, PhtB, PhtD, PhtE (sequences of PhtA, PhtB, PhtD or PhtE are disclosed in WO 00/37105 or WO 00/39299) and fusions of Pht proteins for example PhtDE fusions, PhtBE fusions, Pht A-E (WO 01/98334, WO 03/54007, WO2009/000826), OMPC (meningococcal outer membrane protein-usually extracted from *N. meningitidis* serogroup B-EP0372501), PorB (from *N. meningitidis*), PD (*Haemophilus influenzae* protein D-see, e.g., EP 0 594 610 B), or immunologically functional equivalents thereof, synthetic peptides (EP0378881, EP0427347), heat shock proteins (WO 93/17712, WO 94/03208), pertussis proteins (WO 98/58668, EP0471177), cytokines, lymphokines, growth factors or hormones (WO 91/01146), artificial proteins comprising multiple human CD4+ T cell epitopes from various pathogen derived antigens (Falugi et al (2001) Eur J Immunol 31; 3816-3824) such as N19 protein (Baraldoi et al (2004) Infect Immun 72; 4884-7) pneumococcal surface protein PspA (WO 02/091998), iron uptake proteins (WO 01/72337), toxin A or B of *C. difficile* (WO 00/61761), transferrin binding proteins, pneumococcal adhesion protein (PsaA), recombinant *Pseudomonas aeruginosa* exotoxin A (in particular non-toxic mutants thereof (such as exotoxin A bearing a substitution at glutamic acid 553 (Uchida Cameron D M, RJ Collier. 1987. J. Bacteriol. 169:4967-4971)). Other proteins, such as ovalbumin, keyhole limpet hemocyanin (KLH), bovine serum albumin (BSA) or purified protein derivative of tuberculin (PPD) also can be used as carrier proteins. Other suitable carrier proteins include inactivated bacterial toxins such as cholera toxoid (e.g., as described in Int'l Patent Application No. WO 2004/083251), *E. coli* LT, *E. coli* ST, and exotoxin A from *Pseudomonas aeruginosa*.

In some embodiments, the carrier protein is selected from any one of, for example, $CRM_{197}$, diphtheria toxin fragment B (DTFB), DTFB C8, Diphtheria toxoid (DT), tetanus toxoid (TT), fragment C of TT, pertussis toxoid, cholera toxoid, or exotoxin A from *Pseudomonas aeruginosa*; detoxified Exotoxin A of *P. aeruginosa* (EPA), maltose binding protein (MBP), flagellin, detoxified hemolysin A of *S. aureus*, clumping factor A, clumping factor B, Cholera toxin B subunit (CTB), *Streptococcus pneumoniae* Pneumolysin and detoxified variants thereof, *C. jejuni* AcrA, and *C. jejuni* natural glycoproteins. In one embodiment, the carrier protein is detoxified *Pseudomonas* exotoxin (EPA). In another embodiment, the carrier protein is not detoxified *Pseudomonas* exotoxin (EPA). In one embodiment, the carrier protein is flagellin. In another embodiment, the carrier protein is not flagellin.

In a preferred embodiment, the carrier protein of the glycoconjugates is independently selected from the group consisting of TT, DT, DT mutants (such as $CRM_{197}$), *H. influenzae* protein D, PhtX, PhtD, PhtDE fusions (particularly those described in WO 01/98334 and WO 03/54007), detoxified pneumolysin, PorB, N19 protein, PspA, OMPC, toxin A or B of *C. Difficile* and PsaA. In an embodiment, the carrier protein of the glycoconjugates of the invention is DT (Diphtheria toxoid). In another embodiment, the carrier protein of the glycoconjugates of the invention is TT (tetanus toxoid). In another embodiment, the carrier protein of the glycoconjugates of the invention is PD (*Haemophilus influenzae* protein D-see, e.g., EP 0 594 610 B).

In a preferred embodiment, the capsular saccharides of the invention are conjugated to $CRM_{197}$ protein. The $CRM_{197}$ protein is a nontoxic form of diphtheria toxin but is immunologically indistinguishable from the diphtheria toxin. $CRM_{197}$ is produced by *C. diphtheriae* infected by the nontoxigenic phage β197tox-created by nitrosoguanidine mutagenesis of the toxigenic corynephage beta (Uchida, T. et al. 1971, Nature New Biology 233:8-11). The $CRM_{197}$ protein has the same molecular weight as the diphtheria toxin but differs therefrom by a single base change (guanine to adenine) in the structural gene. This single base change causes an amino acid substitution glutamic acid for glycine) in the mature protein and eliminates the toxic properties of diphtheria toxin. The $CRM_{197}$ protein is a safe and effective T-cell dependent carrier for saccharides. Further details about $CRM_{197}$ and production thereof can be found e.g. in U.S. Pat. No. 5,614,382

Accordingly, in frequent embodiments, the glycoconjugates of the invention comprise $CRM_{197}$ as the carrier protein, wherein the capsular polysaccharide is covalently linked to $CRM_{197}$.

Composition and Vaccine

The inventors further discovered compositions including at least one saccharide described above and compositions including at least one conjugate described above. In a preferred embodiment, the composition is an immunogenic composition. In another embodiment, the composition is a vaccine.

In one aspect, the immunogenic composition includes any of the saccharides disclosed herein. In a preferred aspect, the immunogenic composition includes any one of the conjugates disclosed herein.

In one embodiment, the immunogenic composition includes at least one glycoconjugate from *E. coli* serotype O25, preferably serotype O25b. In one embodiment, the immunogenic composition includes at least one glycoconjugate from *E. coli* serotype O1, preferably serotype O1a. In one embodiment, the immunogenic composition includes at least one glycoconjugate from *E. coli* serotype O2. In one embodiment, the immunogenic composition includes at least one glycoconjugate from *E. coli* serotype O6.

In one embodiment, the immunogenic composition includes at least one glycoconjugate selected from any one of the following *E. coli* serotypes O25, O1, O2, and O6, preferably O25b, O1a, O2, and O6. In one embodiment, the immunogenic composition includes at least two glycoconjugates selected from any one of the following *E. coli* serotypes O25, O1, O2, and O6, preferably O25b, O1a, O2, and O6. In one embodiment, the immunogenic composition includes at least three glycoconjugates selected from any one of the following *E. coli* serotypes O25, O1, O2, and O6, preferably O25b, O1a, O2, and O6. In one embodiment, the immunogenic composition includes a glycoconjugate from each of the following *E. coli* serotypes O25, O1, O2, and O6, preferably O25b, O1a, O2, and O6.

In a preferred embodiment, the glycoconjugate of any of the above immunogenic compositions is individually conjugated to $CRM_{197}$.

Accordingly, the composition includes an O-antigen from at least one *E. coli* serotype. In a preferred embodiment, the composition includes an O-antigen from more than 1 *E. coli* serotype. For example, the composition may include an O-antigen from two different *E. coli* serotypes (or "v", valences) to 12 different serotypes (12 v). In one embodiment, the composition includes an O-antigen from 3 different serotypes. In one embodiment, the composition includes an O-antigen from 4 different *E. coli* serotypes. In one embodiment, the composition includes an O-antigen from 5 different *E. coli* serotypes. In one embodiment, the composition includes an O-antigen from 6 different *E. coli* serotypes. In one embodiment, the composition includes an O-antigen from 7 different *E. coli* serotypes. In one embodiment, the composition includes an O-antigen from 8 different *E. coli* serotypes. In one embodiment, the composition includes an O-antigen from 9 different *E. coli* serotypes. In one embodiment, the composition includes an O-antigen from 10 different *E. coli* serotypes. In one embodiment, the composition includes an O-antigen from 11 different *E. coli* serotypes. In one embodiment, the composition includes an O-antigen from 12 different serotypes. In one embodiment, the composition includes an O-antigen from 13 different serotypes. In one embodiment, the composition includes an O-antigen from 14 different serotypes. In one embodiment, the composition includes an O-antigen from 15 different serotypes. In one embodiment, the composition includes an O-antigen from 16 different serotypes. In one embodiment, the composition includes an O-antigen from 17 different serotypes. In one embodiment, the composition includes an O-antigen from 18 different serotypes. In one embodiment, the composition includes an O-antigen from 19 different serotypes. In one embodiment, the composition includes an O-antigen from 20 different serotypes.

Preferably, the number of *E. coli* saccharides can range from 1 serotype (or "v", valences) to 26 different serotypes (26 v). In one embodiment there is one serotype. In one embodiment there are 2 different serotypes. In one embodiment there are 3 different serotypes. In one embodiment there are 4 different serotypes. In one embodiment there are 5 different serotypes. In one embodiment there are 6 different serotypes. In one embodiment there are 7 different serotypes. In one embodiment there are 8 different serotypes. In one embodiment there are 9 different serotypes. In one embodiment there are 10 different serotypes. In one embodiment there are 11 different serotypes. In one embodiment there are 12 different serotypes. In one embodiment there are 13 different serotypes. In one embodiment there are 14 different serotypes. In one embodiment there are 15 different serotypes. In one embodiment there are 16 different serotypes. In one embodiment there are 17 different serotypes. In one embodiment there are 18 different serotypes. In one embodiment there are 19 different serotypes. In one embodiment there are 20 different serotypes. In one embodiment there are 21 different serotypes. In one embodiment there are 22 different serotypes. In one embodiment there are 23 different serotypes. In one embodiment there are 24 different serotypes. In an embodiment there are 25 different serotypes. In one embodiment there are 26 different serotypes. The saccharides are conjugated to a carrier protein to form glycoconjugates as described herein.

In one aspect, the composition includes a glycoconjugate that includes an O-antigen from at least one *E. coli* serogroup, wherein the O-antigen is conjugated to a carrier protein. In one embodiment, the composition includes an O-antigen from more than 1 *E. coli* serotype, wherein each O-antigen is conjugated to a carrier protein. In one embodiment, the composition includes an O-antigen from 3 different *E. coli* serotypes, wherein each O-antigen is conjugated to a carrier protein. In one embodiment, the composition includes an O-antigen from 4 different *E. coli* serotypes, wherein each O-antigen is conjugated to a carrier protein. In one embodiment, the composition includes an O-antigen from 5 different *E. coli* serotypes, wherein each O-antigen is conjugated to a carrier protein. In one embodiment, the composition includes an O-antigen from 6 different *E. coli* serotypes, wherein each O-antigen is conjugated to a carrier protein. In one embodiment, the composition includes an O-antigen from 7 different *E. coli* serotypes, wherein each O-antigen is conjugated to a carrier protein. In one embodiment, the composition includes an O-antigen from 8 different *E. coli* serotypes, wherein each O-antigen is conjugated to a carrier protein. In one embodiment, the composition includes an O-antigen from 9 different *E. coli* serotypes, wherein each O-antigen is conjugated to a carrier protein. In one embodiment, the composition includes an O-antigen from 10 different *E. coli* serotypes, wherein each O-antigen is conjugated to a carrier protein. In one embodiment, the composition includes an O-antigen from 11 different *E. coli* serotypes, wherein each O-antigen is conjugated to a carrier protein. In one embodiment, the composition includes an O-antigen from 12 different serotypes, wherein each O-antigen is conjugated to a carrier protein. In one embodiment, the composition includes an O-antigen from 13 different serotypes, wherein each O-antigen is conjugated to a carrier protein. In one embodiment, the composition includes an O-antigen from 14 different serotypes, wherein each O-antigen is conjugated to a carrier protein. In one embodiment, the composition includes an O-antigen from 15 different serotypes, wherein each O-antigen is conjugated to a carrier protein. In one embodiment, the composition includes an O-antigen from 16 different serotypes, wherein each O-antigen is conjugated to a carrier protein. In one embodiment, the composition includes an O-antigen from 17 different serotypes, wherein each O-antigen is conjugated to a carrier protein. In one embodiment, the composition includes an O-antigen from 18 different serotypes, wherein each O-antigen is conjugated to a carrier protein. In one embodiment, the composition includes an O-antigen from 19 different serotypes, wherein each O-antigen is conjugated to a carrier protein. In one embodiment, the composition includes an O-antigen from 20 different serotypes, wherein each O-antigen is conjugated to a carrier protein.

In another aspect, the composition includes an O-polysaccharide from at least one *E. coli* serotype. In a preferred embodiment, the composition includes an O-polysaccharide from more than 1 *E. coli* serotype. For example, the composition may include an O-polysaccharide from two different *E. coli* serotypes to 12 different *E. coli* serotypes. In one embodiment, the composition includes an O-polysaccharide from 3 different *E. coli* serotypes. In one embodiment, the composition includes an O-polysaccharide from 4 different *E. coli* serotypes. In one embodiment, the composition includes an O-polysaccharide from 5 different *E. coli* serotypes. In one embodiment, the composition includes an O-polysaccharide from 6 different *E. coli* serotypes. In one embodiment, the composition includes an O-polysaccharide from 7 different *E. coli* serotypes. In one embodiment, the composition includes an O-polysaccharide from 8 different *E. coli* serotypes. In one embodiment, the composition includes an O-polysaccharide from 9 different *E. coli* serotypes. In one embodiment, the composition includes an O-polysaccharide from 10 different *E. coli* serotypes. In one embodiment, the composition includes an O-polysaccharide from 11 different *E. coli* serotypes. In one embodiment, the composition includes an O-polysaccharide from 12 different serotypes. In one embodiment, the composition includes an O-polysaccharide from 13 different serotypes. In one embodiment, the composition includes an O-polysaccharide from 14 different serotypes. In one embodiment, the composition includes an O-polysaccharide from 15 different serotypes. In one embodiment, the composition includes an O-polysaccharide from 16 different serotypes. In one embodiment, the composition includes an O-polysaccharide from 17 different serotypes. In one embodiment, the composition includes an O-polysaccharide from 18 different serotypes. In one embodiment, the composition includes an O-polysaccharide from 19 different serotypes. In one embodiment, the composition includes an O-polysaccharide from 20 different serotypes.

In a preferred embodiment, the composition includes an O-polysaccharide from at least one *E. coli* serotype, wherein the O-polysaccharide is conjugated to a carrier protein. In a preferred embodiment, the composition includes an O-polysaccharide from more than 1 *E. coli* serotype, wherein each O-polysaccharide is conjugated to a carrier protein. For example, the composition may include an O-polysaccharide from two different *E. coli* serotypes to 12 different *E. coli* serotypes, wherein each O-polysaccharide is conjugated to a carrier protein. In one embodiment, the composition includes an O-polysaccharide from 3 different *E. coli* serotypes, wherein each O-polysaccharide is conjugated to a carrier protein. In one embodiment, the composition includes an O-polysaccharide from 4 different *E. coli* serotypes, wherein each O-polysaccharide is conjugated to a carrier protein. In one embodiment, the composition includes an O-polysaccharide from 5 different *E. coli* serotypes, wherein each O-polysaccharide is conjugated to a carrier protein. In one embodiment, the composition includes an O-polysaccharide from 6 different *E. coli* serotypes, wherein each O-polysaccharide is conjugated to a carrier protein. In one embodiment, the composition includes an O-polysaccharide from 7 different *E. coli* serotypes, wherein each O-polysaccharide is conjugated to a carrier protein. In one embodiment, the composition includes an O-polysaccharide from 8 different *E. coli* serotypes, wherein each O-polysaccharide is conjugated to a carrier protein. In one embodiment, the composition includes an O-polysaccharide from 9 different *E. coli* serotypes, wherein each O-polysaccharide is conjugated to a carrier protein. In one embodiment, the composition includes an O-polysaccharide from 10 different *E. coli* serotypes, wherein each O-polysaccharide is conjugated to a carrier protein. In one embodiment, the composition includes an O-polysaccharide from 11 different *E. coli* serotypes, wherein each O-polysaccharide is conjugated to a carrier protein. In one embodiment, the composition includes an O-polysaccharide from 12 different serotypes, wherein each O-polysaccharide is conjugated to a carrier protein. In one embodiment, the composition includes an O-polysaccharide from 13 different serotypes, wherein each O-polysaccharide is conjugated to a carrier protein. In one embodiment, the composition includes an O-polysaccharide from 14 different serotypes, wherein each O-polysaccharide is conjugated to a carrier protein. In one embodiment, the composition includes an O-polysaccharide from 15 different serotypes, wherein each O-polysaccharide is conjugated to a carrier protein. In one embodiment, the composition includes an O-polysaccharide from 16 different serotypes, wherein each O-polysaccharide is conjugated to a carrier protein. In one embodiment, the composition includes an O-polysaccharide from 17 different serotypes, wherein each O-polysaccharide is conjugated to a carrier protein. In one embodiment, the composition includes an O-polysaccharide from 18 different serotypes, wherein each O-polysaccharide is conjugated to a carrier protein. In one embodiment, the composition includes an O-polysaccharide from 19 different serotypes, wherein each O-polysaccharide is conjugated to a carrier protein. In one embodiment, the composition includes an O-polysaccharide from 20 different serotypes, wherein each O-polysaccharide is conjugated to a carrier protein.

In a most preferred embodiment, the composition includes an O-polysaccharide from at least one *E. coli* serotype, wherein the O-polysaccharide is conjugated to a carrier protein, and wherein the O-polysaccharide includes the O-antigen and core saccharide. In a preferred embodiment, the composition includes an O-polysaccharide from more than 1 *E. coli* serotype, wherein each O-polysaccharide is conjugated to a carrier protein, and wherein the O-polysaccharide includes the O-antigen and core saccharide. For example, the composition may include an O-polysaccharide from two different *E. coli* serotypes to 12 different *E. coli* serotypes, wherein each O-polysaccharide is conjugated to a carrier protein, and wherein the O-polysaccharide includes the O-antigen and core saccharide. In one embodiment, the composition includes an O-polysaccharide from 3 different *E. coli* serotypes, wherein each O-polysaccharide is conjugated to a carrier protein, and wherein the O-polysaccharide includes the O-antigen and core saccharide. In one embodiment, the composition includes an O-polysaccharide from 4 different *E. coli* serotypes, wherein each O-polysaccharide is conjugated to a carrier protein, and wherein the O-polysaccharide includes the O-antigen and core saccharide. In one embodiment, the composition includes an O-polysaccharide from 5 different *E. coli* serotypes, wherein each O-polysaccharide is conjugated to a carrier protein, and wherein the O-polysaccharide includes the O-antigen and core saccharide. In one embodiment, the composition includes an O-polysaccharide from 6 different *E. coli* serotypes, wherein each O-polysaccharide is conjugated to a carrier protein, and wherein the O-polysaccharide includes the O-antigen and core saccharide. In one embodiment, the composition includes an O-polysaccharide from 7 different *E. coli* serotypes, wherein each O-polysaccharide is conjugated to a carrier protein, and wherein the O-polysaccharide includes the O-antigen and core saccharide. In one embodiment, the composition includes an O-polysaccharide from 8 different *E. coli* serotypes, wherein each O-polysaccharide is conjugated to a carrier protein, and wherein the O-polysaccharide includes the O-antigen and core saccharide. In one embodiment, the composition includes an O-polysaccharide from 9 different *E. coli* serotypes, wherein each O-polysaccharide is conjugated to a carrier protein, and wherein the O-polysaccharide includes the O-antigen and core saccharide. In one embodiment, the composition includes an O-polysaccharide from 10 different *E. coli* serotypes, wherein each O-polysaccharide is conjugated to a carrier protein, and wherein the O-polysaccharide includes the O-antigen and core saccharide. In one embodiment, the composition includes an O-polysaccharide from 11 different *E. coli* serotypes, wherein each O-polysaccharide is conjugated to a carrier protein, and wherein the O-polysaccharide includes the O-antigen and core saccharide. In one embodiment, the composition includes an O-polysaccharide from 12 different serotypes, wherein each O-polysaccharide is conjugated to a carrier protein, and wherein the O-polysaccharide includes the O-antigen and core saccharide. In one embodiment, the composition includes an O-polysaccharide from 13 different serotypes, wherein each O-polysaccharide is conjugated to a carrier protein, and wherein the O-polysaccharide includes the O-antigen and core saccharide. In one embodiment, the composition includes an O-polysaccharide from 14 different serotypes, wherein each O-polysaccharide is conjugated to a carrier protein, and wherein the O-polysaccharide includes the O-antigen and core saccharide. In one embodiment, the composition includes an O-polysaccharide from 15 different serotypes, wherein each O-polysaccharide is conjugated to a carrier protein, and wherein the O-polysaccharide includes the O-antigen and core saccharide. In one embodiment, the composition includes an O-polysaccharide from 16 different serotypes, wherein each O-polysaccharide is conjugated to a carrier protein, and wherein the O-polysaccharide includes the O-antigen and core saccharide. In one embodiment, the composition includes an O-polysaccharide from 17 different serotypes, wherein each O-polysaccharide is conjugated to a carrier protein, and wherein the O-polysaccharide includes the O-antigen and core saccharide. In one embodiment, the composition includes an O-polysaccharide from 18 different serotypes, wherein each O-polysaccharide is conjugated to a carrier protein, and wherein the O-polysaccharide includes the O-antigen and core saccharide. In one embodiment, the composition includes an O-polysaccharide from 19 different serotypes, wherein each O-polysaccharide is conjugated to a carrier protein, and wherein the O-polysaccharide includes the O-antigen and core saccharide. In one embodiment, the composition includes an O-polysaccharide from 20 different serotypes, wherein each O-polysaccharide is conjugated to a carrier protein, and wherein the O-polysaccharide includes the O-antigen and core saccharide. In a preferred embodiment, the carrier protein is $CRM_{197}$.

In another preferred embodiment, the composition includes an O-polysaccharide conjugated to $CRM_{197}$, wherein the O-polysaccharide includes Formula O25a, wherein n is at least 40, and the core saccharide. In a preferred embodiment, the composition further includes an O-polysaccharide conjugated to $CRM_{197}$, wherein the O-polysaccharide includes Formula O25b, wherein n is at least 40, and the core saccharide. In another embodiment, the composition further includes an O-polysaccharide conjugated to $CRM_{197}$, wherein the O-polysaccharide includes Formula O1a, wherein n is at least 40, and the core saccharide. In another embodiment, the composition further includes an O-polysaccharide conjugated to $CRM_{197}$, wherein the O-polysaccharide includes Formula O2, wherein n is at least 40, and the core saccharide. In another embodiment, the composition further includes an O-polysaccharide conjugated to $CRM_{197}$, wherein the O-polysaccharide includes Formula O6, wherein n is at least 40, and the core saccharide.

In another embodiment, the composition further includes an O-polysaccharide conjugated to $CRM_{197}$, wherein the O-polysaccharide includes Formula O17, wherein n is at least 40, and the core saccharide. In another embodiment, the composition further includes an O-polysaccharide conjugated to $CRM_{197}$, wherein the O-polysaccharide includes Formula O15, wherein n is at least 40, and the core saccharide. In another embodiment, the composition further includes an O-polysaccharide conjugated to $CRM_{197}$, wherein the O-polysaccharide includes Formula O18A, wherein n is at least 40, and the core saccharide. In another embodiment, the composition further includes an O-polysaccharide conjugated to $CRM_{197}$, wherein the O-polysaccharide includes Formula O75, wherein n is at least 40, and the core saccharide. In another embodiment, the composition further includes an O-polysaccharide conjugated to $CRM_{197}$, wherein the O-polysaccharide includes Formula O4, wherein n is at least 40, and the core saccharide. In another embodiment, the composition further includes an O-polysaccharide conjugated to $CRM_{197}$, wherein the O-polysaccharide includes Formula O16, wherein n is at least 40, and the core saccharide. In another embodiment, the composition further includes an O-polysaccharide conjugated to $CRM_{197}$, wherein the O-polysaccharide includes Formula O13, wherein n is at least 40, and the core saccharide. In another embodiment, the composition further includes an O-polysaccharide conjugated to $CRM_{197}$, wherein the O-polysaccharide includes Formula O7, wherein n is at least 40, and the core saccharide.

In another embodiment, the composition further includes an O-polysaccharide conjugated to $CRM_{197}$, wherein the O-polysaccharide includes Formula O8, wherein n is at least 40, and the core saccharide. In another embodiment, the O-polysaccharide includes Formula O8, wherein n is 1-20, preferably 2-5, more preferably 3. Formula O8 is shown, e.g., in FIG. 10B. In another embodiment, the composition further includes an O-polysaccharide conjugated to $CRM_{197}$, wherein the O-polysaccharide includes Formula O9, wherein n is at least 40, and the core saccharide. In another embodiment, the O-polysaccharide includes Formula O9, wherein n is 1-20, preferably 4-8, more preferably 5. Formula O9 is shown, e.g., in FIG. 10B. In another embodiment, the O-polysaccharide includes Formula O9a, wherein n is 1-20, preferably 4-8, more preferably 5. Formula O9a is shown, e.g., in FIG. 10B.

In some embodiments, the O-polysaccharide includes selected from any one of Formula O20ab, Formula O20ac, Formula O52, Formula O97, and Formula O101, wherein n is 1-20, preferably 4-8, more preferably 5. See, e.g., FIG. 10B.

As described above, the composition may include any combination of conjugated O-polysaccharides (antigens). In one exemplary embodiment, the composition includes a polysaccharide that includes Formula O25b, a polysaccharide that includes Formula O1A, a polysaccharide that includes Formula O2, and a polysaccharide that includes Formula O6. More specifically, such as a composition that includes: (i) an O-polysaccharide conjugated to $CRM_{197}$, wherein the O-polysaccharide includes Formula O25b, wherein n is at least 40, and the core saccharide; (ii) an O-polysaccharide conjugated to $CRM_{197}$, wherein the O-polysaccharide includes Formula O1a, wherein n is at least 40, and the core saccharide; (iii) an O-polysaccharide conjugated to $CRM_{197}$, wherein the O-polysaccharide includes Formula O2, wherein n is at least 40, and the core saccharide; and (iv) an O-polysaccharide conjugated to $CRM_{197}$, wherein the O-polysaccharide includes Formula O6, wherein n is at least 40, and the core saccharide.

In one embodiment, the composition includes at least one O-polysaccharide derived from any *E. coli* serotype, wherein the serotype is not O25a. For example, in one embodiment, the composition does not include a saccharide that includes the Formula O25a. Such a composition may include, for example, an O-polysaccharide that includes Formula O25b, an O-polysaccharide that includes Formula O1A, an O-polysaccharide that includes Formula O2, and an O-polysaccharide that includes Formula O6.

In one embodiment, the composition includes an O-polysaccharide from 2 different *E. coli* serotypes, wherein each O-polysaccharide is conjugated to $CRM_{197}$, and wherein the O-polysaccharide includes the O-antigen and core saccharide. In one embodiment, the composition includes an O-polysaccharide from 3 different *E. coli* serotypes, wherein each O-polysaccharide is conjugated to $CRM_{197}$, and wherein the O-polysaccharide includes the O-antigen and core saccharide. In one embodiment, the composition includes an O-polysaccharide from 4 different *E. coli* serotypes, wherein each O-polysaccharide is conjugated to $CRM_{197}$, and wherein the O-polysaccharide includes the O-antigen and core saccharide. In one embodiment, the composition includes an O-polysaccharide from 5 different *E. coli* serotypes, wherein each O-polysaccharide is conjugated to $CRM_{197}$, and wherein the O-polysaccharide includes the O-antigen and core saccharide. In one embodiment, the composition includes an O-polysaccharide from 6 different *E. coli* serotypes, wherein each O-polysaccharide is conjugated to $CRM_{197}$, and wherein the O-polysaccharide includes the O-antigen and core saccharide. In one embodiment, the composition includes an O-polysaccharide from 7 different *E. coli* serotypes, wherein each O-polysaccharide is conjugated to $CRM_{197}$, and wherein the O-polysaccharide includes the O-antigen and core saccharide. In one embodiment, the composition includes an O-polysaccharide from 8 different *E. coli* serotypes, wherein each O-polysaccharide is conjugated to $CRM_{197}$, and wherein the O-polysaccharide includes the O-antigen and core saccharide. In one embodiment, the composition includes an O-polysaccharide from 9 different *E. coli* serotypes, wherein each O-polysaccharide is conjugated to $CRM_{197}$, and wherein the O-polysaccharide includes the O-antigen and core saccharide. In one embodiment, the composition includes an O-polysaccharide from 10 different *E. coli* serotypes, wherein each O-polysaccharide is conjugated to $CRM_{197}$, and wherein the O-polysaccharide includes the O-antigen and core saccharide. In one embodiment, the composition includes an O-polysaccharide from 11 different *E. coli* serotypes, wherein each O-polysaccharide is conjugated to $CRM_{197}$, and wherein the O-polysaccharide includes the O-antigen and core saccharide. In one embodiment, the composition includes an O-polysaccharide from 12 different serotypes, wherein each O-polysaccharide is conjugated to $CRM_{197}$, and wherein the O-polysaccharide includes the O-antigen and core saccharide. In one embodiment, the composition includes an O-polysaccharide from 13 different serotypes, wherein each O-polysaccharide is conjugated to $CRM_{197}$ and wherein the O-polysaccharide includes the O-antigen and core saccharide. In one embodiment, the composition includes an O-polysaccharide from 14 different serotypes, wherein each O-polysaccharide is conjugated to $CRM_{197}$, and wherein the O-polysaccharide includes the O-antigen and core saccharide. In one embodiment, the composition includes an O-polysaccharide from 15 different serotypes, wherein each O-polysaccharide is conjugated to $CRM_{197}$, and wherein the O-polysaccharide includes the O-antigen and core saccharide. In one embodiment, the composition includes an O-polysaccharide from 16 different serotypes, wherein each O-polysaccharide is conjugated to $CRM_{197}$, and wherein the O-polysaccharide includes the O-antigen and core saccharide. In one embodiment, the composition includes an O-polysaccharide from 17 different serotypes, wherein each O-polysaccharide is conjugated to $CRM_{197}$, and wherein the O-polysaccharide includes the O-antigen and core saccharide. In one embodiment, the composition includes an O-polysaccharide from 18 different serotypes, wherein each O-polysaccharide is conjugated to $CRM_{197}$, and wherein the O-polysaccharide includes the O-antigen and core saccharide. In one embodiment, the composition includes an O-polysaccharide from 19 different serotypes, wherein each O-polysaccharide is conjugated to $CRM_{197}$, and wherein the O-polysaccharide includes the O-antigen and core saccharide. In one embodiment, the composition includes an O-polysaccharide from 20 different serotypes, wherein each O-polysaccharide is conjugated to $CRM_{197}$, and wherein the O-polysaccharide includes the O-antigen and core saccharide.

In one aspect, the invention relates to a composition that includes a conjugate including a saccharide covalently bound to a carrier protein, wherein the saccharide includes Formula O25b, wherein n is 15±2. In one aspect, the invention relates to a composition that includes a conjugate including a saccharide covalently bound to a carrier protein, wherein the saccharide includes Formula O25b, wherein n is 17±2. In one aspect, the invention relates to a composition that includes a conjugate including a saccharide covalently bound a carrier protein, wherein the saccharide includes Formula O25b, wherein n is 55±2. In another aspect, the invention relates to a composition that includes a conjugate including a saccharide covalently bound a carrier protein, wherein the saccharide includes Formula O25b, wherein n is 51±2. In one embodiment, the saccharide further includes the *E. coli* R1 core saccharide moiety. In another embodiment, the saccharide further includes the *E. coli* K12 core saccharide moiety. In another embodiment, the saccharide further includes the KDO moiety. Preferably, the carrier protein is $CRM_{197}$. In one embodiment, the conjugate is prepared by single end linked conjugation. In one embodiment, the conjugate is prepared by reductive amination chemistry, preferably in DMSO buffer. In one embodiment, the saccharide is conjugated to the carrier protein through a (2-((2-oxoethyl)thio)ethyl) carbamate (eTEC) spacer. Preferably, the composition further includes a pharmaceutically acceptable diluent.

In one embodiment, the immunogenic composition elicits IgG antibodies in humans, said antibodies being capable of binding an *E. coli* serotype O25B polysaccharide at a concentration of at least 0.2 pg/ml, 0.3 pg/ml, 0.35 pg/ml, 0.4 pg/ml or 0.5 pg/ml as determined by ELISA assay. Therefore, comparison of OPA activity of pre- and post-immunization serum with the immunogenic composition of the invention can be conducted and compared for their response to serotype O25B to assess the potential increase of responders. In one embodiment, the immunogenic composition elicits IgG antibodies in humans, said antibodies being capable of killing *E. coli* serotype O25B as determined by in vitro opsonophagocytic assay. In one embodiment, the immunogenic composition elicits functional antibodies in humans, said antibodies being capable of killing *E. coli* serotype O25B as determined by in vitro opsonophagocytic assay. In one embodiment, the immunogenic composition of the invention increases the proportion of responders against *E. coli* serotype O25B (i.e., individual with a serum having a titer of at least 1:8 as determined by in vitro OPA) as compared to the pre-immunized population. In one embodiment, the immunogenic composition elicits a titer of at least 1:8 against *E. coli* serotype O25B in at least 50% of the subjects as determined by in vitro opsonophagocytic killing assay. In one embodiment, the immunogenic composition of the invention elicits a titer of at least 1:8 against *E. coli* serotype O25B in at least 60%, 70%, 80%, or at least 90% of the subjects as determined by in vitro opsonophagocytic killing assay. In one embodiment, the immunogenic composition of the invention significantly increases the proportion of responders against *E. coli* serotypes O25B (i.e., individual with a serum having a titer of at least 1:8 as determined by in vitro OPA) as compared to the pre-immunized population. In one embodiment, the immunogenic composition of the invention significantly increases the OPA titers of human subjects against *E. coli* serotype O25B as compared to the pre-immunized population.

In one aspect, the invention relates to a composition that includes a conjugate including a saccharide covalently bound a carrier protein, wherein the saccharide includes Formula O1a, wherein n is 39±2. In another aspect, the invention relates to a composition that includes a conjugate including a saccharide covalently bound a carrier protein, wherein the saccharide includes Formula O1a, wherein n is 13±2. In one embodiment, the saccharide further includes the *E. coli* R1 core saccharide moiety. In one embodiment, the saccharide further includes the KDO moiety. Preferably, the carrier protein is $CRM_{197}$. In one embodiment, the conjugate is prepared by single end linked conjugation. In one embodiment, the conjugate is prepared by reductive amination chemistry, preferably in DMSO buffer. In one embodiment, the saccharide is conjugated to the carrier protein through a (2-((2-oxoethyl)thio)ethyl) carbamate (eTEC) spacer. Preferably, the composition further includes a pharmaceutically acceptable diluent.

In one embodiment, the immunogenic composition elicits IgG antibodies in humans, said antibodies being capable of binding an *E. coli* serotype O1A polysaccharide at a concentration of at least 0.2 pg/ml, 0.3 pg/ml, 0.35 pg/ml, 0.4 pg/ml or 0.5 pg/ml as determined by ELISA assay. Therefore, comparison of OPA activity of pre- and post-immunization serum with the immunogenic composition of the invention can be conducted and compared for their response to serotype O1A to assess the potential increase of responders. In one embodiment, the immunogenic composition elicits IgG antibodies in humans, said antibodies being capable of killing *E. coli* serotype O1A as determined by in vitro opsonophagocytic assay. In one embodiment, the immunogenic composition elicits functional antibodies in humans, said antibodies being capable of killing *E. coli* serotype O1A as determined by in vitro opsonophagocytic assay. In one embodiment, the immunogenic composition of the invention increases the proportion of responders against *E. coli* serotype O1A (i.e., individual with a serum having a titer of at least 1:8 as determined by in vitro OPA) as compared to the pre-immunized population. In one embodiment, the immunogenic composition elicits a titer of at least 1:8 against *E. coli* serotype O1A in at least 50% of the subjects as determined by in vitro opsonophagocytic killing assay. In one embodiment, the immunogenic composition of the invention elicits a titer of at least 1:8 against *E. coli* serotype O1A in at least 60%, 70%, 80%, or at least 90% of the subjects as determined by in vitro opsonophagocytic killing assay. In one embodiment, the immunogenic composition of the invention significantly increases the proportion of responders against *E. coli* serotypes O1A (i.e., individual with a serum having a titer of at least 1:8 as determined by in vitro OPA) as compared to the pre-immunized population. In one embodiment, the immunogenic composition of the invention significantly increases the OPA titers of human subjects against *E. coli* serotype O1A as compared to the pre-immunized population.

In one aspect, the invention relates to a composition that includes a conjugate including a saccharide covalently bound a carrier protein, wherein the saccharide includes Formula O2, wherein n is 43±2. In another aspect, the invention relates to a composition that includes a conjugate including a saccharide covalently bound a carrier protein, wherein the saccharide includes Formula O2, wherein n is 47±2. In another aspect, the invention relates to a composition that includes a conjugate including a saccharide covalently bound a carrier protein, wherein the saccharide includes Formula O2, wherein n is 17±2. In another aspect, the invention relates to a composition that includes a conjugate including a saccharide covalently bound a carrier protein, wherein the saccharide includes Formula O2, wherein n is 18±2. In one embodiment, the saccharide further includes the *E. coli* R1 core saccharide moiety. In another embodiment, the saccharide further includes the *E. coli* R4 core saccharide moiety. In another embodiment, the saccharide further includes the KDO moiety. Preferably, the carrier protein is $CRM_{197}$. In one embodiment, the conjugate is prepared by single end linked conjugation. In one embodiment, the conjugate is prepared by reductive amination chemistry, preferably in DMSO buffer. In one embodiment, the saccharide is conjugated to the carrier protein through a (2-((2-oxoethyl)thio)ethyl) carbamate (eTEC) spacer. Preferably, the composition further includes a pharmaceutically acceptable diluent.

In one embodiment, the immunogenic composition elicits IgG antibodies in humans, said antibodies being capable of binding an *E. coli* serotype O2 polysaccharide at a concentration of at least 0.2 pg/ml, 0.3 pg/ml, 0.35 pg/ml, 0.4 pg/ml or 0.5 pg/ml as determined by ELISA assay. Therefore, comparison of OPA activity of pre- and post-immunization serum with the immunogenic composition of the invention can be conducted and compared for their response to serotype O2 to assess the potential increase of responders. In one embodiment, the immunogenic composition elicits IgG antibodies in humans, said antibodies being capable of killing *E. coli* serotype O2 as determined by in vitro opsonophagocytic assay. In one embodiment, the immunogenic composition elicits functional antibodies in humans, said antibodies being capable of killing *E. coli* serotype O2 as determined by in vitro opsonophagocytic assay. In one embodiment, the immunogenic composition of the invention increases the proportion of responders against *E. coli* serotype O2 (i.e., individual with a serum having a titer of at least 1:8 as determined by in vitro OPA) as compared to the pre-immunized population. In one embodiment, the immunogenic composition elicits a titer of at least 1:8 against *E. coli* serotype O2 in at least 50% of the subjects as determined by in vitro opsonophagocytic killing assay. In one embodiment, the immunogenic composition of the invention elicits a titer of at least 1:8 against *E. coli* serotype O2 in at least 60%, 70%, 80%, or at least 90% of the subjects as determined by in vitro opsonophagocytic killing assay. In one embodiment, the immunogenic composition of the invention significantly increases the proportion of responders against *E. coli* serotypes O2 (i.e., individual with a serum having a titer of at least 1:8 as determined by in vitro OPA) as compared to the pre-immunized population. In one embodiment, the immunogenic composition of the invention significantly increases the OPA titers of human subjects against *E. coli* serotype O2 as compared to the pre-immunized population.

In one aspect, the invention relates to a composition that includes a conjugate including a saccharide covalently bound a carrier protein, wherein the saccharide includes Formula O6, wherein n is 42±2. In another aspect, the invention relates to a composition that includes a conjugate including a saccharide covalently bound a carrier protein, wherein the saccharide includes Formula O6, wherein n is 50±2. In another aspect, the invention relates to a composition that includes a conjugate including a saccharide covalently bound a carrier protein, wherein the saccharide includes Formula O6, wherein n is 17±2. In another aspect, the invention relates to a composition that includes a conjugate including a saccharide covalently bound a carrier protein, wherein the saccharide includes Formula O6, wherein n is 18±2. In one embodiment, the saccharide further includes the *E. coli* R1 core saccharide moiety. In one embodiment, the saccharide further includes the KDO moiety. Preferably, the carrier protein is CRM$_{197}$. In one embodiment, the conjugate is prepared by single end linked conjugation. In one embodiment, the conjugate is prepared by reductive amination chemistry, preferably in DMSO buffer. In one embodiment, the saccharide is conjugated to the carrier protein through a (2-((2-oxoethyl)thio)ethyl) carbamate (eTEC) spacer. Preferably, the composition further includes a pharmaceutically acceptable diluent.

In one embodiment, the immunogenic composition elicits IgG antibodies in humans, said antibodies being capable of binding an *E. coli* serotype O6 polysaccharide at a concentration of at least 0.2 pg/ml, 0.3 pg/ml, 0.35 pg/ml, 0.4 pg/ml or 0.5 pg/ml as determined by ELISA assay. Therefore, comparison of OPA activity of pre- and post-immunization serum with the immunogenic composition of the invention can be conducted and compared for their response to serotype O6 to assess the potential increase of responders. In one embodiment, the immunogenic composition elicits IgG antibodies in humans, said antibodies being capable of killing *E. coli* serotype O6 as determined by in vitro opsonophagocytic assay. In one embodiment, the immunogenic composition elicits functional antibodies in humans, said antibodies being capable of killing *E. coli* serotype O6 as determined by in vitro opsonophagocytic assay. In one embodiment, the immunogenic composition of the invention increases the proportion of responders against *E. coli* serotype O6 (i.e., individual with a serum having a titer of at least 1:8 as determined by in vitro OPA) as compared to the pre-immunized population. In one embodiment, the immunogenic composition elicits a titer of at least 1:8 against *E. coli* serotype O6 in at least 50% of the subjects as determined by in vitro opsonophagocytic killing assay. In one embodiment, the immunogenic composition of the invention elicits a titer of at least 1:8 against *E. coli* serotype O6 in at least 60%, 70%, 80%, or at least 90% of the subjects as determined by in vitro opsonophagocytic killing assay. In one embodiment, the immunogenic composition of the invention significantly increases the proportion of responders against *E. coli* serotypes O6 (i.e., individual with a serum having a titer of at least 1:8 as determined by in vitro OPA) as compared to the pre-immunized population. In one embodiment, the immunogenic composition of the invention significantly increases the OPA titers of human subjects against *E. coli* serotype O6 as compared to the pre-immunized population.

In one aspect, the composition includes a conjugate including a saccharide covalently bound to a carrier protein, wherein the saccharide includes a structure selected from any one of Formula O1 (e.g., Formula O1A, Formula O1B, and Formula O1C), Formula O2, Formula O3, Formula O4 (e.g., Formula O4: K52 and Formula O4: K6), Formula O5 (e.g., Formula O5ab and Formula O5ac (strain 180/C3)), Formula O6 (e.g., Formula O6: K2; K13; K15 and Formula O6: K54), Formula O7, Formula O8, Formula O9, Formula O10, Formula O11, Formula O12, Formula O13, Formula O14, Formula O15, Formula O16, Formula O17, Formula O18 (e.g., Formula O18A, Formula O18ac, Formula O18A1, Formula O18B, and Formula O18B1), Formula O19, Formula O20, Formula O21, Formula O22, Formula O23 (e.g., Formula O23A), Formula O24, Formula O25 (e.g., Formula O25a and Formula O25b), Formula O26, Formula O27, Formula O28, Formula O29, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45 (e.g., Formula O45 and Formula O45rel), Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula 62D$_1$, Formula O63, Formula O64, Formula O65, Formula O66, Formula O68, Formula O69, Formula O70, Formula O71, Formula O73 (e.g., Formula O73 (strain 73-1)), Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144, Formula O145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, and Formula O187, wherein n is an integer from 1 to 100. In one embodiment, the saccharide further includes the *E. coli* R1 core saccharide moiety. In one embodiment, the saccharide further includes the *E. coli* R2 core saccharide moiety. In one embodiment, the saccharide further includes the *E. coli* R3 core saccharide moiety. In another embodiment, the saccharide further includes the *E. coli* R4 core saccharide moiety. In one embodiment, the saccharide further includes the *E. coli* K12 core saccharide moiety. In another embodiment, the saccharide further includes the KDO moiety. Preferably, the carrier protein is CRM$_{197}$. In one embodiment, the conjugate is prepared by single end linked conjugation. In one embodiment, the conjugate is prepared by reductive amination chemistry, preferably in DMSO buffer. In one embodiment, the saccharide is conjugated to the carrier protein through a (2-((2-oxoethyl)thio) ethyl) carbamate (eTEC) spacer. Preferably, the composition further includes a pharmaceutically acceptable diluent. In one embodiment, the composition further includes at least 1, 2, 3, 4, 5, 6, 7, 8, 9, 10, 11, 12, 13, 14, 15, 16, 17, 18, 19, 20, 21, 22, 23, 24, 25, 26, 27, 28, 29 additional conjugates to at most 30 additional conjugates, each conjugate including a saccharide covalently bound to a carrier protein, wherein the saccharide includes a structure selected from any one of said Formulas.

Dosages of the Compositions

The amount of glycoconjugate(s) in each dose is selected as an amount which induces an immunoprotective response without significant, adverse side effects in typical vaccines.

Such amount will vary depending upon which specific immunogen is employed and how it is presented.

The amount of a particular glycoconjugate in an immunogenic composition can be calculated based on total polysaccharide for that conjugate (conjugated and non-conjugated). For example, a glycoconjugate with 20% free polysaccharide will have about 80 g of conjugated polysaccharide and about 20 g of non-conjugated polysaccharide in a 100 g polysaccharide dose. The amount of glycoconjugate can vary depending upon the E. coli serotype. The saccharide concentration can be determined by the uronic acid assay.

The "immunogenic amount" of the different polysaccharide components in the immunogenic composition, may diverge and each may comprise about 1.0 g, about 2.0 g, about 3.0 g, about 4.0 g, about 5.0 g, about 6.0 g, about 7.0 g, about 8.0 g, about 9.0 g, about 10.0 g, about 15.0 g, about 20.0 g, about 30.0 g, about 40.0 pg, about 50.0 pg, about 60.0 pg, about 70.0 pg, about 80.0 pg, about 90.0 pg, or about 100.0 g of any particular polysaccharide antigen. Generally, each dose will comprise 0.1 g to 100 g of polysaccharide for a given serotype, particularly 0.5 g to 20 g, more particularly 1 g to 10 g, and even more particularly 2 g to 5 g. Any whole number integer within any of the above ranges is contemplated as an embodiment of the disclosure. In one embodiment, each dose will comprise 1 g, 2 g, 3 g, 4 g, 5 g, 6 g, 7 g, 8 g, 9 g, 10 g, 15 g or 20 g of polysaccharide for a given serotype.

Carrier protein amount. Generally, each dose will comprise 5 g to 150 g of carrier protein, particularly 10 g to 100 g of carrier protein, more particularly 15 g to 100 g of carrier protein, more particularly 25 to 75 g of carrier protein, more particularly 30 g to 70 g of carrier protein, more particularly 30 to 60 g of carrier protein, more particularly 30 g to 50 g of carrier protein and even more particularly 40 to 60 g of carrier protein. In one embodiment, said carrier protein is $CRM_{197}$. In one embodiment, each dose will comprise about 25 g, about 26 g, about 27 g, about 28 g, about 29 g, about 30 g, about 31 g, about 32 g, about 33 g, about 34 g, about 35 g, about 36 g, about 37 g, about 38 g, about 39 g, about 40 g, about 41 g, about 42 g, about 43 g, about 44 g, about 45 g, about 46 g, about 47 g, about 48 g, about 49 g, about 50 g, about 51 g, about 52 g, about 53 g, about 54 g, about 55 g, about 56 g, about 57 g, about 58 g, about 59 g, about 60 g, about 61 g, about 62 g, about 63 g, about 64 g, about 65 g, about 66 g, about 67 g, 68 g, about 69 g, about 70 g, about 71 g, about 72 g, about 73 g, about 74 g or about 75 g of carrier protein. In one embodiment, said carrier protein is $CRM_{197}$.

Adjuvant

In some embodiments, the immunogenic compositions disclosed herein may further comprise at least one, two or three adjuvants. The term "adjuvant" refers to a compound or mixture that enhances the immune response to an antigen. Antigens may act primarily as a delivery system, primarily as an immune modulator or have strong features of both. Suitable adjuvants include those suitable for use in mammals, including humans.

Examples of known suitable delivery-system type adjuvants that can be used in humans include, but are not limited to, alum (e.g., aluminum phosphate, aluminum sulfate or aluminum hydroxide), calcium phosphate, liposomes, oil-in-water emulsions such as MF59 (4.3% w/v squalene, 0.5% w/v polysorbate 80 (Tween 80), 0.5% w/v sorbitan trioleate (Span 85)), water-in-oil emulsions such as Montanide, and poly(D,L-lactide-co-glycolide) (PLG) microparticles or nanoparticles.

In an embodiment, the immunogenic compositions disclosed herein comprise aluminum salts (alum) as adjuvant (e.g., aluminum phosphate, aluminum sulfate or aluminum hydroxide). In a preferred embodiment, the immunogenic compositions disclosed herein comprise aluminum phosphate or aluminum hydroxide as adjuvant. In an embodiment, the immunogenic compositions disclosed herein comprise from 0.1 mg/mL to 1 mg/mL or from 0.2 mg/ml to 0.3 mg/ml of elemental aluminum in the form of aluminum phosphate. In an embodiment, the immunogenic compositions disclosed herein comprise about 0.25 mg/ml of elemental aluminum in the form of aluminum phosphate. Examples of known suitable immune modulatory type adjuvants that can be used in humans include, but are not limited to, saponin extracts from the bark of the Aquilla tree (QS21, Quil A), TLR4 agonists such as MPL (Monophosphoryl Lipid A), 3DMPL (3-O-deacylated MPL) or GLA-AQ, LT/CT mutants, cytokines such as the various interleukins (e.g., IL-2, IL-12) or GM-CSF, AS01, and the like.

Examples of known suitable immune modulatory type adjuvants with both delivery and immune modulatory features that can be used in humans include, but are not limited to, ISCOMS (see, e.g., Sjölander et al. (1998) J. Leukocyte Biol. 64:713; WO 90/03184, WO 96/11711, WO 00/48630, WO 98/36772, WO 00/41720, WO 2006/134423 and WO 2007/026190) or GLA-EM which is a combination of a TLR4 agonist and an oil-in-water emulsion.

For veterinary applications including but not limited to animal experimentation, one can use Complete Freund's Adjuvant (CFA), Freund's Incomplete Adjuvant (IFA), Emulsigen, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-di-palmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion.

Further exemplary adjuvants to enhance effectiveness of the immunogenic compositions disclosed herein include, but are not limited to (1) oil-in-water emulsion formulations (with or without other specific immunostimulating agents such as muramyl peptides (see below) or bacterial cell wall components), such as for example (a) SAF, containing 10% Squalane, 0.4% Tween 80, 5% pluronic-blocked polymer L121, and thr-MDP either microfluidized into a submicron emulsion or vortexed to generate a larger particle size emulsion, and (b) RIBI™ adjuvant system (RAS), (Ribi Immunochem, Hamilton, Mont.) containing 2% Squalene, 0.2% Tween 80, and one or more bacterial cell wall components such as monophosphorylipid A (MPL), trehalose dimycolate (TDM), and cell wall skeleton (CWS), preferably MPL+CWS (DETOX™); (2) saponin adjuvants, such as QS21, STIMULON™ (Cambridge Bioscience, Worcester, Mass.), ABISCO® (Isconova, Sweden), or ISCOMATRIX® (Commonwealth Serum Laboratories, Australia), may be used or particles generated therefrom such as ISCOMs (immunostimulating complexes), which ISCOMS may be devoid of additional detergent (e.g., WO 00/07621); (3) Complete Freund's Adjuvant (CFA) and Incomplete Freund's Adjuvant (IFA); (4) cytokines, such as interleukins (e.g., IL-1, IL-2, IL-4, IL-5, IL-6, IL-7, IL-12 (e.g., WO 99/44636)), interferons (e.g., gamma interferon), macrophage colony stimulating factor (M-CSF), tumor necrosis factor (TNF), etc.; (5) monophosphoryl lipid A (MPL) or 3-O-deacylated MPL (3dMPL) (see, e.g., GB2220211, EP0689454) (see, e.g., WO 00/56358); (6) combinations of 3dMPL with, for example, QS21 and/or oil-in-water emulsions (see, e.g., EP0835318, EP0735898, EP0761231); (7) a polyoxyethylene ether or a polyoxyethylene ester (see, e.g., WO 99/52549); (8) a polyoxyethylene sorbitan ester surfactant in combination with an octoxynol (e.g., WO 01/21207) or a polyoxyethylene alkyl ether or ester surfactant in combination with at least one additional non-ionic surfactant such as an octoxynol (e.g., WO 01/21152); (9) a saponin and an immunostimulatory oligonucleotide (e.g., a CpG oligonucleotide) (e.g., WO 00/62800); (10) an immunostimulant and a particle of metal salt (see, e.g., WO 00/23105); (11) a saponin and an oil-in-water emulsion (e.g., WO 99/11241); (12) a saponin (e.g., QS21)+3dMPL+IM2 (optionally+a sterol) (e.g., WO 98/57659); (13) other substances that act as immunostimulating agents to enhance the efficacy of the composition. Muramyl peptides include N-acetyl-muramyl-L-threonyl-D-isoglutamine (thr-MDP), N-25 acetyl-normuramyl-L-alanyl-D-isoglutamine (nor-MDP), N-acetylmuramyl-L-alanyl-D-isoglutarninyl-L-alanine-2-(1'-2'-dipalmitoyl-sn-glycero-3-hydroxyphosphoryloxy)-ethylamine MTP-PE), etc.

In an embodiment of the present invention, the immunogenic compositions as disclosed herein comprise a CpG Oligonucleotide as adjuvant. A CpG oligonucleotide as used herein refers to an immunostimulatory CpG oligodeoxynucleotide (CpG ODN), and accordingly these terms are used interchangeably unless otherwise indicated. Immunostimulatory CpG oligodeoxynucleotides contain one or more immunostimulatory CpG motifs that are unmethylated cytosine-guanine dinucleotides, optionally within certain preferred base contexts. The methylation status of the CpG immunostimulatory motif generally refers to the cytosine residue in the dinucleotide. An immunostimulatory oligonucleotide containing at least one unmethylated CpG dinucleotide is an oligonucleotide which contains a 5' unmethylated cytosine linked by a phosphate bond to a 3' guanine, and which activates the immune system through binding to Toll-like receptor 9 (TLR-9). In another embodiment the immunostimulatory oligonucleotide may contain one or more methylated CpG dinucleotides, which will activate the immune system through TLR9 but not as strongly as if the CpG motif(s) was/were unmethylated. CpG immunostimulatory oligonucleotides may comprise one or more palindromes that in turn may encompass the CpG dinucleotide. CpG oligonucleotides have been described in a number of issued patents, published patent applications, and other publications, including U.S. Pat. Nos. 6,194,388; 6,207,646; 6,214,806; 6,218,371; 6,239,116; and 6,339,068.

In an embodiment of the present invention, the immunogenic compositions as disclosed herein comprise any of the CpG Oligonucleotide described at page 3, line 22, to page 12, line 36, of WO 2010/125480.

Different classes of CpG immunostimulatory oligonucleotides have been identified. These are referred to as A, B, C and P class, and are described in greater detail at page 3, line 22, to page 12, line 36, of WO 2010/125480. Methods of the invention embrace the use of these different classes of CpG immunostimulatory oligonucleotides.

Formulation

The immunogenic compositions of the invention may be formulated in liquid form (i.e., solutions or suspensions) or in a lyophilized form. Liquid formulations may advantageously be administered directly from their packaged form and are thus ideal for injection without the need for reconstitution in aqueous medium as otherwise required for lyophilized compositions of the invention.

Formulation of the immunogenic composition of the present invention can be accomplished using art-recognized methods. For instance, the individual conjugates can be formulated with a physiologically acceptable vehicle to prepare the composition. Examples of such vehicles include, but are not limited to, water, buffered saline, polyols (e.g., glycerol, propylene glycol, liquid polyethylene glycol) and dextrose solutions.

The present disclosure provides an immunogenic composition comprising any of combination of glycoconjugates disclosed herein and a pharmaceutically acceptable excipient, carrier, or diluent.

In certain embodiments, the immunogenic composition formulations include a pharmaceutically acceptable diluent, excipient or a pharmaceutically acceptable carrier. In one embodiment, the pharmaceutically acceptable diluent includes sterile water, water for injection, sterile isotonic saline or a biological buffer. The polysaccharide-protein conjugates and/or protein immunogens are mixed with such diluents or carriers in a conventional manner. As used herein the language pharmaceutically acceptable "carrier" is intended to include solvents, dispersion media, coatings, antibacterial and antifungal agents, isotonic and absorption delaying agents, and the like, compatible with administration to humans or other vertebrate hosts. The appropriate carrier is evident to those skilled in the art and will depend in large part upon the route of administration.

For example, excipients that may be present in the immunogenic composition formulation include preservatives, chemical stabilizers and suspending or dispersing agents. Typically, stabilizers, preservatives and the like are optimized to determine the best formulation for efficacy in the targeted recipient (e.g., a human subject). Examples of preservatives include chlorobutanol, potassium sorbate, sorbic acid, sulfur dioxide, propyl gallate, the parabens, ethyl vanillin, glycerin, phenol, and parachlorophenol. Examples of stabilizing ingredients include casamino acids, sucrose, gelatin, phenol red, N—Z amine, monopotassium diphosphate, lactose, lactalbumin hydrolysate, and dried milk.

In an embodiment, the immunogenic composition of the invention is in liquid form, preferably in aqueous liquid form.

Immunogenic compositions of the disclosure may comprise one or more of a buffer, a salt, a divalent cation, a non-ionic detergent, a cryoprotectant such as a sugar, and an anti-oxidant such as a free radical scavenger or chelating agent, or any multiple combinations thereof.

In an embodiment, the immunogenic compositions of the invention comprise a buffer. In an embodiment, said buffer has a pKa of about 3.5 to about 7.5. In some embodiments, the buffer is phosphate, succinate, histidine or citrate. In certain embodiments, the buffer is succinate at a final concentration of 1 mM to 10 mM. In one particular embodiment, the final concentration of the succinate buffer is about 5 mM.

In an embodiment, the immunogenic compositions of the invention comprise a salt. In some embodiments, the salt is selected from any one of magnesium chloride, potassium chloride, sodium chloride and a combination thereof. In some embodiments, the salt is selected from the groups consisting of magnesium chloride, potassium chloride, sodium chloride and a combination thereof. In one particular embodiment, the salt is sodium chloride. In one particular embodiment, the immunogenic compositions of the invention comprise sodium chloride at 150 mM.

In an embodiment, the immunogenic compositions of the invention comprise a surfactant. In some embodiments, the composition includes a non-ionic surfactant, including but not limited to polyoxyethylene sorbitan fatty acid esters. In an embodiment, the surfactant is selected from any one of polysorbate 20 (TWEEN™ 20), polysorbate 40 (TWEEN™ 40), polysorbate 60 (TWEEN™ 60), polysorbate 65 (TWEEN™ 65), polysorbate 80 (TWEEN™ 80), polysorbate 85 (TWEEN™ 85), TRITON™ N-101, TRITON™ X-100, oxtoxynol 40, nonoxynol-9, triethanolamine, triethanolamine polypeptide oleate, polyoxyethylene-660 hydroxystearate (PEG-15, Solutol H 15), polyoxyethylene-35-ricinoleate (CREMOPHOR® EL), soy lecithin and a poloxamer. In an embodiment, the surfactant is selected from the group consisting of polysorbate 20 (TWEEN™ 20), polysorbate 40 (TWEEN™ 40), polysorbate 60 (TWEEN™ 60), polysorbate 65 (TWEEN™ 65), polysorbate 80 (TWEEN™ 80), polysorbate 85 (TWEEN™ 85), TRITON™ N-101, TRITON™ X-100, oxtoxynol 40, nonoxynol-9, triethanolamine, triethanolamine polypeptide oleate, polyoxyethylene-660 hydroxystearate (PEG-15, Solutol H 15), polyoxyethylene-35-ricinoleate (CREMOPHOR® EL), soy lecithin and a poloxamer. In some embodiments, the composition further includes any one of the following polyoxyethylene alkyl ethers, including but not limited to BRIJ 58, BRIJ 35, TRITON X-100, TRITON X-114, NP40, SPAN 85, and the pluronic series of non-ionic surfactants, e.g., PLURONIC 121. In one particular embodiment, the surfactant is polysorbate 80. In some said embodiment, the final concentration of polysorbate 80 in the formulation is at least 0.0001% to 10% polysorbate 80 weight to weight (w/w). In some said embodiments, the final concentration of polysorbate 80 in the formulation is at least 0.001% to 1% polysorbate 80 weight to weight (w/w). In some said embodiments, the final concentration of polysorbate 80 in the formulation is at least 0.01% to 1% polysorbate 80 weight to weight (w/w). In other embodiments, the final concentration of polysorbate 80 in the formulation is 0.01%, 0.02%, 0.03%, 0.04%, 0.05%, 0.06%, 0.07%, 0.08%, 0.09% or 0.1% polysorbate 80 (w/w). In another embodiment, the final concentration of the polysorbate 80 in the formulation is 1% polysorbate 80 (w/w).

In certain embodiments, the immunogenic composition of the invention has a pH of 5.5 to 7.5, more preferably a pH of 5.6 to 7.0, even more preferably a pH of 5.8 to 6.0.

In one embodiment, the present invention provides a container filled with any of the immunogenic compositions disclosed herein. In one embodiment, the container is selected from any one of a vial, a syringe, a flask, a fermentor, a bioreactor, a bag, a jar, an ampoule, a cartridge and a disposable pen. In one embodiment, the container is selected from the group consisting of a vial, a syringe, a flask, a fermentor, a bioreactor, a bag, a jar, an ampoule, a cartridge and a disposable pen. In certain embodiments, the container is siliconized. In an embodiment, the container of the present invention is made of glass, metals (e.g., steel, stainless steel, aluminum, etc.) and/or polymers (e.g., thermoplastics, elastomers, thermoplastic-elastomers). In an embodiment, the container of the present invention is made of glass.

In one embodiment, the present invention provides a syringe filled with any of the immunogenic compositions disclosed herein. In certain embodiments, the syringe is siliconized and/or is made of glass.

A typical dose of the immunogenic composition of the invention for injection has a volume of 0.1 mL to 2 mL, more preferably 0.2 mL to 1 mL, even more preferably a volume of about 0.5 mL.

Therefore, the container or syringe as defined above is filed with a volume of 0.1 mL to 2 mL, more preferably 0.2 mL to 1 mL, even more preferably a volume of about 0.5 mL of any of the immunogenic compositions defined herein.

The compositions of the invention can be administered to a subject by one or more known methods, such as parenterally, transmucosally, transdermally, intramuscularly, intravenously, intra-dermally, intra-nasally, subcutaneously, intra-peritoneally, and formulated accordingly.

In one embodiment, compositions of the present invention are administered via epidermal injection, intramuscular injection, intravenous, intra-arterial, subcutaneous injection, or intra-respiratory mucosal injection of a liquid preparation. The composition of the invention can be formulated as single dose vials, multi-dose vials or as pre-filled syringes.

In another embodiment, compositions of the present invention are administered orally, and are thus formulated in a form suitable for oral administration, i.e., as a solid or a liquid preparation. Solid oral formulations include tablets, capsules, pills, granules, pellets and the like. Liquid oral formulations include solutions, suspensions, dispersions, emulsions, oils and the like. Pharmaceutically acceptable carriers for liquid formulations are aqueous or nonaqueous solutions, suspensions, emulsions or oils. Examples of non-aqueous solvents are propylene glycol, polyethylene glycol, and injectable organic esters such as ethyl oleate.

Aqueous carriers include water, alcoholic/aqueous solutions, emulsions or suspensions, including saline and buffered media. Examples of oils are those of animal, vegetable, or synthetic origin, for example, peanut oil, soybean oil, olive oil, sunflower oil, fish-liver oil, another marine oil, or a lipid from milk or eggs.

The pharmaceutical composition may be isotonic, hypotonic or hypertonic. The pharmaceutical composition for infusion or injection is preferably essentially isotonic when it is administrated. For storage, the pharmaceutical composition may preferably be isotonic or hypertonic. If the pharmaceutical composition is hypertonic for storage, it may be diluted to become an isotonic solution prior to administration. The isotonic agent may be an ionic isotonic agent such as a salt or a non-ionic isotonic agent such as a carbohydrate. Examples of ionic isotonic agents include but are not limited to NaCl, $CaCl_3$, KCl and $MgCl_2$. Examples of non-ionic isotonic agents include but are not limited to sucrose, trehalose, mannitol, sorbitol and glycerol.

It is also preferred that at least one pharmaceutically acceptable additive is a buffer. For some purposes, for example, when the pharmaceutical composition is meant for infusion or injection, it is often desirable that the composition comprises a buffer, which is capable of buffering a solution to a pH in the range of 4 to 10, such as 5 to 9, for example 6 to 8. The buffer may for example be selected from any one of Tris, acetate, glutamate, lactate, maleate, tartrate, phosphate, citrate, carbonate, glycinate, L-histidine, glycine, succinate and triethanolamine buffer. The buffer may furthermore for example be selected from USP compatible buffers for parenteral use, in particular, when the pharmaceutical formulation is for parenteral use. For example the buffer may be selected from any one of monobasic acids such as acetic, benzoic, gluconic, glyceric and lactic; dibasic acids such as aconitic, adipic, ascorbic, carbonic, glutamic, malic, succinic and tartaric, polybasic acids such as citric and phosphoric; and bases such as ammonia, diethanolamine, glycine, triethanolamine, and Tris. Parenteral vehicles (for subcutaneous, intravenous, intraarterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, glycols such as propylene glycols or polyethylene glycol, Polysorbate 80 (PS-80), Polysorbate 20 (PS-20), and Poloxamer 188 (PI 88) are preferred liquid carriers, particularly for injectable solutions. Examples of oils are those of animal, vegetable, or synthetic origin, for example, peanut oil, soybean oil, olive oil, sunflower oil, fish-liver oil, another marine oil, or a lipid from milk or eggs.

The formulations may further include a surfactant. Preferred surfactants include, but are not limited to the polyoxyethylene sorbitan esters surfactants (commonly referred to as the TWEENs), especially PS-20 and PS-80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1, 2-ethanediyl) groups, with octoxynol-9 (TRITON X-100, or t-octylphenoxypoly ethoxy ethanol) being of particular interest; (octylphenoxy) polyethoxyethanol (IGEPAL CA-630/NP-40); phospholipids such as phosphatidylcholine (lecithin); nonylphenol ethoxylates, such as the TERGITOL™ NP series; polyoxyethylene fatty ethers derived from lauryl, cetyl, stearyl and oleyl alcohols (known as BRIJ surfactants), such as triethyleneglycol monolauryl ether (BRIJ 30); and sorbitan esters (commonly known as the SPANs), such as sorbitan trioleate (SPAN 85) and sorbitan monolaurate. A preferred surfactant for including in the emulsion is PS-20 or PS-80. Mixtures of surfactants can be used, e.g. PS-80/SPAN 85 mixtures. A combination of a polyoxyethylene sorbitan ester such as polyoxyethylene sorbitan monooleate (PS-80) and an octoxynol such as t-octylphenoxypoly ethoxy ethanol (TRITON X-100) is also suitable. Another useful combination comprises laureth 9 plus a polyoxyethylene sorbitan ester and/or an octoxynol.

The formulation may also include a pH-buffered saline solution. The buffer may, for example, be selected from any one of Tris, acetate, glutamate, lactate, maleate, tartrate, phosphate, citrate, carbonate, glycinate, L-histidine, glycine, succinate, HEPES (4-(2-hydroxyethyl)-I-piperazineethanesulfonic acid), MOPS (3-(N-morpholino) propanesulfonic acid), MES (2-(N-morpholino) ethanesulfonic acid) and triethanolamine buffer. The buffer is capable of buffering a solution to a pH in the range of 4 to 10, 5.2 to 7.5, or 5.8 to 7.0. In certain aspects, the buffer selected from any one of phosphate, succinate, L-histidine, MES, MOPS, HEPES, acetate or citrate. The buffer may furthermore, for example, be selected from USP compatible buffers for parenteral use, in particular, when the pharmaceutical formulation is for parenteral use. The concentrations of buffer will range from 1 mM to 50 mM or 5 mM to 50 mM. In certain aspects, the buffer is L-histidine at a final concentration of 5 mM to 50 mM, or succinate at a final concentration of 1 mM to 10 mM. In certain aspects, the L-histidine is at a final concentration of 20 mM±2 mM.

While the saline solution (i.e., a solution including NaCl) is preferred, other salts suitable for formulation include but are not limited to, $CaCl_3$), KCl and $MgCl_2$ and combinations thereof. Non-ionic isotonic agents including but not limited to sucrose, trehalose, mannitol, sorbitol and glycerol may be used in lieu of a salt. Suitable salt ranges include, but are not limited to 25 mM to 500 mM or 40 mM to 170 mM. In one aspect, the saline is NaCl, optionally present at a concentration from 20 mM to 170 mM. In a preferred embodiment, the formulations comprise a L-histidine buffer with sodium chloride.

In another embodiment, the pharmaceutical composition is delivered in a controlled release system. For example, the agent can be administered using intravenous infusion, a transdermal patch, liposomes, or other modes of administration. In another embodiment, polymeric materials are used; e.g. in microspheres in or an implant.

Activity

In one embodiment, the saccharide described herein is capable of inducing opsonic activity. In another embodiment, the saccharide described herein is capable of inducing opsonic and phagocytic activity (e.g., opsonophagocytic activity).

The inventors surprisingly discovered saccharides having an increase in repeat units as compared to the corresponding wild-type saccharide, induces an increase in immune response in mammals, as compared to wild-type saccharides. The inventors also surprisingly discovered that compositions including a conjugate that includes a carrier protein and a saccharide having an increase in repeat units as compared to the corresponding wild-type saccharide induces an increase in immune response in mammals, as compared to mammals that were administered with a composition including a conjugate that includes a carrier protein and the corresponding wild-type saccharide. Without being bound by mechanism or theory, the saccharides having an increase in repeat units may have an increase in preserved epitopes, which may lead to an increase in immune response.

Opsonic activity or opsonization refers to a process by which an opsonin (for example, an antibody or a complement factor) binds to an antigen (e.g., a saccharide or conjugate thereof described herein), which facilitates attachment of the antigen to a phagocyte or phagocytic cell (e.g., a macrophage, dendritic cell, and polymorphonuclear leukocyte (PMNL). Some bacteria, such as, for example, encapsulated bacteria that are not typically phagocytosed due to the presence of the capsule, become more likely to be recognized by phagocytes when coated with an opsonic antibody. In one embodiment, the saccharide induces an immune response, such as, e.g., an antibody, that is opsonic. In one embodiment, the opsonic activity is against a Gram-negative bacterium, preferably against an *Escherichia* species, more preferably against at least one strain of *E. coli*.

Phagocytic activity or phagocytosis refers to a process by which a phagocytic cell engulfs material and encloses the material in its cytoplasm. In one embodiment, the saccharide induces an immune response, such as, e.g., an antibody, that facilitates phagocytosis. In one embodiment, the phagocytic activity is against a Gram-negative bacterium, preferably against an *Escherichia* species, more preferably against at least one strain of *E. coli*. For example, rabbit antibodies raised against an isolated saccharide described herein may be able to mediate opsonophagocytosis specifically of a strain expressing the saccharide in the presence of complement, as indicated, for example, by an in vitro phagocytosis assay.

In yet another embodiment, the saccharide described herein is capable of inducing a bactericidal immune response. In one embodiment, the bactericidal activity is against a Gram-negative bacterium, preferably against an *Escherichia* species, more preferably against at least one strain of *E. coli*.

Methods for measuring opsonization, phagocytosis, and/or bactericidal activity are known in the art, such as, for example, by measuring reduction in bacterial load in vivo (e.g., by measuring bacteremia levels in mammals challenged with *Escherichia*) and/or by measuring bacterial cell killing in vitro (e.g., an in vitro opsonophagocytic assay). In one embodiment, the saccharide is capable of inducing opsonic, phagocytic, and/or bactericidal activity as compared to an appropriate control, such as, for example, as compared to antisera raised against a heat-killed Gram-negative bacterium.

The opsonophagocytic assay, which measures killing of *E. coli* cells by phagocytic effector cells in the presence of functional antibody and complement, may be a surrogate for evaluating the effectiveness of *E. coli* vaccines to a specific *E. coli* serotype, such as, for example, *E. coli* serotype O25B. In vitro opsonophagocytic assays can be conducted by incubating together a mixture of *E. coli* cells, a heat inactivated human serum to be tested, differentiated HL-60 cells (phagocytes) and an exogenous complement source (e.g., baby rabbit complement). Opsonophagocytosis proceeds during incubation and bacterial cells that are coated with antibody and complement are killed upon opsonophagocytosis. Colony forming units (cfu) of surviving bacteria that escape from opsonophagocytosis are determined by plating the assay mixture. The OPA titer is defined as the reciprocal dilution that results in a 50% reduction in bacterial count over control wells without test serum. The OPA titer is interpolated from the two dilutions that encompass this 50% killing cut-off.

An endpoint titer of 1:8 or greater is considered a positive result in these killing type OPA.

In some embodiments, the subjects may have serotype specific OPA titers prior to vaccination due to, for example, natural exposures to *E. coli* (e.g., in case of adult subjects).

Therefore, comparison of OPA activity of pre- and post-immunization serum with the immunogenic composition of the invention can be conducted and compared for their response to a specific *E. coli* serotype, such as, for example, *E. coli* serotype O25B, to assess the potential increase of responders.

In one embodiment, the immunogenic composition of the invention significantly increases the proportion of responders (i.e., individual with a serum having a titer of at least 1:8 as determined by in vitro OPA) as compared to the pre-immunized population.

Comparison of OPA activity of pre- and post-immunization serum with the immunogenic composition of the invention can also be done by comparing the potential increase in OPA titers.

Therefore, comparison of OPA activity of pre- and post-immunization serum with the immunogenic composition of the invention can be conducted and compared for their response to a specific *E. coli* serotype, such as, for example, *E. coli* serotype O25B, to assess the potential for increase in OPA titers. In one embodiment the immunogenic compositions of the invention are able to significantly increase the OPA titer of human subjects as compared to the pre-immunized population.

In one aspect, the composition induces an immune response against at least one *E. coli* serotype. The *E. coli* serotype may be any serotype, including, for example, any one of the following *E. coli* serotypes: O1 (e.g., O1A, O1B, and O1C), O2, O3, O4 (e.g., O4: K52 and O4: K6), O5 (e.g., O5ab and O5ac (strain 180/C3)), O6 (e.g., O6: K2; K13; K15 and O6: K54), O7, O8, O9, O10, O11, O12, O13, O14, O15, O16, O17, O18 (e.g., O18A, O18ac, O18A1, O18B, and O18B1), O19, O20, O21, O22, O23 (e.g., O23A), O24, O25 (e.g., O25a and O25b), O26, O27, O28, O29, O30, O32, O33, O34, O35, O36, O37, O38, O39, O40, O41, O42, O43, O44, O45 (e.g., O45 and O45rel), O46, O48, O49, O50, O51, O52, O53, O54, O55, O56, O57, O58, O59, O60, O61, O62, 62D$_1$, O63, O64, O65, O66, O68, O69, O70, O71, O73 (e.g., O73 (strain 73-1)), O74, O75, O76, O77, O78, O79, O80, O81, O82, O83, O84, O85, O86, O87, O88, O89, O90, O91, O92, O93, O95, O96, O97, O98, O99, O100, O101, O102, O103, O104, O105, O106, O107, O108, O109, O110, O111, O112, O113, O114, O115, O116, O117, O118, O119, O120, O121, O123, O124, O125, O126, O127, O128, O129, O130, O131, O132, O133, O134, O135, O136, O137, O138, O139, O140, O141, O142, O143, O144, O145, O146, O147, O148, O149, O150, O151, O152, O153, O154, O155, O156, O157, O158, O159, O160, O161, O162, O163, O164, O165, O166, O167, O168, O169, O170, O171, O172, O173, O174, O175, O176, O177, O178, O179, O180, O181, O182, O183, O184, O185, O186, and O187. In one embodiment, the serotype is O25a. In another embodiment, the serotype is O25b. In another embodiment, the serotype is O1A. In another embodiment, the serotype is O2. In another embodiment, the serotype is O6. In another embodiment, the serotype is O6. In another embodiment, the serotype is O17. In another embodiment, the serotype is O15. In another embodiment, the serotype is O18A. In another embodiment, the serotype is O75. In another embodiment, the serotype is O4. In another embodiment, the serotype is O16. In another embodiment, the serotype is O13. In another embodiment, the serotype is O7. In another embodiment, the serotype is O8.

In a preferred embodiment, the composition induces an immune response against at least two *E. coli* serotypes. In another embodiment, the composition induces an immune response against at least 3 different *E. coli* serotypes. In one embodiment, the composition induces an immune response against at least 4 different *E. coli* serotypes. In one embodiment, the composition includes an O-antigen from 5 different *E. coli* serotypes. In one embodiment, the composition induces an immune response against at least 6 different *E. coli* serotypes. In one embodiment, the composition induces an immune response against at least 7 different *E. coli* serotypes. In one embodiment, the composition induces an immune response against at least 8 different *E. coli* serotypes. In one embodiment, the composition induces an immune response against at least 9 different *E. coli* serotypes. In one embodiment, the composition induces an immune response against at least 10 different *E. coli* serotypes. In one embodiment, the composition induces an immune response against at least 11 different *E. coli* serotypes. In one embodiment, the composition induces an immune response against at least 12 different serotypes. In one embodiment, the composition induces an immune response against at least 13 different serotypes. In one embodiment, the composition induces an immune response against at least 14 different serotypes. In one embodiment, the composition induces an immune response against at least 15 different serotypes. In one embodiment, the composition induces an immune response against at least 16 different serotypes. In one embodiment, the composition induces an immune response against at least 17 different serotypes. In one embodiment, the composition induces an immune response against at least 18 different serotypes. In one embodiment, the composition induces an immune response against at least 19 different serotypes. In one embodiment, the composition induces an immune response against at least 20 different serotypes.

In one embodiment, the immunogenic composition of the invention elicits IgG antibodies in humans, said antibodies being capable of binding to a specific *E. coli* serotype saccharide, such as, for example, an *E. coli* serotype O25B saccharide, as determined by an ELISA assay. Preferably, the enhanced immune response may include an increase in the production of IgG1 and/or IgG2a and/or IgM.

In the ELISA (Enzyme-linked Immunosorbent Assay) method, antibodies from the sera of vaccinated subjects are incubated with polysaccharides which have been adsorbed to a solid support. The bound antibodies are detected using enzyme-conjugated secondary detection antibodies. The ELISA measures type specific IgG anti-*E. coli* polysaccharide antibodies present in human serum. When dilutions of human sera are added to type-specific polysaccharide-coated microtiter plates, antibodies specific for that polysaccharide bind to the microtiter plates. The antibodies bound to the plates are detected using a goat anti-human IgG alkaline phosphatase-labeled antibody followed by a p-nitrophenyl phosphate substrate. The optical density of the colored end product is proportional to the amount of anti-O-antigen polysaccharide antibody present in the serum.

In one embodiment, the immunogenic composition of the invention significantly increases the OPA titers of human subjects against *E. coli* serotypes O25B, O1, O2, and O6 as compared to the pre-immunized population.

In some embodiments, the composition of the invention is effective to increase production of antibodies against *E. coli* in a mammal to a geometric mean titer (GMT) level of at least 1,000, preferably at least 5,000 and up to 200,000 initial dosing, such as, for example, about 30 days after initial dosing, preferably about 60 days after initial dosing. In a preferred embodiment, the composition is effective to increase production of antibodies against *E. coli* serotype O25B in a mammal to a geometric mean titer (GMT) level of at least 1,000, preferably at least 5,000 and up to 200,000 after initial dosing.

In one embodiment, the immunogenic composition elicits IgG antibodies in humans, said antibodies being capable of binding an *E. coli* serotype corresponding to the repeat unit of the saccharide in the composition. For example, the composition may elicit IgG antibodies at a concentration of at least 0.2 pg/ml, 0.3 pg/ml, 0.35 pg/ml, 0.4 pg/ml or 0.5 pg/ml as determined by ELISA assay. Therefore, comparison of OPA activity of pre- and post-immunization serum with the immunogenic composition of the invention can be conducted and compared for their response to respective serotype to assess the potential increase of responders. In one embodiment, the immunogenic composition elicits IgG antibodies in humans, said antibodies being capable of killing the *E. coli* serotype corresponding to the repeat unit of the saccharide in the composition, as determined by in vitro opsonophagocytic assay. In one embodiment, the immunogenic composition elicits functional antibodies in humans, said antibodies being capable of killing the *E. coli* serotype corresponding to the repeat unit of the saccharide in the composition, as determined by in vitro opsonophagocytic assay. In one embodiment, the immunogenic composition of the invention increases the proportion of responders (i.e., individual with a serum having a titer of at least 1:8 as determined by in vitro OPA) against the *E. coli* serotype corresponding to the repeat unit of the saccharide in the composition, as compared to the pre-immunized population. In one embodiment, the immunogenic composition elicits a titer of at least 1:8 against the *E. coli* serotype corresponding to the repeat unit of the saccharide in the composition in at least 50% of the subjects as determined by in vitro opsonophagocytic killing assay. In one embodiment, the immunogenic composition of the invention elicits a titer of at least 1:8 against the *E. coli* serotype corresponding to the repeat unit of the saccharide in the composition in at least 60%, 70%, 80%, or at least 90% of the subjects as determined by in vitro opsonophagocytic killing assay. In one embodiment, the immunogenic composition of the invention significantly increases the proportion of responders (i.e., individual with a serum having a titer of at least 1:8 as determined by in vitro OPA) against the *E. coli* serotype corresponding to the repeat unit of the saccharide in the composition, as compared to the pre-immunized population. In one embodiment, the immunogenic composition of the invention significantly increases the OPA titers of human subjects against the *E. coli* serotype corresponding to the repeat unit of the saccharide in the composition as compared to the pre-immunized population.

Methods

In another aspect, the invention relates to methods of preventing infection of a subject, e.g., a human subject, including administering to the subject an effective amount of a composition (e.g., an immunogenic composition) described herein.

In another aspect, the invention relates to methods of treating infection of a subject, e.g., a human subject, including administering to the subject an effective amount of a composition (e.g., an immunogenic composition) described herein.

In another aspect, the invention relates to methods of inducing an immune response in a subject, e.g., a human subject, comprising administering to the subject an effective amount of a composition (e.g., an immunogenic composition) described herein.

In another aspect, the invention relates to methods of inducing production of opsonophagocytic antibodies in a subject, e.g., a human subject, comprising administering to the subject an effective amount of a composition (e.g., an immunogenic composition) described herein.

As used herein, the term "effective amount," in the context of administering a composition described herein to a subject refers to the amount of the composition which has a prophylactic and/or therapeutic effect(s). In certain embodiments, an "effective amount" refers to the amount of a composition which is sufficient to achieve at least one, two, three, four, or more of the following effects: (i) reduce or ameliorate the severity of an *E. coli* infection or symptom associated therewith; (ii) reduce the duration of an *E. coli* infection or symptom associated therewith; (iii) prevent the progression of an *E. coli* infection or symptom associated therewith; (iv) cause regression of an *E. coli* infection or symptom associated therewith; (v) prevent the development or onset of an *E. coli* infection, or symptom associated therewith; (vi) prevent the recurrence of an *E. coli* infection or symptom associated therewith; (vii) reduce organ failure associated with an *E. coli* infection; (viii) reduce hospitalization of a subject having an *E. coli* infection; (ix) reduce hospitalization length of a subject having an *E. coli* infection; (x) increase the survival of a subject with an *E. coli* infection; (xi) eliminate an *E. coli* infection in a subject; (xii) inhibit or reduce *E. coli* replication in a subject; and/or (xiii) enhance or improve the prophylactic or therapeutic effect(s) of another therapy.

In an embodiment, the immunogenic compositions disclosed herein are for use as a medicament. The immunogenic compositions described herein may be used in various therapeutic or prophylactic methods for preventing, treating or ameliorating a bacterial infection, disease or condition in a subject. In particular, immunogenic compositions described herein may be used to prevent, treat or ameliorate a *E. coli* infection, disease or condition in a subject.

Thus, in one aspect, the invention provides a method of preventing, treating or ameliorating an infection, disease or condition associated with *E. coli* in a subject, comprising administering to the subject an immunologically effective amount of an immunogenic composition of the invention.

In one aspect, the invention provides a method of preventing, treating or ameliorating an infection, disease or condition associated with *E. coli* in a subject, comprising administering to the subject an immunologically effective amount of an immunogenic composition of the invention.

In one aspect, the invention provides a method of inducing an immune response to *E. coli* in a subject, comprising administering to the subject an immunologically effective amount of an immunogenic composition of the invention.

In one aspect, the immunogenic compositions of the present invention are for use in a method for preventing, treating or ameliorating an infection, disease or condition caused by *E. coli* in a subject. In another aspect, the compositions of the invention are for use in a method for protecting a mammal against an infection, disease or condition caused by *E. coli*.

In one embodiment, any of the immunogenic compositions disclosed herein is for use in a method of immunizing a subject against infection by *E. coli*.

In one aspect, the present invention is directed toward the use of the immunogenic composition disclosed herein for the manufacture of a medicament for preventing, treating or ameliorating an infection, disease or condition caused by *E. coli* in a subject.

In an embodiment, the present invention is directed toward the use of the immunogenic composition disclosed herein for the manufacture of a medicament for immunizing a subject against infection by *E. coli*.

In an embodiment, the immunogenic compositions disclosed herein are for use as a vaccine. More particularly, the immunogenic compositions described herein may be used to prevent *E. coli* infections in a subject. Thus, in one aspect, the invention provides a method of preventing an infection by *E. coli* in a subject, comprising administering to the subject an immunologically effective amount of an immunogenic composition of the invention.

In some such embodiments, the infection is selected from any one of urinary tract infection, cholecystitis, cholangitis, diarrhea, hemolytic uremic syndrome, neonatal meningitis, urosepsis, intra-abdominal infection, meningitis, complicated pneumonia, wound infection, post-prostate biopsy-related infection, neonatal/infant sepsis, neutropenic fever, pneumonia, bacteremia, and sepsis, and other blood stream infection. For example, *E. coli* serotypes that are associated with neonatal meningitis include serotypes O1, O6, O7, O16, O18 and O83. Accordingly, in one embodiment, the composition includes a conjugate that includes a saccharide having a structure selected from any one of Formula O1, Formula O6, Formula O7, Formula O16, Formula O18, Formula O83, and any combination of conjugates thereof. As another example, *E. coli* serotypes that are associated with bacteremia include serotypes O1, O2, O6, O15 and O75. Accordingly, in another embodiment, the composition includes at least one conjugate that includes a saccharide having a structure selected from any one of Formula O1, O2, O6, O15 and O75, and any combination of conjugates thereof. As a further example, *E. coli* O1 and O2 strains, such as O1: K1: H7 or O2: K1: H4, O2: K1: H5, O2: K1: H6, and O2: K1: $H_7$, were identified as causative agents of urinary tract infection, septicaemia, and neonatal meningitis in humans and animals. Both O1 and O2 serogroups account for the majority of strains causing bacteraemia and sepsis in human patients. Accordingly, in one embodiment, the composition includes a conjugate that includes saccharide having Formula O1 and a conjugate that includes a saccharide having Formula O2.

Accordingly, by raising an immune response in the mammal by these uses and methods, the mammal can be protected against *E. coli* infection, including ExPEC and non-ExPEC strains. The invention is particularly useful for providing broad protection against pathogenic *E. coli*, including intestinal pathotypes such as EPEC, EAEC, EIEC, ETEC and DAEC pathotypes. Thus the mammal may be protected against diseases including, but not limited to peritonitis, pyelonephritis, cystitis, endocarditis, prostatitis, urinary tract infections (UTIs), meningitis (particularly neonatal meningitis), sepsis (or SIRS), dehydration, pneumonia, diarrhea (infantile, travellers', acute, persistent, etc.), bacillary dysentery, hemolytic uremic syndrome (HUS), pericarditis, bacteriuria, etc.

In one aspect, the subject to be vaccinated is a mammal, such as a human, cat, sheep, pig, horse, bovine or dog. Preferably, the subject to be vaccinated is a human. Where the vaccine is for prophylactic use, the human is preferably a child (e.g. a toddler or infant) or a teenager or an adult; where the vaccine is for therapeutic use, the human is preferably a teenager or an adult. A vaccine intended for children may also be administered to adults e.g. to assess safety, dosage, immunogenicity, etc.

Vaccines of the invention may be used to treat both children and adults. Thus a human patient may be less than 1 year old, 1-5 years old, 5-15 years old, 15-55 years old, or at least 55 years old. Preferred patients for receiving the vaccines are the elderly (e.g. ≥50 years old, ≥60 years old, and preferably ≥65 years), the young (e.g. ≤5 years old), hospitalised patients, healthcare workers, armed service and military personnel, pregnant women, the chronically ill, or immunodeficient patients. The vaccines are not suitable solely for these groups, however, and may be used more generally in a population.

Vaccines of the invention are particularly useful for patients who are expecting a surgical operation, or other hospital in-patients. They are also useful in patients who will be catheterized. They are also useful in adolescent females (e.g. aged 11-18) and in patients with chronic urinary tract infections.

In an embodiment, the immunogenic compositions disclosed herein are administered by intramuscular, intraperitoneal, intradermal or subcutaneous routes. In an embodiment, the immunogenic compositions disclosed herein are administered by intramuscular, intraperitoneal, intradermal or subcutaneous injection. In an embodiment, the immunogenic compositions disclosed herein are administered by intramuscular or subcutaneous injection.

In an embodiment, the invention is directed toward a method comprising the step of (i) injecting to a subject an immunologically effective amount of any of the immunogenic compositions defined herein; (ii) collecting a serum sample from said subject; (iii) testing said serum sample for opsonophagocytic killing activity against *E. coli* serotype O25B by in vitro opsonophagocytic killing assay (OPA).

Subjects

As disclosed herein, the immunogenic compositions described herein may be used in various therapeutic or prophylactic methods for preventing, treating or ameliorating a bacterial infection, disease or condition in a subject.

In a preferred embodiment, said subject is a human. In a most preferred embodiment, said subject is a newborn (i.e., under three months of age), an infant (i.e., from 3 months to one year of age) or a toddler (i.e., from one year to four years of age).

In an embodiment, the immunogenic compositions disclosed herein are for use as a vaccine.

In an embodiment, the subject to be vaccinated may be less than 1 year of age. For example, the subject to be vaccinated can be about 1, about 2, about 3, about 4, about 5, about 6, about 7, about 8, about 9, about 10, about 11 or about 12 months of age. In an embodiment, the subject to be vaccinated is about 2, 4 or 6 months of age. In another embodiment, the subject to be vaccinated is less than 2 years of age. For example, the subject to be vaccinated can be about 12 to about 15 months of age. In some cases, as little as one dose of the immunogenic composition according to the invention is needed, but under some circumstances, a second, third or fourth dose may be administered.

In an embodiment, the subject to be vaccinated may be less than 18 years of age. For example, the subject to be vaccinated can be about 1, about 2, about 3, about 4, about 5, about 6, about 7, about 8, about 9, about 10, about 11, about 12, about 13, about 14, about 15, about 16, or about 17 years of age. For example, the subject to be vaccinated can be about 10 to about 18 years of age. In some cases, as little as one dose of the immunogenic composition according to the invention is needed, but under some circumstances, a second, third or fourth dose may be administered.

In another embodiment, the subject to be vaccinated may be a human 18 years of age or order. For example, the subject to be vaccinated can be about 18 to about 50 years of age. In some cases, as little as one dose of the immunogenic composition according to the invention is needed, but under some circumstances, a second, third or fourth dose may be administered.

In an embodiment of the present invention, the subject to be vaccinated is a human 50 years of age or older, more preferably a human 55 years of age or older. In an embodiment, the subject to be vaccinated is a human 65 years of age or older, 70 years of age or older, 75 years of age or older or 80 years of age or older. In an embodiment the subject to be vaccinated is an immunocompromised individual, a human. An immunocompromised individual is generally defined as a person who exhibits an attenuated or reduced ability to mount a normal humoral or cellular defense to challenge by infectious agents.

In an embodiment of the present invention, the immunocompromised subject to be vaccinated suffers from a disease or condition that impairs the immune system and results in an antibody response that is insufficient to protect against or treat a urinary tract infection.

In an embodiment, said disease is a primary immunodeficiency disorder. Preferably, said primary immunodeficiency disorder is selected from any one of combined T- and B-cell immunodeficiencies, antibody deficiencies, well-defined syndromes, immune dysregulation diseases, phagocyte disorders, innate immunity deficiencies, autoinflammatory disorders, and complement deficiencies.

In a particular embodiment of the present invention, the immunocompromised subject to be vaccinated suffers from a disease selected from any one of HIV-infection, acquired immunodeficiency syndrome (AIDS), cancer, chronic heart or lung disorders, congestive heart failure, diabetes mellitus, chronic liver disease, alcoholism, cirrhosis, spinal fluid leaks, cardiomyopathy, chronic bronchitis, emphysema, chronic obstructive pulmonary disease (COPD), spleen dysfunction (such as sickle cell disease), lack of spleen function (asplenia), blood malignancy, leukemia, multiple myeloma, Hodgkin's disease, lymphoma, kidney failure, nephrotic syndrome and asthma.

In an embodiment of the present invention, the subject to be vaccinated suffers from malnutrition.

In an embodiment of the present invention, the subject to be vaccinated is taking a drug or treatment that lowers the body's resistance to infection.

In an embodiment of the present invention, the subject to be vaccinated is a smoker.

In an embodiment of the present invention, the subject to be vaccinated has a white blood cell count (leukocyte count) below $5 \times 10^9$ cells per liter, or below $4 \times 10^9$ cells per liter, or below $3 \times 10^9$ cells per liter, or below $2 \times 10^9$ cells per liter, or below $1 \times 10^9$ cells per liter, or below $0.5 \times 10^9$ cells per liter, or below $0.3 \times 10^9$ cells per liter, or below $0.1 \times 10^9$ cells per liter. White blood cell count (leukocyte count): The number of white blood cells (WBC) in the blood. The WBC is usually measured as part of the CBC (complete blood count). White blood cells are the infection-fighting cells in the blood and are distinct from the red (oxygen-carrying) blood cells known as erythrocytes. There are different types of white blood cells, including neutrophils (polymorphonuclear leukocytes; PMN), band cells (slightly immature neutrophils), T-type lymphocytes (T-cells), B-type lymphocytes (B-cells), monocytes, eosinophils, and basophils. All the types of white blood cells are reflected in the white blood cell count. The normal range for the white blood cell count is usually between 4,300 and 10,800 cells per cubic millimeter of blood. This can also be referred to as the leukocyte count and can be expressed in international units as 4.3-$10.8 \times 10^9$ cells per liter.

In an embodiment, the subject to be vaccinated suffers from neutropenia. For example, the subject to be vaccinated may have a neutrophil count below $2 \times 10^9$ cells per liter, or below $1 \times 10^9$ cells per liter, or below $0.5 \times 10^9$ cells per liter, or below $0.1 \times 10^9$ cells per liter, or below $0.05 \times 10^9$ cells per liter.

A low white blood cell count or "neutropenia" is a condition characterized by abnormally low levels of neutrophils in the circulating blood. Neutrophils are a specific kind of white blood cell that help prevent and fight infections. The most common reason that cancer patients experience neutropenia is as a side effect of chemotherapy. Chemotherapy-induced neutropenia increases a patient's risk of infection and disrupts cancer treatment.

In an embodiment, the subject to be vaccinated has a CD4+ cell count below $500/mm^3$, or CD4+ cell count below $300/mm^3$, or CD4+ cell count below $200/mm^3$, CD4+ cell count below $100/mm^3$, CD4+ cell count below $75/mm^3$, or CD4+ cell count below $50/mm^3$.

CD4 cell tests are normally reported as the number of cells in $mm^3$. Normal CD4 counts are between 500 and 1600, and CD8 counts are between 375 and 1 100. CD4 counts drop dramatically in people with HIV.

In an embodiment of the invention, any of the immunocompromised subject disclosed herein is a human male or a human female.

Regimen

In some cases, as little as one dose of the immunogenic composition according to the invention is effective, under other circumstances, such as conditions of greater immune deficiency, a second, third or fourth dose may be administered. Following an initial vaccination, subjects can receive one or several booster immunizations adequately spaced.

In an embodiment, the schedule of vaccination of the immunogenic composition according to the invention is a single dose. In another embodiment, said single dose schedule is for healthy persons being at least 2 years of age.

In an embodiment, the schedule of vaccination of the immunogenic composition according to the invention is a multiple dose schedule. In another embodiment, said multiple dose schedule includes a series of 2 doses separated by an interval of about 1 month to about 2 months. In an embodiment, said multiple dose schedule includes a series of 2 doses separated by an interval of about 1 month, or a series of 2 doses separated by an interval of about 2 months.

In another embodiment, said multiple dose schedule includes a series of 3 doses separated by an interval of about 1 month to about 2 months. In another embodiment, said multiple dose schedule includes a series of 3 doses separated by an interval of about 1 month, or a series of 3 doses separated by an interval of about 2 months.

In another embodiment, said multiple dose schedule includes a series of 3 doses separated by an interval of about 1 month to about 2 months followed by a fourth dose about 10 months to about 13 months after the first dose. In another embodiment, said multiple dose schedule includes a series of 3 doses separated by an interval of about 1 month followed by a fourth dose about 10 months to about 13 months after the first dose, or a series of 3 doses separated by an interval of about 2 months followed by a fourth dose about 10 months to about 13 months after the first dose.

In an embodiment, the multiple dose schedule includes at least one dose (e.g., 1, 2 or 3 doses) in the first year of age followed by at least one toddler dose.

In an embodiment, the multiple dose schedule includes a series of 2 or 3 doses separated by an interval of about 1 month to about 2 months (for example 28-56 days between doses), starting at 2 months of age, and followed by a toddler dose at 12-18 months of age. In an embodiment, said multiple dose schedule includes a series of 3 doses separated by an interval of about 1 to 2 months (for example 28-56 days between doses), starting at 2 months of age, and followed by a toddler dose at 12-15 months of age. In another embodiment, said multiple dose schedule includes a series of 2 doses separated by an interval of about 2 months, starting at 2 months of age, and followed by a toddler dose at 12-18 months of age.

In an embodiment, the multiple dose schedule includes a 4-dose series of vaccine at 2, 4, 6, and 12-15 months of age.

In an embodiment, a prime dose is given at day 0 and one or more boosts are given at intervals that range from about 2 to about 24 weeks, preferably with a dosing interval of 4-8 weeks.

In an embodiment, a prime dose is given at day 0 and a boost is given about 3 months later.

Kit and Process

In an embodiment, the invention is directed toward a kit comprising an immunogenic composition disclosed herein and an information leaflet.

In an embodiment said information leaflet includes the ability of the composition to elicit functional antibodies against $E.$ $coli$.

In an embodiment said information leaflet includes the ability of the composition to elicit OPA titers against $E.$ $coli$ serotype O25B in a human population. In an embodiment said information leaflet includes the ability of the composition to elicit OPA titers against $E.$ $coli$ serotype O1 in a human population. In an embodiment said information leaflet includes the ability of the composition to elicit OPA titers against $E.$ $coli$ serotype O2 in a human population. In an embodiment said information leaflet includes the ability of the composition to elicit OPA titers against $E.$ $coli$ serotype O6 in a human population.

In an embodiment, the invention is directed toward a process for producing a kit comprising an immunogenic composition and an information leaflet, said process comprising the step of (i) producing an immunogenic composition of the present disclosure and (ii) combining in the same kit said immunogenic composition and information leaflet, wherein said information leaflet mentions the ability of said composition to elicit functional antibodies against $E.$ $coli$.

In an embodiment, the invention is directed toward a process for producing a kit comprising an immunogenic composition and an information leaflet, said process comprising the step of (i) producing an immunogenic composition of the present disclosure and (ii) combining in the same kit said immunogenic composition and information leaflet, wherein said information leaflet mentions the ability of the composition to elicit anti-O-antigen antibodies against $E.$ $coli$ in a human population.

In an embodiment, the invention is directed toward a process for producing a kit comprising an immunogenic composition and an information leaflet, said process comprising the step of (i) producing an immunogenic composition of the present disclosure and (ii) combining in the same kit said immunogenic composition and information leaflet, wherein said information leaflet mentions the ability of the composition to elicit OPA titers against $E.$ $coli$ in a human population.

In an embodiment, the invention is directed toward a process for producing a kit comprising an immunogenic composition and an information leaflet, said process comprising the step of (i) producing an immunogenic composition of the present disclosure; (ii) printing an information leaflet wherein said information leaflet mentions the ability of said composition to elicit functional antibodies against $E.$ $coli$; (iii) combining in the same kit said immunogenic composition and said information leaflet.

In an embodiment, the invention is directed toward a process for producing a kit comprising an immunogenic composition and an information leaflet, said process comprising the step of (i) producing an immunogenic composition of the present disclosure; (ii) printing an information leaflet wherein said information leaflet mentions the ability of the composition to elicit OPA titers against $E.$ $coli$ in a human population; (iii) combining in the same kit said immunogenic composition and said information leaflet.

EXAMPLES

In order that this invention may be better understood, the following examples are set forth. These examples are for purposes of illustration only and are not to be construed as limiting the scope of the invention in any manner. The following Examples illustrate some embodiments of the invention.

Example 1: $E.$ $coli$ and $S.$ $enterica$ Strains

Clinical strains and derivatives are listed in Table 3. Additional reference strains included: O25K5H1, a clinical O25a serotype strain; and $S.$ $enterica$ serovar $Typhimurium$ strain LT2.

Gene knockouts in *E. coli* strains removing the targeted open-reading frame but leaving a short scar sequence were constructed.

The hydrolyzed O-antigen chain and core sugars are indicated subsequently as O-Polysaccharide (OPS) for simplicity.

TABLE 3

*E. coli* Strains

| Strain | Strain Alias | Genotype | Serotype |
|---|---|---|---|
| GAR2401 | PFEEC0100 | wt (blood isolate) | O25b |
| '2401ΔwzzB | — | ΔwzzB | O25b |
| '2401ΔAraAΔ(OPS) | — | ΔAraA Δ(rflB-wzzB) | OPS- |
| O25K5H1 | PFEEC0101 | wt | O25a |
| O25K5H1ΔwzzB | — | ΔwzzB | O25a |
| BD559 | — | W3110 ΔAraA ΔfhuA ΔrecA | OPS- |
| BD559ΔwzzB | — | W3110 ΔAraA ΔfhuA ΔrecAΔwzzB | OPS- |

TABLE 3-continued

*E. coli* Strains

| Strain | Strain Alias | Genotype | Serotype |
|---|---|---|---|
| BD559Δ(OPS) | — | BD559 Δ(rflB-wzzB) | OPS- |
| GAR2831 | PFEEC0102 | wt (blood isolate) | O25b |
| GAR865 | PFEEC0103 | wt (blood isolate) | O2 |
| GAR868 | PFEEC0104 | wt (blood isolate) | O2 |
| GAR869 | PFEEC0105 | wt (blood isolate) | O15 |
| GAR872 | PFEEC0106 | wt (blood isolate) | O1 |
| GAR878 | PFEEC0107 | wt (blood isolate) | O75 |
| GAR896 | PFEEC0108 | wt (blood isolate) | O15 |
| GAR1902 | PFEEC0109 | wt (blood isolate) | O6 |
| Atlas187913 | PFEEC0068 | wt (blood isolate) | O25b |
| *Salmonella enterica* serovar Typhimurium strain LT2 | — | wt | N/A |

Example 2: Oligonucleotide Primers for wzzB, fepE and O-Antigen Gene Cluster Cloning

TABLE 4

Oligonucleotide Primers

| Name | Primer Sequence | Comments |
|---|---|---|
| LT2wzzB_S | GAAGCAAACCGTACGCGTAAAG (SEQ ID NO: 1) | based on Genbank GCA_000006945.2 *Salmonella enterica* serovar Typhimurium strain LT2 |
| LT2wzzB_AS | CGACCAGCTCTTACACGGCG (SEQ ID NO: 2) | |
| O25bFepE_S | GAAATAGGACCACTAATAAATACACAAATTAAT AAC (SEQ ID NO: 3) | Based on Genbank GCA_000285655.3 O25b EC958 strain ST131 assembly and O25b GAR2401 WGS data |
| O25bFepE_A | ATAATTGACGATCCGGTTGCC (SEQ ID NO: 4) | |
| wzzB P1_S | GCTATTTACGCCCTGATTGTCTTTTGT (SEQ ID NO: 5) | based on *E. coli* K-12 strain sequence, Genbank MG1655 NC_000913.3 or W3110 assembly GCA_000010245.1 |
| wzzB P2_AS | ATTGAGAACCTGCGTAAACGGC (SEQ ID NO: 6) | |
| wzzB P3_S | TGAAGAGCGGTTCAGATAACTTCC (SEQ ID NO: 7) (UDP-glucose-6-dehydrogenase) | |
| wzzB P4_AS | CGATCCGGAAACCTCCTACAC (SEQ ID NO: 8) (Phosphoribosyl-AMP cyclohydrolase/ Phosphoribosyl-ATP pyrophosphohydrolase) | |
| O157 FepE_S | GATTATTCGCGCAACGCTAAACAGAT (SEQ ID NO: 9) | *E. coli* O157 fepE (based on Genbank EDL933 strain GCA_000732965.1) |
| O157 FepE_AS | TGATCATTGACGATCCGGTAGCC (SEQ ID NO: 10) | |
| pBAD33_ adaptor_S | CGGTAGCTGTAAAGCCAGGGGCGGTAGCGTG GTTTAAACCCAAGCAACAGATCGGCGTCGTCG GTATGGA (SEQ ID NO: 11) | Adaptor has central PmeI site and homology to conserved 5' OAg operon promoter and 3' gnd gene sequences |
| pBAD33_ada ptor AS | AGCTTCCATACCGACGACGCCGATCTGTTGCT TGGGTTTAAACCACGCTACCGCCCCTGGCTTT ACAGCTACCGAGCT (SEQ ID NO: 12) | |
| JUMPSTART_r | GGTAGCTGTAAAGCCAGGGGCGGTAGCGTG (SEQ ID NO: 13) | Universal Jumpstart (OAg operon promoter) |
| gnd_f | CCATACCGACGACGCCGATCTGTTGCTTGG (SEQ ID NO: 14) | Universal 3' OAg (gnd) operon antisense primer |

Example 3: Plasmids

Figure 1B:
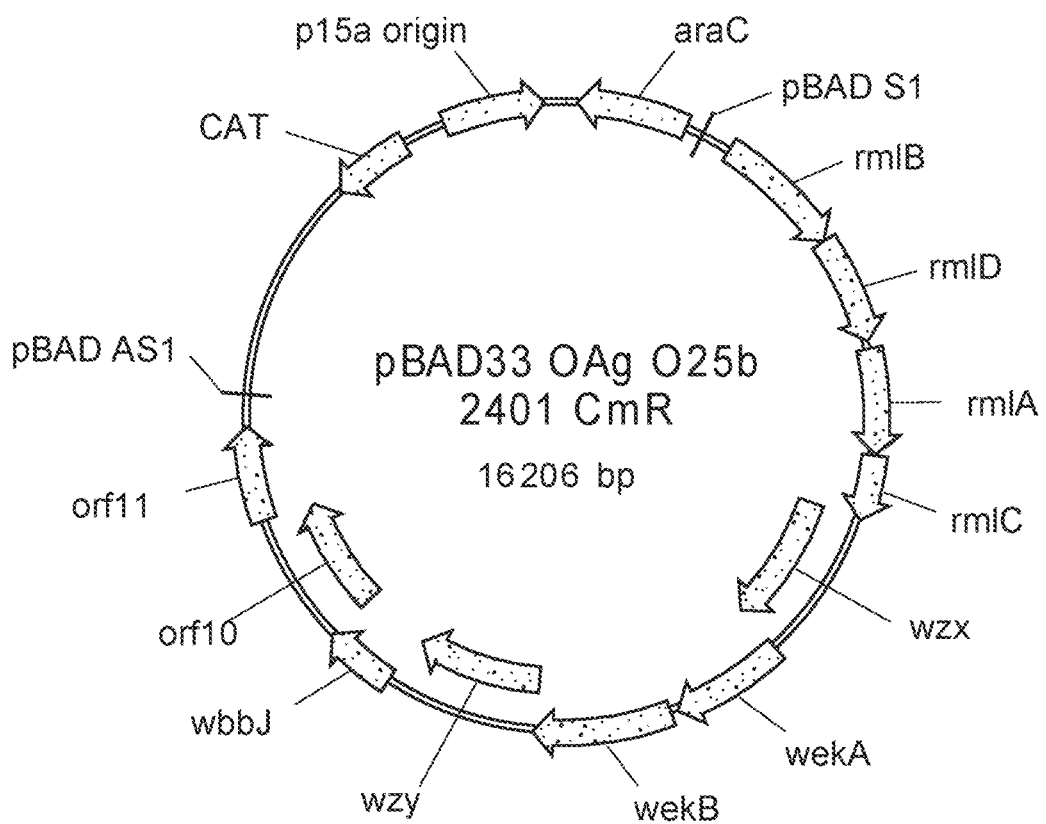

Plasmid vectors and subclones are listed in Table 5. PCR fragments harboring various *E. coli* and *Salmonella* wzzB and fepE genes were amplified from purified genomic DNA and subcloned into the high copy number plasmid provided in the Invitrogen PCR® Blunt cloning kit FIG. 1. This plasmid is based on the pUC replicon. Primers P3 and P4 were used to amplify *E. coli* wzzB genes with their native promoter, and are designed to bind to regions in proximal and distal genes encoding UDP-glucose-6-dehydrogenase and phosphoribosyladenine nucleotide hydrolase respectively (annotated in Genbank MG1655 NC_000913.3). A PCR fragment containing *Salmonella* fepE gene and promoter were amplified using primers previously described. Analogous *E. coli* fepE primers were designed based on available Genbank genome sequences or whole genome data generated internally (in case of GAR2401 and O25K5H$_1$). Low copy number plasmid pBAD33 was used to express O-antigen biosynthetic genes under control of the arabinose promoter. The plasmid was first modified to facilitate cloning (via Gibson method) of long PCR fragments amplified using universal primers homologous to the 5' promoter and 3' 6-phosphogluconate dehydrogenase (gnd) gene Table 5. The pBAD33 subclone containing the O25b biosynthetic operon is illustrated in FIG. 1.

TABLE 5

Plasmids

| Name | Replicon | Resistance marker | Comments |
| --- | --- | --- | --- |
| PCR ® Blunt II TOPO | pUC | KanR | Invitrogen PCR cloning vector |
| pBAD33 | P15a | CamR | Arabinose inducible vector |
| pBAD33-OAg | P15a | CamR | OAg operon Gibson cloning vector |
| pBAD33-O25b | P15a | CamR | O25b 0Ag expression plasmid |
| pBAD33-O21 | P15a | CamR | O21 OAg expression plasmid |
| pBAD33-O16 | P15a | CamR | O16 OAg expression plasmid |
| pBAD33-O75 | P15a | CamR | O75 OAg expression plasmid |
| pBAD33-O1 | P15a | CamR | O1 OAg expression plasmid |
| pBAD33-O2 | P15a | CamR | O2 OAg expression plasmid |
| pTOPO-O25b 2401 wzzB | pUC | KanR | GAR 2401 gDNA template |
| pTOPO-O25b 2401 fepE | pUC | KanR | |
| pTOPO-K12 wzzB | pUC | KanR | *E. coli* K-12 strain gDNA template |
| pTOPO-O25a wzzB | pUC | KanR | *E. coli* O25a strain O25K5H1 gDNA template |
| pTOPO-O25a fepE | pUC | KanR | |
| pTOPO-*Salmonella* LT2 wzzB | pUC | KanR | *Salmonella enterica* serovar *Typhimurium* strain LT2 gDNA template |
| pTOPO-*Salmonella* LT2 fepE | pUC | KanR | |
| pTOPO-O25a ETEC wzzB | pUC | KanR | O25a ETEC strain gDNA |
| pTOPO-O25a ETEC fepE | pUC | KanR | purchased from ATCC ("NR-5" E2539-C1) |
| pTOPO-O157fepE | pUC | KanR | O157:H7:K- *Shigella* toxin strain gDNA purchased from ATCC (EDL933 #43895D-5) |

Example 4: O-Antigen Purification

The fermentation broth was treated with acetic acid to a final concentration of 1-2% (final pH of 4.1). The extraction of OAg and delipidation were achieved by heating the acid treated broth to 100° C. for 2 hours. At the end of the acid hydrolysis, the batch was cooled to ambient temperature and 14% NH$_4$OH was added to a final pH of 6.1. The neutralized broth was centrifuged and the centrate was collected. To the centrate was added CaCl$_2$) in sodium phosphate and the resulting slurry was incubated for 30 mins at room temperature. The solids were removed by centrifugation and the centrate was concentrated 12-fold using a 10 kDa membrane, followed by two diafiltrations against water. The retentate which contained OAg was then purified using a carbon filter. The carbon filtrate was diluted 1:1 (v/v) with 4.0M ammonium sulfate. The final ammonium sulfate concentration was 2M. The ammonium sulfate treated carbon filtrate was further purified using a membrane with 2M ammonium sulfate as the running buffer. The OAg was collected in the flow through. For the long OAg the HIC filtrate was concentrated and then buffer exchanged against water (20 diavolumes) using a 5 kDa membrane. For the short (native) OAg polysaccharide, the MWCO was further reduced to enhance yield.

Example 5: Conjugation of O25b Long O-Antigen to CRM$_{197}$

The first set of long chain O25b polysaccharide-CRM$_{197}$ conjugates were produced using periodate oxidation followed by conjugation using reductive amination chemistry (RAC) (Table 7). Conjugate variants with three activation levels (low, medium and high) by varying the oxidation levels. Conjugates were produced by reacting the lyophilized activated polysaccharides with lyophilized CRM$_{197}$, reconstituted in DMSO medium, using sodium cyanoborohydride as the reducing agent. Conjugation reactions were carried out at 23° C. for 24 hrs, followed by capping using sodium borohydride for 3 hrs. Following the conjugation quenching step, conjugates were purified by ultrafiltration/diafiltration with 100K MWCO regenerated cellulose membrane, using 5 mM Succinate/0.9% NaCl, pH 6.0. Final filtration of the conjugates were performed using a 0.22 µm membrane.

Unless expressly stated otherwise, the conjugates disclosed throughout the following Examples include a core saccharide moiety.

1.1. Long O-Antigen Expression Conferred by Heterologous Polymerase Chain Length Regulators Initial *E. coli* strain construction focused on the O25 serotype. Goal was to overexpress heterologous wzzB or fepE genes to see if they confer longer chain length in O25 wzzB knockout strains. First, blood isolates were screened by PCR to identify strains of the O25a and O25b subtype. Next, strains were screened for sensitivity to ampicillin. A single ampicillin-sensitive O25b isolate GAR2401 was identified into which a wzzB deletion was introduced. Similarly, a wzzB deletion was made in O25a strain O25K5H1. For genetic complementation of these mutations, wzzB genes from GAR 2401 and O25K5H1 were subcloned into the high copy PCR-Blunt II cloning vector and introduced into both strains by electroporation. Additional wzzB genes from *E. coli* K-12 and *S. enterica* serovar *Typhimurium* LT2 were similarly cloned and transferred; likewise fepE genes from *E. coli* O25K5H1, GAR 2401, O25a ETEC NR-5, O157: H7: K- and *S. enterica* serovar *Typhimurium* LT2.

Figure 3A:
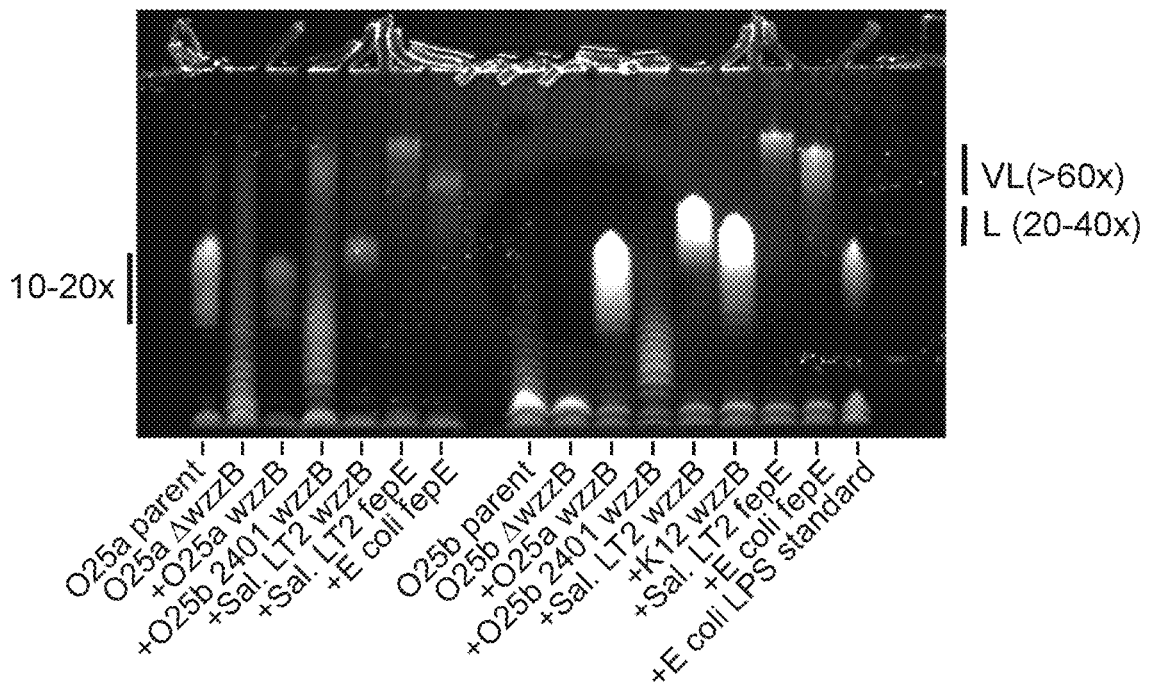
FIG. 3A-B: Modulation of O-antigen chain length in serotype O25a and O25b strains by plasmid-based expression of heterologous wzzB and fepE chain length regulators. Genetic complementation of LPS expression in plasmid transformants of wzzB knockout strains O25K5H1 (O25a) and GAR2401 (O25b) is shown. On the left side of FIG. 3A, LPS profiles of plasmid transformants of O25a O25K5HΔwzzB are shown; and on the right, analogous profiles of O25b GAR 2401ΔwzzB transformants. An immunoblot of a replicate gel probed with O25-specific sera (Statens Serum Institut) is shown in FIG. 3B. O25a ΔwxxB (Knock out) background associated with Lanes 1-7; O25b 2401 ΔwzzB (Knock out) background) associated with Lanes 8-15.
Figure 3B:
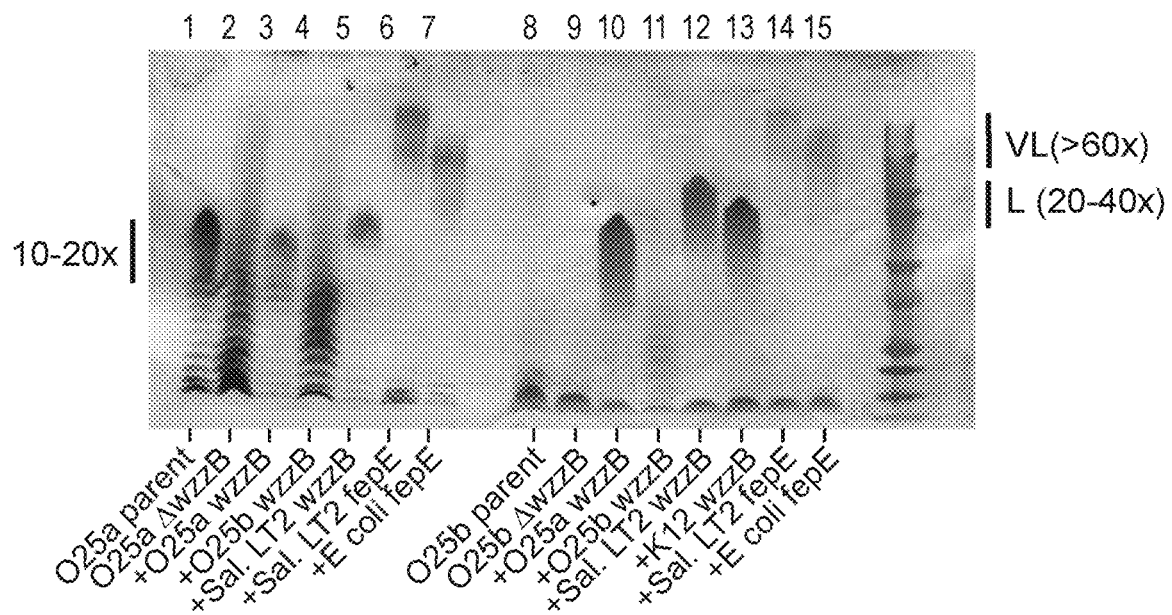

Genetic complementation of LPS expression in plasmid transformants of wzzB knockout strains O25K5H1 (O25a) and GAR2401 (O25b) is shown in FIG. 2. Bacteria were grown overnight in LB medium and LPS was extracted with phenol, resolved by SDS PAGE (4-12% acrylamide) and stained. Each well of the gel was loaded with LPS extracted from the same number of bacterial cells (approximately 2 $OD_{600}$ units). Size of LPS was estimated from an internal native *E. coli* LPS standard and by counting the ladder discernable from a subset of samples showing a broad distribution of chain lengths (differing by one repeat unit). On the left side of panel A of FIG. 3, LPS profiles of plasmid transformants of O25a O25K5HΔwzzB are shown; and on the right, analogous profiles of O25b GAR 2401ΔwzzB transformants. An immunoblot of a replicate gel probed with O25-specific sera is shown in panel B of FIG. 3.

Results from this experiment show that introduction of the homologous wzzB gene into the *E. coli* O25aΔwzzB host restores expression of short O25 LPS (10-20×), as does the *Salmonella* LT2 wzzB. Introduction of the O25b wzzB gene from GAR2401 does not, suggesting the WzzB enzyme from this strain is defective. A comparison of *E. coli* WzzB amino acid sequences suggests that A210E and P253S substitutions may be responsible. Significantly, *Salmonella* LT2 fepE and *E. coli* fepE from O25a O25K5H1 conferred the ability to express very long (VL) OAg LPS, with the *Salmonella* LT2 fepE resulting in OAg exceeding in size that conferred by *E. coli* fepE.

Figure 4:
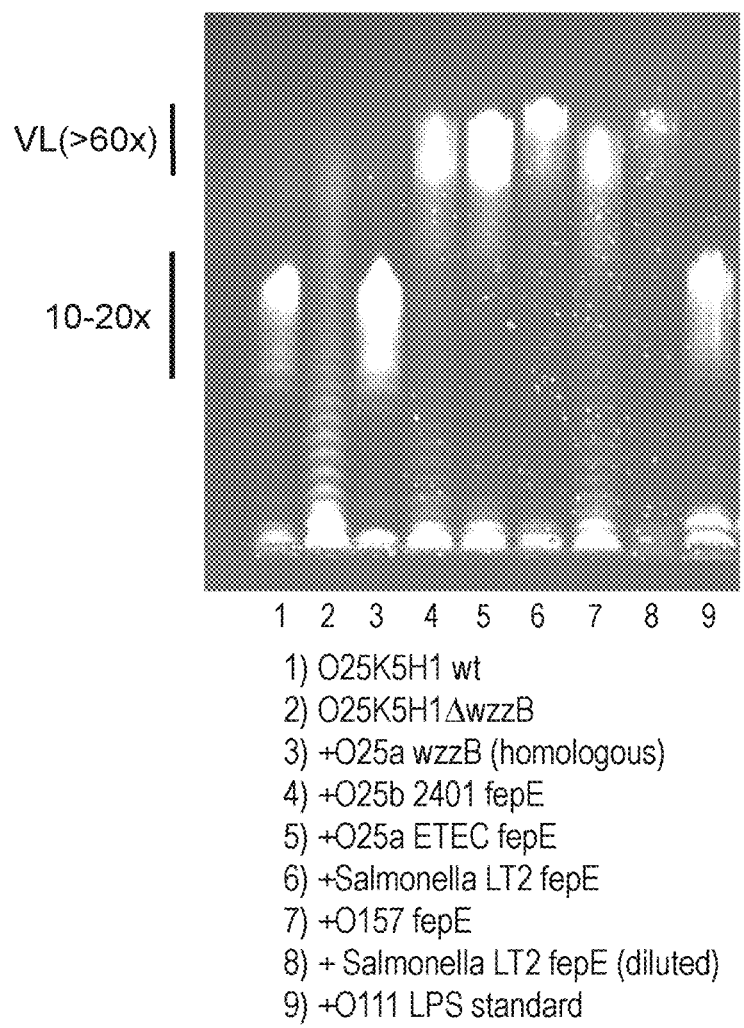
FIG. 4—Long chain O-antigen expression conferred by *E. coli* and *Salmonella* fepE plasmids in host O25K5H1ΔwzzB FIG. 5—FepE amino acid sequence alignments. The O157 FepE amino acid sequence is SEQ ID NO: 18; the O25a ETEC ATCC FepE amino acid sequence is SEQ ID NO: 17; the O25a: K5: H1 FepE amino acid sequence is SEQ ID NO: 16; the O25b 2401 FepE amino acid sequence is SEQ ID NO: 15; the *Salmonella* LT2 FepE amino acid sequence is SEQ ID NO: 19.

A similar pattern of expression was observed with GAR2401ΔwzzB transformants: *E. coli* O25a or K12 strain wzzB restored ability to produce short LPS. The *Salmonella* LT2 fepE generated the longest LPS, the *E. coli* fepE a slightly shorter LPS, while the *Salmonella* LT2 wzzB yielded an intermediate sized long LPS (L). The ability of other *E. coli* fepE genes to produce very long LPS was assessed in a separate experiment with transformants of *E. coli* O25aΔwzzB. The fepE genes from GAR2401, an O25a ETEC strain and an O157 *Shigella* toxin producing strain also conferred the ability to produce very long LPS, but not as long as the LPS generated with the *Salmonella* LT2 fepE (FIG. 4). An alignment of the FepE amino acid sequences is shown in FIG. 5.

Figure 6:
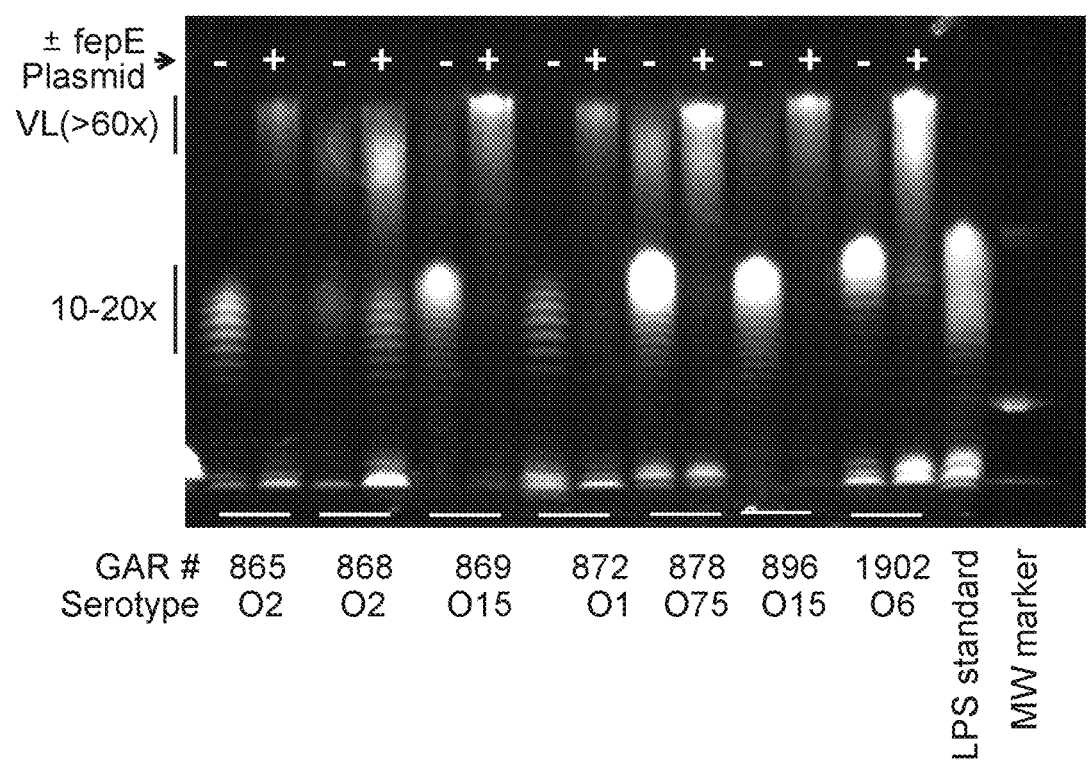
FIG. 6—*Salmonella* fepE expression generates Long O-antigen LPS in a variety of clinical isolates FIG. 7A-B—Plasmid-mediated Arabinose-inducible Expression of O25b Long O-antigen LPS in O25b O-antigen knock-out host strain. Results from an SPS PAGE are shown in FIG. 7A and results from an O25 Immuno-Blot are shown in FIG. 7B, wherein Lane 1 is from Clone 1, no arabinose; Lane 2 is from Clone 1, 0.2% arabinose; Lane 3 is from Clone 9, no Arabinose; Lane 4 is from Clone 9, 0.2% Arabinose; Lane 5 is from O55 *E. coli* LPS Standard; and Lane 6 is from O111 *E. coli* LPS Standard, in both FIG. 7A and in FIG. 7B.

Having established in serotype O25a and O25b strains that *Salmonella* LT2 fepE generates the longest LPS of the polymerase regulators evaluated, we next sought to determine whether it would also produce very long LPS in other *E. coli* serotypes. Wild-type bacteremia isolates of serotype O1, O2, O6, O15 and O75 were transformed with the *Salmonella* fepE plasmid and LPS extracted. The results shown in FIG. 6 confirm that *Salmonella* fepE can confer the ability to make very long LPS in other prevalent serotypes associated with blood-infections. Results also show that plasmid-based expression of *Salmonella* fepE appears to override the control of chain length normally exerted by endogenous wzzB in these strains.

1.2. Plasmid-Based Expression of O-Antigens in a Common *E. coli* Host Strain.

Figure 7A:
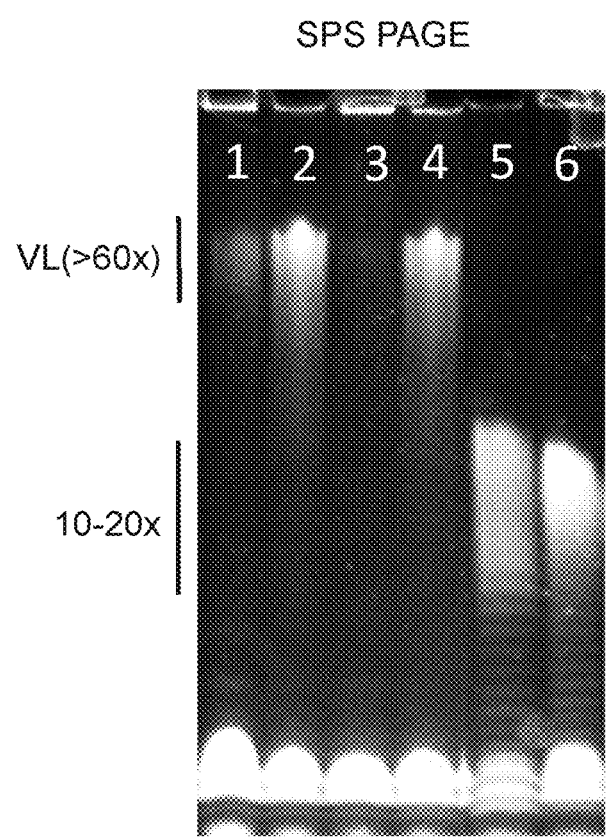
Figure 7B:
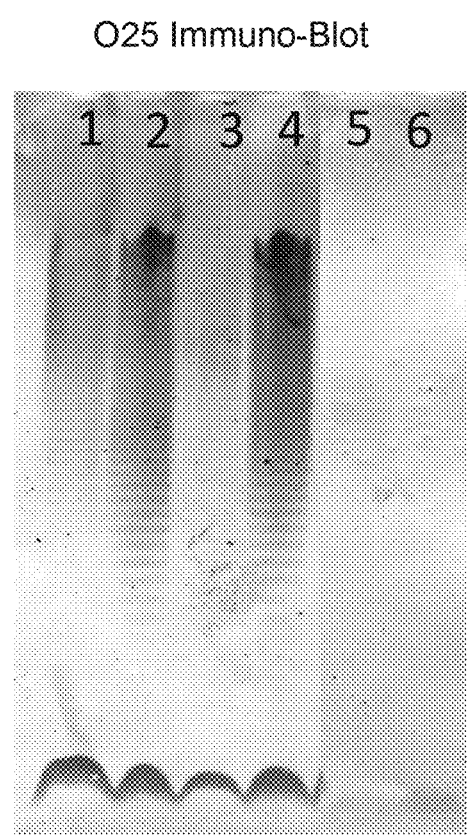

From the perspective of bioprocess development, the ability to produce O-antigens of different serotypes in a common *E. coli* host instead of multiple strains would greatly simplify the manufacturing of individual antigens. To this end, O-antigen gene clusters from different serotypes were amplified by PCR and cloned into a low-copy number plasmid (pBAD33) under control of an arabinose regulated promoter. This plasmid is compatible (can coexist) with the *Salmonella* LT2 fepE plasmid in *E. coli* as it harbors a different (p15a) replicon and different selectable marker (chloramphenicol vs kanamycin). In a first experiment, a pBAD33 O25b operon plasmid subclone was cotransfected with the *Salmonella* LT2 fepE plasmid into GAR2401ΔwzzB and transformants grown in the presence or absence of 0.2% arabinose. Results shown in FIG. 7 demonstrated that very long O-antigen LPS was produced in an arabinose-dependent manner.

Figure 8:
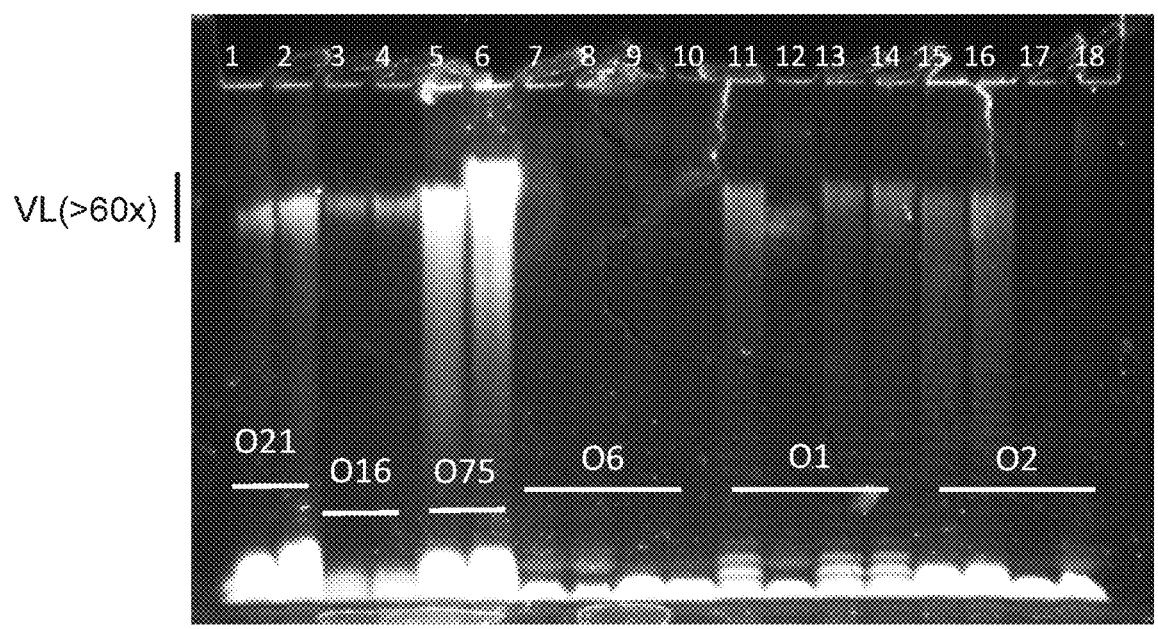
FIG. 8—Plasmid-mediated Arabinose-inducible Expression of Long O-antigen LPS in common host strain FIG. 9A-C—Structures of O-antigens synthesized by the polymerase-dependent pathway with four or less residues in the backbone.
Figure 9B:
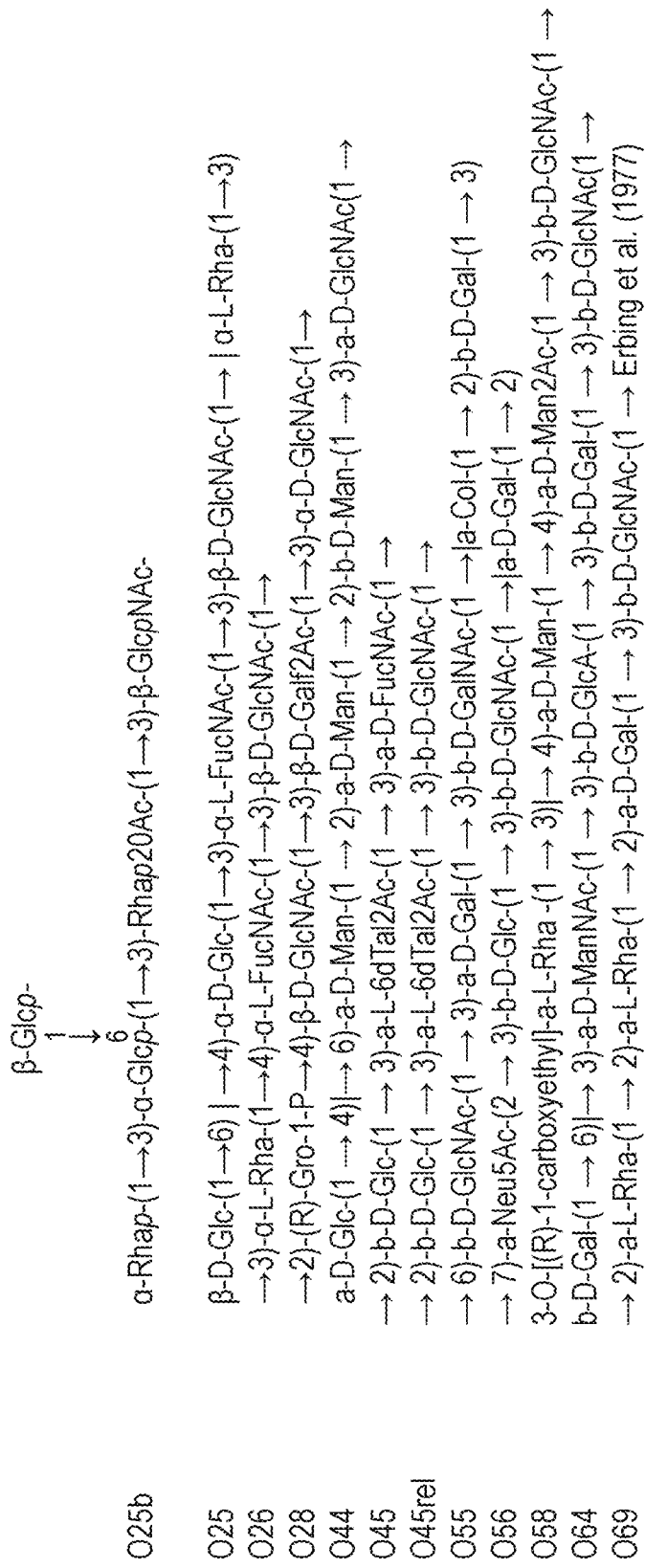

O-antigen gene clusters cloned from other serotypes were similarly evaluated and the results shown in FIG. 8. Co-expression of *Salmonella* LT2 fepE and pBAD33-OAg plasmids resulted in detectable long chain LPS corresponding to O1, O2 (for two out of four clones), O16, O21 and O75 serotypes. For unknown reasons, the pBAD33-06 plasmid failed to yield detectable LPS in all four isolates tested. Although expression level was variable, results show that expression of long chain O-antigens in a common host is feasible. However, in some cases further optimization to improve expression may be required, for example by modification of plasmid promoter sequences.

Figure 11:
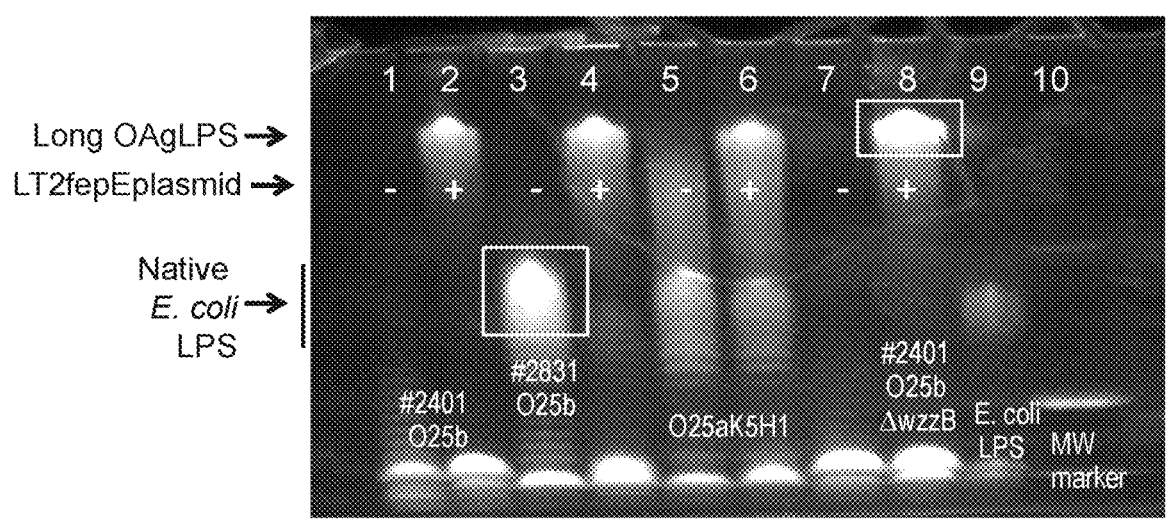
FIG. 11—Expression of O25 O-antigen LPS in Exploratory Bioprocess strains
Figure 12A:
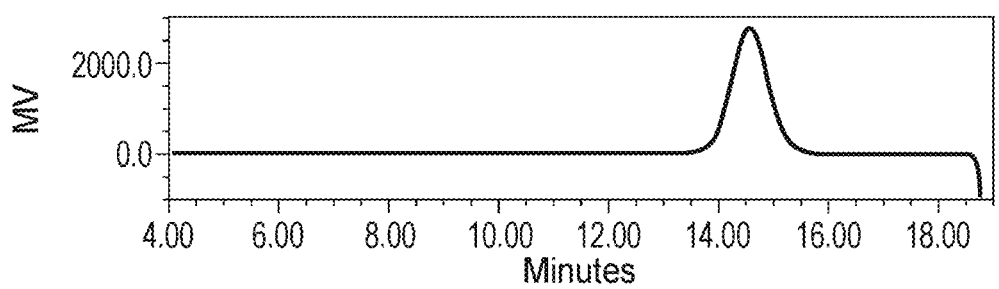
FIG. 12A-B—SEC profiles and properties of short (FIG. 12A, Strain 1 O25b wt 2831) and long O25b O-antigens (FIG. 12B, Strain 2 O25b 2401ΔwzzB/LT2 FepE) purified from strains GAR2831 and '2401ΔwzzB/fepE FIG. 13A-B—(FIG. 13A) Information regarding vaccination schedule for rabbit study 1 VAC-2017-PRL-EC-0723.
Figure 12B:
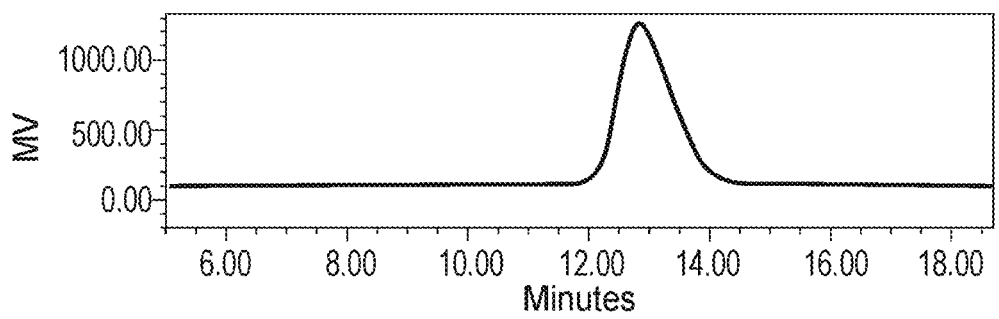

The profiles of LPS from different serotype O25 *E. coli* strains with or without the *Salmonella* LT2 fepE plasmid are shown in FIG. 11. Two strains were studied for fermentation, extraction and purification of O-antigens: GAR2831, for the production of native short O25b OAg; and GAR2401ΔwzzB/fepE, for the production of long O25b OAg. The corresponding short and long form LPSs shown in the FIG. 11 SDS-PAGE gel are highlighted in red. Polysaccharides were extracted directly from fermented bacteria with acetic acid and purified. Size exclusion chromatography profiles of purified short and long or very long O25b polysaccharides are shown in FIG. 12. The properties of two lots of short polysaccharide (from GAR2831) are compared with a single very long polysaccharide preparation (from strain GAR2401ΔwzzB/fepE). The molecular mass of the long O-antigen is 3.3-fold greater than that of the short O-antigen, and the number of repeat units was estimated to be ~65 (very long) vs ~20. See Table 6.

TABLE 6

| Poly Lot # | Native | Native | Modified (long chain) |
|---|---|---|---|
| Poly Lot # | 709766-24A | 709722-24B | 709766-25A |
| Poly MW (kDa) | 17.3 | 16.3 | 55.3 |
| # Repeat Units | 20 | 19 | 64 |

The very long O25b O-antigen polysaccharide was conjugated to diphtheria toxoid $CRM_{197}$ using a conventional reductive amination process. Three different lots of glycoconjugate were prepared with varying degree of periodate activation: medium (5.5%), low (4.4%) and high (8.3%). The resulting preparations and unconjugated polysaccharide were shown to be free of endotoxin contamination) (Table 7).

Figure 13A:
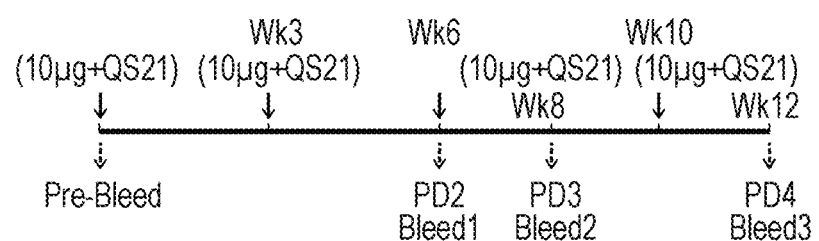
(FIG. 13B) vaccination schedule for rabbit study 2 VAC-2018-PRL-EC-077 FIG. 14A-C—O25b Glycoconjugate IgG responses, wherein —●—represents results from Prebleed; —■—Bleed 1 (6 wk); —▲—Bleed 2 (8 wk); —♦—Bleed 3 (12 wk).

Groups of four rabbits (New Zealand White females) were each vaccinated with 10 mcg of glycoconjugate and 20 mcg of QS21 adjuvant and serum sampled (VAC-2017-PRL-EC-0723) according to the schedule shown in FIG. 13A. It is worth noting that a 10 mcg dose is at the low end of the range customarily given to rabbits in the evaluation of bacterial glycoconjugates (20-50 mcg is more typical). A group of rabbits was also vaccinated in a separate study (VAC-2017-PRL-GB-0698) with unconjugated polysaccharide using the same dose (10 mcg polysaccharide+20 mcg QS21 adjuvant) and identical administration schedule.

Figure 14A:
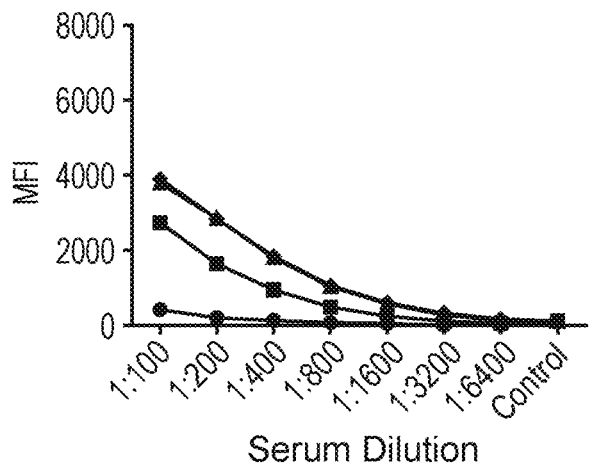
FIG. 14A depicts results from Rabbit 1-3 (Medium Activation)
Figure 14B:
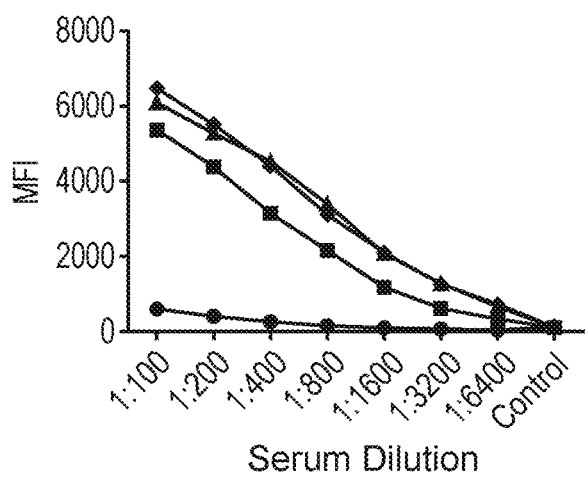
FIG. 14B depicts results from Rabbit 2-3 (Low Activation)
Figure 14C:
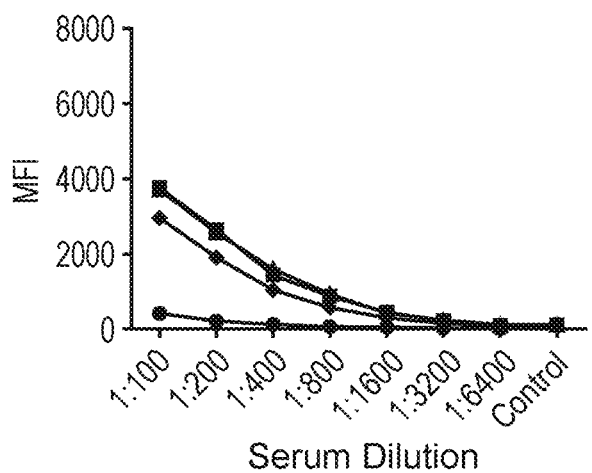
FIG. 14C depicts results from Rabbit 3-1 (High Activation).
Figure 15A:
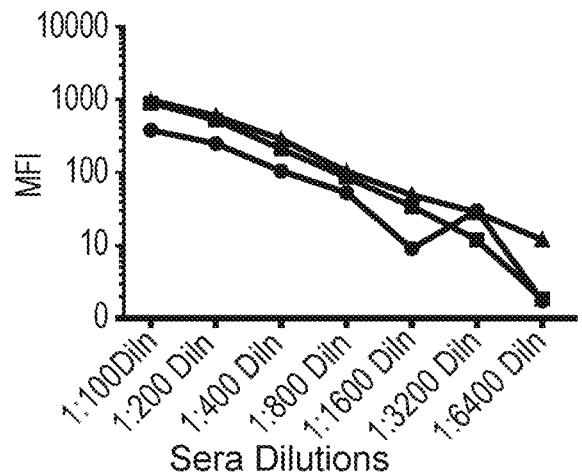
FIG. 15A-F—IgG responses to O25b Long O-antigen Glycoconjugate, i.e., Low activation O25b-CRM$_{197}$ conjugate (FIG. 15D-F, wherein —●—represents results from Prebleed from Rabbit 2-1, —■—Week 12 Antisera from Rabbit 2-1) vs unconjugated polysaccharide, i.e., free O25b polysaccharide (FIG. A-C, wherein —●—represents results from Prebleed from Rabbit A-1, —■—Week 6 Antisera from Rabbit A-1, —▲—Week 8 Antisera from Rabbit A-1). Note that MFIs are plotted on log scale to highlight differences between pre-immune and immune antibodies in the <1000 MFI range.
Figure 15B:
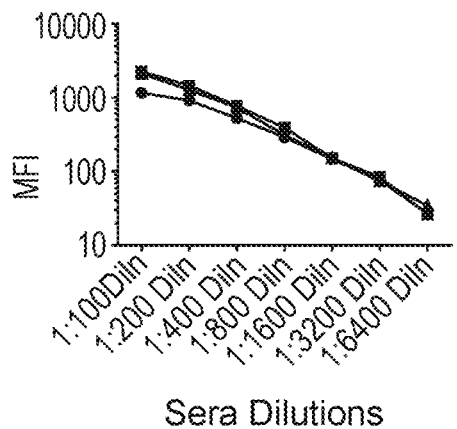
Figure 15C:
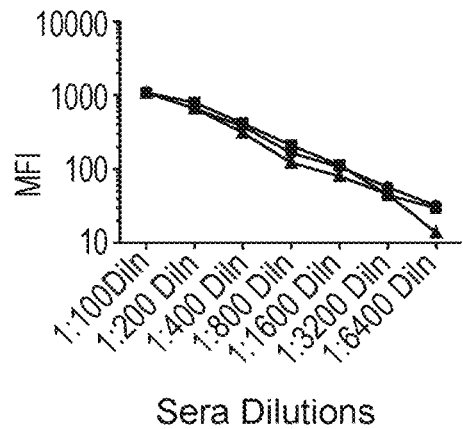
Figure 15D:
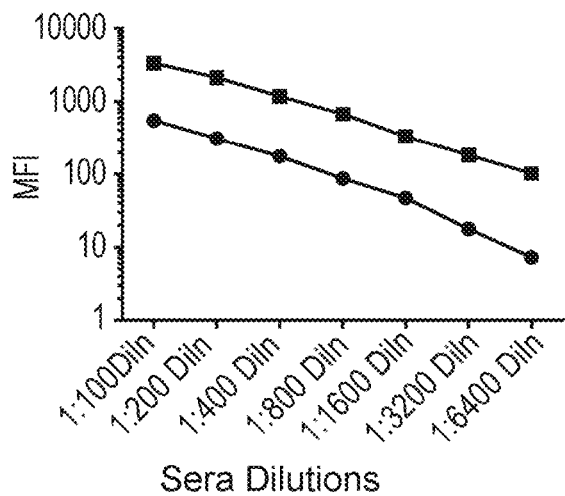
Figure 15E:
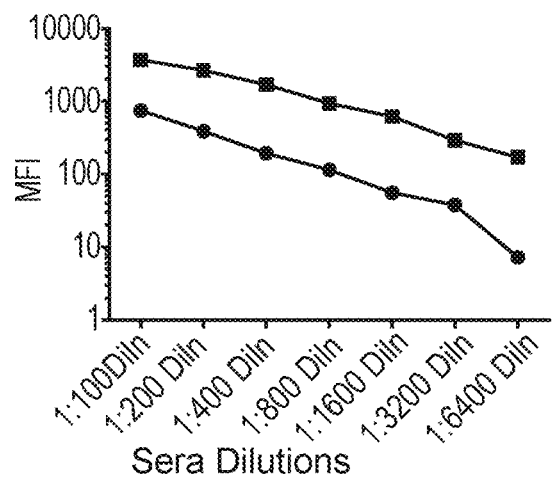
Figure 15F:
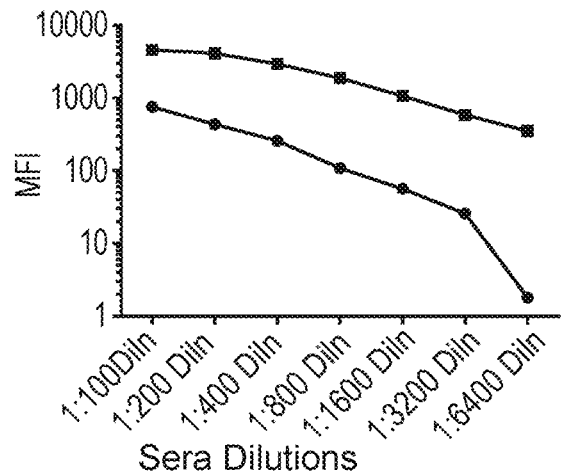

Rabbit antibody responses to the three O25b glycoconjugate preparations were evaluated in a LUMINEX assay in which carboxy beads were coated with methylated human serum albumin prebound with unconjugated O25b long polysaccharide. The presence of O25b-specific IgG antibodies in serum samples was detected with a phycoerythrin (PE)-labelled anti-IgG secondary antibody. The profiles of immune responses observed in sera sampled at week 0 (pre-immune), week 6 (post-dose 2, PD2), week 8 (post-dose 3, PD3) and week 12 (post-dose 4, PD4) in best-responding rabbits (one from each group of four) are shown in FIG. 14. No significant pre-immune serum IgG titers were detected in any of the 12 rabbits. In contrast, O25b antigen-specific antibody responses were detected in post-vaccination sera from rabbits in all three groups, with the low-activation glycoconjugate group responses trending slightly higher than the medium or high activation glycoconjugate groups. Maximal responses were observed by the post-dose 3 timepoint. One rabbit in the low activation group and one rabbit from the high activation group failed to respond to vaccination (non-responders).

To assess the impact of $CRM_{197}$ carrier protein conjugation on immunogenicity of the long O25b OAg polysaccharide, the presence of antibodies in sera from rabbits vaccinated with unconjugated polysaccharide was compared with sera from rabbits vaccinated with the low activation $CRM_{197}$ glycoconjugate FIG. 15. Remarkably, the free polysaccharide was not immunogenic, eliciting virtually no IgG responses in immune vs preimmune sera (panel A). In contrast, O25b OAg-specific IgG mean fluorescence intensity values (MFIs) of approximately ten-fold above pre-immune serum levels were observed in PD4 sera from three out of four rabbits vaccinated with O25b OAg-$CRM_{197}$, across a range of serum dilutions (from 1:100 to 1:6400). These results demonstrate the necessity of carrier protein conjugation to generate IgG antibodies to the O25b OAg polysaccharide at the 10 mcg dose level.

Bacteria grown on TSA plates were suspended in PBS, adjusted to $OD_{600}$ of 2.0 and fixed in 4% paraformaldehyde in PBS. After blocking in 4% BSA/PBS for 1 h, bacteria were incubated with serial dilutions of pre-immune and PD3 immune sera in 2% BSA/PBS, and bound IgG detected with PE-labeled secondary F (ab) antibody.

Specificity of the O25b antibodies elicited by the O25b OAg-$CRM_{197}$ was demonstrated in flow cytometry experiments with intact bacteria. Binding of IgG to whole cells was detected with PE-conjugated F(ab') 2 fragment goat anti-rabbit IgG in an Accuri flow cytometer.

Figure 16A:
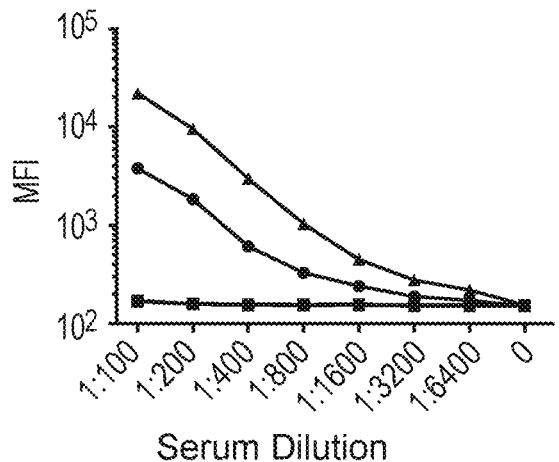
FIG. 16A-C—Surface expression of native vs long O25b O-antigen detected with O25b antisera.
Figure 16B:
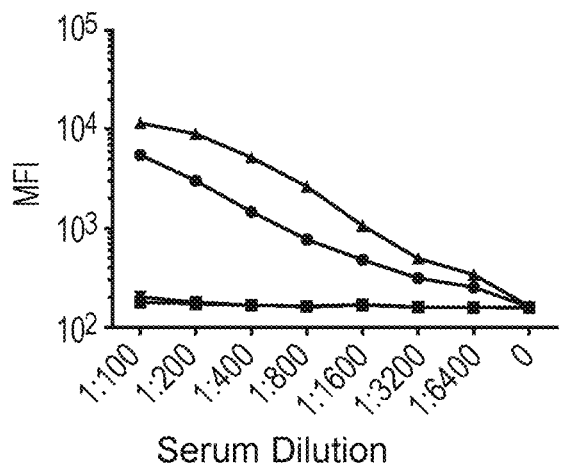
Figure 16C:
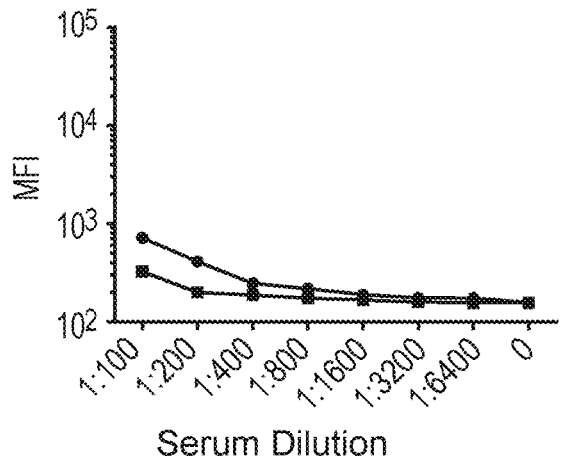

As shown in FIG. 16, pre-immune rabbit antibodies failed to bind to wild-type serotype O25b isolates GAR2831 and GAR2401 or to a K-12 *E. coli* strain, whereas matched PD3 antibodies stained the O25b bacteria in a concentration dependent manner. Negative control K-12 strain which lacks the ability to express OAg showed only very weak binding of PD3 antibodies, most likely due to the presence of exposed inner core oligosaccharide epitopes on its surface. Introduction of the *Salmonella* fepE plasmid into the wild-type O25b isolates resulted in significantly enhanced staining, consistent with the higher density of immunogenic epitopes provided by the longer OAg polysaccharide.

Conclusion: The results described show that not only is *Salmonella* fepE the determinant of very long O-antigen polysaccharides in *Salmonella* species, but that it also can confer on *E. coli* strains of different O-antigen serotypes the ability to make very long OAgs. This property can be exploited to produce O-antigen vaccine polysaccharides with improved properties for bioprocess development, by facilitating purification and chemical conjugation to appropriate carrier proteins, and by potentially enhancing immunogenicity through the formation of higher molecular weight complexes.

Example 6: Initial Rabbit Studies Generated First Polyclonal Antibody Reagents and IgG Responses to RAC 025b OAg-$CRM_{197}$ Long chain O25b polysaccharide-$CRM_{197}$ conjugates were produced using periodate oxidation followed by conjugation using reductive amination chemistry (RAC) (Table 7). See also Table 17.

TABLE 7

| $CRM_{197}$ conjugate | 132242-28 Medium 5.5% activation | 132242-27 Low 4.5% activation | 132242-29 High 8.3% activation | 709766-29 Free O25b polysaccharide |
|---|---|---|---|---|
| Polysaccharide concentration (mg/mL) | 0.7 | 0.6 | 0.67 | 1 |
| Endotoxin (EU/ug) | 0.02 | 0.02 | 0.02 | <0.6 EU |
| Matrix | 5 um Succinate buffer/saline, pH 6.0 | | | |

Figure 18:
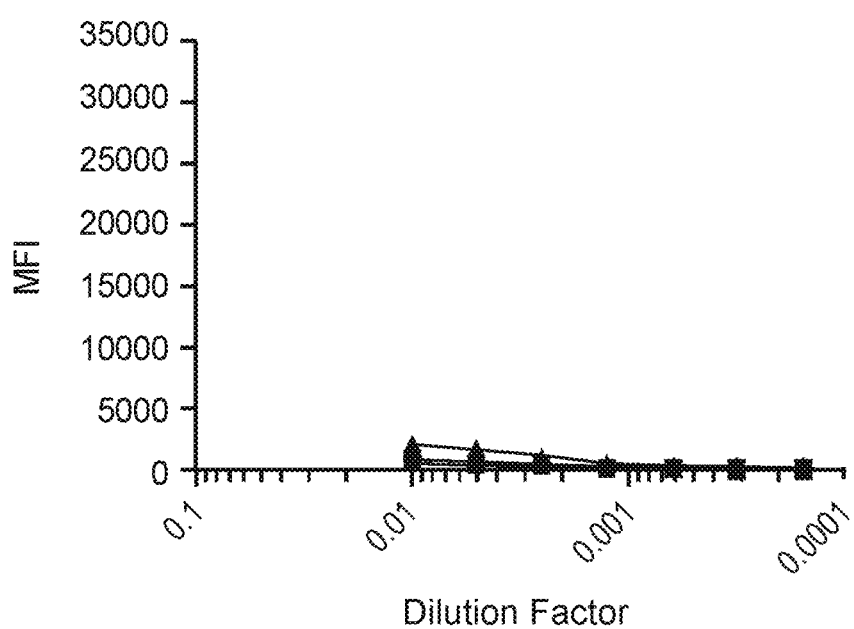
FIG. 18—Unconjugated free O25b polysaccharide is not immunogenic (dLIA), wherein —●— represents results from Week 18 (1 wk=PD4) Antisera from 4-1; —■—Week 18 (1 wk=PD4) Antisera from 4-2; —▲—Week 18 (1 wk=PD4) Antisera from 5-1; —▼—Week 18 (1 wk=PD4) Antisera from 5-2; —*—Week 18 (1 wk=PD4) Antisera from 6-1; —▲—Week 18 (1 wk=PD4) Antisera from 6-2.

In Rabbit Study 1 (VAC-2017-PRL-EC-0723) (also described above in Example 5)—five (5) rabbits/group, with 10 ug L-, M- or H-activation RAC (+QS21) received a composition according to the schedule shown in FIG. 13A. Unconjugated free O25b polysaccharide was observed not to be immunogenic in a follow-up rabbit Study (VAC-2017-PRL-GB-0698) (see FIG. 18).

Figure 13B:
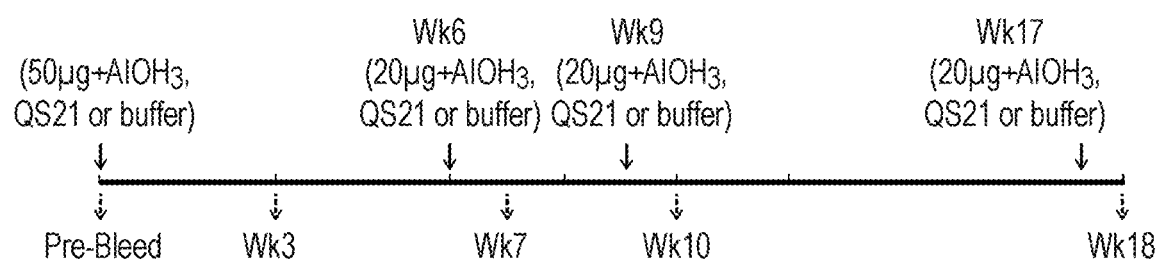

In Rabbit Study 2 (VAC-2018-PRL-EC-077)-2 rabbits/group, with L-RAC ($AlOH_3$, QS21, or no adjuvant) received a composition according to the schedule shown in FIG. 13B. Rabbits 4-1, 4-2, 5-1, 5-2, 6-1, and 6-2 received the very long unconjugated O25b polysaccharide described in Example 5, and week 18 sera were tested.

More specifically, a composition including 50 ug unconjugated O25b, 100 ug $AlOH_3$ adjuvant was administered to Rabbit 4-1. A composition including 50 ug unconjugated O25b, 100 ug $AlOH_3$ adjuvant was administered to Rabbit 4-2. A composition including 50 ug unconjugated O25b, 50 ug QS-21 adjuvant was administered to Rabbit 5-1. A composition including 50 ug unconjugated O25b, 50 ug QS-21 adjuvant was administered to Rabbit 5-2. A composition including 50 ug unconjugated O25b, no adjuvant was administered to Rabbit 6-1. A composition including 50 ug unconjugated O25b, no adjuvant was administered to Rabbit 6-2.

Example 7: Rabbit Studies with O25b RAC Conjugate: dLIA Serum Dilution Titers

Rabbit Study 2 (VAC-2018-PRL-EC-077) O25b dLIA serum dilution titers vs best responding rabbit from study 1 (VAC-2017-PRL-EC-0723). For these experiments a modified direct binding Luminex assay was implemented in which a polylysine conjugate of O25b long O-antigen was passively adsorbed onto the Luminex carboxy beads instead of the methylated serum albumin long O-antigen mixture described previously. The use of the polylysine-O25b conjugate improved the sensitivity of the assay and the quality of IgG concentration dependent responses, permitting determination of serum dilution titers through use of curve-fitting (four parameter non-linear equation). O25b IgG titers in sera from highest titer rabbit from first study is compared with sera from second study rabbits in Table 8.

TABLE 8

| | O25b-CRM Low Activation Conjugate with Alum Adjuvant (EC$_{50}$ as serum dilution) | | O25b-CRM Low Activation Conjugate with QS21 Adjuvant (EC$_{50}$ as serum dilution) | | O25b-CRM Low Activation Conjugate without Adjuvant (EC$_{50}$ as serum dilution) | |
|---|---|---|---|---|---|---|
| | Rabbit 1-1 | Rabbit 1-2 | Rabbit 2-1 | Rabbit 2-2 | Rabbit 3-1 | Rabbit 3-2 |
| Week 3 Antisera (3 wks after primary) | ~1:200 | ~1:200 | <1:100 | <1:100 | ~1:200 | ~1:200 |
| Week 7 Antisera (1 wk after boost 1) | 1:1600 | 1:4000 | 1:250 | 1:500 | 1:250 | 1:1500 |
| Week 10 Antisera (1 wk after boost 2) | 1:1100 | 1:1900 | 1:250 | 1:500 | 1:800 | 1:1200 |
| Week 18 Antisera (1 wk after boost 4) | 1:1600 | 1:4000 | 1:1300 | 1:1200 | 1:1400 | 1:1600 |

Average of 6 replicates of best antisera from rabbit 2-3 (assay standard from first study) EC$_{50}$ = 1:1700

Higher doses in second rabbit study (50/20 ug vs 10 ug) did not improve IgG titers. Two month rest boosts IgG responses (not observed with shorter intervals). Alum appears to enhance IgG response in rabbits compared with QS21 or no adjuvant.

An opsonophagocytic assay (OPA) with baby rabbit complement (BRC) and HL60 cells as source of neutrophils was established to measure the functional immunogenicity of O-antigen glycoconjugates. Pre-frozen bacterial stocks of E. coli GAR2831 were grown in Luria broth (LB) media at 37° C. Cells were pelleted and suspended to a concentration of 1 OD$_{600}$ unit per ml in PBS supplemented with 20% glycerol and frozen. Pre-titered thawed bacteria were diluted to 0.5×10$^5$ CFU/ml in HBSS (Hank's Balanced Salt Solution) with 1% Gelatin) and 10 µL (103 CFU) combined with 20 µL of serially diluted sera in a U-bottomed tissue culture microplate and the mixture shaken at 700 rpm BELLCO Shaker) for 30 min at 37° C. in a 5% CO$_2$ incubator. 10 µl of 2.5% complement (Baby Rabbit Serum, PEL-FREEZ 31061-3, prediluted in HBG) and 20 µL of HL-60 cells (0.75×10$^7$/ml) and 40 µL of HBG added to the U-bottomed tissue culture microplate and the mixture shaken at 700 rpm BELLCO Shaker) for 45 min at 37° C. in a 5% CO$_2$ incubator. Subsequently, 10 µL of each 100 µL reaction was transferred into the corresponding wells of a pre-wetted MILLIPORE MULTISCREENHTS HV filter plate prepared by applying 100 µL water, filter vacuumed, and applying 150 µL of 50% LB. The filter plate was vacuum filtered and incubated overnight at 37° C. in a 5% CO$_2$ incubator. The next day the colonies were enumerated after fixing, staining, and destaining with COOMASSIE dye and Destain solutions, using an IMMUNOSPOT® analyzer and IMMUNO-CAPTURE software. To establish the specificity of OPA activity, immune sera were preincubated with 100 ug/mL purified long O25b O-antigen prior to combining with the other assay components in the OPA reaction. The OPA assay includes control reactions without HL60 cells or complement, to demonstrate dependence of any observed killing on these components.

Figure 19A:
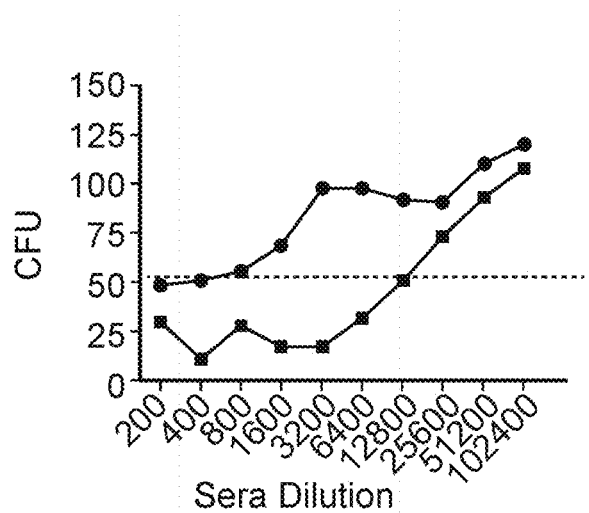
FIG. 19A-C—Graphs illustrating the specificity of BRC Rabbit O25b RAC conjugate immune sera OPA titers.
Figure 19B:
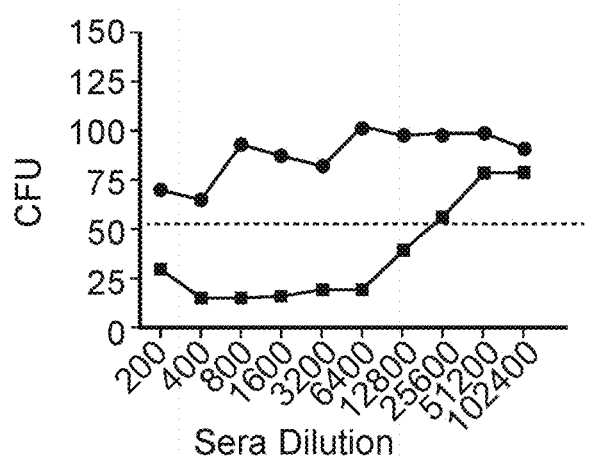
Figure 19C:
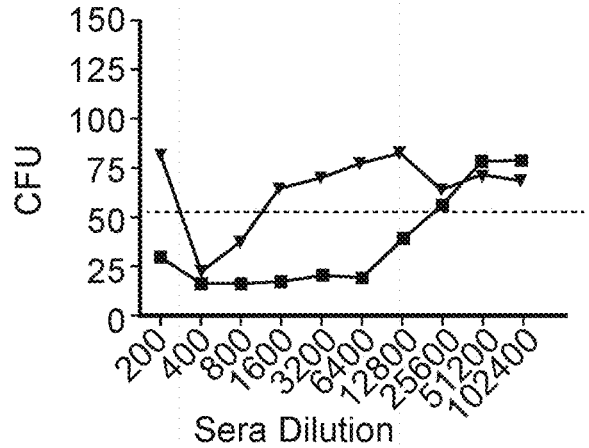

Matched pre-immune and post-vaccination serum samples from representative rabbits from both rabbit studies were evaluated in the assay and serum dilution titers determined (Table 9, FIG. 19A-B). Preincubation with unconjugated O25b long O-antigen polysaccharide blocked bactericidal activity demonstrating specificity of the OPA (FIG. 19C). Table 9 OPA titers Rabbit 2-3 was dosed as follows: Rabbit 2-3 dosing: Oct. 10, 2010/10 ug RAC conjugate+QS21, post-dose (PD) 4 bleed. Rabbit 1-2 was dosed as follows: 50/20/20/20 ug RAC conjugate+Al(OH)3, PD4 bleed.

TABLE 9

| Sample | Titer |
|---|---|
| Rabbit 2-3 Pre-immune serum | 537 |
| Rabbit 2-3 wk 13 serum (terminal bleed) | 13686 |
| Rabbit 1-2 Pre-immune serum | <200 |
| Rabbit 1-2 wk 19 serum (terminal bleed) | 22768 |

Figure 20A:
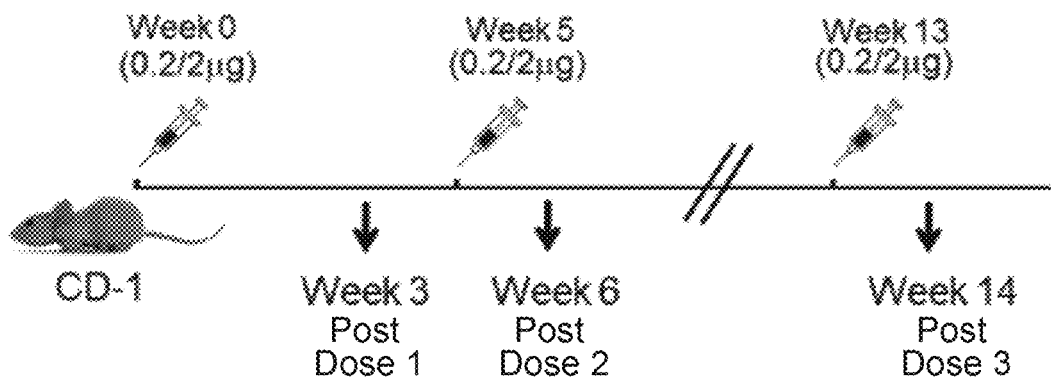
FIG. 20A-C—FIG. 20A Illustration of an exemplary administration schedule.
Figure 20B:
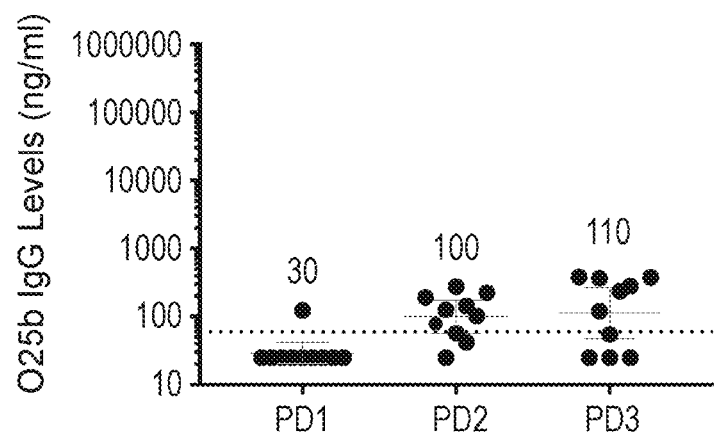
Figure 20C:
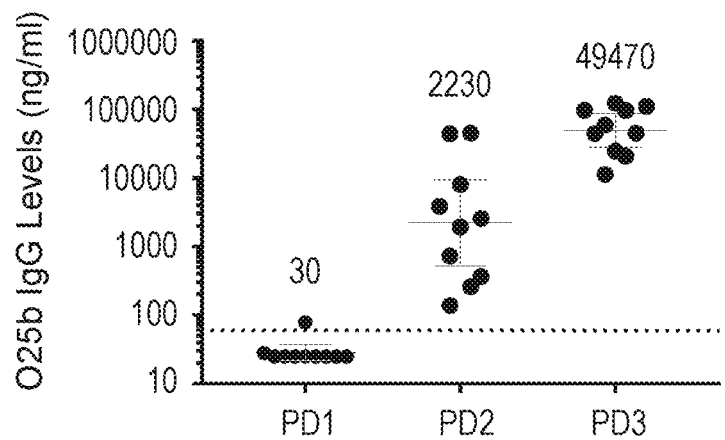

Example 8: O-Antigen O25b IgG Levels Elicited by Unconjugated O25b Long O-Antigen Polysaccharide and Derived O25b RAC/DMSO Long O-Antigen Glycoconjugate Groups of ten CD-1 mice were dosed by sub-cutaneous injection with 0.2 or 2.0 µg/animal of O25b RAC/DMSO long O-antigen glycoconjugate at weeks 0, 5 and 13, with bleeds taken at week 3 (post-dose 1, PD1), week 6 (post-dose 2, PD2) and week 13 (post-dose 3, PD3) timepoints for immunogenicity testing. Levels of antigen-specific IgG were determined by quantitative Luminex assay (see details in Example 7) with O25b-specific mouse mAb as internal standard. Baseline IgG levels (dotted line) were determined in serum pooled from 20× randomly selected unvaccinated mice. The free unconjugated O25b long O-antigen polysaccharide immunogen did not induce IgG above baseline levels at any timepoint. In contrast, IgG responses were observed after two doses of O25b-CRM197 RAC long conjugate glycoconjugate: robust uniform IgG responses were observed by PD3, with intermediate and more variable IgG levels at PD2. GMT IgG values (ng/ml) are indicated with 95% CI error bars. See FIG. 20.

Example 9: Specificity of the O25b Baby Rabbit Complement (BRC) OPA

A-B) O25b RAC/DMSO long O-antigen post-immune serum from rabbits 2-3 and 1-2 (but not matched pre-immune control serum) shows bactericidal OPA activity. C) OPA activity of immune serum from rabbit 1-2 was blocked by pre-incubation with 100 µg/mL long O-antigen O25b polysaccharide. Strain GAR2831 bacteria were incubated with HL60s, 2.5% BRC and serial dilutions of serum for 1 h at 37° C. and surviving bacteria enumerated by counting microcolonies (CFUs) on filter plates. See FIG. 19.

Figure 21A:
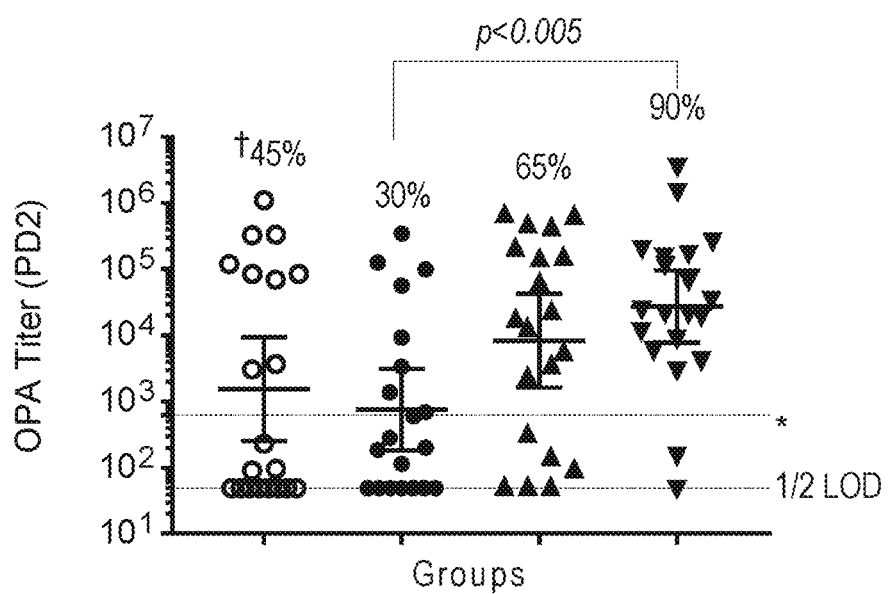
FIG. 21A-B—Graphs depicting OPA immunogenicity of RAC, eTEC O25b long glycoconjugates, and single end glycoconjugates post dose 2 (FIG. 21A) and post dose 3 (FIG. 21B), wherein —○—represents results from single end short 2 µg; —●—single end long 2 µg; —▲—RAC/DMSO long 2 µg; —▼—eTEC long 2 µg; * Background control (n=20). † Responder rates are % mice with titers >2× unvaccinated baseline.
Figure 21B:
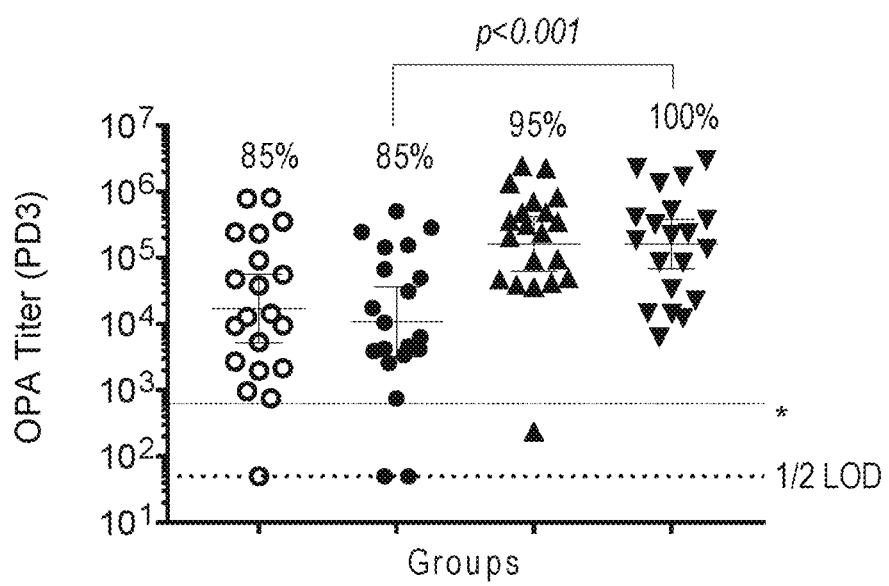

Example 10: RAC and eTEC O25b Long Glycoconjugates are More Immunogenic than Single End Glycoconjugates BRC OPA assay with carbapenem-resistant fluoroquinlone-resistant MDR strain Atlas187913. Groups of 20 CD-1 mice were vaccinated with 2 μg of glycoconjugate according to the same schedule as shown in FIG. 21 and OPA responses determined at post-dose 2 (PD2) (panel A) and post-dose 3 (PD3) (panel B) timepoints. Bars indicate GMTs with 95% Cl. Responder rates above unvaccinated baseline are indicated. Log transformed data from different groups were evaluated to assess if differences were statistically significant using unpaired t-test with Welch's correction (Graphpad Prism). Results are summarized in the Table 10. See FIG. 21. In mice that were vaccinated with 2 μg of eTEC O1a long glycoconjugates, OPA titers against O1a, PD2 and PD3 (data not shown), were observed to be greater than the OPA titers against O25b, PD2 and PD3, respectively, shown in Table 10.

TABLE 10

| DESCRIPTION | % Responders (n/N)* | GEO-MEAN TITER PD2 | % Responders (n/N)* | GEO-MEAN TITER PD3 |
|---|---|---|---|---|
| Single end short, 2 μg | 45 (9/20) | 1,552 | 85 (17/20) | 17,070 |
| Single end long, 2 μg | 30 (6/20) | 763 | 85 (17/20) | 10,838 |
| RAC/DMSO long, 2 μg | 65 (13/20) | 8,297 | 95 (19/20) | 163,210 |
| eTEC (10%) long, 2 μg | 90 (18/20) | 27,368 | 100 (19/19) | 161,526 |

Figure 22:
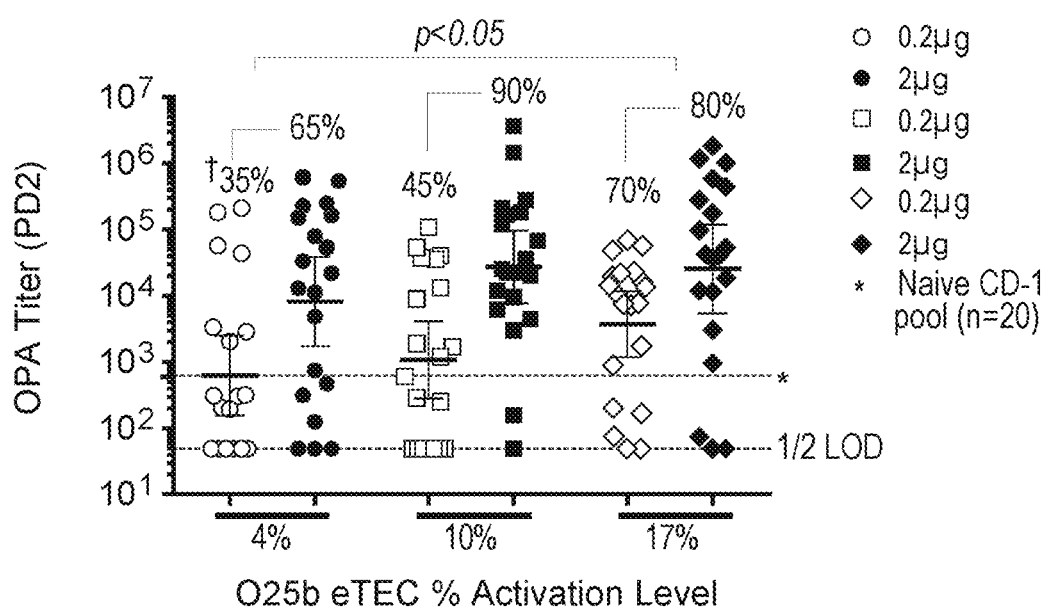
FIG. 22—Graph depicting OPA immunogenicity of eTEC chemistry and modified levels of polysaccharide activation. † Responder rates are % mice with titers >2× unvaccinated baseline.

Example 11: OPA Immunogenicity of eTEC Chemistry May be Improved by Modifying Levels of Polysaccharide Activation BRC OPA assay with carbapenem-resistant fluoroquinlone-resistant MDR strain Atlas187913. Groups of 20 CD-1 mice were vaccinated with 0.2 μg or 2 μg of the indicated long O25b eTEC glycoconjugate and OPA responses determined at PD2 timepoint. Aggregated log transformed data from 4% activation vs 17% activation groups were evaluated to confirm that differences in OPA responses were statistically significant using unpaired t-test with Welch's correction (Graphpad Prism). GMTs and responder rates for individual groups are summarized in Table 11. See FIG. 22.

TABLE 11

| Description | % Responders (n/N) | GeoMean Titer |
|---|---|---|
| eTEC long 4% activation (0.2 μg) | 35 (7/20) | 628 |
| eTEC long 4% activation (0.2 μg) | 65 (13/20) | 8,185 |
| eTEC long 10% activation (0.2 μg) | 45 (9/20) | 1,085 |
| eTEC long 10% activation (0.2 μg) | 90 (18/20) | 27,368 |
| eTEC long 17% activation (0.2 μg) | 70 (14/20) | 3,734 |
| eTEC long 17% activation (0.2 μg) | 80 (16/20) | 25,461 |

Figure 23A:
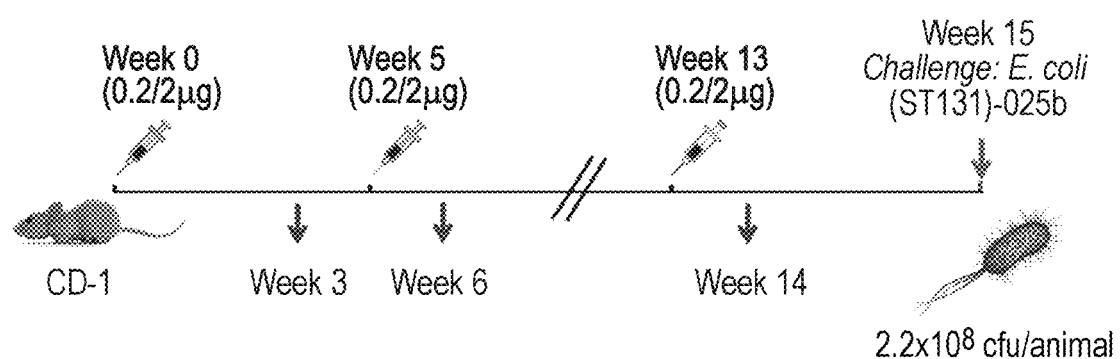
FIG. 23A-B—FIG. 23A Illustration of an exemplary administration schedule and FIG. 23B shows a graph depicting protection of mice immunized with doses of *E. coli* eTEC conjugates from lethal challenge with O25b isolate, wherein —◇—represents eTEC Long Chain 17% activation; —△—eTEC Long Chain 10% activation; —▽—eTEC Long Chain 4% activation; —□—O25b Polysaccharide; —○—Unvaccinated controls.
Figure 23B:
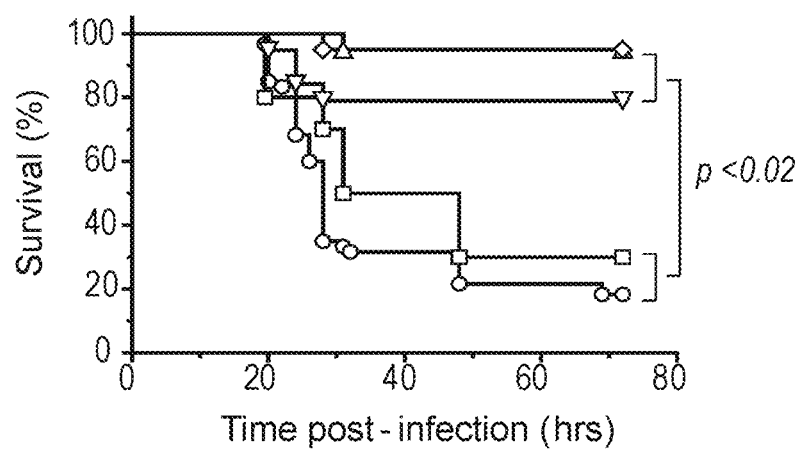

Example 12: Challenge Study Indicates Long *E. coli* O25b eTEC Conjugates Elicit Protection after Three Doses Groups of 20×CD-1 mice immunized with a 2 μg dose according to the indicated schedule were challenged IP with $1\times10^9$ bacteria of strain GAR2831. Subsequent survival was monitored for six days. Groups of mice vaccinated with eTEC glycoconjugates activated at 4%, 10% or 17% levels were protected from lethal infection, whereas unvaccinated control mice or mice vaccinated with 2 μg unconjugated O25b long polysaccharide were not. See FIG. 23.

Example 13: Process for Preparation of eTEC Linked Glycoconjugates

Activation of Saccharide and Thiolation with Cystamine dihydrochloride. The saccharide is reconstituted in anhydrous dimethylsulfoxide (DMSO). Moisture content of the solution is determined by Karl Fischer (KF) analysis and adjusted to reach a moisture content of 0.1 and 1.0%, typically 0.5%.

To initiate the activation, a solution of 1,1'-carbonyl-di-1,2,4-triazole (CDT) or 1,1'-carbonyldiimidazole (CDI) is freshly prepared at a concentration of 100 mg/mL in DMSO. The saccharide is activated with various amounts of CDT/CDI (1-10 molar equivalents) and the reaction is allowed to proceed for 1-5 hours at rt or 35° C. Water was added to quench any residual CDI/CDT in the activation reaction solution. Calculations are performed to determine the added amount of water and to allow the final moisture content to be 2-3% of total aqueous. The reaction was allowed to proceed for 0.5 hour at rt. Cystamine dihydrochloride is freshly prepared in anhydrous DMSO at a concentration of 50 mg/mL. The activated saccharide is reacted with 1-2 mol. eq. of cystamine dihydrochloride. Alternatively, the activated saccharide is reacted with 1-2 mol. eq. of cysteamine hydrochloride. The thiolation reaction is allowed to proceed for 5-20 hours at rt, to produce a thiolated saccharide. The thiolation level is determined by the added amount of CDT/CDI.

Reduction and Purification of Activated Thiolated Saccharide. To the thiolated saccharide reaction mixture a solution of tris(2-carboxyethyl) phosphine (TCEP), 3-6 mol. eq., is added and allowed to proceed for 3-5 hours at rt. The reaction mixture is then diluted 5-10-fold by addition to pre-chilled 10 mM sodium phosphate monobasic, and filtered through a 5 μm filter. Dialfiltration of thiolated saccharide is performed against 30-40-fold diavolume of pre-chilled 10 mM sodium phosphate monobasic. An aliquot of activated thiolated saccharide retentate is pulled to determine the saccharide concentration and thiol content (Ellman) assays.

Activation and Purification of Bromoacetylated Carrier Protein. Free amino groups of the carrier protein are bromoacteylated by reaction with a bromoacetylating agent, such as bromoacetic acid N-hydroxysuccinimide ester (BAANS), bromoacetylbromide, or another suitable reagent.

The carrier protein (in 0.1M Sodium Phosphate, pH 8.0±0.2) is first kept at 8±3° C., at about pH 7 prior to activation. To the protein solution, the N-hydroxysuccinimide ester of bromoacetic acid (BAANS) as a stock dimethylsulfoxide (DMSO) solution (20 mg/mL) is added in a ratio of 0.25-0.5 BAANS:protein (w/w). The reaction is gently mixed at 5±3° C. for 30-60 minutes. The resulting bromoacetylated (activated) protein is purified, e.g., by ultrafiltration/diafiltration using 10 kDa MWCO membrane using 10 mM phosphate (pH 7.0) buffer. Following purification, the protein concentration of the bromoacetylated carrier protein is estimated by Lowry protein assay.

The extent of activation is determined by total bromide assay by ion-exchange liquid chromatography coupled with suppressed conductivity detection (ion chromatography). The bound bromide on the activated bromoacetylated protein is cleaved from the protein in the assay sample preparation and quantitated along with any free bromide that may be present. Any remaining covalently bound bromine on the protein is released by conversion to ionic bromide by heating the sample in alkaline 2-mercaptoethanol.

Activation and Purification of Bromoacetylated $CRM_{197}$. $CRM_{197}$ was diluted to 5 mg/ml with 10 mM phosphate buffered 0.9% NaCl pH 7 (PBS) and then made 0.1 M $NaHCO_3$ PH 7.0 using 1 M stock solution. BAANS was added at a $CRM_{197}$: BAANS ratio 1:0.35 (w: w) using a BAANS stock solution of 20 mg/mL DMSO. The reaction mixture was incubated at between 3° C. and 11° C. for 30 mins-1 hour then purified by ultrafiltration/diafiltration using a 10K MWCO membrane and 10 mM Sodium Phosphate/0.9% NaCl, pH 7.0. The purified activated $CRM_{197}$ was assayed by the Lowry assay to determine the protein concentration and then diluted with PBS to 5 mg/mL. Sucrose was added to 5% wt/vol as a cryoprotectant and the activated protein was frozen and stored at −25° C. until needed for conjugation.

Bromoacetylation of lysine residues of $CRM_{197}$ was very consistent, resulting in the activation of 15 to 25 lysines from 39 lysines available. The reaction produced high yields of activated protein.

Conjugation of Activated Thiolated Saccharide to Bromoacetylated Carrier Protein. Bromoacetylated carrier protein and activated thiolated saccharide are subsequently added. The saccharide/protein input ratio is 0.8±0.2. The reaction pH is adjusted to 9.0±0.1 with 1 M NaOH solution. The conjugation reaction is allowed to proceed at 5° C. for 20±4 hours.

Capping of Residual Reactive Functional Groups. The unreacted bromoacetylated residues on the carrier protein are quenched by reacting with 2 mol. eq. of N-acetyl-L-cysteine as a capping reagent for 3-5 hours at 5° C. Residual free sulfhydryl groups are capped with 4 mol. eq. of iodoacetamide (IAA) for 20-24 hours at 5° C.

Purification of eTEC-linked Glycoconjugate. The conjugation reaction (post-IAA-capped) mixture is filtered through 0.45 μm filter. Ultrafiltration/dialfiltration of the glycoconjugate is performed against 5 mM succinate-0.9% saline, pH 6.0. The glycoconjugate retentate is then filtered through 0.2 μm filter. An aliquot of glycoconjugate is pulled for assays. The remaining glycoconjugate is stored at 5° C. See Table 14, Table 15, Table 16, Table 17, and Table 18.

Example 14: Preparation of *E. coli*-O25B ETEC Conjugates

Activation Process-Activation of *E. coli*-O25b Lipopolysaccharide. The lyophilized *E. coli*-O25b polysaccharide was reconstituted in anhydrous dimethylsulfoxide (DMSO). Moisture content of the lyophilized O25b/DMSO solution was determined by Karl Fischer (KF) analysis. The moisture content was adjusted by adding WFI to the O25b/DMSO solution to reach a moisture content of 0.5%.

To initiate the activation, 1,1'-carbonyldiimidazole (CDI) was freshly prepared as 100 mg/ml in DMSO solution. *E. coli*-O25b polysaccharide was activated with various amounts of CDI prior to the thiolation step. The CDI activation was carried out at rt or 35° C. for 1-3 hours. Water was added to quench any residual CDI in the activation reaction solution. Calculations are performed to determine the added amount of water and to allow the final moisture content to be 2-3% of total aqueous. The reaction was allowed to proceed for 0.5 hour at rt.

Thiolation of Activated *E. coli*-O25b Polysaccharide. Cystamine-dihydrochloride was freshly prepared in anhydrous DMSO and 1-2 mol. eq. of cystamine dihydrochloride was added to the activated polysaccharide reaction solution. The reaction was allowed to proceed for 20±4 hours at rt.

Figure 25A:
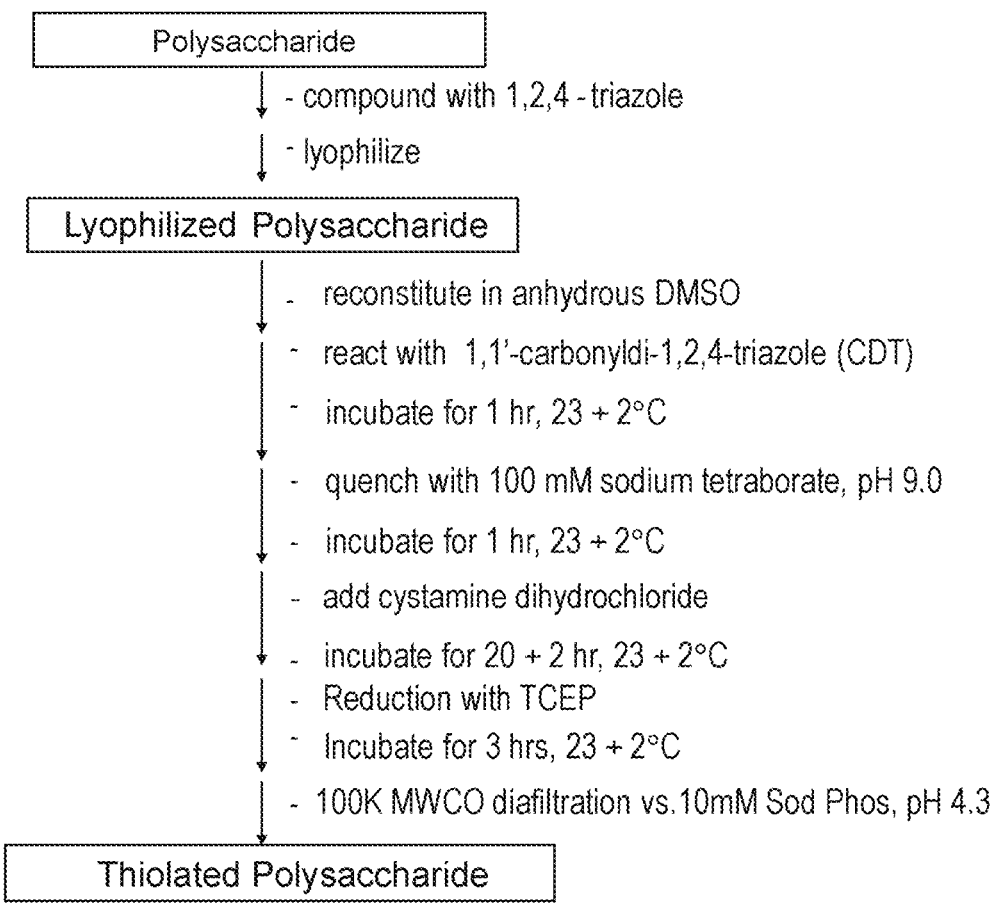
FIG. 25A-B shows an exemplary process flow diagram for the activation (FIG. 25A) and conjugation (FIG. 25B) processes used in the preparation of *E. coli* glycoconjugate to CRM$_{197}$.

Reduction and Purification of Activated Thiolated *E. coli*-O25b Polysaccharide. To the thiolated saccharide reaction mixture a solution of tris(2-carboxyethyl) phosphine (TCEP), 3-6 mol. eq., was added and allowed to proceed for 3-5 hours at rt. The reaction mixture was then diluted 5-10-fold by addition to pre-chilled 10 mM sodium phosphate monobasic and filtered through a 5 μm filter. Dialfiltration of thiolated saccharide was performed against 40-fold diavolume of pre-chilled 10 mM sodium phosphate monobasic with 5K MWCO ultrafilter membrane cassettes. The thiolated O25b polysaccharide retentate was pulled for both saccharide concentration and thiol (Ellman) assays. A flow diagram of the activation process is provided in FIG. 25A).

Conjugation Process-Conjugation of Thiolated *E. coli*-O25b Polysaccharide to Bromoacetylated $CRM_{197}$. The $CRM_{197}$ carrier protein was activated separately by bromoacetylation, as described in Example 13, and then reacted with the activated *E. coli*-O25b polysaccharide for the conjugation reaction. Bromoacetylated $CRM_{197}$ and thiolated O25b polysaccharide were mixed together in a reaction vessel. The saccharide/protein input ratio was 0.8±0.2. The reaction pH was adjusted to 8.0-10.0. The conjugation reaction was allowed to proceed at 5° C. for 20±4 hours.

Capping of Reactive Groups on Bromoacetylated $CRM_{197}$ and Thiolated *E. coli*-O25b Polysaccharide. The unreacted bromoacetylated residues on $CRM_{197}$ proteins were capped by reacting with 2 mol. eq. of N-acetyl-L-cysteine for 3-5 hours at 5° C., followed by capping any residual free sulfhydryl groups of the thiolated O25b-polysaccharide with 4 mol. eq. of iodoacetamide (IAA) for 20-24 hours at 5° C.

Purification of eTEC-linked *E. coli*-O25b Glycoconjugate. The conjugation solution was filtered through a 0.45 μm or 5 μm filter. Dialfiltration of the O25b glycoconjugate was carried out with 100K MWCO ultrafilter membrane cassettes. Diafiltration was performed against 5 mM succinate-0.9% saline, pH 6.0. The *E. coli*-O25b glycoconjugate 100K retentate was then filtered through a 0.22 μm filter and stored at 5° C.

Figure 25B:
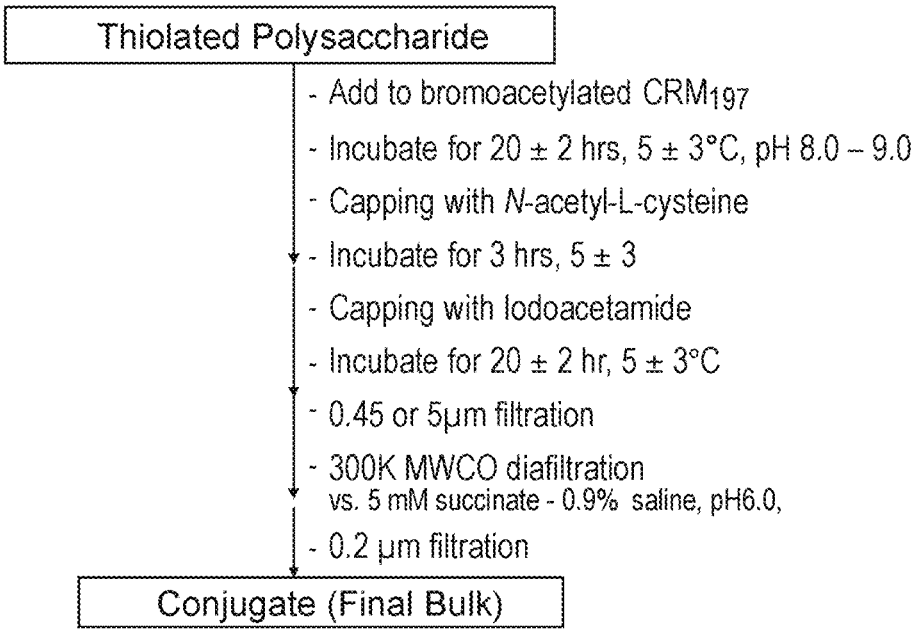

A flow diagram of the conjugation process is provided in FIG. 25B.

Results

The reaction parameters and characterization data for several batches of *E. coli*-O25b eTEC glycoconjugates are shown in Table 12. The CDI activation-thiolation with cystamine dihydrochloride generated glycoconjugates having from 41 to 92% saccharide yields and <5 to 14% free saccharides. See also See Table 14, Table 15, Table 16, Table 17, and Table 18.

TABLE 12

Experimental Parameters and Characterization Data of *E. coli*-O25b eTEC Conjugates

| Conjugate Batch | O25b-1A | O25b-2B | O25b-3C | O25b-4D | O25b-5E | O25b-6F |
|---|---|---|---|---|---|---|
| Activation level (mol of thiol/mol of polysaccharide), % | 10 | 20 | 22 | 17 | 25 | 24 |
| Input Sacc/Prot Ratio | 0.8 | 0.8 | 0.8 | 0.8 | 0.8 | 0.8 |
| Saccharide yield (%) | 56 | 57 | 79 | 92 | 41 | 59 |
| Output Sacc/Prot Ratio | 0.88 | 1 | 1.18 | 1.32 | 2.9 | 1.4 |
| Free Saccharide, % | 8 | <5 | 6 | 5 | 14 | 5 |
| Free Protein, % | <1 | <1 | <1 | <1 | <1 | <1 |
| Conjugate Mw, kDa | 1057 | 4124 | 2259 | 2306 | 1825 | 1537 |
| Total CMCA | 3 | na | na | 7.2 | na | na |

Example 15: Procedure for the Preparation of *E. coli* O-Antigen Polysaccharide-CRM$_{197}$ eTEC Conjugates (Applied to O-Antigens from *E. coli* Serotypes O25b, O1a, O2, and O6)

Activation of Polysaccharide.

The *E. coli* O-antigen polysaccharide is reconstituted in anhydrous dimethylsulfoxide (DMSO). To initiate the activation, various amounts of 1,1'-carbonyldiimidazole (CDI) (1-10 molar equivalents) is added to the polysaccharide solution and the reaction is allowed to proceed for 1-5 hours at rt or 35° C. Then, water (2-3%, v/v) was added to quench any residual CDI in the activation reaction solution. After the reaction was allowed to proceed for 0.5 hour at rt, 1-2 mol. eq. of cystamine dihydrochloride is added. The reaction is allowed to proceed for 5-20 hours at rt, and then treated with 3-6 mol. eq of tris(2-carboxyethyl) phosphine (TCEP) to produce a thiolated saccharide. The thiolation level is determined by the added amount of CDI.

The reaction mixture is then diluted 5-10-fold by addition to pre-chilled 10 mM sodium phosphate monobasic, and filtered through a 5 µm filter. Dialfiltration of thiolated saccharide is performed against 30-40-fold diavolume of pre-chilled 10 mM sodium phosphate monobasic. An aliquot of activated thiolated saccharide retentate is pulled to determine the saccharide concentration and thiol content (Ellman) assays.

Activation of Carrier Protein (CRM$_{197}$)

The CRM$_{197}$ (in 0.1M Sodium Phosphate, pH 8.0±0.2) is first kept at 8±3° C., at about pH 8 prior to activation. To the protein solution, the N-hydroxysuccinimide ester of bromoacetic acid (BAANS) as a stock dimethylsulfoxide (DMSO) solution (20 mg/mL) is added in a ratio of 0.25-0.5 BAANS:protein (w/w). The reaction is gently mixed at 5±3° C. for 30-60 minutes. The resulting bromoacetylated (activated) protein is purified, e.g., by ultrafiltration/diafiltration using 10 kDa MWCO membrane using 10 mM phosphate (pH 7.0) buffer. Following purification, the protein concentration of the bromoacetylated carrier protein is estimated by Lowry protein assay.

Conjugation

Activated CRM$_{197}$ and activated *E. coli* O-antigen polysaccharide are subsequently added to a reactor and mixed. The saccharide/protein input ratio is 1±0.2. The reaction pH is adjusted to 9.0±0.1 with 1 M NaOH solution. The conjugation reaction is allowed to proceed at 5° C. for 20±4 hours. The unreacted bromoacetylated residues on the carrier protein are quenched by reacting with 2 mol. eq. of N-acetyl-L-cysteine as a capping reagent for 3-5 hours at 5° C. Residual free sulfhydryl groups are capped with 4 mol. eq. of iodoacetamide (IAA) for 20-24 hours at 5° C. Then, the reaction mixture is purified using ultrafiltration/dialfiltration performed against 5 mM succinate-0.9% saline, pH 6.0. The purified conjugate is then filtered through 0.2 µm filter. See Table 14, Table 15, Table 16, Table 17, and Table 18.

Example 16: General Procedure-Conjugation of O-Antigen (from *E. coli* Serotypes O1, O2, O6, 25b) Polysaccharide by Reductive Mination Chemistry (RAC)

Conjugation in Dimethylsulfoxide (RAC/DMSO)
Activating Polysaccharide

Polysaccharide oxidation was carried out in 100 mM sodium phosphate buffer (pH 6.0±0.2) by sequential addition of calculated amount of 500 mM sodium phosphate buffer (pH 6.0) and water for injection (WFI) to give final polysaccharide concentration of 2.0 g/L. If required, the reaction pH was adjusted to pH 6.0, approximately. After pH adjustment, the reaction temperature was cooled to 4° C. Oxidation was initiated by the addition of approximately 0.09-0.13 molar equivalents of sodium periodate. The oxidation reaction was performed at 5±3° C. for 20±4 hrs, approximately.

Concentration and diafiltration of the activated polysaccharide was carried out using 5K MWCO ultrafiltration cassettes. Diafiltration was performed against 20-fold diavolumes of WFI. The purified activated polysaccharide was then stored at 5±3° C. The purified activated saccharide is characterized, inter alia, by (i) saccharide concentration by colorimetric assay; (ii) aldehyde concentration by colorimetric assay; (iii) degree of oxidation; and (iv) molecular weight by SEC-MALLS.

Compounding Activated Polysaccharide with Sucrose Excipient, and Lyophilizing

The activated polysaccharide was compounded with sucrose to a ratio of 25 grams of sucrose per gram of activated polysaccharide. The bottle of compounded mixture was then lyophilized. Following lyophilization, bottles containing lyophilized activated polysaccharide were stored at −20±5° C. Calculated amount of CRM$_{197}$ protein was shell-frozen and lyophilized separately. Lyophilized CRM$_{197}$ was stored at −20±5° C.

Reconstituting Lyophilized Activated Polysaccharide and Carrier Protein

Lyophilized activated polysaccharide was reconstituted in anhydrous dimethyl sulfoxide (DMSO). Upon complete dissolution of polysaccharide, an equal amount of anhydrous DMSO was added to lyophilized $CRM_{197}$ for reconstitution.

Conjugating and Capping

Reconstituted activated polysaccharide was combined with reconstituted $CRM_{197}$ in the reaction vessel, followed by mixing thoroughly to obtain a clear solution before initiating the conjugation with sodium cyanoborohydride. The final polysaccharide concentration in reaction solution was approximately 1 g/L. Conjugation was initiated by adding 0.5-2.0 MEq of sodium cyanoborohydride to the reaction mixture and incubating at 23±2° C. for 20-48 hrs. The conjugation reaction was terminated by adding 2 MEq of sodium borohydride ($NaBH_4$) to cap unreacted aldehydes. This capping reaction continued at 23±2° C. for 3±1 hrs.

Purifying the Conjugate

The conjugate solution was diluted 1:10 with chilled 5 mM succinate-0.9% saline (pH 6.0) in preparation for purification by tangential flow filtration using 100-300K MWCO membranes.

The diluted conjugate solution was passed through a 5 μm filter, and diafiltration was performed using 5 mM succinate/0.9% saline (pH 6.0) as the medium. After the diafiltration was completed, the conjugate retentate was transferred through a 0.22 μm filter. The conjugate was diluted further with 5 mM succinate/0.9% saline (pH 6), to a target saccharide concentration of approximately 0.5 mg/mL. Alternatively, the conjugate is purified using 20 mM Histidine-0.9% saline (pH 6.5) by tangential flow filtration using 100-300K MWCO membranes. Final 0.22 μm filtration step was completed to obtain the immunogenic conjugate. See Table 14, Table 15, Table 16, Table 17, and Table 18.

Example 17: Conjugation in Aqueous Buffer (RAC/Aqueous), as Applied to from *E. coli* Serotypes O25B, O1A, O2, and O6

Polysaccharides activation and diafiltration was performed in the same manner as the one for DMSO based conjugation.

The filtered activated saccharide was compounded with $CRM_{197}$ at a polysaccharide to protein mass ratio ranging from 0.4 to 2 w/w depending on the serotype. This input ratio was selected to control the polysaccharide to $CRM_{197}$ ratio in the resulting conjugate.

The compounded mixture was then lyophilized. Upon conjugation, the polysaccharide and protein mixture was dissolved in 0.1M sodium phosphate buffer at the polysaccharide concentration ranging from 5 to 25 g/L depending on the serotype, pH was adjusted between 6.0 to 8.0 depending on the serotype. Conjugation was initiated by adding 0.5-2.0 MEq of sodium cyanoborohydride to the reaction mixture and incubating at 23±2° C. for 20-48 hrs. The conjugation reaction was terminated by adding 1-2 MEq of sodium borohydride ($NaBH_4$) to cap unreacted aldehydes.

Alternatively, the filtered activated saccharide and calculated amount of $CRM_{197}$ protein was shell-frozen and lyophilized separately, and then combined upon dissolving in 0.1M sodium phosphate buffer, subsequent conjugation can then be proceeded as described above.

TABLE 13 summarizes the results from both conjugations prepared in DMSO and aqueous buffer

|  | RAC/DMSO | RAC/Aqueous |
| --- | --- | --- |
| Poly MW (kDa) | 48K | 46K |
| Degree of Oxidation (DO) | 12 | 12 |

TABLE 13-continued summarizes the results from both conjugations prepared in DMSO and aqueous buffer

|  | RAC/DMSO | RAC/Aqueous |
| --- | --- | --- |
| Saccharide/Protein Ratio | 0.8 | 1.0 |
| % Free Saccharide | <5% | 32% |
| Conjugate MW by SEC-MALLS, kDa | 7950 | 260 |

Figure 24:
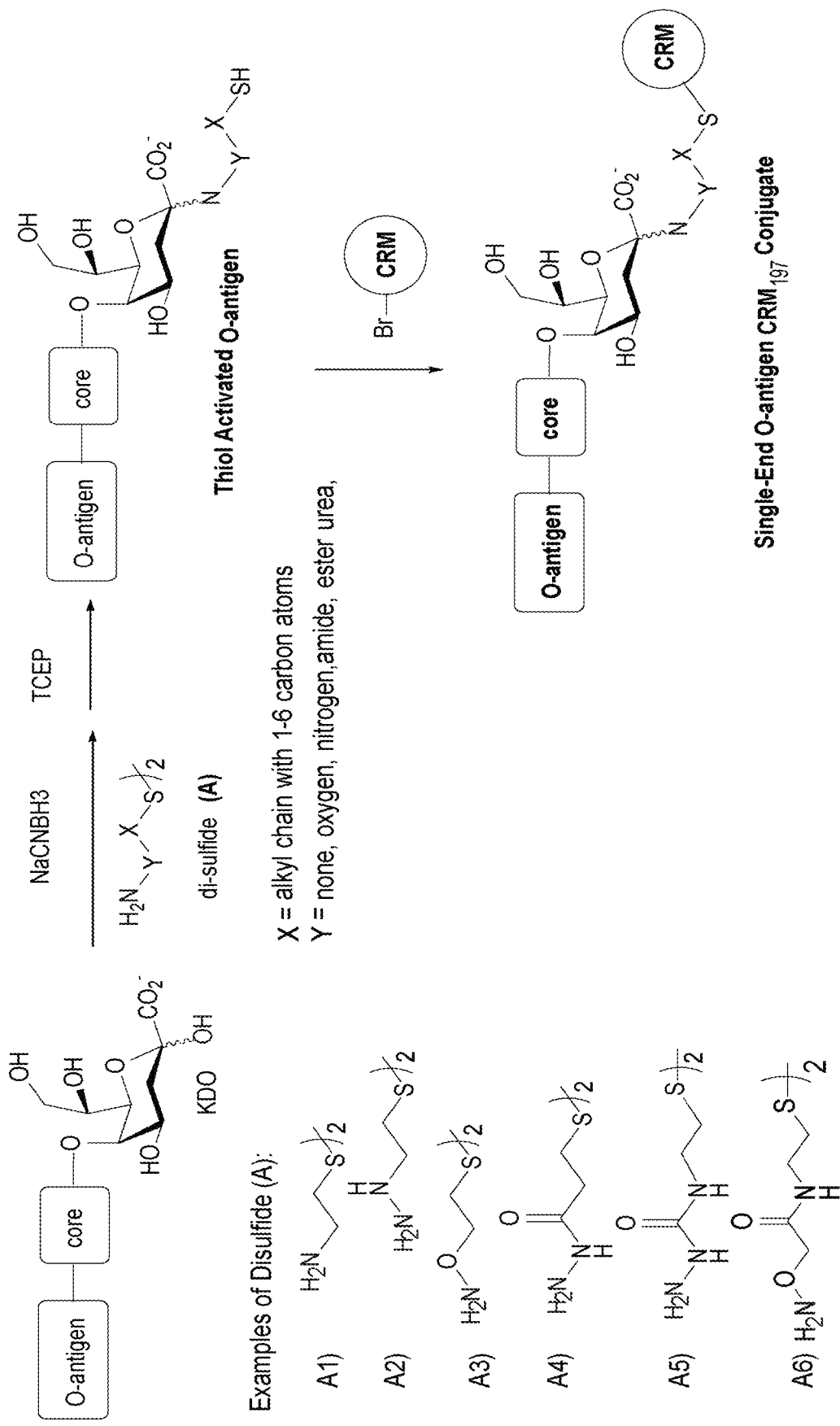
FIG. 24—schematic illustrating an exemplary preparation of single-ended conjugates, wherein the conjugation process involves selective activation of 2-Keto-3-deoxyoctanoic acid (KDO) with a disulfide amine linker, upon unmasking of a thiol functional group. The KDO is then conjugated to bromo activated CRM$_{197}$ protein as depicted in FIG. 24 (Preparation of Single-Ended Conjugates).

Example 18: Procedure for the Preparation of *E. coli* O-Antigen Polysaccharide-$CRM_{197}$ Single-Ended Conjugates Lipopolysaccharides (LPS), which are common components of the outer membrane of Gram-negative bacteria, comprise lipid A, the core region, and the O-antigen (also refer to as the O-specific polysaccharide or O-polysaccharide). Different serotype of O-antigen repeating units differ in their composition, structure and serological features. The O-antigen used in this invention is attached to the core domain which contains a sugar unit called 2-Keto-3-deoxyoctanoic acid (KDO) at its chain terminus. Unlike some conjugation methods based on random activation of the polysaccharide chain (e.g. activation with sodium periodate, or carbodiimide). This invention discloses a conjugation process involving selective activation of KDO with a disulfide amine linker, upon unmasking of thiol functional group, it is then conjugated to bromo activated $CRM_{197}$ protein as depicted in FIG. 24 (Preparation of Single-Ended Conjugates).

Conjugation Based on Cystamine Linker (A1)

O-antigen polysaccharide and cystamine (50-250 mol. eq of KDO) were mixed in phosphate buffer, adjust pH to 6.0-7.0. To the mixture, sodium cyanoborohydride ($NaCNBH_3$) (5-30 mol. eq of KDO) was added and the mixture was stirred at 37° C. for 48-72 hrs. Upon cooling to room temperature and diluted with equal volume of phosphate buffer, the mixture was treated with tris(2-carboxyethyl) phosphine (TCEP) (1.2 mol, eq of cystamine added). The mixture was then purified through diafiltration using 5 KDa MWCO membrane against 10 mM sodium phosphate monobasic solution, to furnish thiol containing O-antigen polysaccharide. The thiol content can be determined by Ellman assays.

The conjugation was then proceeded by mixing above thiol activated O-antigen polysaccharide with bromo activated $CRM_{197}$ protein at a ratio of 0.5-2.0. The pH of the reaction mixture is adjusted to 8.0-10.0 with 1 M NaOH solution. The conjugation reaction was proceeded at 5° C. for 24±4 hours. The unreacted bromo residues on the carrier protein were quenched by reacting with 2 mol. eq. of N-acetyl-L-cysteine for 3-5 hours at 5° C. The addition of 3 mol. eq. of iodoacetamide (related to N-acetyl-L-Cysteine added) wad then followed to cap the residual free sulfhydryl groups. This capping reaction was proceeded for another 3-5 hours at 5° C., and pH of both capping steps was maintained at 8.0-10.0 by addition of 1M NaOH. The resulting conjugate was obtained after ultrafiltration/dialfiltration using 30 KDa MWCO membrane against 5 mM succinate-0.9% saline, pH 6.0. See Table 14, Table 15, Table 16, Table 17, and Table 18.

Example 19: Conjugation Based on 3,3'-Dithio Bis(Propanoic Dihydrazide) Linker (A4)

O-antigen polysaccharide and 3,3'-dithio bis(propanoic dihydrazide) (5-50 mol. eq of KDO) were mixed in acetate buffer, adjust pH to 4.5-5.5. To the mixture, sodium cyanoborohydride (NaCNBH$_3$) (5-30 mol. eq of KDO) was added and the mixture was stirred at 23-37° C. for 24-72 hrs. The mixture was then treated with tris(2-carboxyethyl) phosphine (TCEP) (1.2 mol, eq of 3,3'-dithio bis(propanoicdihydrazide) linker added). The mixture was then purified through diafiltration using 5 KDa MWCO membrane against 10 mM sodium phosphate monobasic solution, to furnish thiol containing O-antigen polysaccharide. The thiol content can be determined by Ellman assays.

The conjugation was then proceeded by mixing above thiol activated O-antigen polysaccharide with bromo activated CRM$_{197}$ protein at a ratio of 0.5-2.0. The pH of the reaction mixture is adjusted to 8.0-10.0 with 1 M NaOH solution. The conjugation reaction was proceeded at 5° C. for 24±4 hours. The unreacted bromo residues on the carrier protein were quenched by reacting with 2 mol. eq. of N-acetyl-L-cysteine for 3-5 hours at 5° C. The addition of 3 mol. eq. of iodoacetamide (related to N-acetyl-L-Cysteine added) wad then followed to cap the residual free sulfhydryl groups. This capping reaction was proceeded for another 3-5 hours at 5° C., and pH of both capping steps was maintained at 8.0-10.0 by addition of 1M NaOH. The resulting conjugate was obtained after ultrafiltration/dialfiltration using 30 KDa MWCO membrane against 5 mM succinate-0.9% saline, pH 6.0.

Example 20: Conjugation Based on 2,2'-dithio-N, N'-bis(ethane-2,1-diyl)bis(2-(aminooxy)acetamide) Linker (A6)

O-antigen polysaccharide and 2,2'-dithio-N,N'-bis(ethane-2,1-diyl)bis(2-(aminooxy) acetamide) (5-50 mol. eq of KDO) were mixed in acetate buffer, adjust pH to 4.5-5.5. The mixture was then stirred at 23-37° C. for 24-72 hrs, followed by the addition of sodium cyanoborohydride (NaCNBH$_3$) (5-30 mol. eq of KDO) and the mixture was stirred for another 3-24 hrs. The mixture was then treated with tris(2-carboxyethyl) phosphine (TCEP) (1.2 mol, eq of linker added). The mixture was then purified through diafiltration using 5 KDa MWCO membrane against 10 mM sodium phosphate monobasic solution, to furnish thiol containing O-antigen polysaccharide. The thiol content can be determined by Ellman assays.

The conjugation was then proceeded by mixing above thiol activated O-antigen polysaccharide with bromo activated CRM$_{197}$ protein at a ratio of 0.5-2.0. The pH of the reaction mixture is adjusted to 8.0-10.0 with 1 M NaOH solution. The conjugation reaction was proceeded at 5° C. for 24±4 hours. The unreacted bromo residues on the carrier protein were quenched by reacting with 2 mol. eq. of N-acetyl-L-cysteine for 3-5 hours at 5° C. The addition of 3 mol. eq. of iodoacetamide (related to N-acetyl-L-Cysteine added) was then followed to cap the residual free sulfhydryl groups. This capping reaction was proceeded for another 3-5 hours at 5° C., and pH of both capping steps was maintained at 8.0-10.0 by addition of 1M NaOH. The resulting conjugate was obtained after ultrafiltration/dialfiltration using 30 KDa MWCO membrane against 5 mM succinate-0.9% saline, pH 6.0.

Example 21: Preparation of Bromo Activated CRM$_{197}$

The CRM$_{197}$ was prepared in 0.1M Sodium Phosphate, pH 8.0±0.2 solution, and was cooled to 5±3° C. To the protein solution, the N-hydroxysuccinimide ester of bromoacetic acid (BAANS) as a stock dimethylsulfoxide (DMSO) solution (20 mg/mL) is added in a ratio of 0.25-0.5 BAANS: protein (w/w). The reaction is gently mixed at 5±3° C. for 30-60 minutes. The resulting bromoacetylated (activated) protein is purified, e.g., by ultrafiltration/diafiltration using 10 kDa MWCO membrane using 10 mM phosphate (pH 7.0) buffer. Following purification, the protein concentration of the bromoacetylated carrier protein is estimated by Lowry protein assay.

TABLE 14

| | O1a Conjugates | | | | |
|---|---|---|---|---|---|
| Conjugate Lot # | 132240-112-2 | 132242-106 | 132242-124 | 132242-127 | 132242-130 |
| Poly Lot # | 709756-160 | 709756-160 | 709756-160 | 710958-116 | 710958-116 |
| Poly Type | | Long Chain | | Short Chain | |
| Poly MW (kDa) | 33 | 33 | 33 | 11 | 11 |
| Variant | eTEC | Single-End | RAC/DMSO | Single-End | RAC/DMSO |
| Activation | 8% SH | 2.1% SH | DO: 13 | 6.4% SH | DO: 16 |
| | | Conjugate Data | | | |
| Yield (%) | 30 | 26 | 77 | 45 | 35 |
| SPRatio | 0.6 | 0.5 | 1.0 | 0.7 | 0.6 |
| Free Sacc (%) | 9 | 9 | 20 | 5 | 6 |
| MW (kDa) | 1035 | 331 | 1284 | 280 | 2266 |
| Sacc Conc (mg · mL) | 0.31 | 0.37 | 0.58 | 0.59 | 0.37 |
| Endotoxin (EU/ug) | 0.03 | 0.02 | 0.01 | 0.01 | 0.01 |
| Buffer | | 5 mM Succ/Saline, pH 6.0 | | | |

TABLE 15

| | O2 Conjugates | | | | |
|---|---|---|---|---|---|
| Conjugate Lot # | 00709749-0003-1 | 132242-161 | 132242-152 | 132242-159 | 132242-157 |
| Poly Lot# | 709766-33 | 709766-65 | | 710958-141-2 | |
| Poly Type | | Long Chain | | Short Chain | |
| Poly MW (kDa) | 36 | 39 | | 14 | |

TABLE 15-continued

| | O2 Conjugates | | | | |
|---|---|---|---|---|---|
| Variant Activation | eTEC 6.8% SH | Single-End 1.6% SH | RAC/DMSO DO: 17 | Single-End 6.3% SH | RAC/DMSO DO: 19 |
| | | Conjugate Data | | | |
| Yield (%) | 26 | 33 | 50 | 38 | 36 |
| SPRatio | 1.5 | 0.8 | 0.8 | 1.0 | 0.6 |
| Free Sacc (%) | 11 | 24% | <5 | <5 | 6 |
| MW (kDa) | 1161 | 422 | 3082 | 234 | 1120 |
| Endotoxin (EU/ug) | 0.025 | 0.02 | 0.01 | 0.01 | 0.01 |
| Buffer | | 5 mM Succ/Saline, pH 6.0 | | | |

TABLE 16

| | O6 Conjugates | | | | |
|---|---|---|---|---|---|
| Conjugate Lot # | 132240-117-1 | 132242-134 | 132242-137 | 132242-146 | 132242-145 |
| Poly Lot # | | 710958-121-1 | | 710958-143-3 | |
| Poly Type | | Long Chain | | Short Chain | |
| Poly MW (kDa) | | 44 | | 15 | |
| Variant Activation | eTEC 18% SH | Single-End 2.2% SH | RAC/DMSO DO: 16.5 | Single-End 6.1% SH | RAC/DMSO DO: 22 |
| | | Conjugate Data | | | |
| Yield (%) | 27 | 23 | 58 | 48 | 30 |
| SPRatio | 0.78 | 0.6 | 0.82 | 0.7 | 0.6 |
| Free Sacc (%) | 9 | 4 | 4 | <5 | 8 |
| MW (kDa) | 1050 | 340 | 1910 | 256 | 2058 |
| Sacc Conc (mg · mL) | 0.39 | 0.45 | 0.59 | 0.88 | 0.41 |
| Endotoxin (EU/ug) | 0.03 | 0.02 | 0.01 | 0.004 | 0.005 |
| Buffer | | 5 mM Succ/Saline, pH 6.0 | | | |

TABLE 17

| | O25b Conjugates | | | | | | | | |
|---|---|---|---|---|---|---|---|---|---|
| Conjugate Lot # | 132242-28 | 132242-98 | 132240-73-1-1 | 132242-62-1 | 132240-81 | 132240-116 | 132242-121 | 132242-27 | 132242-29 |
| Poly Lot # | 709766-28 | 709766-29 | 709766-30 | 709766-30 | 709766-30 | 710958-117/118 | 710958-117/118 | 709766-28 | 709766-28 |
| Poly type | | Long Chain | | | | Short Chain | | Chain Long | Chain Long |
| Poly MW (kDa) | 51 | 48 | 48 | 48 | 48 | 14 | 14 | 51 | 51 |
| Variant Activation | RAC/DMSO DO: 18 | Single-End 2.4% SH | eTEC 10% SH | eTEC 4% SH | eTEC 17% SH | Single-End 6.6% SH | RAC/DMSO DO: 17 | RAC/DMSO 21 | RAC/DMSO 12 |
| | | | | Conjugate Data | | | | | |
| Yield (%) | 82 | 26 | 56 | 32 | 92 | 28 | 18 | 71 | 80 |
| SPRatio | 0.9 | 0.82 | 0.88 | 0.64 | 1.32 | 0.7 | 0.36 | 0.81 | 0.84 |
| Free Sacc (%) | 7.2 | 5 | <5 | 11 | <5 | <5 | <5 | 8.3 | <5 |
| Conjugate MW (kDa) | 4415 | 840 | 1057 | 1029 | 2306 | 380 | 9114 | 3303 | 7953 |
| Sacc Conc (mg · mL) | 0.7 | 0.4 | 0.43 | 0.36 | 0.9 | 0.45 | 0.19 | 0.6 | 0.67 |
| Endotoxin (EU/ug) | 0.01 | 0.02 | 0.08 | 0.08 | 0.01 | 0.01 | 0.01 | 0.02 | 0.22 |
| Conjugate (DS) Buffer matrix | | 5 mM Succ/Saline, pH 6.0 | | | | | | | |

TABLE 18

| O25b K-12 Conjugates | | |
|---|---|---|
| Conjugate Lot # | 709749-015-2 | 709744-0016 |
| Poly Lot # | 710958-137 | |
| Poly Type | Long Chain(K12) | |
| Poly MW (kDa) | 44 | |
| Variant Activation | eTEC SH: 24% | RAC/DMSO DO: 19 |

TABLE 18-continued

O25b K-12 Conjugates

| Conjugate Data | | |
| --- | --- | --- |
| Yield (%) | 59% | 33% |
| SPRatio | 1.4 | 0.83 |
| Free Sacc (%) | 5% | 5.2% |
| MW (kDa) | 1537 | 4775 |
| Sacc Conc (mg · mL) | 0.91 | 0.29 |
| Endotoxin (EU/ug) | 0.08 | 0.01 |
| Buffer | 5 mM Succ/Saline, pH 6.0 | |

Example 22: Preparation of E. coli O—Ag-TT Conjugates

E. coli serotype O25b long polysaccharide, Lot #709766-30 (about 6.92 mg/mL, MW: about 39 kDa), 50 mg, lyophilized was used for Tetanus Toxoid (TT) conjugation.

E. coli serotype O1a long polysaccharide 710958-142-3 (about 6.3 mg/mL, MW: about 44.3 kDa) (50 mg, 7.94 mL) was lyophilized.

E. coli serotype O6 long polysaccharide, 710758-121-1 (about 16.8 mg/mL, MW: about 44 kDa) (50 mg, 2.98 mL) was lyophilized.

Each of the lyophilized polysaccharides listed above was dissolved in WFI to make at approx 5-10 mg/mL to it, 0.5 mL (100 mg (1-cyano-4-dimethylaminopyridinum tetrafluoroborate (CDAP) solution in 1 mL acetonitrile) was added and stirred at RT. Triethylamine (TEA) 0.2M (2 mL) was added and stirred at RT.

Preparation of Tetanus toxoid (TT): TT (100 mg, 47 ml) was concentrated to approximately 20 mL and washed twice with saline (2×50 mL) using filtration tubes. After that it was diluted with HEPES and saline to make final HEPES conc as about 0.25M. TT was prepared as described above and pH of the reaction was adjusted to about 9.1-9.2. The reaction mixture was stirred at RT.

After 20-24 hrs the reaction was quenched with Glycine (0.5 mL). After that it was concentrated to using MWCO regenerated cellulose membranes and diafiltration was performed against saline. Filtered and analyzed. See Table 19.

TABLE 19

| Exemplary embodiments: | |
| --- | --- |
| E. coli serotype O25b-TT conjugate | E. coli serotype O6-TT conjugate |
| Volume: 41 mL | Volume: 42 mL |
| Sacc Conc (Anthrone): 1.122 mg/mL (92% yield) | Sacc Conc (Anthrone): 0.790 mg/mL (66% yield) |
| Protein Conc (Lowry): 1.133 mg/mL | Protein Conc (Lowry): 1.895 mg/mL |
| SPRatio: 0.99 | SPRatio: 0.42 |
| Free Sacc (DOC): 74.7% | Free Sacc (DOC): <5% |
| The product obtained was concentrated to 15 mL using MWCO regenerated cellulose membranes and diafiltration was performed against saline (40X diavolumes). Filtered through 0.22 um filter and analyzed. | MW (kDa): 1192 |
| | Endotoxin (EU/ug:) 0.022 |
| Volume: 27 mL | |
| Sacc Conc (Anthrone): 1.041 mg/mL (56% yield) | |
| Protein Conc (Lowry): 1.012 mg/mL | |
| SPRatio: 1.03 | |
| Free Sacc (DOC): 60.6% (poly recovery 100%) | |

Example 23: Additional Results from O-Antigen Fermentation, Purification, and Conjugation The exemplary processes described below is generally applicable to all E. coli serotypes. The production of each polysaccharide included a batch production fermentation followed by chemical inactivation prior to downstream purification.

Strains and storage. Strains employed for biosynthesis of short chain O-antigen were clinical wild type strains of E. coli. Long chain O-antigen was produced with derivatives of the short chain-producers that had been engineered by the Wanner-Datsenko method to possess a deletion of the native wzzb gene and were complemented by the "long-chain" extender function fepE from Salmonella. The fepE function was expressed from its native promoter on either a high copy colE1-based "topo" vector or a low copy derivative of the colE1-based vector pET30a, from which the T7 promoter region had been deleted.

Cell banks were prepared by growing cells in either animal free LB or minimal medium to an $OD_{600}$ of at least 3.0. The broth was then diluted in fresh medium and combined with 80% glycerol to obtain a 20% glycerol final concentration with 2.0 $OD_{600}$/mL.

Media used for seed culture and fermentation. The seed and fermentation medium employed share the following formulation: $KH_2PO_4$, $K_2HPO_4$, $(NH_4)_2SO_4$, sodium citrate, $Na_2SO_4$, aspartic acid, glucose, $MgSO_4$, $FeSO_4$-$7H_2O$, $Na_2MoO_4$-$2H_2O$, $H_3BO_3$, $CoCl_2$-$6H_2O$, $CuCl_2$-$2H_2O$, $MnCl_2$-$4H_2O$, $ZnCl_2$ and $CaCl_2$)-$2H_2O$.

Seed and fermentation conditions. Seeds were inoculated at 0.1% from a single seed vial. The seed flask was incubated at 37° C. for 16-18 hours and typically achieved 10-20 $OD_{600}$/mL.

Fermentation was performed in a 10 L stainless steel, steam in place fermentor.

Inoculation of the fermentor was typically 1:1000 from a 10 $OD_{600}$ seed. The batch phase, which is the period during which growth proceeds on the 10 g/L batched glucose, typically lasts 8 hours. Upon glucose exhaustion, there was a sudden rise in dissolved oxygen, at which point glucose was fed to the fermentation. The fermentation typically then proceeds for 16-18 hours with harvest giving >120 $OD_{600}$/mL.

Initial evaluation of short/long chain O-antigen production for serotypes O1a, O2, O6 and O25b. Wild type strains for O1a, O2, O6 and O25b were fermented in a supplemented minimal medium in batch mode to an $OD_{600}$=15-20. Upon glucose exhaustion, which results in a sudden decrease in oxygen consumption, a growth limiting glucose feed was applied from a glucose solution for 16-18 hours. Cell densities of 124-145 $OD_{600}$ units/mL were reached. The pH of the harvest broths was subsequently adjusted to about 3.8 and heated to 95° C. for 2 hours. The hydrolyzed broth was then cooled to 25° C., brought to pH 6.0 and centrifuged to remove solids. The resulting supernatant was then applied to a SEC-HPLC column for quantitation of the O-antigen. Productivities in the range of 2240-4180 mg/L were obtained. The molecular weight of purified short-chain O-antigen from these batches was found to range from 10-15 kDa. It was also noted that SEC chromatography of the O2 and O6 hydrolysates revealed a distinct and separable contaminating polysaccharide that was not evident in the O1a and O25b hydrolysates.

Long chain versions of the O1a, O2, O6 and O25b O-antigens where accessed through fermentation of a wzzb deletion version of each strain which carried a heterologous, complementing fepE gene on a high-copy, kanamycin-selectable topo plasmid. Fermentation was performed as for the short chain, albeit with kanamycin selection. The final cell densities observed at 124-177 $OD_{600}$/mL were associated with O-antigen productivities of 3500-9850 mg/L. The complementation-based synthesis of long chain O-antigen was at least as productive as in the parental short chain strain and in some cases more so. The molecular weights of purified O-antigen polysaccharide were 33-49 kDa or about 3 times the size of the corresponding short chain.

It was noted that the long chain hydrolysates for O2 and O6 showed evidence of a contaminating polysaccharide peak that, in the case of long chain antigen, was observed as a shoulder on the main O-antigen peak; O1 and O25b showed no evidence of production of a contaminating polysaccharide, as was seen earlier with the short chain parent.

Growth rate suppression was found to be associated with the presence of the topo replicon absent the fepE. Additionally, the Δwzzb mutation itself had not adverse effect on growth rate, indicating that the disturbed growth rates were conveyed by the plasmid vector.

Evaluation of strains for production of O11, O13, O16, O21 and O75 O-antigen. Multiple wild-type strains of serotypes O11, O13, O16, O21 and O75 were evaluated for their propensity to produce unwanted polysaccharide in fermentation by SEC-HPLC. Strains for O11, O13, O16, O21 and O75 were selected as absent contaminating polysaccharide, as well as for their ability to produce >1000 mg/L O-antigen and for the display of an antibiotic sensitivity profile that allowed Wanner-Datsenko recombineering for introduction of the Δwzzb trait.

Chloramphenicol-selectable versions of topo-fepE and pET-fepE were constructed that allowed for the introduction of fepE into the O11, O13, O16, O21 and O75 Δwzzb strains that in general were found to be kanamycin-resistant. The resulting topo-fepE and pET-fepE bearing strains were fermented with chloramphenicol selection and the supernatant from acid-hydrolyzed broth was evaluated by SEC-HPLC. Both the high (topo) and low copy (pET) fepE constructs directed the synthesis of O-antigen with productivities for each that were equivalent to the parental wild-type. Expression of potentially interfering polysaccharides was not observed.

An evaluation of growth rates for wzzb plasmid-bearing strains showed that the O11, O13 and O21 were retarded by the presence of topo-fepE but not by pET-fepE; strains O16 and O75 strains showed acceptable growth rates irrespective of replicon choice.

TABLE 20

| O-antigen type | IHMA type | short (SC) or long chain (LC) | fep E plasmid type | marker | final cell density $OD_{600}$ | final Oag productivity (mg/L) | MW-kDa | SEC impurity |
|---|---|---|---|---|---|---|---|---|
| O1a | wt | SC | None | None | 125 | 2550 | 11 | N |
| O1a | Δwzzb/fepE | LC | topo | Kana | 130 | 5530 | 33 | N |
| O1a | Δwzzb/fepE | LC | pET | Kana | Not done (ND) | ND | ND | ND |
| O2 | wt | SC | None | None | 127 | 2240 | 13 | Y |
| O2 | Δwzzb/fepE | LC | topo | Kana | 177 | 3750 | 49 | Y |
| O2 | x | LC | pET | x | NA | NA | NA | NA |
| O6 | wt | SC | None | None | 145 | 4180 | 16 | Y |
| O6 | Δwzzb/fepE | LC | topo | Kana | 124 | 9850 | 44 | Y |
| O6 | Δwzzb/fepE | LC | pET | Kana | ND | ND | ND | ND |
| O11 | wt | SC | None | None | 194 | 4720 | x | N |
| O11 | Δwzzb/fepE | LC | topo | Kana | 142 | 7220 | x | N |
| O11 | x | LC | pET | x | NA | NA | NA | NA |
| O13 | wt | SC | None | x | 113 | 4770 | x | N |
| O13 | Δwzzb/fepE | LC | topo | cam | 101 | 4680 | x | N |
| O13 | Δwzzb/fepE | LC | pET | cam | 108 | 4600 | x | N |
| O16 | wt | SC | None | x | 154 | 1870 | x | N |
| O16 | Δwzzb/fepE | LC | topo | cam | 129 | 1180 | x | N |
| O16 | Δwzzb/fepE | LC | pET | cam | 137 | 1280 | x | N |
| O21 | wt | SC | None | x | 140 | 1180 | x | N |
| O21 | Δwzzb/fepE | LC | topo | cam | ND | ND | x | N |
| O21 | Δwzzb/fepE | LC | pET | cam | 131 | 820 | x | N |
| O25b | 2831 | SC | None | None | 126 | 3550 | 10 | N |
| O25b | Δwzzb/fepE | LC | topo | Kana | 152 | 3500 | 49 | N |
| O25b | x | LC | pET | x | NA | NA | NA | NA |
| O75 | wt | SC | None | x | 149 | 1690 | x | N |
| O75 | Δwzzb/fepE | LC | topo | cam | 132 | 1500 | x | N |
| O75 | Δwzzb/fepE | LC | pET | cam | 138 | 1520 | x | N |

The purification process for the polysaccharides included acid hydrolysis to release the O-antigens. A crude suspension of serotype specific *E. coli* culture in fermentation reactor was directly treated with acetic acid to the final pH of 3.5±0.5 and the acidified broth was heated to the temperature of 95±5° C. for at least one hour. This treatment cleaves the labile linkage between KDO, at the proximal end of the oligosaccharide and the lipid A, thus releasing the O—Ag chain. The acidified broth that contains the released O—Ag was cooled to 20±10° C. before being neutralized to pH 7±1.0 using $NH_4OH$. The process further included several centrifugation, filtration, and concentration/diafiltration operations steps.

TABLE 21

| Serotype (core) | Description | Expected Poly size | Titer (g/L) | Purified Poly M.W. (kDa) | Number of Repeat Units | Increase in M.W. (kDa) over short | NMR | Purified Conjugate M.W. (kDa) | Conjugation Lot # |
|---|---|---|---|---|---|---|---|---|---|
| O25b (R1) | ΔwzzB + LT2FepE | Long | 5.3 | 47 | 55 | 34 | ✓ | 5365 | 132242-28 (RAC/DMSO) |
| | | | | | | | | 1423 | 132242-98 (Single-end) |
| | | | | | | | | 1258 | 132240-73-1-1 (eTEC) |
| | ΔwzzB + O25a wzzB | Short | 2.3 | 13/14 | 15 | NA | ✓ | 380 | 132242-116 (Single-end) |
| | | | | | | | | 9114 | 132242-121 (RAC/DMSO) |
| O25b (K12) | ΔwzzB + LT2FepE | Long | 3.5 | 44 | 51 | 27 | ✓ | 1537 | 709749-015-2 (eTEC) |
| | | | | | | | | 4775 | 709744-0016 (RAC/DMSO |
| | wt | Short | 3.5 | 17 | 17 | NA | ✓ | | |
| O1a (R1) | ΔwzzB + LT2FepE | Long | 5.5 | 33 | 39 | 22 | ✓ | 1035 | 132240-112-2 (eTEC) |
| | | | | | | | | 331 | 132242-106 (Single-end) |
| | | | | | | | | 1284 | 132242-124 (RAC/DMSO) |
| | wt | Short | 2.5 | 11 | 13 | NA | ✓ | 280 | 132242-127 (Single-end) |
| | | | | | | | | 2266 | 132242-130 (RAC/DMSO) |
| O2 (R1) | ΔwzzB + LT2FepE | Long | 4.9 | 36 | 43 | 22 | ✓ | 1161 | 00707947-0003-1 (eTEC) |
| | | | | 39 | 47 | 25 | | 422 | 132242-161 (single-end) |
| | | | | | | | | 3082 | 132242-152 (RAC/DMSO) |
| | wt | Short | 2.8 | 14 | 17 | NA | ✓ | 234 | 132242-159 (single-end) |
| | | | | | | | | 1120 | 1322421-157 (RAC/DMSO) |
| O2 (R4) | ΔwzzB + LT2FepE | Long | 5.1 | NA | NA | NA | NA | | |
| | wt | Short | 2.1 | 14.7 | 18 | NA | ✓ | | |
| O6 (R1) | ΔwzzB + LT2FepE | Long | 6.9 | 37.2 | 42 | 22.2 | ✓ | | |
| | wt | Short | 3.5 | 15 | 17 | NA | ✓ | 256 | 132242-146 (Single-end_ |
| | | | | | | | | 2058 | 123342-145 (RAC/DMSO) |
| O6 (R1) | ΔwzzB + LT2FepE | Long | 8.4 | 44.4 | 50 | 28.2 | ✓ | 1050 | 132240-117-1 (eTEC) |
| | | | | | | | | 340 | 132242-134 (Single-end) |
| | | | | | | | | 1910 | 132242-137 (RAC/DMSO) |
| | wt | Short | 3.6 | 16.2 | 18 | NA | ✓ | | |

The following clauses describe additional embodiments of the invention:

C1. A saccharide comprising a structure selected from any one of Formula O1 (e.g., Formula O1A, Formula O1B, and Formula O1C), Formula O2, Formula O3, Formula O4 (e.g., Formula O4: K52 and Formula O4: K6), Formula O5 (e.g., Formula O5ab and Formula O5ac (strain 180/C3)), Formula O6 (e.g., Formula O6: K2; K13; K15 and Formula O6: K54), Formula O7, Formula O8, Formula O9, Formula O10, Formula O11, Formula O12, Formula O13, Formula O14, Formula O15, Formula O16, Formula O17, Formula O18 (e.g., Formula O18A, Formula O18ac, Formula O18A1, Formula O18B, and Formula O18B1), Formula O19, Formula O20, Formula O21, Formula O22, Formula O23 (e.g., Formula O23A), Formula O24, Formula O25 (e.g., Formula O25a and Formula O25b), Formula O26, Formula O27, Formula O28, Formula O29, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45 (e.g., Formula O45 and Formula O45rel), Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula 62D$_1$, Formula O63, Formula O64, Formula O65, Formula O66, Formula O68, Formula O69, Formula O70, Formula O71, Formula O73 (e.g., Formula O73 (strain 73-1)), Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144, Formula O145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, and Formula O187, wherein n is an integer from 1 to 100.

C2. The saccharide according to clause C1, comprising a structure selected from Formula O1 (e.g., Formula O1A, Formula O1B, and Formula O1C), Formula O2, Formula O3, Formula O4 (e.g., Formula O4: K52 and Formula O4: K6), Formula O5 (e.g., Formula O5ab and Formula O5ac (strain 180/C3)), Formula O6 (e.g., Formula O6: K2; K13; K15 and Formula O6: K54), Formula O7, Formula O10, Formula O16, Formula O17, Formula O18 (e.g., Formula O18A, Formula O18ac, Formula O18A1, Formula O18B, and Formula O18B1), Formula O21, Formula O23 (e.g., Formula O23A), Formula O24, Formula O25 (e.g., Formula O25a and Formula O25b), Formula O26, Formula O28, Formula O44, Formula O45 (e.g., Formula O45 and Formula O45rel), Formula O55, Formula O56, Formula O58, Formula O64, Formula O69, Formula O73 (e.g., Formula O73 (strain 73-1)), Formula O75, Formula O77, Formula O78, Formula O86, Formula O88, Formula O90, Formula O98, Formula O104, Formula O111, Formula O113, Formula O114, Formula O119, Formula O121, Formula O124, Formula O125, Formula O126, Formula O127, Formula O128, Formula O136, Formula O138, Formula O141, Formula O142, Formula O143, Formula O147, Formula O149, Formula O152, Formula O157, Formula O158, Formula O159, Formula O164, Formula O173, Formula $62D_1$, Formula O22, Formula O35, Formula O65, Formula O66, Formula O83, Formula O91, Formula O105, Formula O116, Formula O117, Formula O139, Formula O153, Formula O167, and Formula O172, wherein n is an integer from 20 to 100.

C3. The saccharide according to clause C2, comprising a structure selected from Formula O1 (e.g., Formula O1A, Formula O1B, and Formula O1C), Formula O2, Formula O3, Formula O4 (e.g., Formula O4: K52 and Formula O4: K6), Formula O5 (e.g., Formula O5ab and Formula O5ac (strain 180/C3)), Formula O6 (e.g., Formula O6: K2; K13; K15 and Formula O6: K54), Formula O7, Formula O10, Formula O16, Formula O17, Formula O18 (e.g., Formula O18A, Formula O18ac, Formula O18A1, Formula O18B, and Formula O18B1), Formula O21, Formula O23 (e.g., Formula O23A), Formula O24, Formula O25 (e.g., Formula O25a and Formula O25b), Formula O26, Formula O28, Formula O44, Formula O45 (e.g., Formula O45 and Formula O45rel), Formula O55, Formula O56, Formula O58, Formula O64, Formula O69, Formula O73 (e.g., Formula O73 (strain 73-1)), Formula O75, Formula O77, Formula O78, Formula O86, Formula O88, Formula O90, Formula O98, Formula O104, Formula O111, Formula O113, Formula O114, Formula O119, Formula O121, Formula O124, Formula O125, Formula O126, Formula O127, Formula O128, Formula O136, Formula O138, Formula O141, Formula O142, Formula O143, Formula O147, Formula O149, Formula O152, Formula O157, Formula O158, Formula O159, Formula O164, Formula O173, and Formula $62D_1$, wherein n is an integer from 20 to 100.

C4. The saccharide according to clause C2, comprising a structure selected from Formula O1 (e.g., Formula O1A, Formula O1B, and Formula O1C), Formula O2, Formula O6 (e.g., Formula O6: K2; K13; K15 and Formula O6: K54), Formula O15, Formula O16, Formula O21, Formula O25 (e.g., Formula O25a and Formula O25b), and Formula O75.

C5. The saccharide according to clause C1, wherein the saccharide does not comprise a structure selected from Formula O8, Formula O9a, Formula O9, Formula O20ab, Formula O20ac, Formula O52, Formula O97, and Formula O101.

C6. The saccharide according to clause C1, wherein the saccharide does not comprise a structure selected from Formula O12.

C7. The saccharide according to clause C4, wherein the saccharide is produced by expressing a wzz family protein in a Gram-negative bacterium to generate said saccharide.

C8. The saccharide according to clause C7, wherein the wzz family protein is selected from the group consisting of wzzB, wzz, $wzz_{SF}$, $wzz_{ST}$, fepE, $wzz_{fcpE}$, wzz1 and wzz2.

C9. The saccharide according to clause C7, wherein the wzz family protein is wzzB.

C10. The saccharide according to clause C7, wherein the wzz family protein is fepE.

C11. The saccharide according to clause C7, wherein the wzz family protein is wzzB and fepE.

C12. The saccharide according to clause C7, wherein the wzz family protein is derived from *Salmonella enterica*.

C13. The saccharide according to clause C7, wherein the wzz family protein comprises a sequence selected from any one of SEQ ID NO: 20, SEQ ID NO: 21, SEQ ID NO: 22, SEQ ID NO: 23, SEQ ID NO: 24, SEQ ID NO: 15, SEQ ID NO: 16, SEQ ID NO: 17, SEQ ID NO: 18, and SEQ ID NO: 19.

C14. The saccharide according to clause C7, wherein the wzz family protein comprises a sequence having at least 90% sequence identity to any one of SEQ ID NO: 15, SEQ ID NO: 16, SEQ ID NO: 17, SEQ ID NO: 18, and SEQ ID NO: 19.

C15. The saccharide according to clause C7, wherein the wzz family protein comprises a sequence selected from any one of SEQ ID NO: 20, SEQ ID NO: 21, SEQ ID NO: 22, SEQ ID NO: 23, SEQ ID NO: 24, SEQ ID NO: 15, SEQ ID NO: 16, SEQ ID NO: 17, SEQ ID NO: 18, and SEQ ID NO: 19.

C16. The saccharide according to clause C1, wherein the saccharide is synthetically synthesized.

C17. The saccharide according to any one of clauses C1 to C16, wherein the saccharide further comprises an *E. coli* R1 moiety.

C18. The saccharide according to any one of clauses C1 to C16, wherein the saccharide further comprises an *E. coli* R2 moiety.

C19. The saccharide according to any one of clauses C1 to C16, wherein the saccharide further comprises an *E. coli* R3 moiety.

C20. The saccharide according to any one of clauses C1 to C16, wherein the saccharide further comprises an *E. coli* R4 moiety.

C21. The saccharide according to any one of clauses C1 to C16, wherein the saccharide further comprises an *E. coli* K-12 moiety.

C22. The saccharide according to any one of clauses C1 to C21, wherein the saccharide further comprises a 3-deoxy-d-manno-oct-2-ulosonic acid (KDO) moiety.

C23. The saccharide according to any one of clauses C1 to C16, wherein the saccharide does not further comprise an *E. coli* R1 moiety.

C24. The saccharide according to any one of clauses C1 to C16, wherein the saccharide does not further comprise an *E. coli* R2 moiety.

C25. The saccharide according to any one of clauses C1 to C16, wherein the saccharide does not further comprise an *E. coli* R3 moiety.

C26. The saccharide according to any one of clauses C1 to C16, wherein the saccharide does not further comprise an *E. coli* R4 moiety.

C27. The saccharide according to any one of clauses C1 to C16, wherein the saccharide does not further comprise an *E. coli* K-12 moiety.

C28. The saccharide according to any one of clauses C1 to C21, wherein the saccharide does not further comprise a 3-deoxy-d-manno-oct-2-ulosonic acid (KDO) moiety.

C29. The saccharide according to any one of clauses C1 to C22, wherein the saccharide does not comprise a Lipid A.

C30. The saccharide according to any one of clauses C1 to C29, wherein the polysaccharide has a molecular weight of between 10 kDa and 2,000 kDa, or between 50 kDa and 2,000 kDa.

C31. The saccharide according to any one of clauses C1 to C30, wherein the saccharide has an average molecular weight of 20-40 kDa.

C32. The saccharide according to any one of clauses C1 to C31, wherein the saccharide has an average molecular weight of 40,000 to 60,000 kDa.

C33. The saccharide according to any one of clauses C1 to C32, wherein n is an integer 31 to 90.

C34. A conjugate comprising a saccharide covalently bound a carrier protein, wherein the saccharide is derived from *E. coli*.

C35. A conjugate comprising a saccharide according to any one of clause C1 to clause C33, covalently bound a carrier protein.

C36. The conjugate according to any one of clause C34 to clause C35, wherein the carrier protein is selected from any one of $CRM_{197}$, diphtheria toxin fragment B (DTFB), DTFB C8, Diphtheria toxoid (DT), tetanus toxoid (TT), fragment C of TT, pertussis toxoid, cholera toxoid, or exotoxin A from *Pseudomonas aeruginosa*; detoxified Exotoxin A of *P. aeruginosa* (EPA), maltose binding protein (MBP), detoxified hemolysin A of *S. aureus*, clumping factor A, clumping factor B, Cholera toxin B subunit (CTB), *Streptococcus pneumoniae* Pneumolysin and detoxified variants thereof, *C. jejuni* AcrA, and *C. jejuni* natural glycoproteins.

C37. The conjugate according to any one of clause C34 to clause C36, wherein the carrier protein is $CRM_{197}$.

C38. The conjugate according to any one of clause C34 to clause C36, wherein the carrier protein is tetanus toxoid (TT).

C39. The conjugate according to any one of clause C34 to clause C38, wherein the conjugate is prepared by reductive amination.

C40. The conjugate according to any one of clause C34 to clause C38, wherein the conjugate is prepared by CDAP chemistry.

C41. The conjugate according to any one of clause C34 to clause C38, wherein the conjugate is a single-end linked conjugated saccharide.

C42. The conjugate according to any one of clause C34 to clause C38, wherein the saccharide is conjugated to the carrier protein through a (2-((2-oxoethyl)thio)ethyl) carbamate (eTEC) spacer.

C43. The conjugate according to clause C42, wherein the saccharide is conjugated to the carrier protein through a (2-((2-oxoethyl)thio)ethyl) carbamate (eTEC) spacer, wherein the saccharide is covalently linked to the eTEC spacer through a carbamate linkage, and wherein the carrier protein is covalently linked to the eTEC spacer through an amide linkage.

C44. The conjugate according to any one of clause C42 to clause C43, wherein the $CRM_{197}$ comprises 2 to 20, or 4 to 16, lysine residues covalently linked to the polysaccharide through an eTEC spacer.

C45. The conjugate according to any one of clause C34 to clause C44, wherein the saccharide: carrier protein ratio (w/w) is between 0.2 and 4.

C46. The conjugate according to any one of clause C34 to clause C44, wherein the ratio of saccharide to protein is at least 0.5 and at most 2.

C47. The conjugate according to any one of clause C34 to clause C44, wherein the ratio of saccharide to protein is between 0.4 and 1.7

C48. The conjugate according to any one of clause C41 to clause C47, wherein the saccharide is conjugated to the carrier protein through a 3-deoxy-d-manno-oct-2-ulosonic acid (KDO) residue.

C49. A conjugate comprising a saccharide covalently bound a carrier protein, wherein the saccharide comprises a structure selected from Formula O8, Formula O9a, Formula O9, Formula O20ab, Formula O20ac, Formula O52, Formula O97, and Formula O101, wherein n is an integer from 1 to 10.

C50. A composition comprising a saccharide according to any one of clause C1 to clause C33, and a pharmaceutically acceptable diluent.

C51. A composition comprising a conjugate according to any one of clause C34 to clause C49, and a pharmaceutically acceptable diluent.

C52. The composition according to clause C51, comprising at most about 25% free saccharide as compared to the total amount of saccharide in the composition.

C53. The composition according to any one of clause C50 to clause C51, further comprising an adjuvant.

C54. The composition according to any one of clause C50 to clause C51, further comprising aluminum.

C55. The composition according to any one of clause C50 to clause C51, further comprising QS-21.

C56. The composition according to any one of clause C50 to clause C51, further comprising a CpG oligonucleotide.

C57. The composition according to any one of clause C50 to clause C51, wherein the composition does not include an adjuvant.

C58. A composition comprising a saccharide derived from *E. coli*, conjugated to a carrier protein through a (2-((2-oxoethyl)thio)ethyl) carbamate (eTEC) spacer, wherein the polysaccharide is covalently linked to the eTEC spacer through a carbamate linkage, and wherein the carrier protein is covalently linked to the eTEC spacer through an amide linkage.

C59. The composition according to clause C58, wherein the saccharide is an O-antigen derived from *E. coli*.

C60. The composition according to clause C58, further comprising a pharmaceutically acceptable excipient, carrier or diluent.

C61. The composition according to clause C58, wherein the saccharide is an O-antigen derived from *E. coli*.

C62. A composition comprising a saccharide is according to any one of clause C1 to clause C16, conjugated to a carrier protein through a (2-((2-oxoethyl)thio)ethyl) carbamate (eTEC) spacer, wherein the polysaccharide is covalently linked to the eTEC spacer through a carbamate linkage, and wherein the carrier protein is covalently linked to the eTEC spacer through an amide linkage.

C63. A composition comprising (i) a conjugate of an *E. coli* O25B antigen covalently coupled to a carrier protein, (ii) a conjugate of an *E. coli* O1A antigen covalently coupled to a carrier protein, (iii) a conjugate of an *E. coli* O2 antigen covalently coupled to a carrier protein, and (iv) a conjugate of an O6 antigen covalently coupled to a carrier protein, wherein the *E. coli* O25B antigen comprises the structure of Formula O25B, wherein n is an integer greater than 30.

C64. The composition of clause C63, wherein the O1A antigen, O6 antigen, and O2 antigen comprise the following formulas, respectively:

C65. The composition of clause C63, wherein the carrier protein is selected from any one of $CRM_{197}$, diphtheria toxin fragment B (DTFB), DTFB C8, Diphtheria toxoid (DT), tetanus toxoid (TT), fragment C of TT, pertussis toxoid, cholera toxoid, or exotoxin A from *Pseudomonas aeruginosa*; detoxified Exotoxin A of *P. aeruginosa* (EPA), maltose binding protein (MBP), detoxified hemolysin A of *S. aureus*, clumping factor A, clumping factor B, Cholera toxin B subunit (CTB), *Streptococcus pneumoniae* Pneumolysin and detoxified variants thereof, *C. jejuni* AcrA, and *C. jejuni* natural glycoproteins.

C66. A method of making a conjugate comprising a saccharide conjugated to a carrier protein through a (2-((2-oxoethyl)thio)ethyl) carbamate (eTEC) spacer, comprising the steps of a) reacting a saccharide with 1,1'-carbonyl-di-(1,2,4-triazole) (CDT) or 1,1'-carbonyldiimidazole (CDI), in an organic solvent to produce an activated saccharide; b) reacting the activated saccharide with cystamine or cysteamine or a salt thereof, to produce a thiolated saccharide; c) reacting the thiolated saccharide with a reducing agent to produce an activated thiolated saccharide comprising one or more free sulfhydryl residues; d) reacting the activated thiolated saccharide with an activated carrier protein comprising one or more α-haloacetamide groups, to produce a thiolated saccharide-carrier protein conjugate; and e) reacting the thiolated saccharide-carrier protein conjugate with (i) a first capping reagent capable of capping unconjugated α-haloacetamide groups of the activated carrier protein; and/or (ii) a second capping reagent capable of capping unconjugated free sulfhydryl residues; whereby an eTEC linked glycoconjugate is produced, wherein the saccharide is derived from *E. coli*.

C67. The method according to clause C66, wherein the saccharide comprises the saccharide according to any one of clause C1 to clause C33.

C68. The method according to any of one clause C66 to clause C67, wherein the capping step e) comprises reacting the thiolated saccharide-carrier protein conjugate with (i) N-acetyl-L-cysteine as a first capping reagent, and/or (ii) iodoacetamide as a second capping reagent.

C69. The method according to any of one clause C66 to clause C68, further comprising a step of compounding the saccharide by reaction with triazole or imidazole to provide a compounded saccharide, wherein the compounded saccharide is shell frozen, lyophilized and reconstituted in an organic solvent prior to step a).

C70. The method according to any of one clause C66 to clause C69, further comprising purification of the thiolated polysaccharide produced in step c), wherein the purification step comprises diafiltration.

C71. The method according to any of one clause C66 to clause C70, wherein the method further comprises purification of the eTEC linked glycoconjugate by diafiltration.

C72. The method according to any of one clause C66 to clause C71, wherein the organic solvent in step a) is a polar aprotic solvent selected from any one of dimethyl sulfoxide (DMSO), dimethylformamide (DMF), dimethylacetamide (DMA), N-methyl-2-pyrrolidone (NMP), acetonitrile, 1,3-Dimethyl-3,4,5,6-tetrahydro-2(1H)-pyrimidinone (DMPU) and hexamethylphosphoramide (HMPA), or a mixture thereof.

C73. A medium comprising $KH_2PO_4$, $K2HPO_4$, $(NH_4)_2SO_4$, sodium citrate, $Na_2SO_4$, aspartic acid, glucose, $MgSO_4$, $FeSO_4\text{-}7H_2O$, $Na_2MoO_{4\text{-}2}H_2O$, $H3BO_3$, $CoCl_2\text{-}6H_2O$, $CuCl_2\text{-}2H_2O$, $MnCl_2\text{-}4H_2O$, $ZnCl_2$ and $CaCl_2)\text{-}2H_2O$.

C74. The medium according to clause C73, wherein the medium is used for culturing *E. coli*.

C75. A method for producing a saccharide according to any one of clause C1 to clause C33, comprising culturing a recombinant *E. coli* in a medium; producing said saccharide by culturing said cell in said medium; whereby said cell produces said saccharide.

C76. The method according to clause C75, wherein the medium comprises an element selected from any one of $KH_2PO_4$, $K2HPO_4$, $(NH_4)_2SO_4$, sodium citrate, $Na_2SO_4$, aspartic acid, glucose, $MgSO_4$, $FeSO_4\text{-}7H_2O$, $Na_2MoO_{4\text{-}2}H_2O$, $H3BO_3$, $CoCl_2\text{-}6H_2O$, $CuCl_2\text{-}2H_2O$, $MnCl_2\text{-}4H_2O$, $ZnCl_2$ and $CaCl_2)\text{-}2H_2O$.

C77. The method according to clause C75, wherein the medium comprises soy hydrolysate.
C78. The method according to clause C75, wherein the medium comprises yeast extract.
C79. The method according to clause C75, wherein the medium does not further comprise soy hydrolysate and yeast extract.
C80. The method according to clause C75, wherein the *E. coli* cell comprises a heterologous wzz family protein selected from any one of wzzB, wzz, $wzz_{SF}$, $wzz_{ST}$, fepE, $wzz_{fepE}$, wzz1 and wzz2.
C81. The method according to clause C75, wherein the *E. coli* cell comprises a *Salmonella enterica* wzz family protein selected from any one of wzzB, wzz, $wzz_{SF}$, $wzz_{ST}$, fepE, $wzz_{fepE}$, wzz1 and wzz2.
C82. The method according to clause C81, wherein the wzz family protein comprises a sequence selected from any one of SEQ ID NO: 20, SEQ ID NO: 21, SEQ ID NO: 22, SEQ ID NO: 23, SEQ ID NO: 24, SEQ ID NO: 15, SEQ ID NO: 16, SEQ ID NO: 17, SEQ ID NO: 18, and SEQ ID NO: 19.
C83. The method according to clause C75, wherein the culturing produces a yield of >120 $OD_{600}$/mL.
C84. The method according to clause C75, further comprising purifying the saccharide.
C85. The method according to clause C75, wherein the purifying step comprises any one of the following: dialysis, concentration operations, diafiltration operations, tangential flow filtration, precipitation, elution, centrifugation, precipitation, ultra-filtration, depth filtration, and column chromatography (ion exchange chromatography, multimodal ion exchange chromatography, DEAE, and hydrophobic interaction chromatography).
C86. A method for inducing an immune response in a mammal comprising administering to the subject a composition according to any one of clause C50 to clause C62.
C87. The method according to clause C73, wherein the immune response comprises induction of an anti-*E. coli* O-specific polysaccharide serum antibody.
C88. The method according to clause C73, wherein the immune response comprises induction of an anti-*E. coli* IgG antibody.
C89. The method according to clause C73, wherein the immune response comprises induction of bactericidal activity against *E. coli*.
C90. The method according to clause C73, wherein the immune response comprises induction of opsonophagocytic antibodies against *E. coli*.
C91. The method according to clause C73, wherein the immune response comprises a geometric mean titer (GMT) level of at least 1,000 to 200,000 after initial dosing.
C92. The method according to clause C73, wherein the composition comprises a saccharide comprising the Formula O25, wherein n is an integer 40 to 100, wherein the immune response comprises a geometric mean titer (GMT) level of at least 1,000 to 200,000 after initial dosing.
C93. The method according to clause C73, wherein the mammal is at risk of any one of the conditions selected from urinary tract infection, cholecystitis, cholangitis, diarrhea, hemolytic uremic syndrome, neonatal meningitis, urosepsis, intra-abdominal infection, meningitis, complicated pneumonia, wound infection, post-prostate biopsy-related infection, neonatal/infant sepsis, neutropenic fever, and other blood stream infection; pneumonia, bacteremia, and sepsis.
C94. The method according to clause C73, wherein the mammal is has any one of the conditions selected from urinary tract infection, cholecystitis, cholangitis, diarrhea, hemolytic uremic syndrome, neonatal meningitis, urosepsis, intra-abdominal infection, meningitis, complicated pneumonia, wound infection, post-prostate biopsy-related infection, neonatal/infant sepsis, neutropenic fever, and other blood stream infection; pneumonia, bacteremia, and sepsis.
C95. A method for (i) inducing an immune response in a subject against extra-intestinal pathogenic *Escherichia coli*, (ii) inducing an immune response in a subject against extra-intestinal pathogenic *Escherichia coli*, or (iii) inducing the production of opsonophagocytic antibodies in a subject that are specific to extra-intestinal pathogenic *Escherichia coli*, wherein the method comprises administering to the subject an effective amount of the composition according to any one of clause C50 to clause C65.
C96. The method of clause C95, wherein the subject is at risk of developing a urinary tract infection.
C97. The method of clause C95, wherein the subject is at risk of developing bacteremia.
C98. The method of clause C95, wherein the subject is at risk of developing sepsis.
C99. A composition comprising (i) a conjugate of an an *E. coli* O25B antigen covalently coupled to a carrier protein, (ii) a conjugate of an *E. coli* O1A antigen covalently coupled to a carrier protein, (iii) a conjugate of an *E. coli* O2 antigen covalently coupled to a carrier protein, and (iv) a conjugate of an O6 antigen covalently coupled to a carrier protein, wherein the *E. coli* O25B antigen comprises the structure of Formula O25B, wherein n is an integer greater than 30.
C100. The composition of clause C1, wherein the O1A antigen, O6 antigen, and O2 antigen comprise the following formulas, respectively:
C101. The composition of clause C1, wherein the carrier protein is selected from the group consisting of detoxified Exotoxin A of *P. aeruginosa* (EPA), $CRM_{197}$, maltose binding protein (MBP). Diphtheria toxoid, Tetanus toxoid, detoxified hemolysin A of *S. aureus*, clumping factor A, clumping factor B, Cholera toxin B subunit (CTB), cholera toxin, detoxified variants of cholera toxin, *Streptococcus pneumoniae* Pneumolysin and detoxified variants thereof, *C. jejuni* AcrA, and *C. jejuni* natural glycoproteins.
C102. A method for (i) inducing an immune response in a subject against extra-intestinal pathogenic *Escherichia coli*, (ii) inducing an immune response in a subject against extra-intestinal pathogenic *Escherichia coli*, or (iii) inducing the production of opsonophagocytic antibodies in a subject that are specific to extra-intestinal pathogenic *Escherichia coli*, wherein the method comprises administering to the subject an effective amount of the composition of clause C1.
C103. The method of clause C102, wherein the subject is at risk of developing a urinary tract infection.
C104. The method of clause C102, wherein the subject is at risk of developing bacteremia. C105. The method of clause C102, wherein the subject is at risk of developing sepsis.
C106. A saccharide comprising an increase of at least 5 repeating units, compared to the corresponding wild-type O-polysaccharide of an *E. coli*.

C107. The saccharide according to clause C106, wherein the saccharide comprises Formula O25a and the *E. coli* is an *E. coli* serotype O25a.

C108. The saccharide according to clause C106, wherein the saccharide comprises Formula O25b and the *E. coli* is an *E. coli* serotype O25b.

C109. The saccharide according to clause C106, wherein the saccharide comprises Formula O2 and the *E. coli* is an *E. coli* serotype O2.

C110. The saccharide according to clause C106, wherein the saccharide comprises Formula O6 and the *E. coli* is an *E. coli* serotype O6.

C111. The saccharide according to clause C106, wherein the saccharide comprises Formula O1 and the *E. coli* is an *E. coli* serotype O1.

C112. The saccharide according to clause C106, wherein the saccharide comprises Formula O17 and the *E. coli* is an *E. coli* serotype O17.

C113. The saccharide according to clause C106, wherein the saccharide comprises a structure selected from: Formula O1, Formula O2, Formula O3, Formula O4, Formula O5, Formula O6, Formula O7, Formula O8, Formula O9, Formula O10, Formula O11, Formula O12, Formula O13, Formula O14, Formula O15, Formula O16, Formula O17, Formula O18, Formula O19, Formula O20, Formula O21, Formula O22, Formula O23, Formula O24, Formula O25, Formula O25b, Formula O26, Formula O27, Formula O28, Formula O29, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45, Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula O63, Formula O64, Formula O65, Formula O66, Formula O68, Formula O69, Formula O70, Formula O71, Formula O73, Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144, Formula O145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, and Formula O187, wherein n is an integer from 5 to 1000.

C114. The saccharide according to clause C106, wherein the *E. coli* is *E. coli* serotype selected from the group consisting of: O1, O2, O3, O4, O5, O6, O7, O8, O9, O10, O11, O12, O13, O14, O15, O16, O17, O18, O19, O20, O21, O22, O23, O24, O25, O25b, O26, O27, O28, O29, O30, O32, O33, O34, O35, O36, O37, O38, O39, O40, O41, O42, O43, O44, O45, O46, O48, O49, O50, O51, O52, O53, O54, O55, O56, O57, O58, O59, O60, O61, O62, O63, O64, O65, O66, O68, O69, O70, O71, O73, O74, O75, O76, O77, O78, O79, O80, O81, O82, O83, O84, O85, O86, O87, O88, O89, O90, O91, O92, O93, O95, O96, O97, O98, O99, O100, O101, O102, O103, O104, O105, O106, O107, O108, O109, O110, O111, O112, O113, O114, O115, O116, O117, O118, O119, O120, O121, O123, O124, O125, O126, O127, O128, O129, O130, O131, O132, O133, O134, O135, O136, O137, O138, O139, O140, O141, O142, O143, O144, O145, O146, O147, O148, O149, O150, O151, O152, O153, O154, O155, O156, O157, O158, O159, O160, O161, O162, O163, O164, O165, O166, O167, O168, O169, O170, O171, O172, O173, O174, O175, O176, O177, O178, O179, O180, O181, O182, O183, O184, O185, O186, and O187.

C115. The saccharide according to clause C106, wherein the saccharide is produced by increasing repeating units of O-polysaccharides produced by a Gram-negative bacterium in culture comprising overexpressing wzz family proteins in a Gram-negative bacterium to generate said saccharide.

C116. The saccharide according to clause C115, wherein the overexpressed wzz family protein is selected from the group consisting of wzzB, wzz, $wzz_{SF}$, $wzz_{ST}$, fepE, $wzz_{fcpE}$, wzz1 and wzz2.

C117. The saccharide according to clause C115, wherein the overexpressed wzz family protein is wzzB.

C118. The saccharide according to clause C115, wherein the overexpressed wzz family protein is fepE.

C119. The saccharide according to clause C115, wherein the overexpressed wzz family protein is wzzB and fepE.

C120. The saccharide according to clause C106, wherein the saccharide is synthetically synthesized.

C121. A conjugate comprising a saccharide according to clause C106, covalently bound to a carrier protein.

C122. The conjugate according to clause C121, wherein the carrier protein is $CRM_{197}$. C123. The conjugate according to clause C121, wherein the saccharide comprises a structure selected from: Formula O1, Formula O2, Formula O3, Formula O4, Formula O5, Formula O6, Formula O7, Formula O8, Formula O9, Formula O10, Formula O11, Formula O12, Formula O13, Formula O14, Formula O15, Formula O16, Formula O17, Formula O18, Formula O19, Formula O20, Formula O21, Formula O22, Formula O23, Formula O24, Formula O25, Formula O25b, Formula O26, Formula O27, Formula O28, Formula O29, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45, Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula O63, Formula O64, Formula O65, Formula O66, Formula O68, Formula O69, Formula O70, Formula O71, Formula O73, Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144, O145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, and Formula O187, wherein n is an integer from 5 to 1000.

C124. The conjugate according to clause C121, wherein said saccharide comprises an increase of at least 5 repeating units, compared to the corresponding wild-type O-polysaccharide.

C125. A composition comprising a saccharide according to clause 1, further comprising a pharmaceutically acceptable diluent.

C126. The composition according to clause C125, further comprising an adjuvant.

C127. The composition according to clause C125, further comprising aluminum.

C128. The composition according to clause C125, further comprising QS-21.

C129. The composition according to clause C125, wherein the composition does not include an adjuvant.

C130. A method for inducing an immune response in a subject comprising administering to the subject a composition according to clause C125.

C131. A composition comprising a conjugate according to clause C121, further comprising a pharmaceutically acceptable diluent.

C132. A method for inducing an immune response in a subject comprising administering to the subject a composition according to clause C131.

C133. The method according to clauses C130 or C132, wherein the immune response comprises induction of an anti-*E. coli* O-specific polysaccharide serum antibody.

C134. The method according to clause C133, wherein the anti-*E. coli* O-specific polysaccharide serum antibody is an IgG antibody.

C135. The method according to clause C133, wherein the anti-*E. coli* O-specific polysaccharide serum antibody is an IgG antibody has bactericidal activity against *E. coli*.

C136. An immunogenic composition comprising a saccharide derived from *E. coli*, conjugated to a carrier protein through a (2-((2-oxoethyl)thio)ethyl) carbamate (eTEC) spacer, wherein the polysaccharide is covalently linked to the eTEC spacer through a carbamate linkage, and wherein the carrier protein is covalently linked to the eTEC spacer through an amide linkage.

C137. The immunogenic composition according to clause C136, further comprising a pharmaceutically acceptable excipient, carrier or diluent.

C138. The immunogenic composition according to clause C136, wherein the saccharide is an O-antigen derived from *E. coli*.

C139. The immunogenic composition according to clause C136, wherein the saccharide comprises a structure selected from: Formula O1, Formula O2, Formula O3, Formula O4, Formula O5, Formula O6, Formula O7, Formula O8, Formula O9, Formula O10, Formula O11, Formula O12, Formula O13, Formula O14, Formula O15, Formula O16, Formula O17, Formula O18, Formula O19, Formula O20, Formula O21, Formula O22, Formula O23, Formula O24, Formula O25, Formula O25b, Formula O26, Formula O27, Formula O28, Formula O29, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45, Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula O63, Formula O64, Formula O65, Formula O66, Formula O68, Formula O69, Formula O70, Formula O71, Formula O73, Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144, O145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, and Formula O187, wherein n is an integer from 5 to 1000.

C140. The immunogenic composition according to clause C136, wherein the saccharide has a degree of O-acetylation between 75-100%.

C141. The immunogenic composition according to clause C136, wherein the carrier protein is $CRM_{197}$.

C142. The immunogenic composition according to clause C141, wherein the $CRM_{197}$ comprises 2 to 20 lysine residues covalently linked to the polysaccharide through an eTEC spacer.

C143. The immunogenic composition according to clause C141, wherein the $CRM_{197}$ comprises 4 to 16 lysine residues covalently linked to the polysaccharide through an eTEC spacer.

C144. The immunogenic composition according to clause C136, further comprising an additional antigen.

C145. The immunogenic composition according to clause C136, further comprising an adjuvant.

C146. The immunogenic composition according to clause C145, wherein the adjuvant is an aluminum-based adjuvant selected from the group consisting of aluminum phosphate, aluminum sulfate and aluminum hydroxide.

C147. The immunogenic composition according to clause C136, wherein the composition does not comprise an adjuvant.

C148. An immunogenic composition comprising a glycoconjugate comprising a saccharide derived from *E. coli* conjugated to a carrier protein, wherein the glycoconjugate is prepared using reductive amination.

C149. The immunogenic composition according to clause C148, further comprising a pharmaceutically acceptable excipient, carrier or diluent.

C150. The immunogenic composition according to clause C148, wherein the saccharide is an O-antigen derived from *E. coli*.

C151. The immunogenic composition according to clause C148, wherein the saccharide comprises a structure selected from: Formula O1, Formula O2, Formula O3, Formula O4, Formula O5, Formula O6, Formula O7, Formula O8, Formula O9, Formula O10, Formula O11, Formula O12, Formula O13, Formula O14, Formula O15, Formula O16, Formula O17, Formula O18, Formula O19, Formula O20, Formula O21, Formula O22, Formula O23, Formula O24, Formula O25, Formula O25b, Formula O26, Formula O27, Formula O28, Formula O29, Formula O30, Formula O32, Formula O33, Formula O34, Formula O35, Formula O36, Formula O37, Formula O38, Formula O39, Formula O40, Formula O41, Formula O42, Formula O43, Formula O44, Formula O45, Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula O63, Formula O64, Formula O65, Formula O66, Formula O68, Formula O69, Formula O70, Formula O71, Formula O73, Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O93, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O144, O145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, and Formula O187, wherein n is an integer from 5 to 1000.

C152. The immunogenic composition according to clause C148, wherein the saccharide has a degree of O-acetylation between 75-100%.

C153. The immunogenic composition according to clause C148, wherein the carrier protein is $CRM_{197}$.

C154. The immunogenic composition according to clause C148, further comprising an additional antigen.

C155. The immunogenic composition according to clause C148, further comprising an adjuvant.

C156. The immunogenic composition according to clause C155, wherein the adjuvant is an aluminum-based adjuvant selected from the group consisting of aluminum phosphate, aluminum sulfate and aluminum hydroxide.

C157. The immunogenic composition according to clause C148, wherein the composition does not comprise an adjuvant.

C158. A method for inducing an immune response in a subject comprising administering to the subject a composition according to any one of clauses C136-C157.

C159. The method according to clause C158, wherein the immune response comprises induction of an anti-*E. coli* O-specific polysaccharide serum antibody.

C160. The method according to clause C133, wherein the anti-*E. coli* O-specific polysaccharide serum antibody is an IgG antibody.

C161. The method according to clause C133, wherein the anti-*E. coli* O-specific polysaccharide serum antibody is an IgG antibody has bactericidal activity against *E. coli*.

What is claimed is:

1. A saccharide comprising a structure selected from any one of Formula O1, Formula O1A, Formula O1B, Formula O1C, Formula O2, Formula O3, Formula O4, Formula O4: K52, Formula O4: K6, Formula O5, Formula O5ab, Formula O5ac, Formula O6, Formula O6: K2, Formula O6: K13, Formula O6: K15, Formula O6: K54, Formula O7, Formula O8, Formula O9, Formula O10, Formula O11, Formula O12, Formula O13, Formula O14, Formula O15, Formula O16, Formula O17, Formula O18, Formula O18A, Formula O18ac, Formula O18A1, Formula O18B, Formula O18B1, Formula O19, Formula O20, Formula O21, Formula O22, Formula O23, Formula O23A, Formula O24, Formula O25, Formula O25a, Formula O25b, Formula O26, Formula O27, Formula O28, Formula O29, Formula O30, Formula O32, Formula O33, Formula O35, Formula O36, Formula O37, Formula O38, Formula O39, Formula O40, Formula O41, Formula O42, Formula O43, Formula O44, Formula O45, Formula O45rel, Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula 62D$_1$, Formula O63, Formula O64, Formula O65, Formula O66, Formula O68, Formula O69, Formula O70, Formula O71, Formula O73, Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O89, Formula O90, Formula O91, Formula O92, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, and Formula O187, wherein n is an integer consisting of 31 to 100 in the Formula thereof for each saccharide molecule.

2. The saccharide according to claim 1, wherein the saccharide is produced in a recombinant host cell that expresses a wzz family protein having at least 90% sequence identity to any one of SEQ ID NO: 20, SEQ ID NO: 21, SEQ ID NO: 22, SEQ ID NO: 23, SEQ ID NO: 24, SEQ ID NO: 15, SEQ ID NO: 16, SEQ ID NO: 17, SEQ ID NO: 18, and SEQ ID NO: 19.

3. The saccharide according to claim 2, wherein the wzz family protein comprises any one of SEQ ID NO: 15, SEQ ID NO: 16, SEQ ID NO: 17, SEQ ID NO: 18, and SEQ ID NO: 19.

4. The saccharide according to claim 1, wherein the saccharide is synthetically synthesized.

5. A conjugate comprising a carrier protein covalently bound to a saccharide, said saccharide comprising a structure selected from any one of Formula O1, Formula O1A, Formula O1B, Formula O1C, Formula O2, Formula O3, Formula O4, Formula O4: K52, Formula O4: K6, Formula O5, Formula O5ab, Formula O5ac, Formula O6: K2, Formula O6: K13, Formula O6: K15, Formula O6: K54, Formula O7, Formula O8, Formula O9, Formula O10, Formula O11, Formula O12, Formula O13, Formula O15, Formula O16, Formula O17, Formula O18, Formula O18A, Formula O18ac, Formula O18A1, Formula O18B, Formula O18B1, Formula O19, Formula O20, Formula O21, Formula O22, Formula O23, Formula O23A, Formula O24, Formula O25, Formula O25a, Formula O25b, Formula O26, Formula O27, Formula O28, Formula O29, Formula O30, Formula O32, Formula O33, Formula O35, Formula O36, Formula O37, Formula O38, Formula O39, Formula O40, Formula O41, Formula O42, Formula O43, Formula O44, Formula O45, Formula O45rel, Formula O46, Formula O48, Formula O49, Formula O50, Formula O51, Formula O52, Formula O53, Formula O54, Formula O55, Formula O56, Formula O57, Formula O58, Formula O59, Formula O60, Formula O61, Formula O62, Formula 62D$_1$, Formula O63, Formula O64, Formula O65, Formula O66, Formula O68, Formula O69, Formula O70, Formula O71, Formula O72, Formula O73, Formula O74, Formula O75, Formula O76, Formula O77, Formula O78, Formula O79, Formula O80, Formula O81, Formula O82, Formula O83, Formula O84, Formula O85, Formula O86, Formula O87, Formula O88, Formula O90, Formula O91, Formula O92, Formula O95, Formula O96, Formula O97, Formula O98, Formula O99, Formula O100, Formula O101, Formula O102, Formula O103, Formula O104, Formula O105, Formula O106, Formula O107, Formula O108, Formula O109, Formula O110, Formula O111, Formula O112, Formula O113, Formula O114, Formula O115, Formula O116, Formula O117, Formula O118, Formula O119, Formula O120, Formula O121, Formula O123, Formula O124, Formula O125, Formula O126, Formula O127, Formula O128, Formula O129, Formula O130, Formula O131, Formula O132, Formula O133, Formula O134, Formula O135, Formula O136, Formula O137, Formula O138, Formula O139, Formula O140, Formula O141, Formula O142, Formula O143, Formula O145, Formula O146, Formula O147, Formula O148, Formula O149, Formula O150, Formula O151, Formula O152, Formula O153, Formula O154, Formula O155, Formula O156, Formula O157, Formula O158, Formula O159, Formula O160, Formula O161, Formula O162, Formula O163, Formula O164, Formula O165, Formula O166, Formula O167, Formula O168, Formula O169, Formula O170, Formula O171, Formula O172, Formula O173, Formula O174, Formula O175, Formula O176, Formula O177, Formula O178, Formula O179, Formula O180, Formula O181, Formula O182, Formula O183, Formula O184, Formula O185, Formula O186, and Formula O187, wherein n is an integer consisting of 31 to 100 in the Formula thereof for each saccharide molecule.

6. The conjugate according to claim 5, wherein the saccharide further comprises any one of an *E. coli* R1 moiety, *E. coli* R2 moiety, *E. coli* R3 moiety, *E. coli* R4 moiety, and *E. coli* K-12 moiety.

7. The conjugate according to claim 5, wherein the saccharide does not further comprise an *E. coli* R2 moiety.

8. The conjugate according to claim 5, wherein the saccharide further comprises a 3-deoxy-d-manno-oct-2-ulosonic acid (KDO) moiety.

9. The conjugate according to claim 5, wherein the carrier protein is selected from any one of diphtheria toxin CRM$_{197}$, diphtheria toxin fragment B (DTFB), DTFB C8, Diphtheria toxoid (DT), tetanus toxoid (TT), fragment C of TT, pertussis toxoid, cholera toxoid, exotoxin A from *Pseudomonas aeruginosa*, detoxified Exotoxin A of *P. aeruginosa* (EPA), maltose binding protein (MBP), detoxified hemolysin A of *S. aureus*, clumping factor A, clumping factor B, Cholera toxin B subunit (CTB), *Streptococcus pneumoniae* Pneumolysin or detoxified variants thereof, *C. jejuni* AcrA, and *C. jejuni* natural glycoproteins.

10. The conjugate according to claim 5, wherein the carrier protein is diphtheria toxin CRM$_{197}$.

11. The conjugate according to claim 5, wherein the carrier protein is tetanus toxoid.

12. The conjugate according to claim 5, wherein the mass ratio of saccharide to the carrier protein is at least 0.5 to at most 2.

13. The conjugate according to claim 5, wherein the conjugate is prepared via reductive amination.

14. The conjugate according to claim 5, wherein the saccharide is conjugated to the carrier protein through a (2-((2-oxoethyl)thio)ethyl) carbamate (eTEC) spacer.

15. The conjugate according to claim 5, wherein the saccharide is a single-end linked conjugated saccharide.

16. The conjugate according to claim 8, wherein the saccharide is conjugated to the carrier protein through a 3-deoxy-d-manno-oct-2-ulosonic acid (KDO) residue.

17. The conjugate according to claim 5, wherein the conjugate is prepared via 1-cyano-4-dimethylamino pyridinium tetrafluoroborate (CDAP) chemistry.

18. A composition comprising the conjugate according to claim 5 and a pharmaceutically acceptable carrier.

19. The composition according to claim 18, further comprising a second conjugate comprising a carrier protein covalently bound to a saccharide comprising a structure selected from any one of the following: Formula O25b, Formula O1A, Formula O2, Formula O6, Formula O15, Formula O16, Formula O17, Formula O18 and Formula O75, wherein n is an integer from 31 to 90.

20. The composition according to claim 18, wherein the composition comprises at most 25% free saccharide as compared to the total amount of saccharide in the composition.

21. A method of eliciting an immune response against *Escherichia coli* in a mammal, comprising administering to the mammal an effective amount of the composition according to claim 18.

22. The method according to claim 21, wherein the immune response comprises opsonophagocytic antibodies against *E. coli*.

23. The method according to claim 21, wherein the immune response protects the mammal from an *E. coli* infection.

24. A method of eliciting an immune response against *Escherichia coli* in a mammal, comprising administering to the mammal an effective amount of the composition according to claim 19.

25. The method according to claim 24, wherein the immune response comprises opsonophagocytic antibodies against *E. coli*.

26. The method according to claim 24, wherein the immune response protects the mammal from an *E. coli* infection.

27. A method of eliciting an immune response against *Escherichia coli* in a mammal, comprising administering to the mammal an effective amount of the composition according to claim 20.

28. The method according to claim 27, wherein the immune response comprises opsonophagocytic antibodies against *E. coli*.

29. The method according to claim 27, wherein the immune response protects the mammal from an *E. coli* infection.

* * * * *

SEQUENCE LISTING

<160> NUMBER OF SEQ ID NOS: 24

<210> SEQ ID NO 1
<211> LENGTH: 22
<212> TYPE: DNA
<213> ORGANISM: Artificial Sequence
<220> FEATURE:
<223> OTHER INFORMATION: Synthetic sequence; LT2wzzB_S

<400> SEQUENCE: 1
gaagcaaacc gtacgcgtaa ag                                          22

<210> SEQ ID NO 2
<211> LENGTH: 20
<212> TYPE: DNA
<213> ORGANISM: Artificial Sequence
<220> FEATURE:
<223> OTHER INFORMATION: Synthetic sequence; LT2wzzB_AS

<400> SEQUENCE: 2
cgaccagctc ttacacggcg                                             20

<210> SEQ ID NO 3
<211> LENGTH: 36
<212> TYPE: DNA
<213> ORGANISM: Artificial Sequence
<220> FEATURE:
<223> OTHER INFORMATION: Synthetic sequence; O25bFepE_S

<400> SEQUENCE: 3
gaaataggac cactaataaa tacacaaatt aataac                           36

<210> SEQ ID NO 4
<211> LENGTH: 21
<212> TYPE: DNA
<213> ORGANISM: Artificial Sequence
<220> FEATURE:
<223> OTHER INFORMATION: Synthetic sequence; O25bFepE_A

<400> SEQUENCE: 4
ataattgacg atccggttgc c                                           21

<210> SEQ ID NO 5
<211> LENGTH: 27
<212> TYPE: DNA
<213> ORGANISM: Artificial Sequence
<220> FEATURE:
<223> OTHER INFORMATION: Synthetic sequence; wzzB P1_S

<400> SEQUENCE: 5
gctatttacg ccctgattgt cttttgt                                     27

<210> SEQ ID NO 6
<211> LENGTH: 22
<212> TYPE: DNA
<213> ORGANISM: Artificial Sequence
<220> FEATURE:
<223> OTHER INFORMATION: Synthetic sequence; wzzB P2_AS

<400> SEQUENCE: 6 attgagaaacc tgcgtaaacg gc                                         22

<210> SEQ ID NO 7
<211> LENGTH: 24
<212> TYPE: DNA
<213> ORGANISM: Artificial Sequence -continued

```
<220> FEATURE:
<223> OTHER INFORMATION: Synthetic sequence; wzzB P3_S

<400> SEQUENCE: 7
tgaagagcgg ttcagataac ttcc                                            24

<210> SEQ ID NO 8
<211> LENGTH: 21
<212> TYPE: DNA
<213> ORGANISM: Artificial Sequence
<220> FEATURE:
<223> OTHER INFORMATION: Synthetic sequence; wzzB P4_AS

<400> SEQUENCE: 8
cgatccggaa acctcctaca c                                               21

<210> SEQ ID NO 9
<211> LENGTH: 26
<212> TYPE: DNA
<213> ORGANISM: Artificial Sequence
<220> FEATURE:
<223> OTHER INFORMATION: Synthetic sequence; O157 FepE_S

<400> SEQUENCE: 9
gattattcgc gcaacgctaa acagat                                          26

<210> SEQ ID NO 10
<211> LENGTH: 23
<212> TYPE: DNA
<213> ORGANISM: Artificial Sequence
<220> FEATURE:
<223> OTHER INFORMATION: Synthetic sequence; O157 FepE_AS

<400> SEQUENCE: 10
tgatcattga cgatccggta gcc                                             23

<210> SEQ ID NO 11
<211> LENGTH: 70
<212> TYPE: DNA
<213> ORGANISM: Artificial Sequence
<220> FEATURE:
<223> OTHER INFORMATION: Synthetic sequence; pBAD33_adaptor_S

<400> SEQUENCE: 11
cggtagctgt aaagccaggg gcggtagcgt ggtttaaacc caagcaacag atcggcgtcg     60
tcggtatgga                                                            70

<210> SEQ ID NO 12
<211> LENGTH: 78
<212> TYPE: DNA
<213> ORGANISM: Artificial Sequence
<220> FEATURE:
<223> OTHER INFORMATION: Synthetic sequence; pBAD33_adaptor_AS

<400> SEQUENCE: 12
agcttccata ccgacgacgc cgatctgttg ctgggttta aaccacgcta ccgcccctgg      60
ctttacagct accgagct                                                   78

<210> SEQ ID NO 13
<211> LENGTH: 30
<212> TYPE: DNA
<213> ORGANISM: Artificial Sequence
<220> FEATURE:
<223> OTHER INFORMATION: Synthetic sequence; JUMPSTART_r
```

<400> SEQUENCE: 13
ggtagctgta aagccagggg cggtagcgtg                                              30

<210> SEQ ID NO 14
<211> LENGTH: 30
<212> TYPE: DNA
<213> ORGANISM: Artificial Sequence
<220> FEATURE:
<223> OTHER INFORMATION: Synthetic sequence; gnd_f

<400> SEQUENCE: 14
ccataccgac gacgccgatc tgttgcttgg                                              30

<210> SEQ ID NO 15
<211> LENGTH: 377
<212> TYPE: PRT
<213> ORGANISM: Escherichia coli

<400> SEQUENCE: 15

Met Ser Ser Leu Asn Ile Lys Gln Gly Ser Asp Ala His Phe Pro Asp
1               5                   10                  15

Tyr Pro Leu Ala Ser Pro Ser Asn Asn Glu Ile Asp Leu Leu Asn Leu
            20                  25                  30

Ile Ser Val Leu Trp Arg Ala Lys Lys Thr Val Met Ala Val Val Phe
        35                  40                  45

Ala Phe Ala Cys Ala Gly Leu Leu Ile Ser Phe Ile Leu Pro Gln Lys
    50                  55                  60

Trp Thr Ser Ala Ala Val Val Thr Pro Pro Glu Pro Val Gln Trp Gln
65                  70                  75                  80

Glu Leu Glu Lys Ser Phe Thr Lys Leu Arg Val Leu Asp Leu Asp Ile
                85                  90                  95

Lys Ile Asp Arg Thr Glu Ala Phe Asn Leu Phe Ile Lys Lys Phe Gln
            100                 105                 110

Ser Val Ser Leu Leu Glu Glu Tyr Leu Arg Ser Ser Pro Tyr Val Met
        115                 120                 125

Asp Gln Leu Lys Glu Ala Lys Ile Asp Glu Leu Asp Leu His Arg Ala
    130                 135                 140

Ile Val Ala Leu Ser Glu Lys Met Lys Ala Val Asp Asp Asn Ala Ser
145                 150                 155                 160

Lys Lys Lys Asp Glu Pro Ser Leu Tyr Thr Ser Trp Thr Leu Ser Phe
                165                 170                 175

Thr Ala Pro Thr Ser Glu Glu Ala Gln Thr Val Leu Ser Gly Tyr Ile
            180                 185                 190

Asp Tyr Ile Ser Thr Leu Val Val Lys Glu Ser Leu Glu Asn Val Arg
        195                 200                 205

Asn Lys Leu Glu Ile Lys Thr Gln Phe Glu Lys Glu Lys Leu Ala Gln
    210                 215                 220

Asp Arg Ile Lys Thr Lys Asn Gln Leu Asp Ala Asn Ile Gln Arg Leu
225                 230                 235                 240

Asn Tyr Ser Leu Asp Ile Ala Asn Ala Ala Gly Ile Lys Lys Pro Val
                245                 250                 255

Tyr Ser Asn Gly Gln Ala Val Lys Asp Asp Pro Asp Phe Ser Ile Ser
            260                 265                 270

Leu Gly Ala Asp Gly Ile Glu Arg Lys Leu Glu Ile Glu Lys Ala Val
        275                 280                 285

Thr Asp Val Ala Glu Leu Asn Gly Glu Leu Arg Asn Arg Gln Tyr Leu

```
                     290                 295                 300

Val Glu Gln Leu Thr Lys Ala His Val Asn Asp Val Asn Phe Thr Pro
305                 310                 315                 320

Phe Lys Tyr Gln Leu Ser Pro Ser Leu Pro Val Lys Lys Asp Gly Pro
                325                 330                 335

Gly Lys Ala Ile Ile Val Ile Leu Ser Ala Leu Ile Gly Gly Met Val
                340                 345                 350

Ala Cys Gly Gly Val Leu Leu Arg Tyr Ala Met Ala Ser Arg Lys Gln
                355                 360                 365

Asp Ala Met Met Ala Asp His Leu Val
                370                 375

<210> SEQ ID NO 16
<211> LENGTH: 377
<212> TYPE: PRT
<213> ORGANISM: Escherichia coli

<400> SEQUENCE: 16

Met Ser Ser Leu Asn Ile Lys Gln Gly Ser Glu Ala His Phe Pro Glu
1               5                   10                  15

Tyr Pro Leu Ala Ser Pro Ser Asn Asn Glu Ile Asp Leu Leu Asn Leu
                20                  25                  30

Ile Glu Val Leu Trp Arg Ala Lys Lys Thr Val Met Ala Val Val Phe
            35                  40                  45

Ala Phe Ala Cys Ala Gly Leu Leu Ile Ser Phe Ile Leu Pro Gln Lys
        50                  55                  60

Trp Thr Ser Ala Ala Val Val Thr Pro Pro Glu Pro Val Gln Trp Gln
65                  70                  75                  80

Glu Leu Glu Lys Thr Phe Thr Lys Leu Arg Val Leu Asp Leu Asp Ile
                85                  90                  95

Lys Ile Asp Arg Thr Glu Ala Phe Asn Leu Phe Ile Lys Lys Phe Gln
                100                 105                 110

Ser Val Ser Leu Leu Glu Glu Tyr Leu Arg Ser Ser Pro Tyr Val Met
            115                 120                 125

Asp Gln Leu Lys Glu Ala Lys Ile Asp Pro Leu Asp Leu His Arg Ala
        130                 135                 140

Ile Val Ala Leu Ser Glu Lys Met Lys Ala Val Asp Asp Asn Ala Ser
145                 150                 155                 160

Lys Lys Lys Asp Glu Ser Ala Leu Tyr Thr Ser Trp Thr Leu Ser Phe
                165                 170                 175

Thr Ala Pro Thr Ser Glu Glu Ala Gln Lys Val Leu Ala Gly Tyr Ile
                180                 185                 190

Asp Tyr Ile Ser Ala Leu Val Val Lys Glu Ser Ile Glu Asn Val Arg
            195                 200                 205

Asn Lys Leu Glu Ile Lys Thr Gln Phe Glu Lys Glu Lys Leu Ala Gln
        210                 215                 220

Asp Arg Ile Lys Thr Lys Asn Gln Leu Asp Ala Asn Ile Gln Arg Leu
225                 230                 235                 240

Asn Tyr Ser Leu Asp Ile Ala Asn Ala Ala Gly Ile Lys Lys Pro Val
                245                 250                 255

Tyr Ser Asn Gly Gln Ala Val Lys Asp Asp Pro Asp Phe Ser Ile Ser
                260                 265                 270

Leu Gly Ala Asp Gly Ile Glu Arg Lys Leu Glu Ile Glu Lys Ala Val
            275                 280                 285
```

```
Thr Asp Val Ala Glu Leu Asn Gly Glu Leu Arg Asn Arg Gln Tyr Leu
            290                 295                 300

Val Glu Gln Leu Thr Lys Thr Asn Ile Asn Asp Val Asn Phe Thr Pro
305                 310                 315                 320

Phe Lys Tyr Gln Leu Arg Pro Ser Leu Pro Val Lys Lys Asp Gly Gln
                325                 330                 335

Gly Lys Ala Ile Ile Val Ile Leu Ser Ala Leu Val Gly Gly Met Val
                340                 345                 350

Ala Cys Gly Gly Val Leu Leu Arg His Ala Met Ala Ser Arg Lys Gln
            355                 360                 365

Asp Ala Met Met Ala Asp His Leu Val
            370                 375

<210> SEQ ID NO 17
<211> LENGTH: 377
<212> TYPE: PRT
<213> ORGANISM: Escherichia coli

<400> SEQUENCE: 17

Met Ser Ser Leu Asn Ile Lys Gln Gly Ser Asp Ala His Phe Pro Asp
1               5                   10                  15

Tyr Pro Leu Ala Ser Pro Ser Asn Asn Glu Ile Asp Leu Leu Asn Leu
                20                  25                  30

Ile Ser Val Leu Trp Arg Ala Lys Lys Thr Val Met Ala Val Val Phe
            35                  40                  45

Ala Phe Ala Cys Ala Gly Leu Leu Ile Ser Phe Ile Leu Pro Gln Lys
50                  55                  60

Trp Thr Ser Ala Ala Val Val Thr Pro Pro Glu Pro Val Gln Trp Gln
65                  70                  75                  80

Glu Leu Glu Lys Ser Phe Thr Lys Leu Arg Val Leu Asp Leu Asp Ile
                85                  90                  95

Lys Ile Asp Arg Thr Glu Ala Phe Asn Leu Phe Ile Lys Lys Phe Gln
                100                 105                 110

Ser Val Ser Leu Leu Glu Glu Tyr Leu Arg Ser Ser Pro Tyr Val Met
            115                 120                 125

Asp Gln Leu Lys Glu Ala Lys Ile Asp Glu Leu Asp Leu His Arg Ala
130                 135                 140

Ile Val Ala Leu Ser Glu Lys Met Lys Ala Val Asp Asp Asn Ala Ser
145                 150                 155                 160

Lys Lys Lys Asp Glu Pro Ser Leu Tyr Thr Ser Trp Thr Leu Ser Phe
                165                 170                 175

Thr Ala Pro Thr Ser Glu Glu Ala Gln Thr Val Leu Ser Gly Tyr Ile
            180                 185                 190

Asp Tyr Ile Ser Thr Leu Val Val Lys Glu Ser Leu Glu Asn Val Arg
            195                 200                 205

Asn Lys Leu Glu Ile Lys Thr Gln Phe Glu Lys Glu Lys Leu Ala Gln
210                 215                 220

Asp Arg Ile Lys Thr Lys Asn Gln Leu Asp Ala Asn Ile Gln Arg Leu
225                 230                 235                 240

Asn Tyr Ser Leu Asp Ile Ala Asn Ala Ala Gly Ile Lys Lys Pro Val
                245                 250                 255

Tyr Ser Asn Gly Gln Ala Val Lys Asp Asp Pro Asp Phe Ser Ile Ser
            260                 265                 270

Leu Gly Ala Asp Gly Ile Glu Arg Lys Leu Glu Ile Glu Lys Ala Val
            275                 280                 285
```

```
Thr Asp Val Ala Glu Leu Asn Gly Glu Leu Arg Asn Arg Gln Tyr Leu
    290                 295                 300

Val Glu Gln Leu Thr Lys Ala His Val Asn Asp Val Asn Phe Thr Pro
305                 310                 315                 320

Phe Lys Tyr Gln Leu Ser Pro Ser Leu Pro Val Lys Lys Asp Gly Pro
                325                 330                 335

Gly Lys Ala Ile Ile Val Ile Leu Ser Ala Leu Ile Gly Gly Met Val
                340                 345                 350

Ala Cys Gly Gly Val Leu Leu Arg Tyr Ala Met Ala Ser Arg Lys Gln
                355                 360                 365

Asp Ala Met Met Ala Asp His Leu Val
    370                 375

<210> SEQ ID NO 18
<211> LENGTH: 377
<212> TYPE: PRT
<213> ORGANISM: Escherichia coli

<400> SEQUENCE: 18

Met Ser Ser Leu Asn Ile Lys Gln Gly Ser Asp Ala His Phe Pro Asp
1               5                   10                  15

Tyr Pro Leu Ala Ser Pro Ser Asn Asn Glu Ile Asp Leu Leu Asn Leu
                20                  25                  30

Ile Ser Val Leu Trp Arg Ala Lys Lys Thr Val Met Ala Val Val Phe
            35                  40                  45

Ala Phe Ala Cys Ala Gly Leu Leu Ile Ser Phe Ile Leu Pro Gln Lys
        50                  55                  60

Trp Thr Ser Ala Ala Val Val Thr Pro Pro Glu Pro Val Gln Trp Gln
65                  70                  75                  80

Glu Leu Glu Lys Thr Phe Thr Lys Leu Arg Val Leu Asp Leu Asp Ile
                85                  90                  95

Lys Ile Asp Arg Thr Glu Ala Phe Asn Leu Phe Ile Lys Lys Phe Gln
                100                 105                 110

Ser Val Ser Leu Leu Glu Glu Tyr Leu Arg Ser Ser Pro Tyr Val Met
                115                 120                 125

Asp Gln Leu Lys Glu Ala Lys Ile Asp Glu Leu Asp Leu His Arg Ala
    130                 135                 140

Ile Val Ala Leu Ser Glu Lys Met Lys Ala Val Asp Asp Asn Ala Ser
145                 150                 155                 160

Lys Lys Lys Asp Glu Pro Ser Leu Tyr Thr Ser Trp Thr Leu Ser Phe
                165                 170                 175

Thr Ala Pro Thr Ser Glu Glu Ala Gln Thr Val Leu Ser Gly Tyr Ile
                180                 185                 190

Asp Tyr Ile Ser Ala Leu Val Val Lys Glu Ser Ile Glu Asn Val Arg
            195                 200                 205

Asn Lys Leu Glu Ile Lys Thr Gln Phe Glu Lys Glu Lys Leu Ala Gln
    210                 215                 220

Asp Arg Ile Lys Met Lys Asn Gln Leu Asp Ala Asn Ile Gln Arg Leu
225                 230                 235                 240

Asn Tyr Ser Leu Asp Ile Ala Asn Ala Ala Gly Ile Lys Lys Pro Val
                245                 250                 255

Tyr Ser Asn Gly Gln Ala Val Lys Asp Asp Pro Asp Phe Ser Ile Ser
                260                 265                 270

Leu Gly Ala Asp Gly Ile Glu Arg Lys Leu Glu Ile Glu Lys Ala Val
```

```
            275                 280                 285
Thr Asp Val Ala Glu Leu Asn Gly Glu Leu Arg Asn Arg Gln Tyr Leu
290                 295                 300
Val Glu Gln Leu Thr Lys Ala Asn Ile Asn Asp Val Asn Phe Thr Pro
305                 310                 315                 320
Phe Lys Tyr Gln Leu Ser Pro Ser Leu Pro Val Lys Lys Asp Gly Pro
                325                 330                 335
Gly Lys Ala Ile Ile Val Ile Leu Ser Ala Leu Ile Gly Gly Met Val
                340                 345                 350
Ala Cys Gly Ser Val Leu Leu Arg Tyr Ala Met Ala Ser Arg Lys Gln
                355                 360                 365
Asp Ala Met Met Ala Asp His Leu Val
370                 375

<210> SEQ ID NO 19
<211> LENGTH: 378
<212> TYPE: PRT
<213> ORGANISM: Salmonella enterica

<400> SEQUENCE: 19

Met Pro Ser Leu Asn Val Lys Gln Glu Lys Asn Gln Ser Phe Ala Gly
1               5                   10                  15
Tyr Ser Leu Pro Pro Ala Asn Ser His Glu Ile Asp Leu Phe Ser Leu
                20                  25                  30
Ile Glu Val Leu Trp Gln Ala Lys Arg Arg Ile Leu Ala Thr Val Phe
            35                  40                  45
Ala Phe Ala Cys Val Gly Leu Leu Ser Phe Leu Leu Pro Gln Lys
50                  55                  60
Trp Thr Ser Gln Ala Ile Val Thr Pro Ala Glu Ser Val Gln Trp Gln
65                  70                  75                  80
Gly Leu Glu Arg Thr Leu Thr Ala Leu Arg Val Leu Asp Met Glu Val
                85                  90                  95
Ser Val Asp Arg Gly Ser Val Phe Asn Leu Phe Ile Lys Lys Phe Ser
                100                 105                 110
Ser Pro Ser Leu Glu Glu Tyr Leu Arg Ser Pro Tyr Val Met
            115                 120                 125
Asp Gln Leu Lys Gly Ala Gln Ile Asp Glu Gln Asp Leu His Arg Ala
130                 135                 140
Ile Val Leu Leu Ser Glu Lys Met Lys Ala Val Asp Ser Asn Val Gly
145                 150                 155                 160
Lys Lys Asn Glu Thr Ser Leu Phe Thr Ser Trp Thr Leu Ser Phe Thr
                165                 170                 175
Ala Pro Thr Arg Glu Glu Ala Gln Lys Val Leu Ala Gly Tyr Ile Gln
                180                 185                 190
Tyr Ile Ser Asp Ile Val Lys Glu Thr Leu Glu Asn Ile Arg Asn
            195                 200                 205
Gln Leu Glu Ile Lys Thr Arg Tyr Glu Gln Glu Lys Leu Ala Met Asp
210                 215                 220
Arg Val Arg Leu Lys Asn Gln Leu Asp Ala Asn Ile Gln Arg Leu His
225                 230                 235                 240
Tyr Ser Leu Glu Ile Ala Asn Ala Ala Gly Ile Lys Arg Pro Val Tyr
                245                 250                 255
Ser Asn Gly Gln Ala Val Lys Asp Asp Pro Asp Phe Ser Ile Ser Leu
                260                 265                 270
```

```
Gly Ala Asp Gly Ile Ser Arg Lys Leu Glu Ile Glu Lys Gly Val Thr
            275                 280                 285

Asp Val Ala Glu Ile Asp Gly Asp Leu Arg Asn Arg Gln Tyr His Val
        290                 295                 300

Glu Gln Leu Ala Ala Met Asn Val Ser Asp Val Lys Phe Thr Pro Phe
305                 310                 315                 320

Lys Tyr Gln Leu Ser Pro Ser Leu Pro Val Lys Lys Asp Gly Pro Gly
                325                 330                 335

Lys Ala Ile Ile Ile Leu Ala Ala Leu Ile Gly Gly Met Met Ala
                340                 345                 350

Cys Gly Gly Val Leu Leu Arg His Ala Met Val Ser Arg Lys Met Glu
            355                 360                 365

Asn Ala Leu Ala Ile Asp Glu Arg Leu Val
        370                 375

<210> SEQ ID NO 20
<211> LENGTH: 325
<212> TYPE: PRT
<213> ORGANISM: Escherichia coli

<400> SEQUENCE: 20

Met Arg Val Glu Asn Asn Val Ser Gly Gln Asn His Asp Pro Glu
1               5                   10                  15

Gln Ile Asp Leu Ile Asp Leu Leu Val Gln Leu Trp Arg Gly Lys Met
                20                  25                  30

Thr Ile Ile Ile Ser Val Ile Val Ala Ile Ala Leu Ala Ile Gly Tyr
            35                  40                  45

Leu Ala Val Ala Lys Glu Lys Trp Thr Ser Thr Ala Ile Ile Thr Gln
50                  55                  60

Pro Asp Val Gly Gln Ile Ala Gly Tyr Asn Asn Ala Met Asn Val Ile
65                  70                  75                  80

Tyr Gly Gln Ala Ala Pro Lys Val Ser Asp Leu Gln Glu Thr Leu Ile
                85                  90                  95

Gly Arg Phe Ser Ser Ala Phe Ser Ala Leu Ala Glu Thr Leu Asp Asn
            100                 105                 110

Gln Glu Glu Pro Glu Lys Leu Thr Ile Glu Pro Ser Val Lys Asn Gln
        115                 120                 125

Gln Leu Pro Leu Thr Val Ser Tyr Val Gly Gln Thr Ala Glu Gly Ala
    130                 135                 140

Gln Met Lys Leu Ala Gln Tyr Ile Gln Gln Val Asp Asp Lys Val Asn
145                 150                 155                 160

Gln Glu Leu Glu Lys Asp Leu Lys Asp Asn Ile Ala Leu Gly Arg Lys
                165                 170                 175

Asn Leu Gln Asp Ser Leu Arg Thr Gln Glu Val Val Ala Gln Glu Gln
            180                 185                 190

Lys Asp Leu Arg Ile Arg Gln Ile Gln Glu Ala Leu Gln Tyr Ala Asn
        195                 200                 205

Gln Glu Gln Val Thr Lys Pro Gln Val Gln Gln Thr Glu Asp Val Thr
    210                 215                 220

Gln Asp Thr Leu Phe Leu Leu Gly Ser Glu Ala Leu Glu Ser Met Ile
225                 230                 235                 240

Lys His Glu Ala Thr Arg Pro Leu Val Phe Ser Ser Asn Tyr Tyr Gln
                245                 250                 255

Thr Arg Gln Asn Leu Leu Asp Ile Glu Ser Leu Lys Val Asp Asp Leu
            260                 265                 270
```

```
Asp Ile His Ala Tyr Arg Tyr Val Met Lys Pro Thr Leu Pro Ile Arg
        275                 280                 285

Arg Asp Ser Pro Lys Lys Ala Ile Thr Leu Ile Leu Ala Val Leu Leu
    290                 295                 300

Gly Gly Met Val Gly Ala Gly Ile Val Leu Gly Arg Asn Ala Leu Arg
305                 310                 315                 320

Asn Tyr Asn Ala Lys
            325

<210> SEQ ID NO 21
<211> LENGTH: 326
<212> TYPE: PRT
<213> ORGANISM: Escherichia coli

<400> SEQUENCE: 21

Met Arg Val Glu Asn Asn Val Ser Gly Gln Asn Asn Asp Pro Glu
1               5                   10                  15

Gln Ile Asp Leu Ile Asp Leu Leu Val Gln Leu Trp Arg Gly Lys Met
            20                  25                  30

Thr Ile Ile Ile Ser Val Ile Val Ala Ile Ala Leu Ala Ile Gly Tyr
        35                  40                  45

Leu Ala Val Ala Lys Glu Lys Trp Thr Ser Thr Ala Ile Ile Thr Gln
50                  55                  60

Pro Asp Val Gly Gln Ile Ala Gly Tyr Asn Asn Ala Met Asn Val Ile
65                  70                  75                  80

Tyr Gly Gln Ala Ala Pro Lys Val Ser Asp Leu Gln Glu Thr Leu Ile
                85                  90                  95

Gly Arg Phe Ser Ser Ala Phe Ser Ala Leu Ala Glu Thr Leu Asp Asn
            100                 105                 110

Gln Asp Glu Pro Glu Lys Leu Thr Ile Glu Pro Ser Val Lys Asn Gln
        115                 120                 125

Gln Leu Pro Leu Thr Val Ser Tyr Val Gly Gln Thr Ala Glu Gly Ala
    130                 135                 140

Gln Met Lys Leu Ala Gln Tyr Ile Gln Gln Val Asp Asp Lys Val Asn
145                 150                 155                 160

Gln Glu Leu Glu Lys Asp Leu Lys Asp Asn Ile Ala Leu Gly Arg Lys
                165                 170                 175

Asn Leu Gln Asp Ser Leu Arg Thr Gln Glu Val Val Ala Gln Glu Gln
            180                 185                 190

Lys Asp Leu Arg Ile Arg Gln Ile Gln Glu Ala Leu Gln Tyr Ala Asn
        195                 200                 205

Gln Ala Gln Val Thr Lys Pro Gln Ile Gln Thr Gly Glu Asp Ile
    210                 215                 220

Thr Gln Asp Thr Leu Phe Leu Leu Gly Ser Glu Ala Leu Glu Ser Met
225                 230                 235                 240

Ile Lys His Glu Ala Thr Arg Pro Leu Val Phe Ser Pro Asn Tyr Tyr
                245                 250                 255

Gln Thr Arg Gln Asn Leu Leu Asp Ile Glu Ser Leu Lys Val Asp Asp
            260                 265                 270

Leu Asp Ile His Ala Tyr Arg Tyr Val Met Lys Pro Thr Leu Pro Ile
        275                 280                 285

Arg Arg Asp Ser Pro Lys Lys Ala Ile Thr Leu Ile Leu Ala Val Leu
    290                 295                 300

Leu Gly Gly Met Val Gly Ala Gly Ile Val Leu Gly Arg Asn Ala Leu
```

-continued

```
                305                 310                 315                 320

Arg Asn Tyr Asn Ala Lys
                325

<210> SEQ ID NO 22
<211> LENGTH: 326
<212> TYPE: PRT
<213> ORGANISM: Escherichia coli

<400> SEQUENCE: 22

Met Arg Val Glu Asn Asn Val Ser Gly Gln Asn His Asp Pro Glu
1               5                   10                  15

Gln Ile Asp Leu Ile Asp Leu Leu Val Gln Leu Trp Arg Gly Lys Met
                20                  25                  30

Thr Ile Ile Ile Ser Val Val Ala Ile Ala Leu Ala Ile Gly Tyr
                35                  40                  45

Leu Ala Val Ala Lys Glu Lys Trp Thr Ser Thr Ala Ile Ile Thr Gln
50                  55                  60

Pro Asp Val Gly Gln Ile Ala Gly Tyr Asn Asn Ala Met Asn Val Ile
65                  70                  75                  80

Tyr Gly Gln Ala Ala Pro Lys Val Ser Asp Leu Gln Glu Thr Leu Ile
                85                  90                  95

Gly Arg Phe Ser Phe Ala Phe Ser Ala Leu Ala Glu Thr Leu Asp Asn
                100                 105                 110

Gln Lys Glu Pro Glu Lys Leu Thr Ile Glu Pro Ser Val Lys Asn Gln
                115                 120                 125

Gln Leu Pro Leu Thr Val Ser Tyr Val Gly Gln Thr Ala Glu Asp Ala
                130                 135                 140

Gln Met Lys Leu Ala Gln Tyr Ile Gln Gln Val Asp Asp Lys Val Asn
145                 150                 155                 160

Gln Glu Leu Glu Lys Asp Leu Lys Asp Asn Leu Ala Leu Gly Arg Lys
                165                 170                 175

Asn Leu Gln Asp Ser Leu Arg Thr Gln Glu Val Val Ala Gln Glu Gln
                180                 185                 190

Lys Asp Leu Arg Ile Arg Gln Ile Gln Glu Ala Leu Gln Tyr Ala Asn
                195                 200                 205

Gln Ala Gln Val Thr Lys Pro Gln Ile Gln Gln Thr Gly Glu Asp Ile
                210                 215                 220

Thr Gln Asp Thr Leu Phe Leu Leu Gly Ser Glu Ala Leu Glu Ser Met
225                 230                 235                 240

Ile Lys His Glu Ala Thr Arg Pro Leu Val Phe Ser Pro Asn Tyr Tyr
                245                 250                 255

Gln Thr Arg Gln Asn Leu Leu Asp Ile Glu Asn Leu Lys Val Asp Asp
                260                 265                 270

Leu Asp Ile His Ala Tyr Arg Tyr Val Met Lys Pro Thr Leu Pro Ile
                275                 280                 285

Arg Arg Asp Ser Pro Lys Lys Ala Ile Thr Leu Ile Leu Ala Val Leu
                290                 295                 300

Leu Gly Gly Met Val Gly Ala Gly Ile Val Leu Gly Arg Asn Ala Leu
305                 310                 315                 320

Arg Asn Tyr Asn Ser Lys
                325

<210> SEQ ID NO 23
<211> LENGTH: 326
```

```
<212> TYPE: PRT
<213> ORGANISM: Escherichia coli

<400> SEQUENCE: 23

Met Arg Val Glu Asn Asn Val Ser Gly Gln Asn His Asp Pro Glu
1               5                   10                  15

Gln Ile Asp Leu Ile Asp Leu Leu Val Gln Leu Trp Arg Gly Lys Met
            20                  25                  30

Thr Ile Ile Ile Ser Val Ile Val Ala Ile Leu Ala Ile Gly Tyr
        35                  40                  45

Leu Ala Val Ala Lys Glu Lys Trp Thr Ser Thr Ala Ile Ile Thr Gln
    50                  55                  60

Pro Asp Val Gly Gln Ile Ala Gly Tyr Asn Asn Ala Met Asn Val Ile
65                  70                  75                  80

Tyr Gly Gln Ala Ala Pro Lys Val Ser Asp Leu Gln Glu Thr Leu Ile
                85                  90                  95

Gly Arg Phe Ser Ser Ala Phe Ser Ala Leu Ala Glu Thr Leu Asp Asn
            100                 105                 110

Gln Glu Glu Arg Glu Lys Leu Thr Ile Glu Pro Ser Val Lys Asn Gln
        115                 120                 125

Gln Leu Pro Leu Thr Val Ser Tyr Val Gly Gln Thr Ala Glu Gly Ala
    130                 135                 140

Gln Met Lys Leu Ala Gln Tyr Ile Gln Gln Val Asp Asp Lys Val Asn
145                 150                 155                 160

Gln Glu Leu Glu Lys Asp Leu Lys Asp Asn Ile Ala Leu Gly Arg Lys
                165                 170                 175

Asn Leu Gln Asp Ser Leu Arg Thr Gln Glu Val Val Ala Gln Glu Gln
            180                 185                 190

Lys Asp Leu Arg Ile Arg Gln Ile Gln Glu Ala Leu Gln Tyr Ala Asn
        195                 200                 205

Gln Ala Gln Val Thr Lys Pro Gln Ile Gln Gln Thr Gly Glu Asp Ile
    210                 215                 220

Thr Gln Asp Thr Leu Phe Leu Leu Gly Ser Glu Ala Leu Glu Ser Met
225                 230                 235                 240

Ile Lys His Glu Ala Thr Arg Pro Leu Val Phe Ser Pro Asn Tyr Tyr
                245                 250                 255

Gln Thr Arg Gln Asn Leu Leu Asp Ile Glu Ser Leu Lys Val Asp Asp
            260                 265                 270

Leu Asp Ile His Ala Tyr Arg Tyr Val Met Lys Pro Met Leu Pro Ile
        275                 280                 285

Arg Arg Asp Ser Pro Lys Lys Ala Ile Thr Leu Ile Leu Ala Val Leu
    290                 295                 300

Leu Gly Gly Met Val Gly Ala Gly Ile Val Leu Gly Arg Asn Ala Leu
305                 310                 315                 320

Arg Asn Tyr Asn Ala Lys
                325

<210> SEQ ID NO 24
<211> LENGTH: 327
<212> TYPE: PRT
<213> ORGANISM: Salmonella enterica

<400> SEQUENCE: 24

Met Thr Val Asp Ser Asn Thr Ser Ser Gly Arg Gly Asn Asp Pro Glu
1               5                   10                  15
```

-continued

```
Gln Ile Asp Leu Ile Glu Leu Leu Gln Leu Trp Arg Gly Lys Met
             20                  25                  30
Thr Ile Ile Val Ala Val Ile Ile Ala Ile Leu Leu Ala Val Gly Tyr
             35                  40                  45
Leu Met Ile Ala Lys Glu Lys Trp Thr Ser Thr Ala Ile Ile Thr Gln
 50                  55                  60
Pro Asp Ala Ala Gln Val Ala Thr Tyr Thr Asn Ala Leu Asn Val Leu
 65                  70                  75                  80
Tyr Gly Gly Asn Ala Pro Lys Ile Ser Glu Val Gln Ala Asn Phe Ile
                     85                  90                  95
Ser Arg Phe Ser Ser Ala Phe Ser Ala Leu Ser Glu Val Leu Asp Asn
                 100                 105                 110
Gln Lys Glu Arg Glu Lys Leu Thr Ile Glu Gln Ser Val Lys Gly Gln
                 115                 120                 125
Ala Leu Pro Leu Ser Val Ser Tyr Val Ser Thr Thr Ala Glu Gly Ala
 130                 135                 140
Gln Arg Arg Leu Ala Glu Tyr Ile Gln Gln Val Asp Glu Glu Val Ala
 145                 150                 155                 160
Lys Glu Leu Glu Val Asp Leu Lys Asp Asn Ile Thr Leu Gln Thr Lys
                 165                 170                 175
Thr Leu Gln Glu Ser Leu Glu Thr Gln Glu Val Val Ala Gln Glu Gln
                 180                 185                 190
Lys Asp Leu Arg Ile Lys Gln Ile Glu Glu Ala Leu Arg Tyr Ala Asp
                 195                 200                 205
Glu Ala Lys Ile Thr Gln Pro Gln Ile Gln Gln Thr Gln Asp Val Thr
 210                 215                 220
Gln Asp Thr Met Phe Leu Leu Gly Ser Asp Ala Leu Lys Ser Met Ile
 225                 230                 235                 240
Gln Asn Glu Ala Thr Arg Pro Leu Val Phe Ser Pro Ala Tyr Tyr Gln
                 245                 250                 255
Thr Lys Gln Thr Leu Leu Asp Ile Lys Asn Leu Lys Val Thr Ala Asp
                 260                 265                 270
Thr Val His Val Tyr Arg Tyr Val Met Lys Pro Thr Leu Pro Val Arg
                 275                 280                 285
Arg Asp Ser Pro Lys Thr Ala Ile Thr Leu Val Leu Ala Val Leu Leu
 290                 295                 300
Gly Gly Met Ile Gly Ala Gly Ile Val Leu Gly Arg Asn Ala Leu Arg
 305                 310                 315                 320
Ser Tyr Lys Pro Lys Ala Leu
                 325
```

UNITED STATES PATENT AND TRADEMARK OFFICE
CERTIFICATE OF CORRECTION

| | |
|---|---|
| PATENT NO. | : 12,128,095 B2 |
| APPLICATION NO. | : 17/672126 |
| DATED | : October 29, 2024 |
| INVENTOR(S) | : Robert G. K. Donald et al. |

Page 1 of 1

It is certified that error appears in the above-identified patent and that said Letters Patent is hereby corrected as shown below:

In the Claims

<u>Column 145, Claim 1, Line 61:</u>
Delete "[Formula O14]"

<u>Column 146, Claim 1, Line 66:</u>
Delete "[Formula O89]"

Signed and Sealed this
Fourth Day of March, 2025

Coke Morgan Stewart
*Acting Director of the United States Patent and Trademark Office*